(12) United States Patent
Litosh et al.

(10) Patent No.: US 9,200,319 B2
(45) Date of Patent: Dec. 1, 2015

(54) NUCLEOTIDES AND NUCLEOSIDES AND METHODS FOR THEIR USE IN DNA SEQUENCING

(71) Applicant: Lasergen, Inc., Houston, TX (US)

(72) Inventors: Vladislav A. Litosh, Cypress, TX (US); Megan N. Hersh, Houston, TX (US); Brian P. Stupi, Cypress, TX (US); Weidong Wu, Houston, TX (US); Michael L. Metzker, Houston, TX (US)

(73) Assignee: Lasergen, Inc., Houston, TX (US)

( * ) Notice: Subject to any disclaimer, the term of this patent is extended or adjusted under 35 U.S.C. 154(b) by 0 days.

(21) Appl. No.: 14/519,616

(22) Filed: Oct. 21, 2014

(65) Prior Publication Data

US 2015/0140559 A1 May 21, 2015

Related U.S. Application Data

(60) Continuation of application No. 13/929,305, filed on Jun. 27, 2013, now Pat. No. 8,877,905, which is a division of application No. 13/406,934, filed on Feb. 28, 2012, now Pat. No. 8,497,360, which is a division of application No. 12/483,080, filed on Jun. 11, 2009, now Pat. No. 8,148,503.

(60) Provisional application No. 61/184,779, filed on Jun. 5, 2009, provisional application No. 61/060,795, filed on Jun. 11, 2008.

(51) Int. Cl.
| | | |
|---|---|---|
| *C12Q 1/68* | (2006.01) | |
| *C12P 19/34* | (2006.01) | |
| *C07H 21/00* | (2006.01) | |
| *C07H 21/02* | (2006.01) | |
| *C07H 19/04* | (2006.01) | |

(52) U.S. Cl.
CPC ........ *C12Q 1/6869* (2013.01); *C12Q 2525/117* (2013.01); *C12Q 2563/107* (2013.01)

(58) Field of Classification Search
CPC ........... C12Q 1/6869; C12Q 2525/117; C12Q 2563/107
USPC ............ 435/6.12; 536/22.1, 25.32, 26.1, 26.2
See application file for complete search history.

(56) References Cited

U.S. PATENT DOCUMENTS

| | | | |
|---|---|---|---|
| 3,845,035 A | 10/1974 | Kampe et al. | |
| 4,318,846 A | 3/1982 | Khanna et al. | |
| 4,439,356 A | 3/1984 | Khanna et al. | |
| 4,657,897 A | 4/1987 | Bristol et al. | |
| 4,704,381 A | 11/1987 | Schaumann et al. | |
| 5,151,507 A | 9/1992 | Hobbs, Jr. et al. | |
| 5,188,934 A | 2/1993 | Menchen et al. | |
| 5,302,509 A | 4/1994 | Cheeseman | |
| 5,614,386 A | 3/1997 | Metzker et al. | |
| 5,684,142 A | 11/1997 | Mishra et al. | |
| 5,728,529 A | 3/1998 | Metzker et al. | |
| 5,763,594 A | 6/1998 | Hiatt et al. | |
| 5,770,367 A | 6/1998 | Southern et al. | |
| 5,773,423 A | 6/1998 | Jacobson et al. | |
| 5,808,045 A | 9/1998 | Hiatt et al. | |
| 5,824,796 A | 10/1998 | Petrie et al. | |
| 5,861,287 A | 1/1999 | Metzker et al. | |
| 5,872,244 A | 2/1999 | Hiatt et al. | |
| 5,994,063 A | 11/1999 | Metzker et al. | |
| 6,214,987 B1 | 4/2001 | Hiatt et al. | |
| 6,255,083 B1 | 7/2001 | Williams | |
| 6,579,704 B2 | 6/2003 | Short | |
| 6,664,079 B2 | 12/2003 | Ju et al. | |
| RE38,416 E | 2/2004 | Petrie et al. | |
| 6,762,048 B2 | 7/2004 | Williams | |
| 6,812,219 B2 | 11/2004 | LaColla et al. | |
| 6,818,395 B1 | 11/2004 | Quake et al. | |
| 6,833,246 B2 | 12/2004 | Balasubramanian | |
| 6,869,764 B2 | 3/2005 | Williams et al. | |
| 6,875,751 B2 | 4/2005 | Imbach et al. | |
| 6,995,841 B2 | 2/2006 | Scott et al. | |
| 7,057,026 B2 | 6/2006 | Barnes et al. | |
| 7,101,861 B2 | 9/2006 | Sommadossi et al. | |
| 7,105,493 B2 | 9/2006 | Sommadossi et al. | |
| 7,125,660 B2 | 10/2006 | Stanton et al. | |
| 7,148,206 B2 | 12/2006 | Sommadossi et al. | |
| 7,163,929 B2 | 1/2007 | Sommadossi et al. | |
| 7,329,492 B2 | 2/2008 | Briggs et al. | |

(Continued)

FOREIGN PATENT DOCUMENTS

| | | |
|---|---|---|
| EP | 0272007 A2 | 6/1988 |
| EP | 0 640 146 | 3/1995 |

(Continued)

OTHER PUBLICATIONS

Adzamli et al., "Development of phosphonate derivatives of gadolinium chelates for NMRimaging of calcified soft tissues," *J Med. Chem.*, 32(1):139-144, 1989.

Agbanyo et al., "5'-S-(2-aminoethyl )-N 6-( 4-nitrobenzy 1 )-5' - thioadenosine (SAENTA), anovel ligand with high affinity for polypeptides associated with nucleoside transport. Partial purification of the nitrobenzylthioinosine-binding protein of pig erythrocytes by affinity chromatography," *Biochem. J.*, 270:605-614, 1990.

Barltrop et al., "Photosensitive Protecting Groups," *Chem. Commun.*, 822-23, 1966.

Barone et al., "Novel Nucleoside Triphosphate Analogs for the Enzymatic Labeling of Nucleic Acids," *Nucleosides, Nucleotides, and Nucleic Acids*, 20:1141-45, 2001.

Barth et al., "Time-Resolved Infrared Spectroscopy of Intermediates and Products from Photolysis of 1-(2-Nitrophenyl) ethyl Phosphates: Reactions of the 2-Nitrosoacetophenone Byproduct with Thiols," *J. Amer. Chem. Soc.*, 119:4149-59, 1997.

(Continued)

*Primary Examiner* — Jezia Riley
(74) *Attorney, Agent, or Firm* — Parker Highlander PLLC

(57) ABSTRACT

The present invention relates generally to labeled and unlabled cleavable terminating groups and methods for DNA sequencing and other types of DNA analysis. More particularly, the invention relates in part to nucleotides and nucleosides with chemically cleavable, photocleavable, enzymatically cleavable, or non-photocleavable groups and methods for their use in DNA sequencing and its application in biomedical research.

19 Claims, 5 Drawing Sheets

(56) References Cited

U.S. PATENT DOCUMENTS

| | | | |
|---|---|---|---|
| 7,345,159 | B2 | 3/2008 | Edwards et al. |
| 7,355,036 | B2 | 4/2008 | Guimil et al. |
| 7,414,116 | B2 | 8/2008 | Milton et al. |
| 7,476,734 | B2 | 1/2009 | Liu |
| 7,541,444 | B2 | 6/2009 | Milton et al. |
| 7,585,851 | B2 | 9/2009 | Bryant et al. |
| 7,592,435 | B2 | 9/2009 | Milton et al. |
| 7,816,503 | B2 | 10/2010 | Milton et al. |
| 7,893,227 | B2 | 2/2011 | Wu et al. |
| 7,897,737 | B2 | 3/2011 | Wu et al. |
| 7,964,352 | B2 | 6/2011 | Wu et al. |
| 8,148,503 | B2 | 4/2012 | Litosh et al. |
| 8,198,029 | B2 | 6/2012 | Wu et al. |
| 8,212,015 | B2 | 7/2012 | Milton et al. |
| 8,343,937 | B2 | 1/2013 | Sommadossi et al. |
| 8,361,727 | B2 | 1/2013 | Wu et al. |
| 8,497,360 | B2 | 7/2013 | Litosh et al. |
| 2002/0034750 | A1 | 3/2002 | Short |
| 2003/0060400 | A1 | 3/2003 | LaColla et al. |
| 2003/0083306 | A1 | 5/2003 | Imbach et al. |
| 2003/0092668 | A1 | 5/2003 | Liang et al. |
| 2003/0180769 | A1 | 9/2003 | Metzker |
| 2004/0014096 | A1 | 1/2004 | Anderson et al. |
| 2004/0063622 | A1 | 4/2004 | Sommadossi et al. |
| 2004/0097462 | A1 | 5/2004 | Sommadossi et al. |
| 2004/0102414 | A1 | 5/2004 | Sommadossi et al. |
| 2005/0048601 | A1 | 3/2005 | Dellinger et al. |
| 2005/0049407 | A1 | 3/2005 | Dellinger et al. |
| 2005/0049411 | A1 | 3/2005 | Dellinger et al. |
| 2005/0113330 | A1 | 5/2005 | Bryant et al. |
| 2006/0160081 | A1 | 7/2006 | Milton et al. |
| 2006/0166865 | A1 | 7/2006 | Sommadossi et al. |
| 2007/0037773 | A1 | 2/2007 | Sommadossi et al. |
| 2008/0131952 | A1 | 6/2008 | Wu et al. |
| 2008/0132692 | A1 | 6/2008 | Wu et al. |
| 2009/0081686 | A1 | 3/2009 | Wu et al. |
| 2010/0029494 | A1 | 2/2010 | Cherkasov et al. |
| 2010/0041041 | A1 | 2/2010 | Litosh et al. |
| 2011/0200988 | A1 | 8/2011 | Wu et al. |
| 2011/0287427 | A1 | 11/2011 | Wu et al. |
| 2013/0072388 | A1 | 3/2013 | Wu et al. |
| 2013/0095471 | A1 | 4/2013 | Wu et al. |

FOREIGN PATENT DOCUMENTS

| | | |
|---|---|---|
| EP | 0 866 071 | 9/1998 |
| JP | 2002-527524 | 8/2002 |
| JP | 2004-501929 | 1/2004 |
| JP | 2004-534767 | 11/2004 |
| JP | 2011-506265 | 3/2011 |
| SU | 539532 A | 2/1977 |
| WO | WO 91/05060 | 4/1991 |
| WO | WO 97/00967 | 1/1997 |
| WO | WO 98/50047 | 11/1998 |
| WO | WO 01/92282 | 12/2001 |
| WO | WO 01/96353 | 12/2001 |
| WO | WO 02/083937 | 10/2002 |
| WO | WO 02/029003 | 11/2002 |
| WO | WO 03/021212 | 3/2003 |
| WO | WO 03/048387 | 6/2003 |
| WO | WO 03/087302 | 10/2003 |
| WO | WO 03/048178 | 12/2003 |
| WO | WO 2004/018497 | 3/2004 |
| WO | WO 2004/018493 | 4/2004 |
| WO | WO 2004/058791 | 7/2004 |
| WO | WO 2005/044836 | 5/2005 |
| WO | WO 2005/084367 | 9/2005 |
| WO | WO 2006/084281 | 8/2006 |

OTHER PUBLICATIONS

Bartholomew and Broom, "One-step chemical synthesis of ribonucleosides bearing a photolabile ether protecting group," *J. Chem. Soc. Chem. Commun.*, 38, 1975.
Bentley et al., "Accurate Whole Human Genome Sequencing Using Reversible Terminator Chemistry," *Nature*, 456:53-59, 2008.
Berlier et al. "Quantitative comparison of long-wavelength alexa fluor dyes to cy dyes: fluorescence of the dyes and their bioconjugates," *The Journal of Histochemistry & Cytochemistry*, 51(12):1699-1712, 2003.
Berson & Brown, "Studies on Dihydropyridines. I. The Preparation of Unsymmetrical 4-Aryl-1,4-dihydropyridines by the Hantzsch-Beyer Synthesis,"*J. Amer. Chem. Soc.*, 77:447-50, 1955.
Bodepudi et al., "Synthesis of 2'-deoxy-7, 8-dihydro-8-oxoguanosine and 2'-deoxy-7,8-dihydro-8-oxoadenosine and their incorporation into oligomeric DNA," *Chem. Res. Toxicol.*, 5:608-617, 1992.
Bowers et al., "Virtual Terminator Nucleotides for Next-Generation DNA sequencing," *Nature Methods*, 6:593-95, 2009.
Brandis, "Dye structure affects *Taq* DNA polymerase terminator selectivity," *Nucleic Acids Research*, 27(8):1912-1918, 1999.
Bressi et al., "Adenosine analogues as inhibitors of *Trypanosoma brucei* phosphoglycerate kinase: Elucidation of a novel binding mode for a 2-amino-$N_6$ substituted andenosine," *J. Med. Chem.*, 43, 4135-4250, 2000.
Cameron and Frechet, "Photogeneration of Organic Bases from O-nitrobenzyl-derived Carbamates," *J. Am. Chem. Soc.*, 113:4303-13, 1991.
Canard & Sarfati, "DNA Polymerase Fluorescent Substrates with Reversible 3'-tags," *Gene*, 148:1-6, 1994.
Chaulk and MacMillan, "Caged RNA: photo-control of a ribozyme reaction," *Nucleic Acids Res.*, 26:3173-3178, 1998.
Chaves des Neves and Pais, "Identification of a spathe regreening factor in *Zantedeschia aethiopicia*," *Biochemical and Biophysical Research Communications*, 95(4): 1387-1392, 1980.
Cho et al., "$_{15}$N nuclear magnetic resonance studies on the tautomerism of 8-hydroxy-2'-deoxyguanosine, 8-hydroxyguanosine, and other C8-substituted guanine nucleosides," *Chem. Res. Toxicol.*, 3:445-452, 1990.
Cho et al., "Correlation between NMR spectral parameters of nucleosides and its implication to the conformation about the glycosyl bond," *Biochemical and Biophysical Research Communications*, 180(1):273-278, 1991.
Corrie et al., "Synthesis and Absolute Stereochemistry of the two Diastereoisomers of $P_3$-1-(2-nitrophenyl) ethyl adenosine triphosphate ('Caged' ATP),"*J. Chem. Soc., Perkin Trans.* 1, 1015-19, 1992.
Corrie, in *Dynamics studies in biology*, Goeldner and Givens (Eds.), Wiley-VCH Verlag GmbH & Co. KGaA, Weinheim, pp. 1-28, 2005.
Corrigenda for Welch et al., "Synthesis of nucleosides designed for combinatorial DNA sequencing," *Chem. Eur. J.*, 11:7145, 2005.
Dewey et al., "New uridine derivatives for systematic evolution of RNA ligands by exponential enrichment," *J. Am. Chem. Soc.*, 117:8474-8475, 1995.
Dressman et al., "Transforming single DNA molecules into fluorescent magnetic particles for detection and enumeration of genetic variations," *Proc. Natl. Acad. Sci. USA*, 100:8817-8822, 2003.
Dutta et al., "Synthesis and biological activities of some N6-(nitro- and-aminobenzyl) adenosines," *Journal of Medicinal Chemistry*, 18(8):780-783, 1975.
Eid et al., "Real-Time DNA Sequencing from Single Polymerase Molecules," *Science*, 323:133-138, 2009.
Erratum for Welch and Burgess, "Synthesis of fluorescent, photolabile 3'-O-protected nucleoside triphosphates for the base addition sequencing scheme," *Nucleosides, Nucleotides, and Nucleic Acids*, 25:119, 2006.
Evans et al., "Oxidative DNA damage and disease: induction, repair and significance," *Mutation Research*, 567:1-61, 2004.
Extended Search Report and Opinion issued in European Patent Application No. 07854973.0, dated Nov. 25, 2013.
Friest et al., "Valyl-tRNA, Isoleucyl-tRNA and Tyrosyl-tRNA synthetase from Baker's Yeast," *Eur. J. Biochem.*, 66:493-497, 1976.
Gao et al., "Structural determinants of A3 adenosine receptor activation: Nucleoside ligands at the agonist/antagonist boundary,"*J. Med. Chem.*, 45:4471-4484, 2002.
Gardner and Jack, "Determinants of nucleotide sugar recognition in an archaeon DNA polymerase," *Nucleic Acids Research*, 27(12):2545-2553, 1999.

(56) References Cited

OTHER PUBLICATIONS

Gardner and Jack, "Acyclic and dideoxy terminator preferences denote divergent sugar recognition by archaaeon and *Taq* DNA polymerases," *Nucleic Acids Research*, 30(2):605-613, 2002.
Gebeyehu et al., "Novel biotinylated nucleotide—analogs for labeling and colorimetric detection of DNA," *Nucleic Acids Research*, 15(11):4513-4534, 1987.
Gibbs, "Identification of mutations leading to the Lesch-Nyhan syndrome by automated direct DNA sequencing of in vitro amplified cDNA," *Proc. Natl. Acad. Sci. USA*, 86:1919-1923, 1989.
Giegrich et al., "New Photolabile Protecting Groups in Nucleoside and Nucleotide Chemistry-Synthesis, Cleavage Mechanisms, and Applications," *Nucleosides Nucleotides*, 17:1987-1996, 1998.
Golisade et al., "Anti-malarial activity of N6-substituted Adenosine derivatives. Part I.," *Bioorganic & Medicinal Chemistry*, 10:769-777, 2002.
Gommers-Ampt and Borst, "Hypermodified bases in DNA," *FASEB J.*, 9(11):1034-1042, 1995.
Guo et al., "Four-color DNA sequencing with 3'-O-modified Nucleotide Reversible Terminators and Chemically Cleavable Fluorescent Dideoxynucleotides," *Proc. Natl. Acad. Sci. USA*, 105:9145-50, 2008.
Hampton et al., "Species- or isozyme-specific enzyme inhibitors. 4. Design of a two-site inhibitor of adenylate kinase with isozyme selectivity," *J. Med. Chem.*, 25:638-644, 1982.
Harris et al., "Single-molecule DNA sequencing of a viral genome," *Science*, 320:106-109, 2008.
Hasan et al., "Photolabile Protecting Groups for Nucleosides: Synthesis and Photodeprotection Rates," *Tetrahedron*, 53:4247-64, 1997.
Hashizume et al., "Synthesis and cytokinin activity of alpha-anomeric $N_6$-benzyladenosine," *Agric. Biol. Chem.*, 49(1):225-227, 1985.
Henderson et al., "4,4'-Dimethoxytrityl and 4,4',4''-trimethoxytrityl as protecting tropus for amino functions; selectivity for primary amino groups and application in $_{15}$N-labeling," *J. Chem. Soc. Perkin Trans.*, 1:3407-3413, 1997.
Hermanns et al., "Synthesis of 8-[18O]hydroxy-2'-deoxyguanosine," *Journal of Labelled Compounds and Radiopharmaceuticals*, 36(2):191-197, 1993.
Hobarnter and Silverman, "Modulation of RNA tertiary folding by incorporation of caged nucleotides," *Angew. Chem. Int. Ed.*, 44:7305-7309, 2005.
Holmes and Robins, "Purine nucleosides. IX. The synthesis of 9-beta-D-Ribofuranysyl uric acid and other related 8-substituted purine ribonucleosides," *Journal of the American Chemical Society*, 87:8:1772-176, 1965.
Honda et al., "New type of prefabricated fully protected ribonucleotide monomer unites as useful synthetic intermediates in rapid oligoribonucleotide synthesis," *Chemistry Letters*, pp. 15-18, 1982.
International Human Genome Sequencing Consortium., "Initial sequencing and analysis of the human genome," *Nature*, 409:860-921, 2001.
Jacobson et al., "Methancarba analogues of purine nucleosides as potent and selective adenosine receptor agonists," *J. Med. Chem.*, 43:2196-2203, 2000.
Jacobson et al., "A novel pharmacological approach to treading cardiac ischemia," *J. Biol. Chem.*, 275(39): 30272-30279, 2000.
Ju et al., "Fluorescence energy transfer dye-labeled primers for DNA sequencing and analysis," *Proc. Natl. Acad. Sci USA*, 92:4347-4351, 1995.
Ju et al., "Four-color DNA sequencing by synthesis using cleavable fluorescent nucleotide reversible terminators," *Proc. Natl. Acad. Sci. USA*, 103:19635-40, 2006.
Juillerat et al., "Directed evolution of O6-Alkylguanine-DNA alkyltransferase for efficient labeling of fusion proteins with small molecules in vivo," *Chem Biol.*, 10:313-317, 2003.

Kahl and Greenberg, "Introducing structural diversity in oligonucleotides via photolabile, convertible C5-substituted nucleotides," *Journal of the American Chemical Society*, 121(4):597-604, 1999.
Kim et al., "2-Substitution of N6-benzyladenosine-5'-uronamides enhances selectivity for A3 adenosine receptors," *J. Med. Chem.*, 37:3614-3621, 1994.
Kobayashi et al., "A microfluidic device for conducting gas-liquid-solid hydrogenation reactions," *Science*, 304:1305-1308, 2004.
Kong et al., "Characterization of a DNA polymerase from the hyperthermophile archaea *Thermococcus litoralis*," *The Journal of Biological Chemistry*, 268(3):1965-1975, 1993.
Kornher and Livak, "Mutation detection using nucleotide analogs that alter electrophoretic mobility," *Nucleic Acids Research*, 17(19):7779-7784, 1989.
Kulikowski et al., "Structure-activity relationships and conformational features of antiherpetic pyrimidine and purine analogues. A review," *Pharmacy World & Science*, 16(2):127-138, 1994.
Lee et al., "New energy transfer dyes for DNA sequencing," *Nucleic Acids Research*, 25(14):2816-2822, 1997.
Levy et al., "The diploid genome sequence of an individual human," *PLoS Biol.*, 5:e254, 2007.
Lewis et al., "Color-blind fluorescence detection for four-color DNA sequencing," *PNAS*, 102(15):5346-5351, 2005.
Li et al., "A photocleavable fluorescent nucleotide for DNA sequencing and analysis," *PNAS*, 100(2):414-419, 2003.
Limbach, et al., "Summary: the Modified Nucleosides of RNA," *Nucleic Acids Res.*, 22:2183-2196, 1994.
Lin et al., "8-substituted guanosine and 2'-Deoxyguanosine derivatives as potential inducers of the differentiation of friend erythroleukemia cells," *J. Med. Chem.*, 28:1194-1198, 1985.
Liu et al., "A molecular gate which controls unnatural ATP analogue recognition by the tyrosine kinase v-Src," *Bioorganic & Medicinal Chemistry*, 6:1219-1226, 1998.
Malecki et al., "Mutations in NEUROD1 are associated with the development of type 2 diabetes mellitus," *Nature Genetics*, 23:323-328, 1999.
McCray et al., "A New Approach to Time-Resolved Studies of ATP-requiring Biological Systems; Laser Flash Photolysis of Caged ATP," *Proc. Natl. Acad. Sci. USA*, 77:7237-41, 1980.
McDougall et al., "Analogs of Guanine Nucleoside Triphosphates for Sequencing Applications," *Nucleosides, Nucleotides & Nucleic Acids*, 20:501-6, 2001.
McGall et al., "The Efficiency of Light-Directed Synthesis of DNA Arrays on Glass Substrates," *J. Amer. Chem. Soc.*, 119:5081-90, 1997.
McMinn and Greenberg, "Novel solid phase synthesis supports for the preparation of oligonucleotides containing 3'-alkyl amines," *Tetrahedron*, 52(11):3827-3840, 1996.
Metzker et al., "Electrophoretically uniform fluorescent dyes for automated DNA sequencing," *Science*, 271:1420-1422, 1996.
Metzker et al., "Elimination of residual natural nucleotides from 3'-O-modified-dNTP syntheses by enzymatic mop-up," *BioTechniques*, 25:814-817, 1998.
Metzker et al., "Emerging technologies in DNA sequencing," *Genome Research*, 15:1767-1776, 2005.
Metzker et al., "Termination of DNA synthesis by novel 3'-modified-deoxyribonucleoside 5'-triphosphates," *Nucleic Acids Res.*, 22:4259-4267, 1994.
Mitra et al., "Fluorescent In Situ Sequencing on Polymerase Colonies," *Anal. Biochem.*, 320:55-65, 2003.
Molecular Probes™ invitrogen detection technologies, "Alexa Fluor® Dyes—Simply the Best and Brightest, Fluorescent dyes and conjugates," 2005.
Moore and Koreeda, "Application of the change in partition coefficient with pH to the structure determination of alkyl substituted guanosines," *Biochemical and Biophysical Research Communications*, 73(2):459-464, 1976.
Morrison, In: *The chemistry of nitro and nitroso groups*, Feuer (Ed.), Interscience publishers, NY, 165-213, 1969.
Mosher et al., "Photochromotropism of *gamma*-(2,4-dinitrobenzyl)-Pyridine in Solution," *J. Chem. Phys.* 32:1888-89, 1960.

(56) References Cited

OTHER PUBLICATIONS

Mounetou et al., "O6-(alkyl/aralkyl)guanosine and 2'-deoxyguanosine derivatives: synthesis and ability to enhance chloroethylnitrosourea antitumor action," *J. Med. Chem.*, 40:2902-2909, 1997.

Mounteou et al., "Synthesis of three no-carrier-added 06-4-[125I] iodobenzylguanosine derivatives, new reagents for the assay of O6-alkylguanine-DNA alkyltransferase activity," *Journal of Labelled Compounds and Radiopharmaceuticals*, 36(12):1216-1225, 1995.

Nampalli et al., Efficient synthesis of 8-oxo-dGTP: A mutagenic nucleotide, *Bioorganic & Medicinal Chemistry Letters*, 10:1677-1679, 2000.

Notice of Allowance issued in U.S. Appl. No. 12/483,080, dated Dec. 27, 2011.

Notice of Allowance issued in U.S. Appl. No. 12/986,810, dated Feb. 10, 2012.

Notice of Allowance issued in U.S. Appl. No. 11/567,189, dated Oct. 29, 2010.

Notice of Allowance issued in U.S. Appl. No. 12/268,876, dated Feb. 9, 2011.

Notice of Allowance issued in U.S. Appl. No. 11/567,193, dated Nov. 3, 2012.

Office Communication issued in U.S. Appl. No. 11/567,193, mailed Nov. 24, 2008.

Office Communication issued in U.S. Appl. No. 11/567,193, mailed Sep. 26, 2008.

Office Communication issued in Australian Patent Application No. 2009257369 dated Dec. 16, 2013.

Office Communication issued in Chinese Patent Application No. 200780049437.2, dated Jul. 4, 2011. (English translation).

Office Communication issued in Israeli Patent Application No. 199051, dated Jul. 28, 2011. (English summary).

Office Communication issued in New Zealand Patent Application No. 577303, dated Jul. 28, 2010.

Office Communication issued in New Zealand Patent Application No. 590265, dated May 6, 2011.

Office Communication issued in New Zealand Patent Application No. 596122, dated Nov. 7, 2011.

Office Communication issued in New Zealand Patent Application No. 590265, dated Aug. 25, 2011.

Office Communication issued in New Zealand Patent Application No. 594812, dated Aug. 25, 2011.

Office Communication issued in New Zealand Patent Application No. 577303, dated Nov. 8, 2011.

Office Communication issued in U.S. Appl. No. 11/567,189, dated Apr. 15, 2010.

Office Communication issued in U.S. Appl. No. 11/567,193, dated Jul. 14, 2010.

Office Communication issued in U.S. Appl. No. 11/567,193, dated Jun. 15, 2010.

Office Communication issued in U.S. Appl. No. 11/567,193, dated Mar. 26, 2010.

Office Communication issued in U.S. Appl. No. 12/268,876, dated Jul. 12, 2010.

Office Communication issued in U.S. Appl. No. 12/268,876, dated Jun. 17, 2010.

Office Communication issued in U.S. Appl. No. 12/483,080, dated Feb. 15, 2011.

Office Communication issued in U.S. Appl. No. 12/483,080, dated May 13, 2011.

Office Communication issued in U.S. Appl. No. 12/483,080, dated Nov. 4, 2011.

Office Communication issued in U.S. Appl. No. 13/114,270, dated Nov. 17, 2011.

Office Communication issued in U.S. Appl. No. 13/114,270, dated Jan. 26, 2012.

Office Communication issued in U.S. Appl. No. 12/268,876, dated Mar. 11, 2010.

Office Communication issued in U.S. Appl. No. 12/986,810, dated Oct. 6, 2011.

Office Communication issued in U.S. Appl. No. 12/986,810, dated Nov. 21, 2011.

Office Communication issued in U.S. Appl. No. 13/467,885 dated Jul. 31, 2013.

Office Communication issued in U.S. Appl. No. 11/567,189, mailed Dec. 9, 2008.

Office Communication issued in U.S. Appl. No. 11/567,189, mailed Jun. 24, 2009.

Office Communication issued in U.S. Appl. No. 11/567,189, mailed Sep. 25, 2008.

Office Communication issued in U.S. Appl. No. 11/567,193, mailed Jun. 22, 2009.

Office Communication issued in U.S. Appl. No. 12/268,876, mailed Jun. 25, 2009.

Office Communication issued in U.S. Appl. No. 12/268,876, mailed Mar. 5, 2009.

Office Communication, issued in Japanese Patent Application No. 2011-513695, mailed on Apr. 4, 2012.

Ohtsuka et al., "Studies on transfer ribonucleic acids and related compounds. IX. Ribooligonucleotide synthesis using a photosensitive o-nitrobenzyl protection at the 2'-hydroxyl group," *Nucleic Acids Res.*, 1:1351-1357, 1974.

Panchuk-Voloshina et al., "Alexa dyes, a series of new fluorescent dyes that yield exceptionally bright, photostable conjugates," *The Journal of Histochemistry & Cytochemistry*, 47(9):1179-1188, 1999.

Patchornik et al., "Photosensitive Protecting Groups," *J. Am. Chem. Soc.*, 92:6333-35, 1970.

PCT International Preliminary Report on Patentability, issued in International Application No. PCT/US2007/086559, mailed Jun. 18, 2009.

PCT International Search Report and Written Opinion, issued in International Application No. PCT/US2009/047071, dated Jul. 9, 2013.

PCT International Search Report issued in International Application No. PCT/US07/86559, mailed Aug. 21, 2008.

PCT International Search Report issued in International Application No. PCT/US12/55231, mailed Nov. 14, 2012.

PCT Invitation to Pay Additional Fees and Partial International Search Report, issued in International application No. PCT/US2009/047071, dated May 11, 2011.

Pease et al., "Light-generated oligonucleotide arrays for rapid DNA sequence analysis," *Proc. Natl. Acad. Sci. USA*, 91:5022-5026, 1994.

Perler et al., "Intervening sequences in an Archaea DNA polymerase gene," *Proc. Natl. Acad. Sci. USA*, 89:5577-5581, 1992.

Perler et al., "Thermostable DNA polymerases," *Adv. Protein Chem.*, 48:377-435, 1996.

Pillai et al., "Photoremovable protecting groups in organic synthesis," *Synthesis*, 1-26, 1980.

Prober et al., "A system for rapid DNA sequencing with fluorescent chain-terminating dideoxynucleotides," *Science*, 4825:336-341, 1987.

Redon et al., "Global variation in copy number in the human genome," *Nature*, 444:444-454, 2006.

Reeve and Fuller, "A novel thermostable polymerase for DNA sequencing," *Nature*, 376:796-797, 1995.

Reichmanis et al., "O-nitrobenzyl Photochemistry: Solutions vs. Solid-State Behavior," *J. Polymer Sci.*, 23:1-8, 1985.

Response to Office Communication submitted in U.S. Appl. No. 11/567,189, filed Mar. 9, 2009.

Response to Office Communication submitted in U.S. Appl. No. 11/567,193, dated May 26, 2010.

Response to Office Communication submitted in U.S. Appl. No. 11/567,193, dated Dec. 22, 2009.

Response to Office Communication submitted in U.S. Appl. No. 12/268,876, dated Sep. 20, 2010.

Response to Office Communication submitted in U.S. Appl. No. 11/567,189, dated Sep. 13, 2010.

Response to Office Communication submitted in U.S. Appl. No. 12/986,080, filed Nov. 7, 2011.

Response to Office Communication submitted in U.S. Appl. No. 12/986,810, filed Jan. 23, 2012.

(56) References Cited

OTHER PUBLICATIONS

Response to Office Communication submitted in U.S. Appl. No. 12/483,080, filed Aug. 15, 2011.
Response to Office Communication submitted in U.S. Appl. No. 12/483,080, filed Mar. 11, 2011.
Response to Office Communication submitted in New Zealand Patent Application No. 577303, dated Oct. 17, 2011.
Response to Office Communication submitted in Israeli Patent Application No. 199051, dated Nov. 10, 2011. (English translation).
Response to Office Communication submitted in New Zealand Patent Application No. 590265, dated Aug. 24, 2011.
Response to Office Communication submitted in New Zealand Patent Application o. 577303, dated Nov. 9, 2011.
Response to Office Communication submitted in U.S. Appl. No. 12/268,876, dated Nov. 24, 2009.
Response to Office Communication submitted in U.S. Appl. No. 11/567,193, filed Oct. 27, 2008.
Response to Office Communication submitted in U.S. Appl. No. 11/567,189, filed Sep. 29, 2009.
Response to Office Communication submitted in U.S. Appl. No. 11/567,189, filed Dec. 28, 2009.
Response to Office Communication submitted in U.S. Appl. No. 11/567,189, filed Oct. 27, 2008.
Response to Office Communication submitted in U.S. Appl. No. 12/268,876, filed Apr. 6, 2009.
Response to Office Communication submitted in U.S. Appl. No. 12/268,876, dated Apr. 6, 2010.
Response to Office Communication submitted in U.S. Appl. No. 11/567,193, filed Sep. 22, 2009.
Response to Office Communication submitted in U.S. Appl. No. 11/567,193, filed Feb. 24, 2009.
Response to Office Communication submitted in U.S. Appl. No. 13/114,270, dated Dec. 19, 2011.
Response to Office Communication submitted in U.S. Appl. No. 12/483,080, filed Dec. 7, 2011.
Robins and Trip, "Sugar-modified N6-(3-methyl-2-butenyl) adenosine derivatives, N6-benzyl analogs, and cytokinin-related nucleosides containing sulfur or formycin," 12(12):2179-2187, 1973.
Ruparel et al.,"Design and synthesis of a 3'-O-allyl photocleavable fluorescent nucleotide as a reversible terminator for DNA sequencing by synthesis," PNAS 102(17): 5932-5937 (2005).
Sachidanadam et al., "A map of human genome sequence variation containing 1.42 million single nucleotide polymorphisms," Nature, 409(6822):928-933, 2001.
Sanger et al., "DNA sequencing with chain-terminating inhibitors," Proc. Natl. Acad. Sci. USA 74:5463-5467, 1977.
Schold et al., "Treatment of human brain tumor xenografts with O6-benzyl-2'-deoxyguanosine and BCNU," Cancer Research, 56:2076-2081, 1996.
Search Report by Eurasian Patent Office, issued in Eurasian Application No. 2430-187921EA, dated Jun. 19, 2012.
Sebat et al., "Large-scale copy number polymorphism in the human genome," Science, 305:525-528, 2004.
Seela and Peng, In: Current Protocols in Nucleic Acid Chemistry, Beaucage et al. (Eds.), John Wiley & Sons, Inc., 1.10.1, 2005.
Seio et al., "Synthesis and properties of new nucleotide analogues processing squaramide moieties as new phosphate isosters," Eur. J. Org. Chem., 5163-5170, 2005.
Seo et al., "Photocleavable fluorescent nucleotides for DNA sequencing on a chip constructed by site-specific coupling chemistry," PNAS, 101(15):5488-5493, 2004.
Seo et al., "Four-color DNA sequencing by synthesis on a chip using photocleavable fluorescent nucleotides," PNAS, 102(17):5926-5931, 2005.
Shankar et al., "O6-3-[$_{125}$I]iodobenzyl-2'-deoxyguanosine ([125I]IBdG): synthesis and evaluation of its usefulness as an agent for quantification of alkylguanine-DNA alkyltransferase (AGT)," Bioorganic & Medicinal Chemistry, 13:3889-3898, 2005.
Shapiro and Shiuey, "Reactions of cytidine with 7-bromomethylbenz[a]anthracene, benzyl bromide, and p-methoxybenzyl bromide. Ratio of Amino to 3 substitution," J. Org. Chem., 41(9): 1597-1600, 1976.
Sierzchala et al., "Solid-phase oligodeoxynucleotide synthesis: A two-step cycle using peroxy anion deprotection," J. Am. Chem. Soc., 125:13427-13441, 2003.
Silhar et al., "Synthesis, cytostatic and anti-HCV activity of 6-(N-substituted aminomethyl)-, 6-(O-substituted hydroxymethyl)- and 6-(S-substituted sulfanylmethyl) purine nucleosides," Bioorganic & Medicinal Chemistry, 16:2329-2366, 2008.
Sousa & Weinstein, "Photoisomerization of 2-(2,4-dinitrobenzyl)pyridine and 2-(2-nitro-4-cyanobenzyl)pyridine," J. Org. Chem., 27:3155-59, 1962.
Southworth et al., "Cloning of thermostable DNA polymerases from hyperthermophilic marine Archaea with emphasis on Thermococcus sp. 9°N-7 and mutations affecting 3'-5' exonuclease activity," Proc. Natl. Acad. Sci. USA, 93:5281-5285, 1996.
Stranger et al., "Relative impact of nucleotide and copy number variation on gene expression phenotypes," Science, 315:848-853, 2007.
Stupi et al., "Stereochemistry of Benzylic Carbon Substitution Coupled with Ring Modification of 2-Nitrobenzyl Groups as Key Determinants for Fast-Cleaving Reversible Terminators," Angew. Chem. Int. Ed., 51:1724-1727, 2012.
Supporting information for Ju et al., "Four-color DNA cleavable sequencing by synthesis using cleavable fluorescent nucleotide reversible terminators," PNAS, 103(52):19635-19640, 2006. Supporting information is available online at pnas.org/content/103/52/19635/suppl/DC1.
Tabor and Richardson, "A single residue in DNA polymerases of the Escherichia coli DNA polymerase I family is critical for distinguishing between deoxy- and dideoxyribonucleotides," Proc. Natl. Acad. Sci. USA, 92:6339-6343, 1995.
Terrashima et al., "Substrate specificity of human $O_6$-methylguanine-DNA methyltransferase for $O_6$-benzylguanine derivatives in oligodeoxynucleotides," Chem. Res. Toxicol., 10:1234-1239, 1997.
Turcatti et al., "A new class of cleavable fluorescent nucleotides: synthesis and optimization as reversible terminators for DNA sequencing by synthesis," Nucleic Acids Research, 36(4):e25, doi:10.1093/nar/gkn021, 13 pages, 2008.
van Tilburg et al., "N6,5'-disubstituted adenosine derivatives as partial agonists for the human adenosine $A_3$ receptor," J. Med. Chem., 42:1393-1400, 1999.
Vander Horn et al., "Thermo Sequenase™ DNA polymerase and T. acidophilum pyrophosphatase: new thermo-stable enzymes for DNA sequencing," BioTechniques, 22:758-765, 1997.
Walker et al., "Photolabile Protecting Groups for an Acetylcholine Receptor Ligand. Synthesis and Photochemistry of a New Class of O-nitrobenzyl Derivatives and Their Effects on Receptor Function," Biochemistry, 25:1799-1805, 1986.
Weinstein et al. "Substituent Effects in Photochromic Nitrobenzylpyridines," J. Org. Chem., 31:1983-1985, 1966.
Welch and Burgess, "Synthesis of fluorescent, photolabile 3'-O-protected nucleoside triphosphates for the base addition sequencing scheme," Nucleosides & Nucleotides, 18(2):197-201, 1999.
Welch et al., "Synthesis of nucleosides designed for combinatorial DNA sequencing," Chem. Eur. J., 5(3):951-960, 1999.
Wettermark, "Photochromism of O-nitrotoluenes," Nature, 194:677, 1962.
Wootton & Trentham, In: Photochemical probes in biochemistry (NATO Science Series C), Nielsen (Ed)., Kluwer Academic Publishers, Ann Arbor, 272:277-296, 1989.
Wu et al., "Termination of DNA synthesis by $N_6$-alkylated, not 3'-O-alkylated, photocleavable 2'-deoxyadenosine triphosphates," Nucleic Acids Research, 35(19):6339-6349, 2007.
Yamashita et al., "Studies on antitumor agents. IX. Synthesis of 3'-O-benzyl-2'-deoxy-5-trifluoromethyluridine," Chem Pharm. Bull., 37(9):2287-2292, 1989.
Yu et al., "Synthesis of 3,7,8-$_{15}$N$_3$-N$_1$-(beta-D-erythro-pentofuranosyl)-5-guanidinohydantoin," Journal of Labelled Compounds and Radiopharmaceuticals, 46:1269-1277, 2003.

NUCLEOTIDES AND NUCLEOSIDES AND METHODS FOR THEIR USE IN DNA SEQUENCING

The present application is a continuation application of U.S. patent application Ser. No. 13/929,305, filed Jun. 27, 2013, which is a divisional application of U.S. patent application Ser. No. 13/406,934 filed Feb. 28, 2012, issued as U.S. Pat. No. 8,497,360, which is a divisional application of U.S. patent application Ser. No. 12/483,080 filed Jun. 11, 2009, issued as U.S. Pat. No. 8,148,503, which claims the priority to U.S. Provisional Application Nos. 61/060,795 and 61/184,779, filed Jun. 11, 2008 and Jun. 5, 2009, respectively, the entire contents of which are each incorporated herein by reference.

BACKGROUND OF THE INVENTION

I. Field of the Invention

The present invention relates generally to compositions and methods for DNA sequencing and other types of DNA analysis. More particularly, the invention relates in part to nucleotides and nucleosides with chemically cleavable, photocleavable, enzymatically cleavable, or non-photocleavable groups and methods for their use in a number of DNA sequencing methods and their applications in biomedical research.

II. Description of Related Art

Methods for rapidly sequencing DNA have become needed for analyzing diseases and mutations in the population and developing therapies. Commonly observed forms of human sequence variation are single nucleotide polymorphisms (SNPs), which occur in approximately 1-in-300 to 1-in-1000 base pairs of genomic sequence and structural variants (SVs) including block substitutions, insertion/deletions, inversions, segmental duplications, and copy number variants. Structural variants can accounted for 22% of all variable events and more variant bases than those contributed by SNPs (Levy et al., 2007, which is incorporated herein by reference.). This finding is consistent with that of Scherer, Hurles, and colleagues who analyzed 270 individuals using microarray-based methods (Redon et al. 2006, which is incorporated herein by reference). Building upon the complete sequence of the human genome, efforts are underway to identify the underlying genetic link to common diseases by SNP mapping or direct association. Technology developments focused on rapid, high-throughput, and low cost DNA sequencing would facilitate the understanding and use of genetic information, such as SNPs, in applied medicine.

In general, 10%-to-15% of SNPs will affect protein function by altering specific amino acid residues, will affect the proper processing of genes by changing splicing mechanisms, or will affect the normal level of expression of the gene or protein by varying regulatory mechanisms. SVs may also play an important role in human biology and disease (Iafrate et al., 2004; Sebat et al., 2004; Tuzun et al., 2005; Stranger et al., 2007, which are incorporated herein by reference). It is envisioned that the identification of informative SNPs and SVs will lead to more accurate diagnosis of inherited disease, better prognosis of risk susceptibilities, or identity of sporadic mutations in tissue. One application of an individual's SNP and SV profile would be to significantly delay the onset or progression of disease with prophylactic drug therapies. Moreover, an SNP and SV profile of drug metabolizing genes could be used to prescribe a specific drug regimen to provide safer and more efficacious results. To accomplish these ambitious goals, genome sequencing will move into the resequencing phase with the potential of partial sequencing of a large majority of the population, which would involve sequencing specific regions in parallel, which are distributed throughout the human genome to obtain the SNP and SV profile for a given complex disease.

Sequence variations underlying most common diseases are likely to involve multiple SNPs, SVs, and a number of combinations thereof, which are dispersed throughout associated genes and exist in low frequency. Thus, DNA sequencing technologies that employ strategies for de novo sequencing are more likely to detect and/or discover these rare, widely dispersed variants than technologies targeting only known SNPs.

Traditionally, DNA sequencing has been accomplished by the "Sanger" or "dideoxy" method, which involves the chain termination of DNA synthesis by the incorporation of 2',3'-dideoxynucleotides (ddNTPs) using DNA polymerase (Sanger et al., 1997, which is incorporated herein by reference). The reaction also includes the natural 2'-deoxynucleotides (dNTPs), which extend the DNA chain by DNA synthesis. Balanced appropriately, competition between chain extension and chain termination results in the generation of a set of nested DNA fragments, which are uniformly distributed over thousands of bases and differ in size as base pair increments. Electrophoresis is used to resolve the nested DNA fragments by their respective size. The ratio of dNTP/ddNTP in the sequencing reaction determines the frequency of chain termination, and hence the distribution of lengths of terminated chains. The fragments are then detected via the prior attachment of four different fluorophores to the four bases of DNA (i.e., A, C, G, and T), which fluoresce their respective colors when irradiated with a suitable laser source. Currently, Sanger sequencing has been the most widely used method for discovery of SNPs by direct PCR sequencing (Gibbs et al., 1989, which is incorporated herein by reference) or genomic sequencing (Hunkapiller et al., 1991; International Human Genome Sequencing Consortium, 2001, which are incorporated herein by reference).

Advantages of next-generation sequencing (NGS) technologies include the ability to produce an enormous volume of data cheaply, in some cases in excess of a hundred million short sequence reads per instrument run. Many of these approaches are commonly referred to as sequencing-by-synthesis (SBS), which does not clearly delineate the different mechanics of sequencing DNA (Metzker, 2005, which is incorporated herein by reference). Here, the DNA polymerase-dependent strategies are classified as cyclic reversible termination (CRT), single nucleotide addition (SNA, e.g., pyrosequencing), and real-time sequencing. An approach whereby DNA polymerase is replaced by DNA ligase is referred to as sequencing-by-ligation (SBL).

There is a great need for developing new sequencing technologies, with potential applications spanning diverse research sectors including comparative genomics and evolution, forensics, epidemiology, and applied medicine for diagnostics and therapeutics. Current sequencing technologies are often too expensive, labor intensive, and time consuming for broad application in human sequence variation studies. Genome center cost is calculated on the basis of dollars per 1,000 $Q_{20}$ bases and can be generally divided into the categories of instrumentation, personnel, reagents and materials, and overhead expenses. Currently, these centers are operating at less than one dollar per 1,000 $Q_{20}$ bases with at least 50% of the cost resulting from DNA sequencing instrumentation alone. Developments in novel detection methods, miniaturization in instrumentation, microfluidic separation technologies, and an increase in the number of assays per run will most likely have the biggest impact on reducing cost.

SUMMARY OF THE INVENTION

In some aspects, the present disclosure provides novel compounds and compositions that are useful in efficient sequencing of genomic information in high throughput sequencing reactions. In another aspect, reagents and combinations of reagents that can efficiently and affordably provide genomic information are provided. In further aspects, the present invention provides libraries and arrays of reagents for diagnostic methods and for developing targeted therapeutics for individuals.

In some aspects, the present disclosure provides new compounds that may be used in DNA sequencing. For example, in some embodiments, the invention provides compounds of the formula:

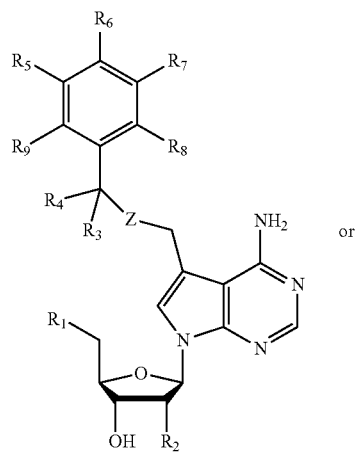
(A)

or

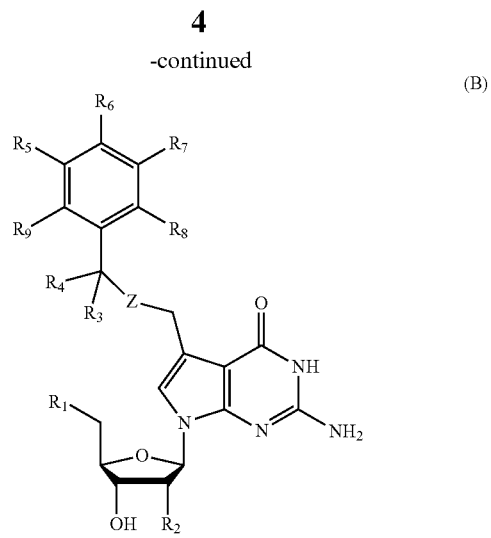
(B)

wherein:
Z is —O—, —S—, —NH—, —OC(O)O—, —NHC(O)O—, —OC(O)NH— or —NHC(O)NH—;
$R_1$ is hydroxy, monophosphate, diphosphate, triphosphate or polyphosphate;
$R_2$ is hydrogen or hydroxy;
$R_3$ and $R_4$ are each independently:
  hydrogen, hydroxy, halo or amino; or
  $alkyl_{(C\leq12)}$, $alkenyl_{(C\leq12)}$, $alkynyl_{(C\leq12)}$, $aryl_{(C\leq12)}$, $aralkyl_{(C\leq12)}$, $hetero\text{-}aryl_{(C\leq12)}$, $heteroaralkyl_{(C\leq12)}$, $alkoxy_{(C\leq12)}$, $aryloxy_{(C\leq12)}$, $aralkoxy_{(C\leq12)}$, $heteroaryloxy_{(C\leq12)}$, $heteroaralkoxy_{(C\leq12)}$, $alkylamino_{(C\leq12)}$, $dialkylamino_{(C\leq12)}$, $arylamino_{(C\leq12)}$, $aralkylamino_{(C\leq12)}$, or a substituted version of any of these groups; or
$R_5$, $R_6$, $R_7$, $R_8$ and $R_9$ are each independently:
  hydrogen, hydroxy, halo, amino, nitro, cyano or mercapto;
  $alkyl_{(C\leq12)}$, $alkenyl_{(C\leq12)}$, $alkynyl_{(C\leq12)}$, $aryl_{(C\leq12)}$, $aralkyl_{(C\leq12)}$, $hetero\text{-}aryl_{(C\leq12)}$, $heteroaralkyl_{(C\leq12)}$, $alkenyl\text{-}acyl_{(C\leq12)}$, $alkoxy_{(C\leq12)}$, $alkenyl\text{-}oxy_{(C\leq12)}$, $alkynyloxy_{(C\leq12)}$, $aryloxy_{(C\leq12)}$, $aralkoxy_{(C\leq12)}$, $hetero\text{-}aryloxy_{(C\leq12)}$, $heteroaralkoxy_{(C\leq12)}$, $acyloxy_{(C\leq12)}$, $alkylamino_{(C\leq12)}$, $dialkylamino_{(C\leq12)}$, $alkoxyamino_{(C\leq12)}$, $alkenylamino_{(C\leq12)}$, $alkynylamino_{(C\leq12)}$, $arylamino_{(C\leq12)}$, $aralkylamino_{(C\leq12)}$, $heteroaryl\text{-}amino_{(C\leq12)}$, $heteroaralkylamino_{(C\leq12)}$, $alkylsulfonylamino_{(C\leq12)}$, $amido_{(C\leq12)}$, $alkylthio_{(C\leq12)}$, $alkenylthio_{(C\leq12)}$, $alkynylthio_{(C\leq12)}$, $aryl\text{-}thio_{(C\leq12)}$, $aralkylthio_{(C\leq12)}$, $heteroarylthio_{(C\leq12)}$, $heteroaralkyl\text{-}thio_{(C\leq12)}$, $acylthio_{(C\leq12)}$, $thioacyl_{(C\leq12)}$, $alkylsulfonyl_{(C\leq12)}$, $aryl\text{-}sulfonyl_{(C\leq12)}$, $alkylammonium_{(C\leq12)}$, $alkylsulfonium_{(C\leq12)}$, $alkyl\text{-}silyl_{(C\leq12)}$, or a substituted version of any of these groups;
a group of formula:

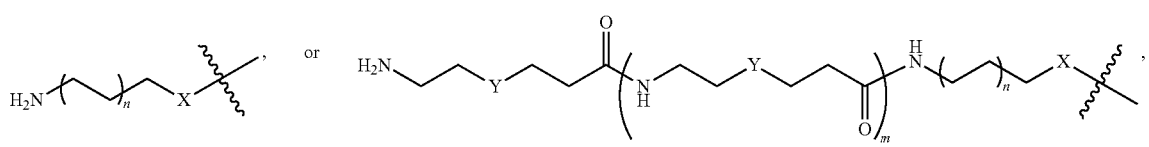

wherein
X is
—O—, —S—, or —NH—; or alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, or a substituted version of any of these groups;

Y is —O—, —NH—, alkanediyl$_{(C\leq12)}$ or substituted alkanediyl$_{(C\leq12)}$;

n is an integer from 0-12; and m is an integer from 0-12; or a -linker-reporter;

or a salt, esters, hydrates, solvates, tautomers, prodrugs, or optical isomers thereof.

In some aspects the invention provides a compound of formula:

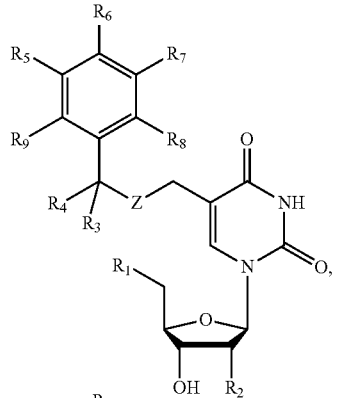

(C)

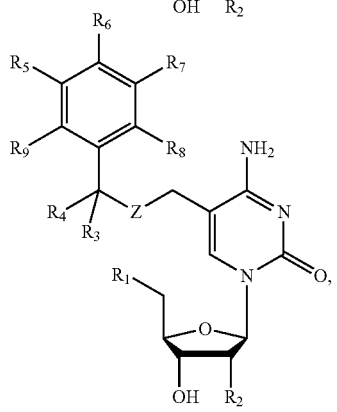

(D)

wherein:

Z is —O—, —S—, —NH—, —OC(O)O—, —NHC(O)O—, —OC(O)NH— or —NHC(O)NH—;

$R_1$ is hydroxy, monophosphate, diphosphate, triphosphate or polyphosphate;

$R_2$ is hydrogen or hydroxy;

$R_3$ and $R_4$ are each independently:

hydrogen, hydroxy, halo or amino; or alkyl$_{(C\leq12)}$, alkenyl$_{(C\leq12)}$, alkynyl$_{(C\leq12)}$, aryl$_{(C\leq12)}$, aralkyl$_{(C\leq12)}$, hetero-aryl$_{(C\leq12)}$, heteroaralkyl$_{(C\leq12)}$, alkoxy$_{(C\leq12)}$, aryloxy$_{(C\leq12)}$, aralkoxy$_{(C\leq12)}$, heteroaryloxy$_{(C\leq12)}$, heteroaralkoxy$_{(C\leq12)}$, alkylamino$_{(C\leq12)}$, dialkylamino$_{(C\leq12)}$, arylamino$_{(C\leq12)}$, aralkylamino$_{(C\leq12)}$, or a substituted version of any of these groups;

$R_5$, $R_6$, $R_7$ and $R_8$ are each independently:

hydrogen, hydroxy, halo, amino, nitro, cyano or mercapto; or alkyl$_{(C\leq12)}$, alkenyl$_{(C\leq12)}$, alkynyl$_{(C\leq12)}$, aryl$_{(C\leq12)}$, aralkyl$_{(C\leq12)}$, hetero-aryl$_{(C\leq12)}$, heteroaralkyl$_{(C\leq12)}$, acyl$_{(C\leq12)}$, alkoxy$_{(C\leq12)}$, alkenyl-oxy$_{(C\leq12)}$, alkynyloxy$_{(C\leq12)}$, aryloxy$_{(C\leq12)}$, aralkoxy$_{(C\leq12)}$, hetero-aryloxy$_{(C\leq12)}$, heteroaralkoxy$_{(C\leq12)}$, acyloxy$_{(C\leq12)}$, alkylamino$_{(C\leq12)}$, dialkylamino$_{(C\leq12)}$, alkoxyamino$_{(C\leq12)}$, alkenylamino$_{(C\leq12)}$, alkynylamino$_{(C\leq12)}$, arylamino$_{(C\leq12)}$, aralkylamino$_{(C\leq12)}$, heteroaryl-amino$_{(C\leq12)}$, heteroaralkylamino$_{(C\leq12)}$, alkylsulfonylamino$_{(C\leq12)}$, amido$_{(C\leq12)}$, alkylthio$_{(C\leq12)}$, alkenylthio$_{(C\leq12)}$, alkynylthio$_{(C\leq12)}$, aryl-thio$_{(C\leq12)}$, aralkylthio$_{(C\leq12)}$, heteroarylthio$_{(C\leq12)}$, heteroaralkyl-thio$_{(C\leq12)}$, acylthio$_{(C\leq12)}$, thioacyl$_{(C\leq12)}$, alkylsulfonyl$_{(C\leq12)}$, aryl-sulfonyl$_{(C\leq12)}$, alkylammonium$_{(C\leq12)}$, alkylsulfonium$_{(C\leq12)}$, alkyl-silyl$_{(C\leq12)}$, or a substituted version of any of these groups; or a group of formula:

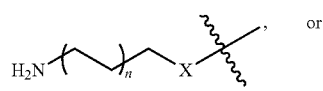

(V)

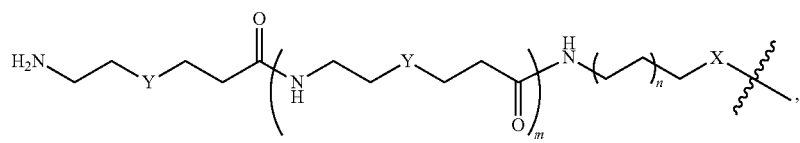

(VI)

wherein
X is
—O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups;
Y is —O—, —NH—, alkanediyl$_{(C\leq 12)}$ or substituted alkanediyl$_{(C\leq 12)}$;
n is an integer from 0-12; and
m is an integer from 0-12; or
a -linker-reporter; and
$R_9$ is alkyl$_{(C\leq 12)}$, aryl$_{(C\leq 12)}$ or a substituted version of either of these groups;
or a salt, esters, hydrates, solvates, tautomers, prodrugs, or optical isomers thereof.

In some embodiments, the compound is further defined as a compound of formula A. In some embodiments, the compound is of formula B. In some embodiments, the compound is further defined as a compound of formula C. In some embodiments, the compound is of formula D. In some embodiments Z is —O—. In some embodiments $R_1$ is hydroxy. In some embodiments, $R_1$ is a monophosphate. In some embodiments $R_1$ is a diphosphate. In some embodiments $R_1$ is a triphosphate. In some embodiments $R_1$ is a polyphosphate. In some embodiments $R_2$ is hydrogen. In some embodiments $R_2$ is hydroxy. In some embodiments $R_3$ is hydrogen. In some embodiments $R_3$ is alkyl$_{(C\leq 12)}$ or a substituted version thereof. In some embodiments $R_3$ is alkyl$_{(C\leq 8)}$. In some embodiments $R_3$ is alkyl$_{(C\leq 6)}$. In some embodiments $R_3$ is selected from the group consisting of methyl, ethyl, n-propyl, isopropyl and tert-butyl. In some embodiments $R_3$ is methyl. In some embodiments $R_3$ is alkyl$_{(C2-6)}$. In some embodiments $R_3$ is alkyl$_{(C3-5)}$. In some embodiments $R_3$ is isopropyl. In some embodiments $R_3$ is tert-butyl. In some embodiments $R_4$ is hydrogen. In some embodiments $R_4$ is alkyl$_{(C\leq 12)}$ or a substituted version thereof. In some embodiments $R_4$ is alkyl$_{(C\leq 8)}$. In some embodiments $R_4$ is alkyl$_{(C\leq 6)}$. In some embodiments $R_4$ is selected from the group consisting of methyl, ethyl, n-propyl, isopropyl and tert-butyl. In some embodiments $R_4$ is methyl. In some embodiments $R_4$ is alkyl$_{(C2-6)}$. In some embodiments $R_4$ is alkyl$_{(C3-5)}$. In some embodiments $R_4$ is isopropyl. In some embodiments $R_4$ is tert-butyl. In some embodiments $R_5$ is hydrogen. In some embodiments $R_5$ is cyano. In some embodiments $R_5$ is alkoxy$_{(C\leq 12)}$ or a substituted version thereof. In some embodiments $R_5$ is alkoxy$_{(C\leq 8)}$. In some embodiments $R_5$ is alkoxy$_{(C\leq 6)}$. In some embodiments $R_5$ is alkoxy$_{(C\leq 3)}$. In some embodiments $R_5$ is methoxy. In some embodiments $R_5$ is a group of formula:

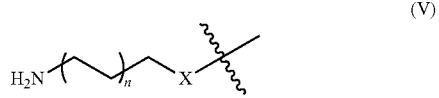

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; and n is an integer from 0-12.

In some embodiments X is alkynediyl$_{(C\leq 12)}$. In some embodiments X is alkynediyl$_{(C2-8)}$. In some embodiments X is —C≡C—. In some embodiments n is zero. In some embodiments $R_5$ is a group of formula:

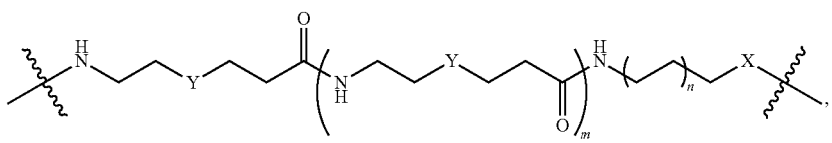

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; Y is —O—, —NH—, alkanediyl$_{(C\leq 12)}$ or substituted alkanediyl$_{(C\leq 12)}$; n is an integer from 0-12; and m is an integer from 0-12. In some embodiments X is alkynediyl$_{(C\leq 12)}$. In some embodiments X is alkynediyl$_{(C2-8)}$. In some embodiments X is —C≡C—. In some embodiments Y is —CH$_2$—. In some embodiments n is zero. In some embodiments m is zero. In some embodiments $R_6$ is a -linker-reporter. In some embodiments the linker is:

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; and n is an integer from 0-12. In some embodiments X is alkynediyl$_{(C\leq 12)}$. In some embodiments X is alkynediyl$_{(C2-8)}$. In some embodiments X is —C≡C—. In some embodiments n is zero. In some embodiments the linker is:

wherein X is —O—, —S—, or —NH—; or alkanediyl$_{(C\le12)}$, alkenediyl$_{(C\le12)}$, alkynediyl$_{(C\le12)}$, arenediyl$_{(C\le12)}$, heteroarenediyl$_{(C\le12)}$, or a substituted version of any of these groups; Y is —O—, —NH—, alkanediyl$_{(C\le12)}$ or substituted alkanediyl$_{(C\le12)}$; n is an integer from 0-12; and m is an integer from 0-12. In some embodiments X is alkynediyl$_{(C\le12)}$. In some embodiments X is alkynediyl$_{(C2-8)}$. In some embodiments X is —C≡C—. In some embodiments Y is —CH$_2$—. In some embodiments n is zero. In some embodiments m is zero. In some embodiments the linker is:

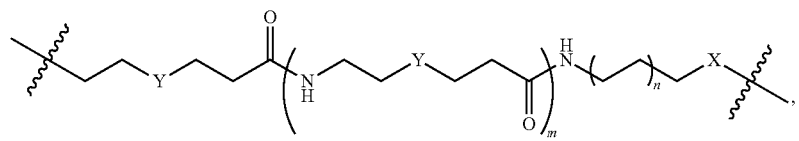

wherein X is —O—, —S—, or —NH—; or alkanediyl$_{(C\le12)}$, alkenediyl$_{(C\le12)}$, alkynediyl$_{(C\le12)}$, arenediyl$_{(C\le12)}$, heteroarenediyl$_{(C\le12)}$, or a substituted version of any of these groups; Y is —O—, —NH—, alkanediyl$_{(C\le12)}$ or substituted alkanediyl$_{(C\le12)}$; n is an integer from 0-12; and m is an integer from 0-12. In some embodiments X is alkynediyl$_{(C\le12)}$. In some embodiments X is alkynediyl$_{(C2-8)}$. In some embodiments X is —C≡C—. In some embodiments Y is —CH$_2$—. In some embodiments n is zero. In some embodiments m is zero. In some embodiments the reporter is based on a dye, wherein the dye is zanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, or a squaraine dye. In some embodiments the reporter is:

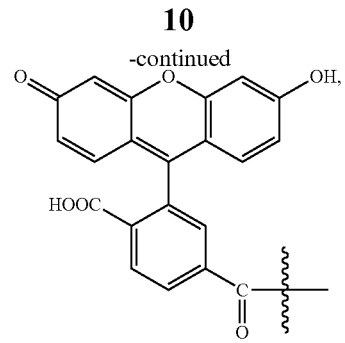

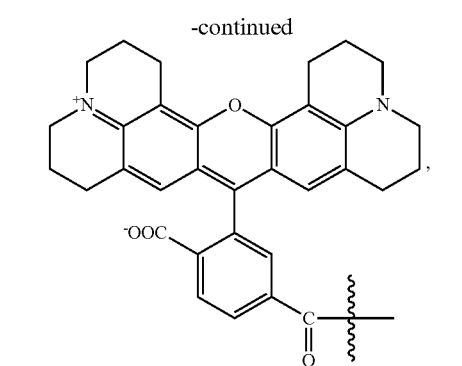

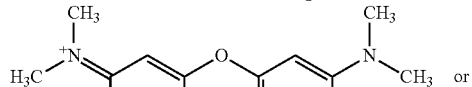

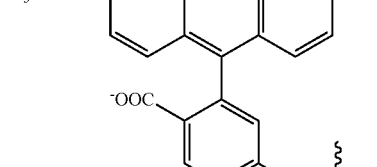

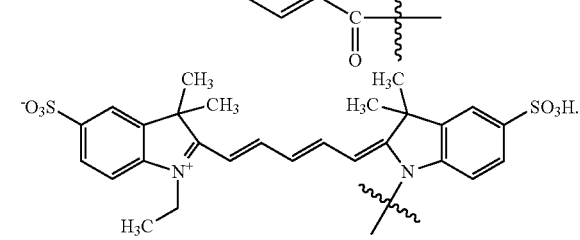

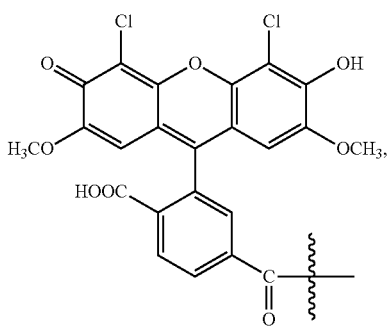

In some embodiments R$_6$ is hydrogen. In some embodiments R$_6$ is alkoxy$_{(C\le12)}$ or a substituted version thereof. In some embodiments R$_6$ is alkoxy$_{(C\le8)}$. In some embodiments R$_6$ is alkoxy$_{(C\le6)}$. In some embodiments R$_6$ is alkoxy$_{(C\le3)}$. In some embodiments R$_6$ is methoxy. In some embodiments R$_6$ is a group of formula:

(V)

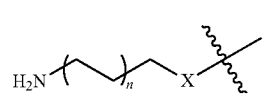

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; and n is an integer from 0-12. In some embodiments X is alkynediyl$_{(C\leq 12)}$. In some embodiments X is alkynediyl$_{(C2-8)}$. In some embodiments X is —C≡C—. In some embodiments n is zero. In some embodiments R$_6$ is a group of formula:

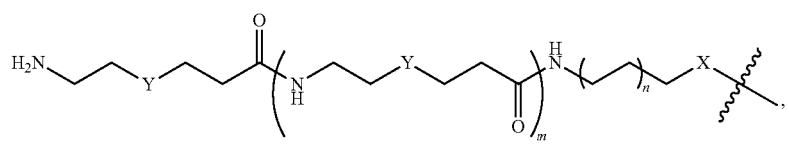

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; Y is —O—, —NH—, alkanediyl$_{(C\leq 12)}$ or substituted alkanediyl$_{(C\leq 12)}$; n is an integer from 0-12; and m is an integer from 0-12. In some embodiments X is alkynediyl$_{(C\leq 12)}$. In some embodiments X is alkynediyl$_{(C2-8)}$. In some embodiments X is —C≡C—. In some embodiments Y is —CH$_2$—. In some embodiments n is zero. In some embodiments m is zero. In some embodiments R$_6$ is a -linker-reporter. In some embodiments the linker is:

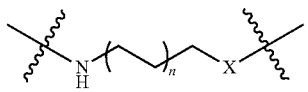

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; and n is an integer from 0-12. In some embodiments X is alkynediyl$_{(C\leq 12)}$. In some embodiments X is alkynediyl$_{(C2-8)}$. In some embodiments X is —C≡C—. In some embodiments n is zero. In some embodiments the linker is:

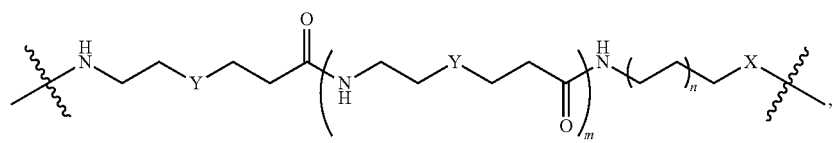

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; Y is —O—, —NH—, alkanediyl$_{(C\leq 12)}$ or substituted alkanediyl$_{(C\leq 12)}$; n is an integer from 0-12; and m is an integer from 0-12. In some embodiments X is alkynediyl$_{(C\leq 12)}$. In some embodiments X is alkynediyl$_{(C2-8)}$. In some embodiments X is —C≡C—. In some embodiments Y is —CH$_2$—. In some embodiments n is zero. In some embodiments m is zero. In some embodiments the linker is:

(VI)

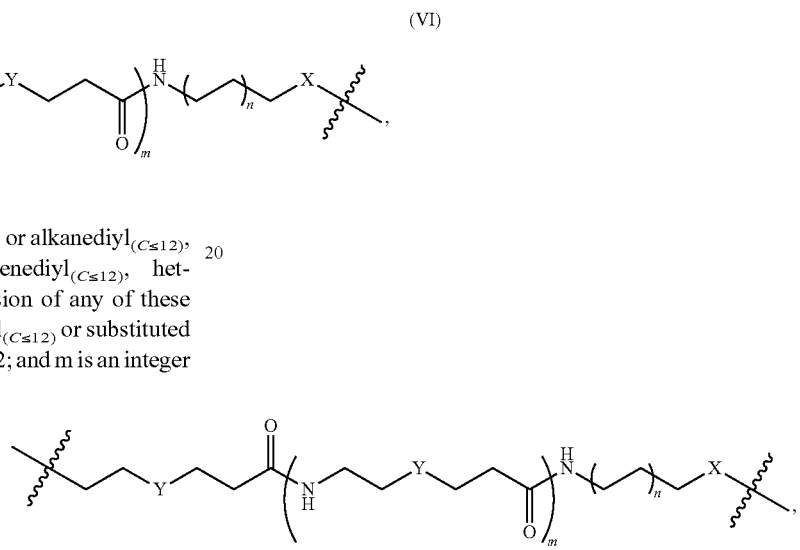

wherein X is —O—, —S—, or —NH—; or alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, or a substituted version of any of these groups; Y is —O—, —NH—, alkanediyl$_{(C\leq 12)}$ or substituted alkanediyl$_{(C\leq 12)}$; n is an integer from 0-12; and m is an integer from 0-12. In some embodiments X is alkynediyl$_{(C\leq 12)}$. In some embodiments X is alkynediyl$_{(C2-8)}$. In some embodiments X is —C≡C—. In some embodiments Y is —CH$_2$—. In some embodiments n is zero. In some embodiments m is zero. In some embodiments the reporter is based on a dye, wherein the dye is zanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR®

680, ALEXA FLUOR® 700, ALEXA FLUOR® 750, or a squaraine dye. In some embodiments the reporter is:

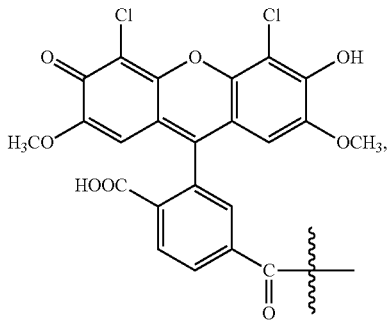

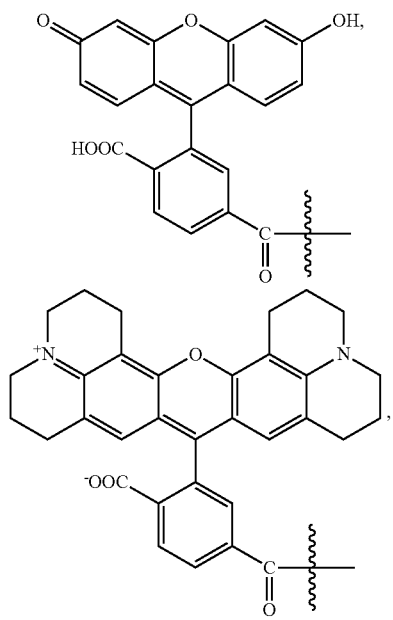

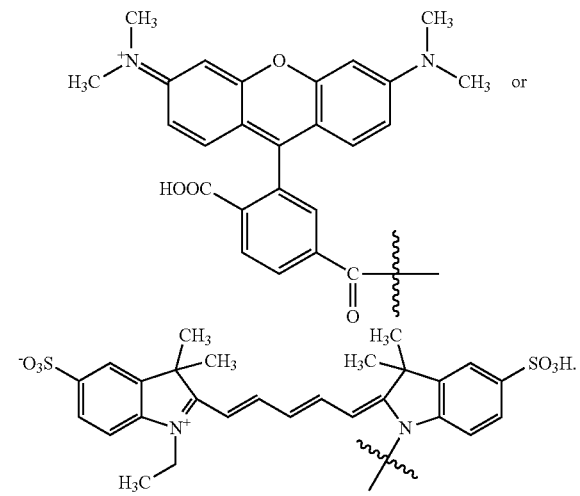

In some embodiments $R_7$ is hydrogen. In some embodiments $R_8$ is hydrogen. In some embodiments $R_8$ is nitro. In some embodiments $R_8$ is alkyl$_{(C \leq 12)}$ or a substituted version thereof. In some embodiments $R_8$ is alkyl$_{(C \leq 8)}$. In some embodiments $R_8$ is alkyl$_{(C \leq 6)}$. In some embodiments $R_8$ is alkyl$_{(C \leq 3)}$. In some embodiments $R_8$ is methyl. In some embodiments $R_9$ is hydrogen. In some embodiments $R_9$ is nitro. In some embodiments $R_9$ is alkyl$_{(C \leq 12)}$ or a substituted version thereof. In some embodiments $R_9$ is alkyl$_{(C \leq 8)}$. In some embodiments $R_9$ is alkyl$_{(C \leq 6)}$. In some embodiments $R_9$ is selected from the group consisting of methyl, ethyl, n-propyl, isopropyl and tert-butyl. In some embodiments $R_9$ is methyl. In some embodiments $R_9$ is alkyl$_{(C2-6)}$. In some embodiments $R_9$ is alkyl$_{(C3-5)}$. In some embodiments $R_9$ is isopropyl. In some embodiments $R_9$ is tert-butyl. In some embodiments $R_9$ is aryl$_{(C \leq 12)}$ or a substituted version thereof. In some embodiments $R_9$ is aryl$_{(C \leq 8)}$. In some embodiments $R_9$ is phenyl.

In some embodiments, the invention provides a compound of the formula:

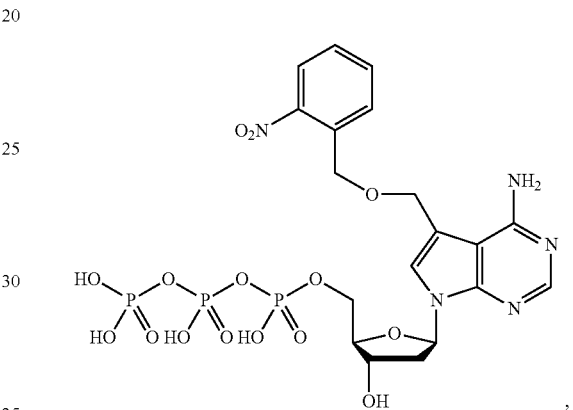

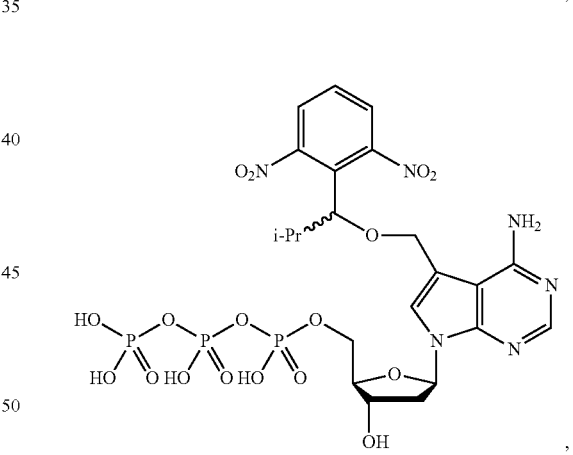

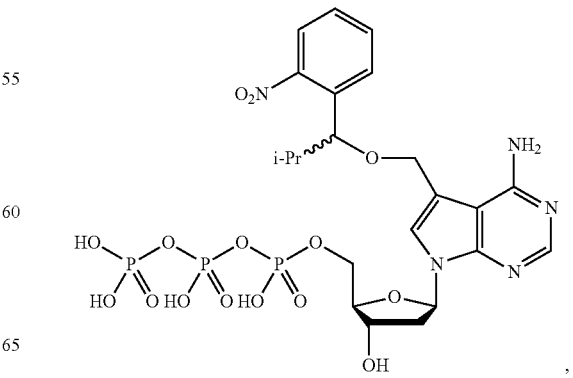

15
-continued
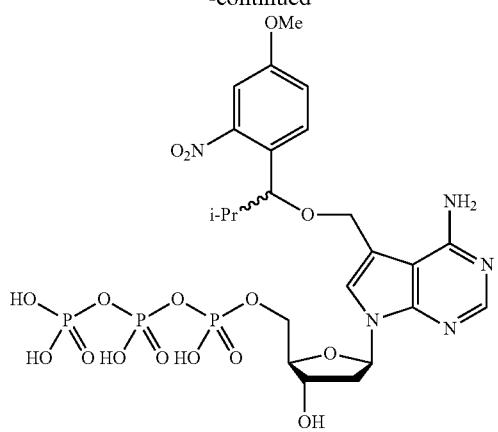
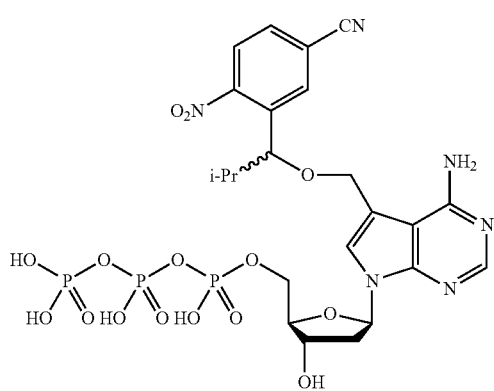
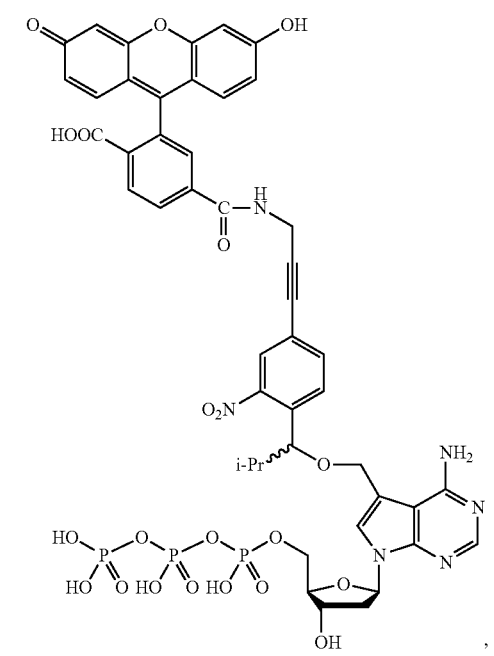
16
-continued
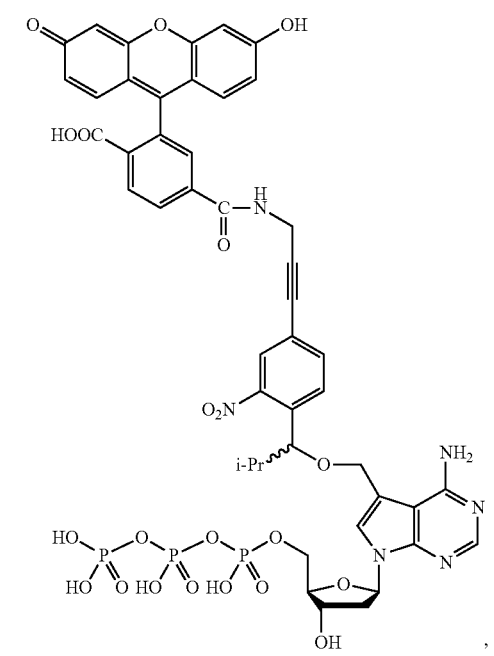

17
-continued
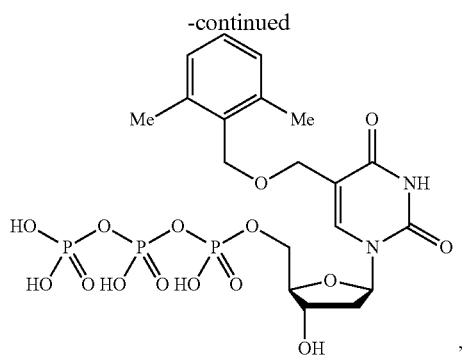
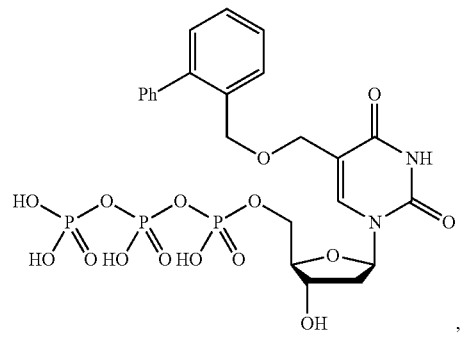
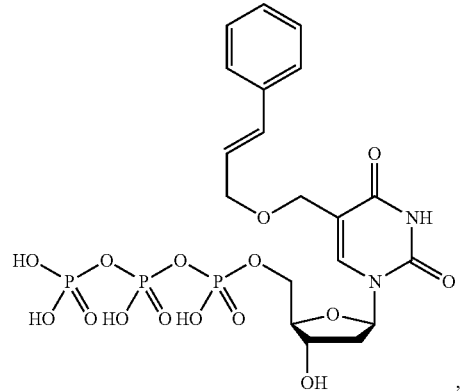
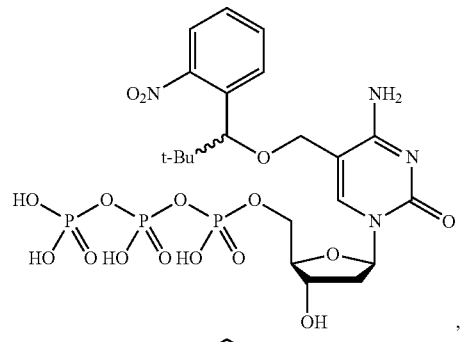
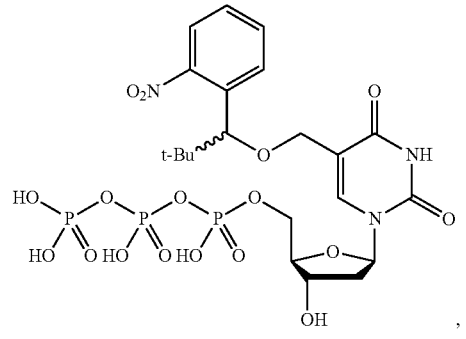
18
-continued
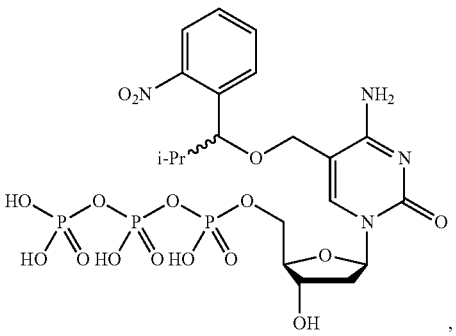
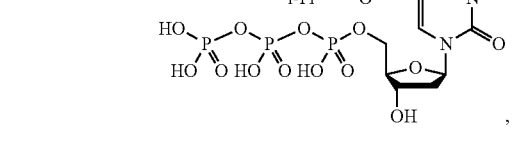
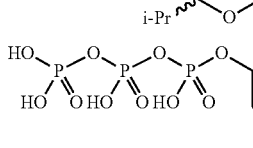
or

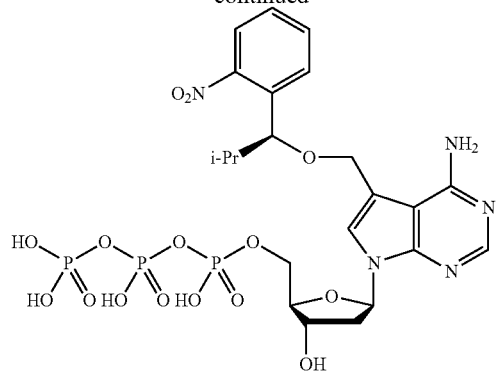

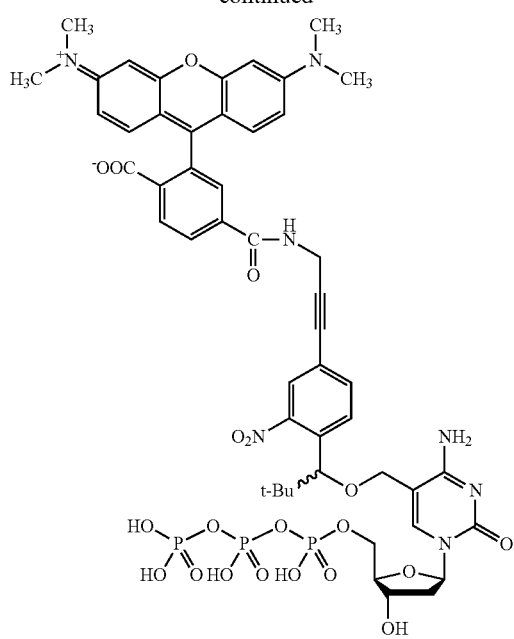

In some embodiments the compound is a salt of a formula above. In some embodiments, the compound is a 50:50 R:S-at-the-α-carbon-mixture of diastereomers of any of the formulas above, or salts thereof, that have a stereocenter at the α-carbon. In some embodiments, the compound is predominantly one diastereomer substantially free from other optical isomers thereof. For example, in some embodiments the present disclosure provides any of the following diastereomers, or salts thereof, substantially free from other optical isomers thereof:

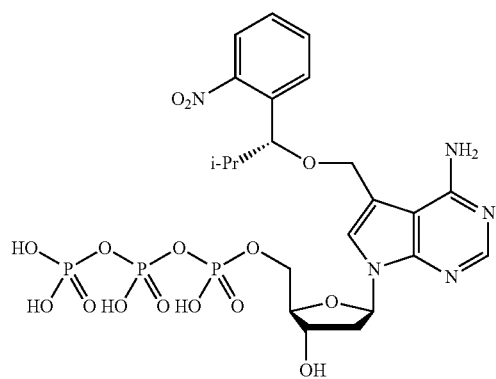

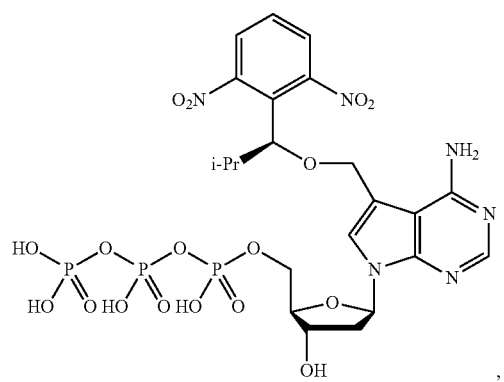

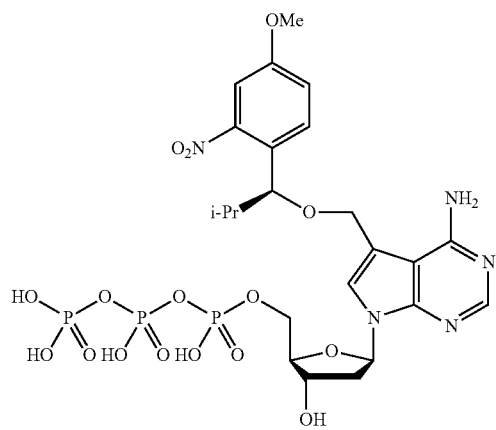

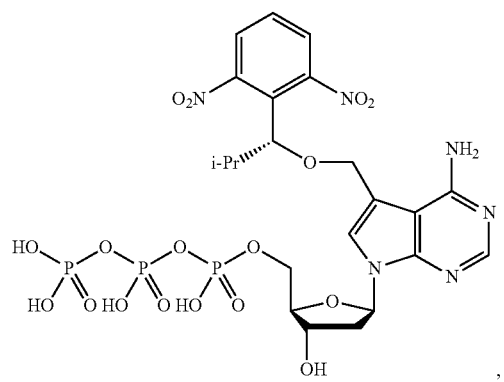

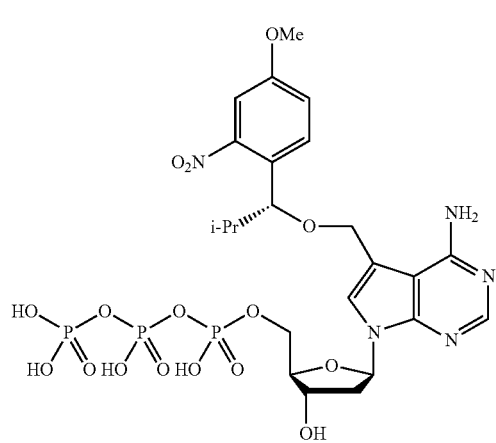

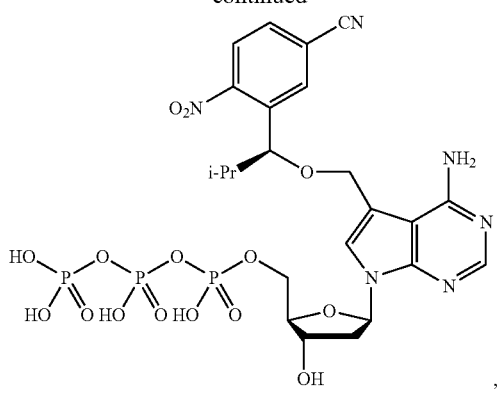
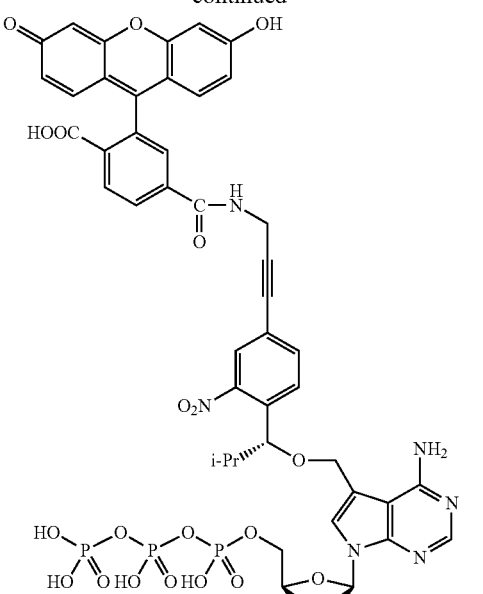
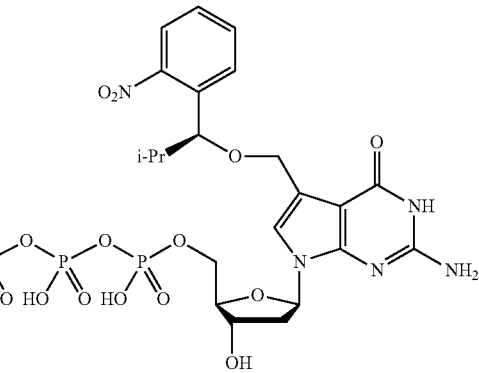
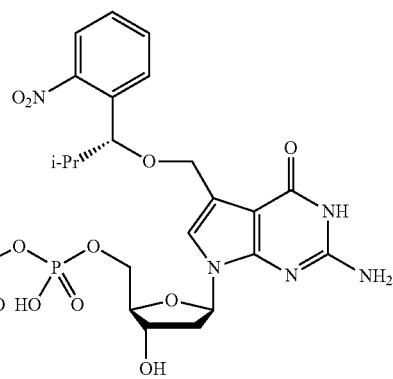

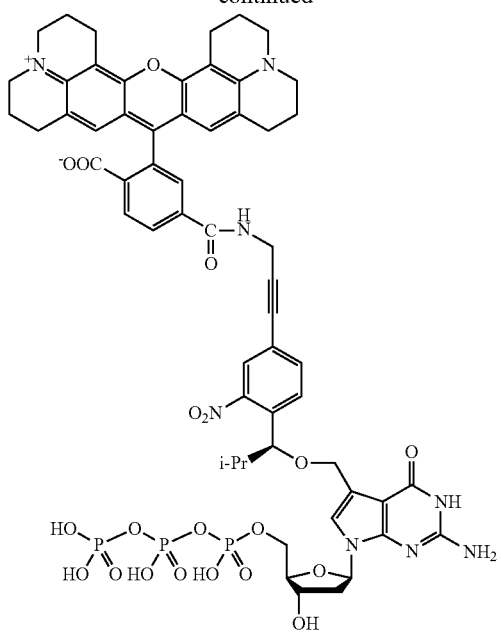
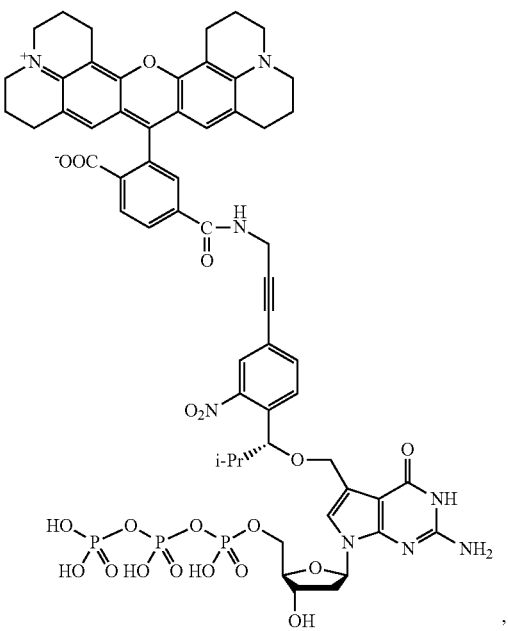
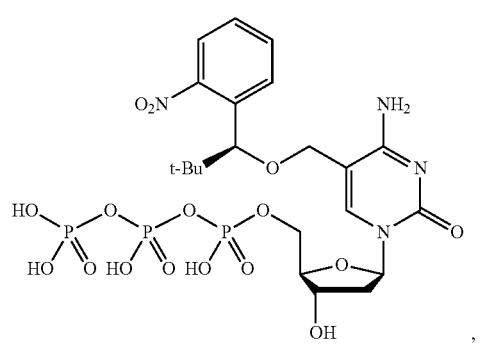
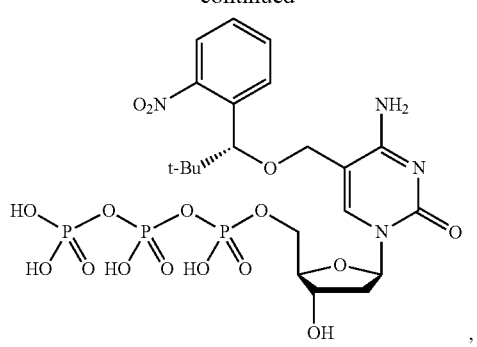
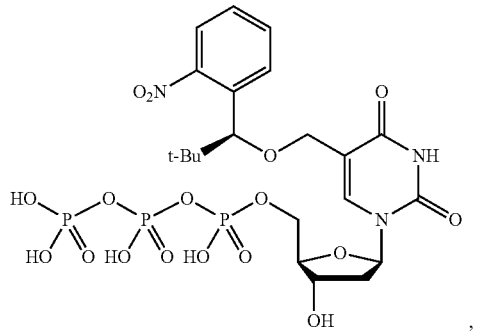
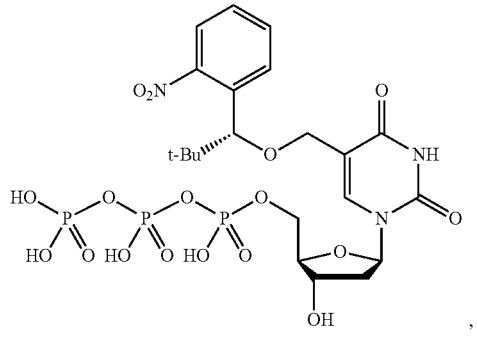
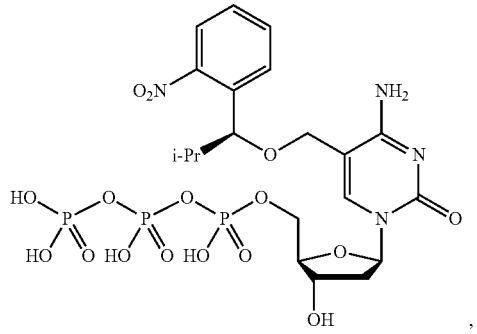

25
-continued
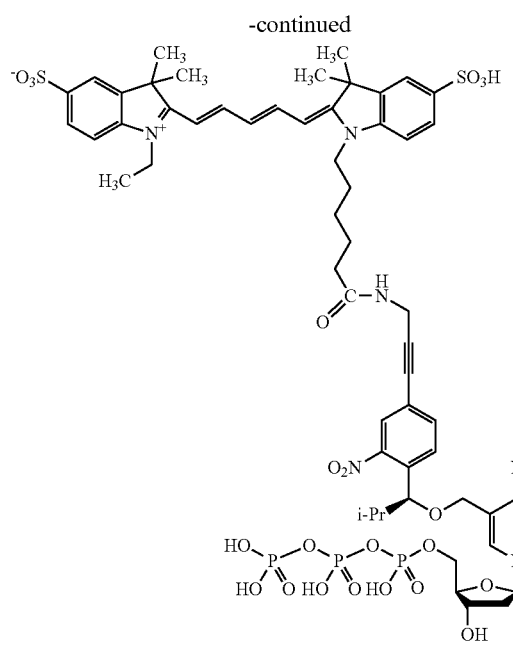
,
26
-continued
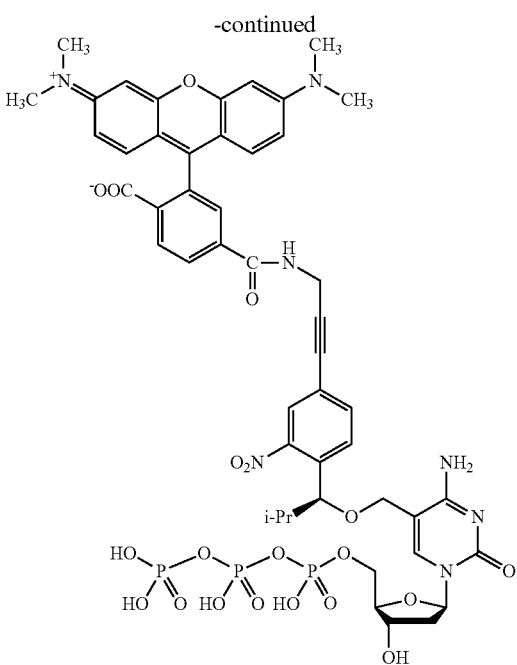
,
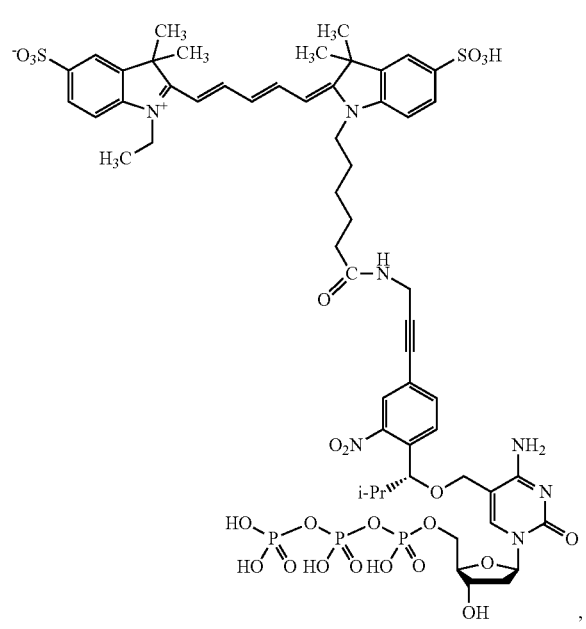
,
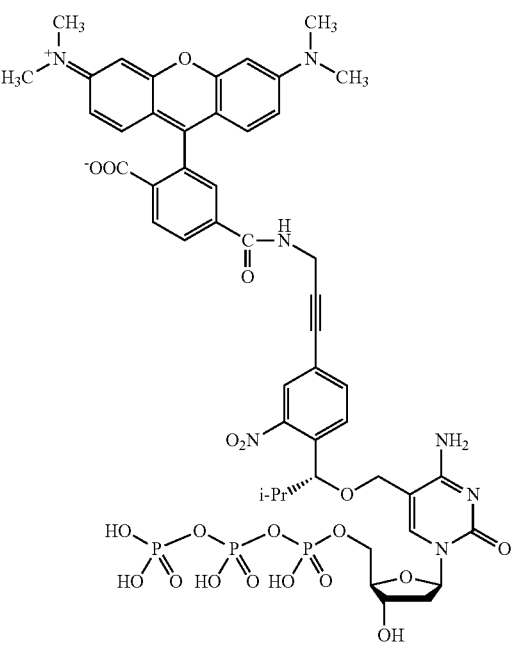
,

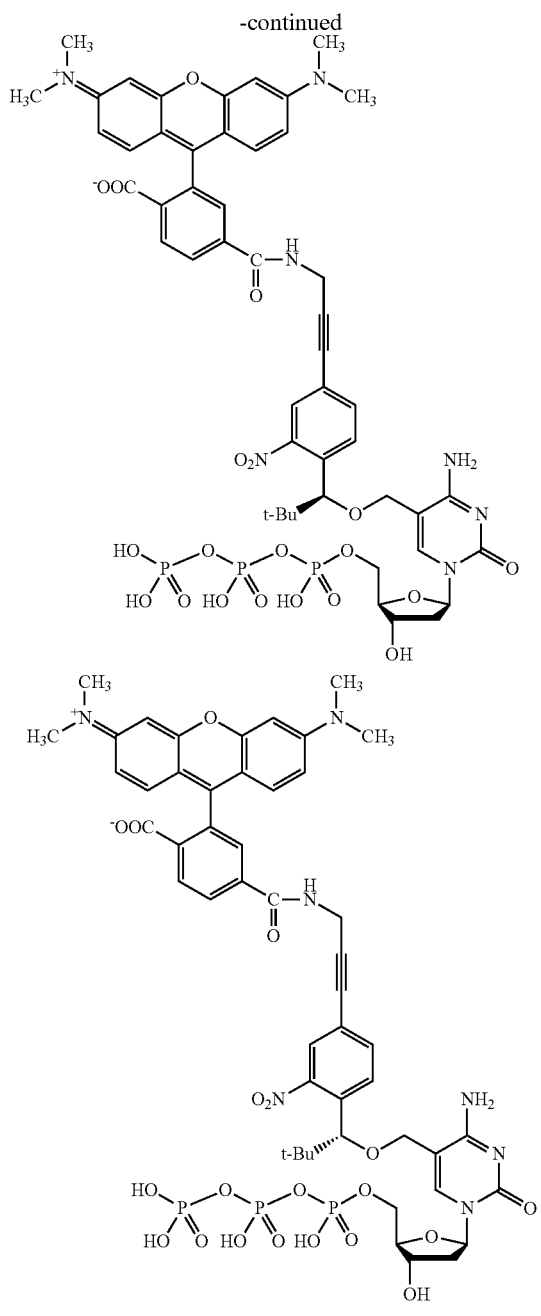

In some embodiments the salt of any of the formulas or diastereomers above comprises a monovalent cation. In some embodiments the monovalent cation is lithium. In some embodiments the monovalent cation is sodium. In some embodiments the monovalent cation is potassium. In some embodiments the salt comprises a divalent cation. In some embodiments the divalent cation is calcium, magnesium or manganese(II). In some embodiments the salt comprises a cation selected from the group consisting of ammonium, tri-n-butyl ammonium and $(HOCH_2)_3CNH_3^+$.

In another aspect the invention provides a method of sequencing a target nucleic acid comprising the following steps:
(i) attaching the 5'-end of a primer to a solid surface;
(ii) hybridizing a target nucleic acid to the primer attached to the solid surface;
(iii) adding a compound according to any of the claims, with the proviso that where more than one type of base is present, each base is attached to a different reporter group;
(iv) adding a nucleic acid replicating enzyme to the hybridized primer/target nucleic acid complex to incorporate the composition of step (iii) into the growing primer strand, wherein the incorporated composition of step (iii) terminates the polymerase reaction at an efficiency of between about 70% to about 100%;
(v) washing the solid surface to remove unincorporated components;
(vi) detecting the incorporated reporter group to identify the incorporated composition of step (iii);
(vii) a cleavage step to remove the terminating moiety resulting in an extended primer with naturally-occurring bases;
(viii) washing the solid surface to remove the cleaved terminating group; and
(ix) repeating steps (iii) through (viii) one or more times to identify the plurality of bases in the target nucleic acid.

In another aspect the invention provides a method of sequencing a target nucleic acid comprising the following steps:
(i) attaching the 5'-end of a target nucleic acid to a solid surface;
(ii) hybridizing a primer to the target nucleic acid attached to the solid surface;
(iii) adding a compound according to any of the claims, with the proviso that where more than one type of base is present, each base is attached to a different reporter group;
(iv) adding a nucleic acid replicating enzyme to the hybridized primer/target nucleic acid complex to incorporate the composition of step (iii) into the growing primer strand, wherein the incorporated composition of step (iii) terminates the polymerase reaction at an efficiency of between about 70% to about 100%;
(v) washing the solid surface to remove unincorporated components;
(vi) detecting the incorporated reporter group to identify the incorporated composition of step (iii);
(vii) optionally adding one or more chemical compounds to permanently cap unextended primers;
(viii) a cleavage step to remove the terminating moiety resulting in an extended primer with naturally-occurring bases;
(ix) washing the solid surface to remove the cleaved terminating group; and
(x) repeating steps (iii) through (ix) one or more times to identify the plurality of bases in the target nucleic acid.

In some embodiments the compound is incorporated by a nucleic acid replicating enzyme that is a DNA polymerase. In some embodiments the DNA polymerase is selected from the group consisting of Taq DNA polymerase, Klenow(exo-) DNA polymerase, Bst DNA polymerase, VENT® (exo-) DNA polymerase (DNA polymerase A cloned from *Thermococcus litoralis* and containing the D141A and E143A mutations), Pfu(exo-) DNA polymerase, and DEEPVENT™ (exo-) DNA polymerase (DNA polymerase A, cloned from the *Pyrococcus* species GB-D, and containing the D141A and E143A mutations). In some embodiments the DNA polymerase is selected from the group consisting of AMPLI-TAQ® DNA polymerase, FS (Taq DNA polymerase that contains the G46D and F667Y mutations), THERMOSEQUENASE™ DNA polymerase (Taq DNA polymerase that contains the F667Y mutation), THER- MOSEQUENASE™ II DNA polymerase (blend of THERMOSEQUENASE™ DNA polymerase and *T. acidophilum* pyrophosphatase), THERMINATOR™ DNA polymerase (DNA polymerase A, cloned from the *Thermococcus* species 9° N-7 and containing the D141A, E143A and A485L mutations), THERMINATOR™ II DNA polymerase (THERMINATOR™ DNA polymerase that contains the additional Y409V mutation), and VENT® (exo-) A488L DNA polymerase (VENT® (exo-) DNA polymerase that contains the A488L mutation). In some embodiments the cleavage of the terminating moiety is a chemical cleavage, a photo-cleavage, electrochemical or an enzymatic cleavage. In some embodiments the chemical cleavage is performed using a catalyst or stoichiometric reagent. In some embodiments the catalyst homogeneous or heterogeneous. In some embodiments the heterogeneous catalyst comprises Palladium. In some embodiments the homogeneous catalyst comprises Palladium. In some embodiments 85% to 100% of the photocleavable terminating moieties are removed by means of the photo-cleavage. In some embodiments the photo-cleavage is performed using a wavelength of light ranging between 300 nm to 400 nm. In some embodiments 85% to 100% of the photocleavable terminating moieties are removed by means of the photo-cleavage. In some embodiments the invention provides a method of performing Sanger or Sanger-type sequencing using a compound disclosed herein. In some embodiments the invention provides a method of performing pyrosequencing or pyrosequencing-type sequencing using a compound disclosed herein.

Non-limiting examples of compounds provided by this invention include the compounds according to the formulas shown below. In certain embodiments, these compounds are substantially free from other optical isomers thereof.

| WW# | Chemical Name | Diastereomer |
|---|---|---|
| 1p129 | $N^6$-(2-nitrobenzyl)-2'-dATP | |
| 2p108 | $O^6$-(2-nitrobenzyl)-2'-dGTP | |
| 2p143 | $O^6$-(α-methyl-2-nitrobenzyl)-2'-dGTP | mixture |
| 2p148 | 5-(α-isopropyl-2-nitrobenzyloxy)methyl-2'-dUTP | mixture |
| 3p006 | $N^6$-(α-methyl-2-nitrobenzyl)-2'-dATP | mixture |
| 3p063 | 5-(α-isopropyl-2-nitrobenzyloxy)methyl-2'-dUTP | single |
| 3p065 | 5-(α-isopropyl-2-nitrobenzyloxy)methyl-2'-dCTP | single |
| 3p075 | 5-(α-tert-butyl-2-nitrobenzyloxy)methyl-2'-dUTP | single |
| 3p085 | 5-(α-tert-butyl-2-nitrobenzyloxy)methyl-2'-dCTP | single |
| 4p135 | 5-(α-isopropyl-2-nitrobenzyloxy)methyl-2'-dCTP-linker | single |
| 5p085 | $C^7$-(2-nitrobenzyloxy)methyl-2'-dATP | |
| 5p098-ds1 | $C^7$-(α-isopropyl-2-nitrobenzyloxy)methyl-2'-dATP (ds1) | single |
| 5p098-ds2 | $C^7$-(α-isopropyl-2-nitrobenzyloxy)methyl-2'-dATP (ds2) | single |
| 5p107 | $C^7$-(2-nitrobenzyloxy)methyl-2'-dGTP | |
| 5p111 | 5-(α-isopropyl-benzyloxy)methyl-2'-dUTP | mixture |
| 5p127 | $C^7$-(α-isopropyl-2-nitrobenzyloxy)methyl-2'-dATP-6-FAM | single |
| 5p130-LP2 | $C^7$-(α-isopropyl-2-nitrobenzyloxy)methyl-2'-dATP-6-CR110 | single |
| 5p143 | $C^7$-(α-isopropyl-2-nitrobenzyloxy)methyl-2'-dGTP | mixture |
| 5p143-ds1 | $C^7$-(α-isopropyl-2-nitrobenzyloxy)methyl-2'-dGTP (ds1) | single |
| 5p143-ds2 | $C^7$-(α-isopropyl-2-nitrobenzyloxy)methyl-2'-dGTP (ds2) | single |
| 5p145 | 5-(benzyloxy)methyl-2'-dUTP | |
| 5p147 | 5-(2-methylbenzyloxy)methyl-2'-dUTP | |
| 5p149 | 5-(2-isopropylbenzyloxy)methyl-2'-dUTP | |
| 6p005 | 5-(α-isopropyl-2-nitrobenzyloxy)methyl-2'-dUTP-5-R6G | single |
| 6p008 | 5-(α-isopropyl-2-nitrobenzyloxy)methyl-2'-dUTP-6-JOE | single |
| 6p010 | 5-(2-phenylbenzyloxy)methyl-2'-dUTP | |
| 6p015 | 5-(2,6-dimethylbenzyloxy)methyl-2'-dUTP | |
| 6p017 | 5-(α-isopropyl-2-nitrobenzyloxy)methyl-2'-dCTP-Cy5 | single |
| 6p024 | 5-(2-tert-butylbenzyloxy)methyl-2'-dUTP | |
| 6p034 | $C^7$-(α-isopropyl-2-nitrobenzyloxy)methyl-2'-dGTP-6-ROX | single |
| 6p036 | $C^7$-(α-isopropyl-2-nitrobenzyloxy)methyl-2'-dGTP-dTAMRA-1 | single |
| 6p044 | 5-(α-isopropyl-2-nitrobenzyloxy)methyl-2'-dUTP-6-ROX | single |
| 6p057-ds1 | $C^7$-(α-isopropyl-2,6-dinitrobenzyloxy)methyl-2'-dATP (ds1) | single |
| 6p057-ds2 | $C^7$-(α-isopropyl-2,6-dinitrobenzyloxy)methyl-2'-dATP (ds2) | single |
| 6p063 | $N^6$-(α-isopropyl-2-nitrobenzyl)-2'-dATP | single |
| 6p071 | $C^7$-(α-isopropyl-2-nitrobenzyloxy)methyl-2'-dGTP-alexa-fluor-530 | single |
| 6p073 | $C^7$-(α-isopropyl-2-nitrobenzyloxy)methyl-2'-dGTP-6-JOE | single |
| 6p087-ds1 | $C^7$-(α-isopropyl-4-methoxy-2-nitrobenzyloxy)methyl-2'-dATP (ds1) | single |
| 6p087-ds2 | $C^7$-(α-isopropyl-4-methoxy-2-nitrobenzyloxy)methyl-2'-dATP (ds2) | single |
| 6p094 | 5-(α-isopropyl-2-nitrobenzyloxy)methyl-2'-dUTP-6-FAM | single |

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

I. Definitions

Figure 1:
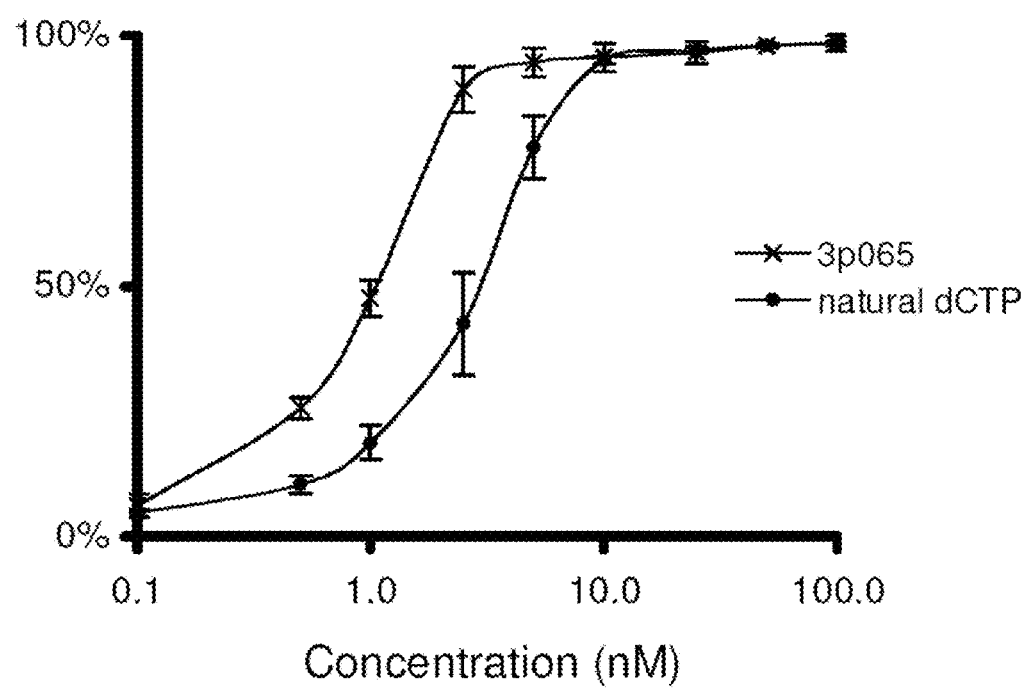
FIG. 1. Incorporation Assay: Natural dCTP and a modified dCTP analog were assayed for incorporation on a template with complementary base "G".

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O) (OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS (O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

The symbol "—" means a single bond, "=" means a double bond, and "≡" means triple bond. The symbol "⚌" represents a single bond or a double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄■" means a single bond where the group attached to the thick end of the wedge is "out of the page." The symbol "⌇" means a single bond where the group attached to the thick end of the wedge is "into the page". The symbol "⌇" means a single bond where the conformation is unknown (e.g., either R or S), the geometry is unknown (e.g., either E or Z) or the compound is present as mixture of conformation or geometries (e.g., a 50%/50% mixture).

When a group "R" is depicted as a "floating group" on a ring system, for example, in the formula:

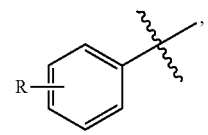

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

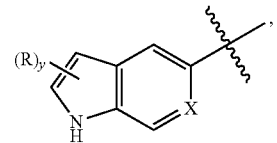

then R may replace any hydrogen attached to any of the ring atoms of either of the fuzed rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

When y is 2 and "(R)$_y$" is depicted as a floating group on a ring system having one or more ring atoms having two replaceable hydrogens, e.g., a saturated ring carbon, as for example in the formula:

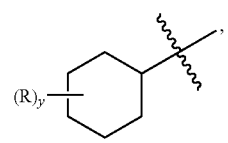

then each of the two R groups can reside on the same or a different ring atom. For example, when R is methyl and both R groups are attached to the same ring atom, a geminal dimethyl group results. Where specifically provided for, two R groups may be taken together to form a divalent group, such as one of the divalent groups further defined below. When such a divalent group is attached to the same ring atom, a spirocyclic ring structure will result.

When the point of attachment is depicted as "floating", for example, in the formula:

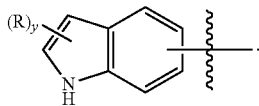

then the point of attachment may replace any replaceable hydrogen atom on any of the ring atoms of either of the fuzed rings unless specified otherwise.

In the case of a double-bonded R group (e.g., oxo, imino, thio, alkylidene, etc.), any pair of implicit or explicit hydrogen atoms attached to one ring atom can be replaced by the R group. This concept is exemplified below:

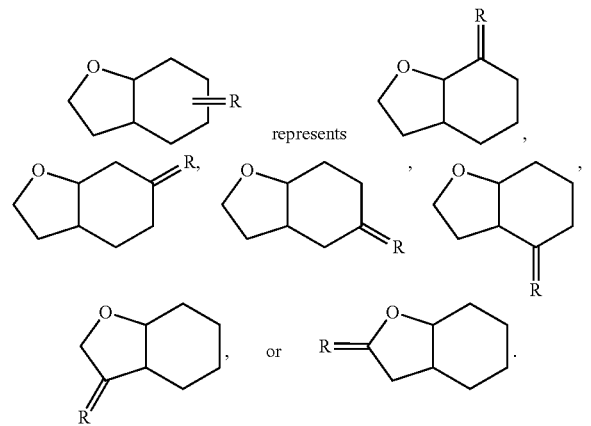

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question. E.g., it is understood that the minimum number of carbon atoms in the group "alkenyl$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkanediyl" when used without the "substituted" modifier refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, —CH$_2$CH$_2$CH$_2$—, and

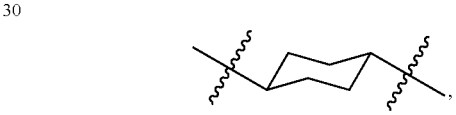

are non-limiting examples of alkanediyl groups. The term "substituted alkanediyl" refers to a non-aromatic monovalent group, wherein the alkynediyl group is attached with two σ-bonds, with one or two saturated carbon atom(s) as the point(s) of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkanediyl groups: —CH(F)—, —CF$_2$—, —CH(Cl)—, —CH(OH)—, —CH(OCH$_3$)—, and —CH$_2$CH(Cl)—.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkenediyl" when used without the "substituted" modifier refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

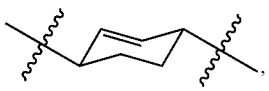 [SMILES: *C1C=CC(*)CC1]

are non-limiting examples of alkenediyl groups. The term "substituted alkenediyl" refers to a non-aromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and at least one atom independently selected from the group consisting of N, O, F, Cl, Br, I, Si, P, and S. The following groups are non-limiting examples of substituted alkenediyl groups: —CF=CH—, —C(OH)=CH—, and —CH$_2$CH=C(Cl)—.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkynediyl" when used without the "substituted" modifier refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH$_2$—, and —C≡CCH(CH$_3$)— are non-limiting examples of alkynediyl groups. The term "substituted alkynediyl" refers to a non-aromatic divalent group, wherein the alkynediyl group is attached with two σ-bonds, with two carbon atoms as points of attachment, a linear or branched, cyclo, cyclic or acyclic structure, at least one carbon-carbon triple bond, and at least one atom independently selected from the group consisting of N, O, F, Cl, Br, I, Si, P, and S. The groups —C≡CCFH— and —C≡CHCH(Cl)— are non-limiting examples of substituted alkynediyl groups.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$—CH$_2$CH$_3$ (ethylphenyl), —C$_6$H$_4$—CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH=CH$_2$ (vinylphenyl), —C$_6$H$_4$CH=CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S. Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "arenediyl" when used without the "substituted" modifier refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. Non-limiting examples of arenediyl groups include:

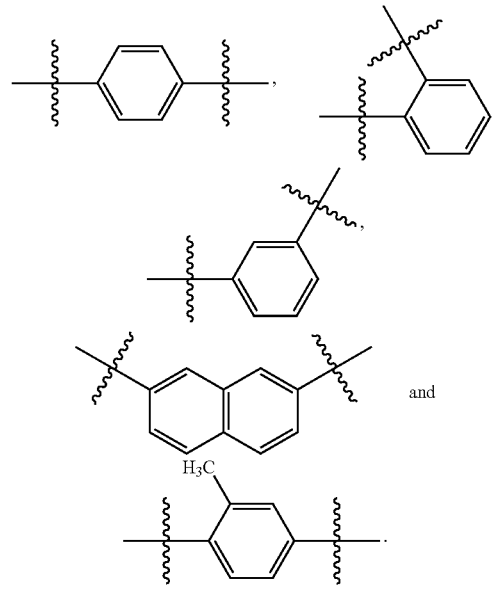

The term "substituted arenediyl" refers to a divalent group, wherein the arenediyl group is attached with two σ-bonds, with two aromatic carbon atoms as points of attachment, said carbon atoms forming part of one or more six-membered aromatic rings structure(s), wherein the ring atoms are carbon, and wherein the divalent group further has at least one atom independently selected from the group consisting of N, O, F, Cl, Br, I, Si, P, and S.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn), 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms. When the term "aralkyl" is used with the "substituted" modifier, either one or both the alkanediyl and the aryl is substituted. Non-limiting examples of substituted aralkyls are: (3-chlorophenyl)-methyl, 2-oxo-2-phenyl-ethyl (phenylcarbonylmethyl), 2-chloro-2-phenyl-ethyl, chromanyl where the point of attachment is one of the saturated carbon atoms, and tetrahydroquinolinyl where the point of attachment is one of the saturated atoms.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "heteroarenediyl" when used without the "substituted" modifier refers to a divalent group, wherein the heteroarenediyl group is attached with two σ-bonds, with an aromatic carbon atom or nitrogen atom as the point of attachment, said carbon atom or nitrogen atom forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. Non-limiting examples of heteroarenediyl groups include:

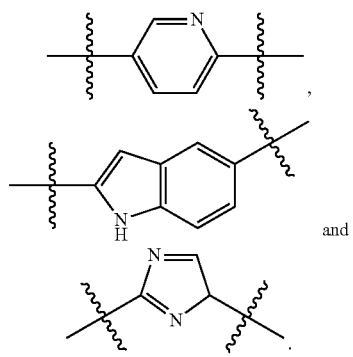

The term "substituted heteroarenediyl" refers to a divalent group, wherein the heteroarenediyl group is attached with two σ-bonds, with an aromatic carbon atom or nitrogen atom as points of attachment, said carbon atom or nitrogen atom forming part of one or more six-membered aromatic ring structure(s), wherein at least one of the ring atoms is nitrogen, oxygen or sulfur, and wherein the divalent group further has at least one atom independently selected from the group consisting of non-aromatic nitrogen, non-aromatic oxygen, non aromatic sulfur F, Cl, Br, I, Si, and P.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of aralkyls are: pyridylmethyl, and thienylmethyl. When the term "heteroaralkyl" is used with the "substituted" modifier, either one or both the alkanediyl and the heteroaryl is substituted.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkylidene" when used without the "substituted" modifier refers to the divalent group =CRR', wherein the alkylidene group is attached with one σ-bond and one π-bond, in which R and R' are independently hydrogen, alkyl, or R and R' are taken together to represent alkanediyl. Non-limiting examples of alkylidene groups include: =CH$_2$, =CH(CH$_2$CH$_3$), and =C(CH$_3$)$_2$. The term "substituted alkylidene" refers to the group =CRR', wherein the alkylidene group is attached with one σ-bond and one π-bond, in which R and R' are independently hydrogen, alkyl, substituted alkyl, or R and R' are taken together to represent a substituted alkanediyl, provided that either one of R and R' is a substituted alkyl or R and R' are taken together to represent a substituted alkanediyl.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

Similarly, the terms "alkenyloxy", "alkynyloxy", "aryloxy", "aralkoxy", "heteroaryloxy", "heteroaralkoxy" and "acyloxy", when used without the "substituted" modifier, refers to groups, defined as —OR, in which R is alkenyl, alkynyl, aryl, aralkyl, heteroaryl, heteroaralkyl and acyl, respectively, as those terms are defined above. When any of the terms alkenyloxy, alkynyloxy, aryloxy, aralkyloxy and acyloxy is modified by "substituted," it refers to the group —OR, in which R is substituted alkenyl, alkynyl, aryl, aralkyl, heteroaryl, heteroaralkyl and acyl, respectively.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

The terms "alkoxyamino", "alkenylamino", "alkynylamino", "arylamino", "aralkylamino", "heteroarylamino", "heteroaralkylamino", and "alkylsulfonylamino" when used without the "substituted" modifier, refers to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$. When any of the terms alkoxyamino, alkenylamino, alkynylamino, arylamino, aralkylamino, heteroarylamino, heteroaralkylamino and alkylsulfonylamino is modified by "substituted," it refers to the group —NHR, in which R is substituted alkoxy, alkenyl, alkynyl, aryl, aralkyl, heteroaryl, heteroaralkyl and alkylsulfonyl, respectively.

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkylimino" when used without the "substituted" modifier refers to the group =NR, wherein the alkylimino group is attached with one σ-bond and one π-bond, in which R is an alkyl, as that term is defined above. Non-limiting examples of alkylimino groups include: =NCH$_3$, =NCH$_2$CH$_3$ and =N-cyclohexyl. The term "substituted alkylimino" refers to the group =NR, wherein the alkylimino group is attached with one σ-bond and one π-bond, in which R is a substituted alkyl, as that term is defined above. For example, =NCH$_2$CF$_3$ is a substituted alkylimino group.

Similarly, the terms "alkenylimino", "alkynylimino", "arylimino", "aralkylimino", "heteroarylimino", "heteroaralkylimino" and "acylimino", when used without the "substituted" modifier, refers to groups, defined as =NR, wherein the alkylimino group is attached with one σ-bond and one π-bond, in which R is alkenyl, alkynyl, aryl, aralkyl, heteroaryl, heteroaralkyl and acyl, respectively, as those terms are defined above. When any of the terms alkenylimino, alkynylimino, arylimino, aralkylimino and acylimino is modified by "substituted," it refers to the group =NR, wherein the alkylimino group is attached with one σ-bond and one π-bond, in which R is substituted alkenyl, alkynyl, aryl, aralkyl, heteroaryl, heteroaralkyl and acyl, respectively.

The term "fluoroalkyl" when used without the "substituted" modifier refers to an alkyl, as that term is defined above, in which one or more fluorines have been substituted for hydrogens. The groups, —CH$_2$F, —CF$_2$H, —CF$_3$, and —CH$_2$CF$_3$ are non-limiting examples of fluoroalkyl groups. The term "substituted fluoroalkyl" refers to a non-aromatic monovalent group with a saturated carbon atom as the point of attachment, a linear or branched, cyclo, cyclic or acyclic structure, at least one fluorine atom, no carbon-carbon double or triple bonds, and at least one atom independently selected from the group consisting of N, O, Cl, Br, I, Si, P, and S. The following group is a non-limiting example of a substituted fluoroalkyl: —CFHOH.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "substituted alkylphosphate" refers to the group —OP(O)(OH)(OR), in which R is a substituted alkyl, as that term is defined above.

The term "dialkylphosphate" when used without the "substituted" modifier refers to the group —OP(O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include: —OP(O)(OMe)$_2$, —OP(O)(OEt)(OMe) and —OP(O)(OEt)$_2$. The term "substituted dialkylphosphate" refers to the group —OP(O)(OR)(OR'), in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached via the oxygen atoms to the phosphorous.

The term "alkylthio" when used without the "substituted" modifier refers to the group —SR, in which R is an alkyl, as that term is defined above. Non-limiting examples of alkylthio groups include: —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl. The term "substituted alkylthio" refers to the group —SR, in which R is a substituted alkyl, as that term is defined above. For example, —SCH$_2$CF$_3$ is a substituted alkylthio group.

Similarly, the terms "alkenylthio", "alkynylthio", "arylthio", "aralkylthio", "heteroarylthio", "heteroaralkylthio", and "acylthio", when used without the "substituted" modifier, refers to groups, defined as —SR, in which R is alkenyl, alkynyl, aryl, aralkyl, heteroaryl, heteroaralkyl and acyl, respectively, as those terms are defined above. When any of the terms alkenylthio, alkynylthio, arylthio, aralkylthio, heteroarylthio, heteroaralkylthio, and acylthio is modified by "substituted," it refers to the group —SR, in which R is substituted alkenyl, alkynyl, aryl, aralkyl, heteroaryl, heteroaralkyl and acyl, respectively.

The term "thioacyl" when used without the "substituted" modifier refers to a monovalent group with a carbon atom of a thiocarbonyl group as the point of attachment, further having a linear or branched, cyclo, cyclic or acyclic structure, further having no additional atoms that are not carbon or hydrogen, beyond the sulfur atom of the carbonyl group. The groups, —CHS, —C(S)CH$_3$, —C(S)CH$_2$CH$_3$, —C(S)CH$_2$CH$_2$CH$_3$, —C(S)CH(CH$_3$)$_2$, —C(S)CH(CH$_2$)$_2$, —C(S)C$_6$H$_5$, —C(S)C$_6$H$_4$CH$_3$, —C(S)C$_6$H$_4$CH$_2$CH$_3$, —C(S)C$_6$H$_3$(CH$_3$)$_2$, and —C(S)CH$_2$C$_6$H$_5$, are non-limiting examples of thioacyl groups. The term "thioacyl" therefore encompasses, but is not limited to, groups sometimes referred to as "alkyl thiocarbonyl" and "aryl thiocarbonyl" groups. The term "substituted thioacyl" refers to a radical with a carbon atom as the point of attachment, the carbon atom being part of a thiocarbonyl group, further having a linear or branched, cyclo, cyclic or acyclic structure, further having at least one atom, in addition to the sulfur atom of the carbonyl group, independently selected from the group consisting of N, O, F, Cl, Br, I, Si, P, and S. The groups, —C(S)CH$_2$CF$_3$, —C(S)O$_2$H, —C(S)OCH$_3$, —C(S)OCH$_2$CH$_3$, —C(S)OCH$_2$CH$_2$CH$_3$, —C(S)OC$_6$H$_5$, —C(S)OCH(CH$_3$)$_2$, —C(S)OCH(CH$_2$)$_2$, —C(S)NH$_2$, and —C(S)NHCH$_3$, are non-limiting examples of substituted thioacyl groups. The term "substituted thioacyl" encompasses, but is not limited to, "heteroaryl thiocarbonyl" groups.

The term "alkylsulfonyl" when used without the "substituted" modifier refers to the group —S(O)$_2$R, in which R is an alkyl, as that term is defined above. Non-limiting examples of alkylsulfonyl groups include: —S(O)$_2$CH$_3$, —S(O)$_2$CH$_2$CH$_3$, —S(O)$_2$CH$_2$CH$_2$CH$_3$, —S(O)$_2$CH(CH$_3$)$_2$, —S(O)$_2$CH(CH$_2$)$_2$, —S(O)$_2$-cyclopentyl, and —S(O)$_2$-cyclohexyl. The term "substituted alkylsulfonyl" refers to the group —S(O)$_2$R, in which R is a substituted alkyl, as that term is defined above. For example, —S(O)$_2$CH$_2$CF$_3$ is a substituted alkylsulfonyl group.

Similarly, the terms "alkenylsulfonyl", "alkynylsulfonyl", "arylsulfonyl", "aralkylsulfonyl", "heteroarylsulfonyl", and "heteroaralkylsulfonyl" when used without the "substituted" modifier, refers to groups, defined as —S(O)$_2$R, in which R is alkenyl, alkynyl, aryl, aralkyl, heteroaryl, and heteroaralkyl, respectively, as those terms are defined above. When any of the terms alkenylsulfonyl, alkynylsulfonyl, arylsulfonyl, aralkylsulfonyl, heteroarylsulfonyl, and heteroaralkylsulfonyl is modified by "substituted," it refers to the group —S(O)$_2$R, in which R is substituted alkenyl, alkynyl, aryl, aralkyl, heteroaryl and heteroaralkyl, respectively.

The term "alkylsulfinyl" when used without the "substituted" modifier refers to the group —S(O)R, in which R is an alkyl, as that term is defined above. Non-limiting examples of alkylsulfinyl groups include: —S(O)CH$_3$, —S(O)CH$_2$CH$_3$, —S(O)CH$_2$CH$_2$CH$_3$, —S(O)CH(CH$_3$)$_2$, —S(O)CH(CH$_2$)$_2$, —S(O)-cyclopentyl, and —S(O)-cyclohexyl. The term "substituted alkylsulfinyl" refers to the group —S(O)R, in which R is a substituted alkyl, as that term is defined above. For example, —S(O)CH$_2$CF$_3$ is a substituted alkylsulfinyl group.

Similarly, the terms "alkenylsulfinyl", "alkynylsulfinyl", "arylsulfinyl", "aralkylsulfinyl", "heteroarylsulfinyl", and "heteroaralkylsulfinyl" when used without the "substituted" modifier, refers to groups, defined as —S(O)R, in which R is alkenyl, alkynyl, aryl, aralkyl, heteroaryl, and heteroaralkyl, respectively, as those terms are defined above. When any of the terms alkenylsulfinyl, alkynylsulfinyl, arylsulfinyl, aralkylsulfinyl, heteroarylsulfinyl, and heteroaralkylsulfinyl is modified by "substituted," it refers to the group —S(O)R, in which R is substituted alkenyl, alkynyl, aryl, aralkyl, heteroaryl and heteroaralkyl, respectively.

The term "alkylammonium" when used without the "substituted" modifier refers to a group, defined as —NH$_2$R$^+$, —NHRR'$^+$, or —NRR'R''$^+$, in which R, R' and R'' are the same or different alkyl groups, or any combination of two of R, R' and R'' can be taken together to represent an alkanediyl. Non-limiting examples of alkylammonium cation groups include: —NH$_2$(CH$_3$)$^+$, —NH$_2$(CH$_2$CH$_3$)$^+$, —NH$_2$(CH$_2$CH$_2$CH$_3$)$^+$, —NH(CH$_3$)$_2$$^+$, —NH(CH$_2$CH$_3$)$_2$$^+$, —NH(CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)$^+$, —NH$_2$C(CH$_3$)$_3$$^+$, —NH(cyclopentyl)$_2$$^+$, and —NH$_2$(cyclohexyl)$^+$. The term "substituted alkylammonium" refers —NH$_2$R$^+$, —NHRR'$^+$, or —NRR'R''$^+$, in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent a alkanediyl with two or more carbon atoms, at least two of which are attached to the nitrogen atom shown in the formula.

The term "alkylsulfonium" when used without the "substituted" modifier refers to the group —SRR'$^+$, in which R and R' can be the same or different alkyl groups, or R and R' can be taken together to represent an alkanediyl. Non-limiting examples of alkylsulfonium groups include: —SH(CH$_3$)$^+$, —SH(CH$_2$CH$_3$)$^+$, —SH(CH$_2$CH$_2$CH$_3$)$^+$, —S(CH$_3$)$_2$$^+$, —S(CH$_2$CH$_3$)$_2$$^+$, —S(CH$_2$CH$_2$CH$_3$)$_2$$^+$, —SH(cyclopentyl)$^+$, and —SH(cyclohexyl)$^+$. The term "substituted alkylsulfonium" refers to the group —SRR'$^+$, in which R and R' can be the same or different substituted alkyl groups, one of R or R' is an alkyl and the other is a substituted alkyl, or R and R' can be taken together to represent a substituted alkanediyl. For example, —SH(CH$_2$CF$_3$)$^+$ is a substituted alkylsulfonium group.

The term "alkylsilyl" when used without the "substituted" modifier refers to a monovalent group, defined as —SiH$_2$R, —SiHRR', or —SiRR'R'', in which R, R' and R'' can be the same or different alkyl groups, or any combination of two of R, R' and R'' can be taken together to represent an alkanediyl. The groups, —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups. The term "substituted alkylsilyl" refers —SiH$_2$R, —SiHRR', or —SiRR'R'', in which at least one of R, R' and R'' is a substituted alkyl or two of R, R' and R'' can be taken together to represent a substituted alkanediyl. When more than one of R, R' and R'' is a substituted alkyl, they can be the same of different. Any of R, R' and R'' that are not either substituted alkyl or substituted alkanediyl, can be either alkyl, either the same or different, or can be taken together to represent a alkanediyl with two or more saturated carbon atoms, at least two of which are attached to the silicon atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

A compound having a formula that is represented with a dashed bond is intended to include the formulae optionally having zero, one or more double bonds. Thus, for example, the structure

includes the structures

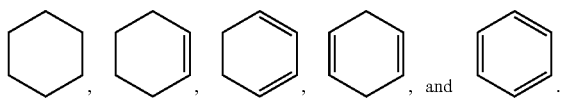

As will be understood by a person of skill in the art, no one such ring atom forms part of more than one double bond.

Any undefined valency on an atom of a structure shown in this application implicitly represents a hydrogen atom bonded to the atom.

As used herein, a "chiral auxiliary" refers to a removable chiral group that is capable of influencing the stereoselectivity of a reaction. Persons of skill in the art are familiar with such compounds, and many are commercially available.

The terms "nucleotide base", "nucleobase" or simply "base", as used herein, refers to a substituted or unsubstituted nitrogen-containing parent heteroaromatic ring of a type that is commonly found in nucleic acids, as well as natural, substituted, modified, or engineered variants or analogs of the same. In a typical embodiment, the nucleobase is capable of forming Watson-Crick and/or Hoogsteen hydrogen bonds with an appropriately complementary nucleobase. Exemplary nucleobases include, but are not limited to, purines such as 2-aminopurine, 2,6-diaminopurine, adenine (A), ethenoadenine, $N^6$-$\Delta^2$-isopentenyladenine (6iA), $N^6$-$\Delta^2$-isopentenyl-2-methylthioadenine (2 ms6iA), $N^6$-methyladenine, guanine (G), isoguanine, $N^2$-dimethylguanine (dmG), 7-methylguanine (7mG), 2-thiopyrimidine, 6-thioguanine (6sG), hypoxanthine and $O^6$-methylguanine;

7-deaza-purines such as 7-deazaadenine (7-deaza-A), 7-deazaguanine (7-deaza-G), 7-deaza-7-hydroxymethyladenine, 7-deaza-7-aminomethyladenine and 7-deaza-7-hydroxymethylguanine;

pyrimidines such as cytosine (C), 5-propynylcytosine, isocytosine, 5-hydroxymethylcytosine (HOMeC), 5-aminomethyl-cytosine, thymine (T), 4-thiothymine (4sT), 5,6-dihydrothymine, $O^4$-methylthymine, uracil (U), 4-thiouracil (4sU), 5-hydroxymethyluracil (HOMeU), 5-aminomethyl-uracil, and 5,6-dihydrouracil (dihydrouracil; D);

indoles such as nitroindole and 4-methylindole; pyrroles such as nitropyrrole; nebularine; base (Y); etc.

Additional exemplary nucleobases can be found in Lehninger, 2005, which is incorporated by reference, and the references cited therein.

The term "nucleoside" as used herein, refers to a glycosylamine consisting of a nucleobase bound to a five-carbon sugar, typically a ribose or a deoxyribose. Examples of these include, but are not limited to, cytidine, 2'-deoxycytidine, 5-hydroxymethylcytidine, 2'-deoxy-5-hydroxylmethylcytidine, 5-aminomethylcytidine, 2'-deoxy-5-aminomethylcytidine, uridine, 2'-deoxyuridine, 5-hydroxylmethyluridine, 2'-deoxy-5-hydroxylmethyluridine, 5-aminomethyluridine, 2'-deoxy-5-aminomethyluridine, adenosine, 2'-deoxyadenosine, 7-deaza-7-hydroxymethyladenosine, 2'-deoxy-7-deaza-7-hydroxymethyladenosine, 7-deaza-7-aminomethyladenosine, 2'-deoxy-7-deaza-7-amino-methyladenosine, guanosine, 2'-deoxyguanosine, 7-deaza-7-hydroxymethyl guanosine, 2'-deoxy-7-deaza-7-hydroxymethyl, 7-deaza-7-aminomethyl guanosine, 2'-deoxy-7-deaza-7-aminomethyl guanosine, thymidine, and 2'-deoxythymidine.

A "nucleotide" is composed of a nucleoside with one, two, three or more phosphate groups bound in a chain to the 5-carbon sugar of the nucleoside.

Unless specified otherwise, a "linker" refers to one or more divalent groups (linking members) that function as a covalently-bonded molecular bridge between two other groups. A linker may contain one or more linking members and one or more types of linking members. Exemplary linking members include: —C(O)NH—, —C(O)O—, —NH—, —S—, —S(O)$_n$— where n is 0, 1 or 2, —O—, —OP(O)(OH)O—, —OP(O)(O$^-$)O—, alkanediyl, alkenediyl, alkynediyl, arenediyl, heteroarenediyl, or combinations thereof. Some linkers have pendant side chains or pendant functional groups (or both). Examples of such pendant moieties are hydrophilicity modifiers, for example, solubilizing groups like, e.g., —SO$_3$H or —SO$_3^-$. In some embodiments, a linker may connect a reporter to another moiety such as a chemically, photochemically or enzymatically reactive group (e.g., a cleavable or non-cleavable terminating moiety). In other embodiments, a linker connects a reporter to a biological and non-biological component, for example, a nucleobase, a nucleoside or a nucleotide. In further embodiments, a linker connects chemically reactive groups to a nucleobase, a nucleoside or a nucleotide. The moiety formed by a linker bonded to a reporter may be designated -L-Reporter. Depending on such factors as the molecules to be linked and the conditions in which the method of strand synthesis is performed, the linker may vary in length and composition for optimizing properties such as stability, length, FRET efficiency, resistance to certain chemicals and/or temperature parameters, and be of sufficient stereo-selectivity or size to operably link a label to a nucleotide such that the resultant conjugate is useful in optimizing a polymerization reaction. Linkers can be employed using standard chemical techniques and include but not limited to, amine linkers for attaching labels to nucleotides (see, for example, Hobbs and Trainor, U.S. Pat. No. 5,151,507, which is incorporated herein by reference); a linker typically contain a primary or secondary amine for operably linking a label to a nucleotide; and a rigid hydrocarbon arm added to a nucleotide base (see, for example, Service, 1998, which is incorporated herein by reference). Some exemplary linking methodologies for attachment of reporters to base molecules are provided in U.S. Pat. Nos. 4,439,356 and 5,188,934; European Patent Application 87310256.0; International Application PCT/US90/05565 and Barone et al., 2001, each of which is incorporated herein by reference in its entirety.

A "cleavable linker" is a linker that has one or more cleavable groups that may be broken by the result of a reaction or condition. The term "cleavable group" refers to a moiety that allows for release of a portion, e.g., a fluorogenic or fluorescent moiety. Such cleavage is typically chemically, photochemically or enzymatically mediated. Exemplary enzymatically cleavable groups include phosphates, or peptide sequences.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to but not limited to the concentration of a nucleotide analog at which its incorporation on a primer-template complex yields equal numbers of moles of substrate and product and/or could be defined, but not limited to, incorporation efficiency measured by determining the concentration at which the compound incorporates on half the primer-template complexes.

As used herein, the term "oligonucleotide" refers to DNA fragments of 2 to 200 covalently linked nucleotides.

As used herein, the term "template" refers to an oligonucleotide serving as the complimentary strand for DNA synthesis (incorporation).

As used herein, the term "primer" refers to an oligonucleotide that is hybridized to a complement sequence on the template strand used to initiate DNA synthesis (incorporation).

When used herein in the scientific or technical sense, the term "incorporation" refers to a nucleotide or nucleotide analog forming a complement base-pair with the template strand and a covalent bond to a primer strand by a polymerase. The primer-template complex is extended one or more bases from the initial primer strand.

As used herein, the term "cleavage" refers to the removal of the terminating group by photo-cleavage, chemical cleavage, enzymatic cleavage or the like.

As used herein, the term "incorporation cycle" refers to the incorporation of a nucleotide or nucleotide analog by a polymerase, the detection and identification of said nucleotide or nucleotide analog, and if a nucleotide analog, cleavage of the terminating group from said analog.

As used herein, the term "misincorporation" refers to a nucleotide or nucleotide analog forming a non-complement base-pair with the template strand and a covalent bond to a primer by a polymerase. The primer-template complex is extended one or more bases from the initial primer strand.

As used herein, the term "discrimination" refers the $IC_{50}$ concentration differences for misincorporation versus incorporation of nucleotide or nucleotide analogs by a polymerase.

As used herein, the term "termination" refers to the incorporation of a nucleotide or nucleotide analog forming a complement or non-complement base-pair with the template strand and a covalent bond to a primer by a polymerase. The primer-template complex is extended only one base from the initial primer strand for any given incorporation cycle.

As used herein, the term "$DT_{50}$" refers to the amount of time required to cleavage 50% of the base analog incorporated in the primer-template complex.

The term "analog" as used herein, is understood as being a substance which does not comprise the same basic carbon skeleton and carbon functionality in its structure as a "given compound", but which can mimic the given compound by incorporating one or more appropriate substitutions such as for example substituting carbon for heteroatoms.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

When used in reference to a compound, composition, method or device, "pharmaceutically acceptable" means generally safe, non-toxic and neither biologically nor otherwise undesirable and includes that which is acceptable for veterinary use as well as human pharmaceutical use.

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

Compounds of the present disclosure may be made using the methods outlined in the Examples section. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated herein by reference.

III. Biological Function and Cleavage Rates

As shown in some aspects of the present disclosure, substitution and its stereochemistry of the α-carbon of the 2-nitrobenzyl group affects biological function and cleavage rates of reaction of 3'-unblocked, base-modified dNTPs.

In one embodiment, sample components enable the determination of SNPs. The method may be for the high-throughput identification of informative SNPs. The SNPs may be obtained directly from genomic DNA material, from PCR amplified material, or from cloned DNA material and may be assayed using a single nucleotide primer extension method. The single nucleotide primer extension method may comprise using single unlabeled dNTPs, single labeled dNTPs, single 3'-modified dNTPs, single base-modified 3'-dNTPs, single alpha-thio-dNTPs or single labeled 2',3'-dideoxynucleotides. The mini-sequencing method may comprise using single unlabeled dNTPs, single labeled dNTPs, single 3'-modified dNTPs, single base-modified 2'-dNTPs, single alpha-thio-dNTPs or single labeled 2',3'-dideoxynucleotides. The SNPs may be obtained directly from genomic DNA material, from PCR amplified material, or from cloned DNA materials.

The present disclosure further provides nucleotide and nucleoside compounds as well as salts, esters and phosphates thereof, that can be used in rapid DNA sequencing technology. The compounds are optionally in the form of ribonucleoside triphosphates (NTPs) and deoxyribonucleoside triphosphates (dNTP). The nucleotide and nucleoside compounds in some cases include a photocleavable group labeled with a reporter group such as a fluorescent dye. The nucleotide and nucleoside compounds include photoremovable protecting groups that are designed to terminate DNA synthesis as well as cleave rapidly, so that these monomers can be used for rapid sequencing in a parallel format. The presence of such rapidly cleavable groups labeled with fluorescent dyes on the nucleotide and nucleoside compounds can enhance the speed and accuracy of sequencing of large oligomers of DNA in parallel, to allow, for example, rapid whole genome sequencing, and the identification of polymorphisms and other valuable genetic information.

In certain aspects, the present disclosure relates to compounds wherein the base of the nucleoside is covalently attached with a 2-nitrobenzyl group, and the alpha carbon position of the 2-nitrobenzyl group is optionally substituted with one alkyl or aryl group as described herein. In certain examples, the base of the nucleoside is covalently attached with a 2-nitrobenzyl group, and the 2-nitrobenzyl group is optionally substituted with one or more of an electron donating and electron withdrawing group as described herein. The 2-nitrobenzyl group can be functionalized to enhance the termination properties as well as the light catalyzed deprotection rate. The termination properties of the 2-nitrobenzyl and alpha carbon substituted 2-nitrobenzyl group attached to the nucleobase occur even when the 3'-OH group on the ribose sugar is unblocked. These 3'-OH unblocked terminators are well-tolerated by a number of commercially available DNA polymerases, representing a key advantage over 3'-O-blocked terminators. The alpha carbon substituted 2-nitrobenzyl group also can be derivatized to include a selected fluorescent dye or other reporter group.

A. Nucleotide and Nucleoside Compounds and their Use in DNA Sequencing

Nucleotide and nucleoside compounds are provided which are useful in DNA sequencing technology. One aspect of the present invention is directed towards the use of the promising sequencing approach, cyclic reversible termination (CRT). CRT is a cyclic method of detecting the synchronistic, single base additions of multiple templates. This approach differentiates itself from the Sanger method (Metzker, 2005, which is incorporated herein by reference) in that it can be performed without the need for gel electrophoresis, a major bottleneck in advancing this field. Like Sanger sequencing, however, longer read-lengths translates into fewer sequencing assays needed to cover the entire genome. The CRT cycle typically comprises three steps, incorporation, imaging, and deprotection. For this procedure, cycle efficiency, cycle time, and sensitivity are important factors. The cycle efficiency is the product of deprotection and incorporation efficiencies and determines the CRT read-length. The CRT cycle time is the sum of incorporation, imaging, and deprotection times. For rapid CRT for whole genome sequencing, the nucleotide and nucleoside compounds as disclosed herein may be used, which can exhibit fast and efficient deprotection properties. These compounds can be labeled with reporter groups such as fluorescent dyes, attached directly to the 2-nitrobenzyl, providing, e.g., fluorescent, reversible terminators with similar deprotection properties. It has remained difficult to accomplish the goal of long CRT reads because reversible terminators typically act as poor substrates with commercially available DNA polymerases. Modified nucleotide analogs of the present invention may be used to improve this technology by providing substrates that incorporate as well or better than a natural nucleotide with commercially available DNA polymerases.

When applied to genomic DNA, the compounds can be used in CRT to read directly from genomic DNA. Fragmented genomic DNA can be hybridized to a high-density oligonucleotide chip containing priming sites that span selected chromosomes. Each priming sequence is separated by the estimated read-length of the CRT method. Between base additions, a fluorescent imager can simultaneously image the entire high-density chip, marking significant improvements in speed and sensitivity. In specific embodiments, a fluorophore, which is attached to the 2-nitrobenzyl group or its derivatives described herein, is removed by UV irradiation releasing the 2-nitrobenzyl group for the next round of base addition. After approximately 500 CRT cycles, the complete and contiguous genome sequence information can then be compared to the reference human genome to determine the extent and type of sequence variation in an individual's sample. Reversible terminators that exhibit higher incorporation and deprotection efficiencies will typically achieve higher cycle efficiencies, and thus longer read-lengths.

CRT Efficiency is defined by the formula: $(RL)^{Ceff}=0.5$, where RL is the read-length in bases and Ceff is the overall cycle efficiency. In other words, a read-length of 7 bases could be achieved with an overall cycle efficiency of 90%, 70 bases could be achieved with a cycle efficiency of 99% and 700 bases with a cycle efficiency of 99.9%. The efficiency of incorporation of compounds according to the invention may range from about 70% to about 100% of the incorporation of the analogous native nucleoside. Preferably, the efficiency of incorporation will range from about 85% to about 100%. Photocleavage efficiencies will preferably range from about 85% to about 100%. Further, termination of nucleic acid extension will range from about 90% to about 100% upon incorporation of compounds according to the invention. Nucleotide and nucleoside compounds in one embodiment have a cycle efficiency of at least 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%.

Another aspect of the present invention is directed towards the use of pyrosequencing, which is a non-electrophoretic, bioiluminescence method that measures the release of inorganic pyrophosphate (PPi) by proportionally converting it into visible light by a series of enzymatic reactions (Ronaghi et al., 1998, which is incorporated herein by reference). Unlike other sequencing approaches that use modified nucleotides to terminate DNA synthesis, the pyrosequencing assay manipulates DNA polymerase by the single addition of a dNTP in limiting amounts. DNA polymerase then extends the primer upon incorporation of the complementary dNTP and pauses. DNA synthesis is reinitiated following the addition of the next complementary dNTP in the dispensing cycle. The order and intensity of the light peaks are recorded as flowgrams, revealing the underlying DNA sequence. For homopolymer repeats up to six nucleotides, the number of dNTPs added is directly proportional to the light signal. Homopolymer repeats greater than six nucleotide can result in insertional errors, which are the most common error type for pyrosequencing. Modified nucleotide analogs of the present invention may improve this technology by accurate sequencing through homopolymer repeats, particularly those greater than six nucleotides in length.

Another aspect of the present invention is directed towards the use of Sanger sequencing, particularly in heterozygote detection. Despite much advancement, improvements in the dideoxy-BigDye terminator sequencing chemistry for accurate heterozygote detection are needed. It is generally believed that a uniform peak height distribution in the primary data makes base-calling and heterozygote detection more reliable and accurate. The termination pattern in Sanger sequencing is primarily due to sequence-dependent bias incorporation by DNA polymerase, which can selectively incorporate natural nucleotides over modified nucleotides (Metzker et al., 1998, which is incorporated herein by reference). These bias incorporation effects are more pronounced with the dye-terminator chemistry than with the dye-primer chemistry. This can be attributed to effects of the large fluorescent dye structures attached to the terminating nucleotide, lowering enzyme activity at least 10-fold to that of the natural substrate. Thus, the reduction of bias incorporation effects by DNA polymerase towards dye-labeled terminators could lead to improved heterozygote detection. Modified nucleotide analogs of the present invention may improve this technology by incorporating as well or better than a natural nucleotide, thus eliminating incorporation bias in Sanger sequencing.

Another aspect of the present invention is directed towards the use of clonally amplified templates and single DNA molecule templates. The front-end of NGS technologies can be partitioned into two camps: clonally amplified templates from single DNA molecules and single DNA molecule templates. It is well recognized in the art that DNA can be immobilized to a solid surface by either attaching a primer to said surface and hybridizing a target nucleic acid to said primer (Southern and Cummins, 1998, U.S. Pat. No. 5,770,367; Harris et al., 2008, which are incorporated herein by reference) or by attaching a target nucleic acid to said surface by clonally amplification and hybridizing a primer to said target nucleic acid (Dressman et al., 2003; Margulies et al., 2005, which are incorporated herein by reference). Either immobilization configuration can be used in the present invention for then binding a DNA polymerase to initiate either the CRT method or the pyrosequencing method.

For CRT terminators to function properly, the protecting group must be efficiently cleaved under mild conditions. The removal of a protecting group generally involves either treatment with strong acid or base, catalytic or chemical reduction, or a combination of these methods. These conditions may be reactive to the DNA polymerase, nucleotides, oligonucleotide-primed template, or the solid support creating undesirable outcomes. The use of photochemical protecting groups is an attractive alternative to rigorous chemical treatment and can be employed in a non-invasive manner.

A number of photoremovable protecting groups including, but not limited to 2-nitrobenzyl, benzyloxycarbonyl, 3-nitrophenyl, phenacyl, 3,5-dimethoxybenzoinyl, 2,4-dinitrobenzenesulphenyl, and their respective derivatives have been used for the synthesis of peptides, polysaccharides, and nucleotides (Pillai, 1980, which is incorporated herein by reference). Of these, the light sensitive 2-nitrobenzyl protecting group has been successfully applied to the 2'-OH of ribonucleosides for diribonucleoside synthesis (Ohtsuka et al., 1974, which is incorporated herein by reference), the 2'-OH of ribophosphoramidites in automated ribozyme synthesis (Chaulk and MacMillan, 1998, which is incorporated herein by reference), the 3'-OH of phosphoramidites for oligonucleotide synthesis in the Affymetrix chemistry (Pease et al., 1994, which is incorporated herein by reference), and to the 3'-OH group for DNA sequencing applications (Metzker et al., 1994, which is incorporated herein by reference). Under deprotection conditions (ultraviolet light>300 nm), the 2-nitrobenzyl group can be efficiently cleaved without affecting either the pyrimidine or purine bases (Pease et al., 1994 and Bartholomew and Broom, 1975, which are incorporated by reference).

In one aspect, the present invention is directed towards the use of chemically cleavable reversible terminators. For example, the benzyl protecting group has been widely used in organic synthesis as a result of its stability and ease of mild and selective deprotection by catalytic hydrogenolysis (Green and Wuts, 1999, which is incorporated herein by reference). Hydrogenolysis, which can be conducted under neutral conditions, is advantageous when working with nucleosides containing phosphoanhydride bonds, since nucleoside diphosphates, and especially nucleoside triphosphates, degrade under acidic conditions (Wu et al., 2004;

Johnson et al., 2004, which are incorporated herein by reference). Removal of a benzyl protecting group from solid-supported compounds by hydrogenolysis using Palladium nano-particles (Kanie et al., 2000, which is incorporated herein by reference) and hydrogenation conducted on a microfluidic device with immobilized Palladium catalyst (Kobayashi et al. 2004, which is incorporated herein by reference) have also been reported in addition to hydrogenolysis using conventional Palladium catalyst.

B. Polymerase Assays

Natural and modified nucleotides were tested for incorporation efficiency using the "polymerase end point assay" (Wu et al., 2007, which is incorporated herein by reference). This assay examines incorporation efficiency on matched and mismatched template bases. Incorporation efficiency is measured by determining the concentration at which the compound incorporates on half the primer-template complexes ($IC_{50}$). Titrations of increasing compound concentration were performed to generate curves from which the $IC_{50}$ can be determined.

The sequence of the template DNA is selected depending on which compound will be tested. For example, the first interrogation base after the primer in the template sequence is the complement base of the compound when measuring incorporation efficiency, and one of three mismatched bases when measuring mismatch discrimination properties.

To the annealed reaction, a DNA polymerase (e.g., THERMINATOR™ DNA polymerase, 0.25 units per reaction, New England Biolabs), 1× Thermopol Buffer, and a known concentration of either natural or modified nucleotide are added to each 10 µL reaction and incubated at 75° C. for 10 minutes, cooled on ice, and quenched with 10 µL of stop solution (98% formamide: 10 mM $Na_2EDTA$, pH=8.0, 25 mg/ml Blue Dextran). Stopped reactions are heated to 75° C. for 30 seconds to denature the DNA, and then placed on ice. The extension products are analyzed on a 10% Long Ranger (Lonza) polyacrylamide gel using an ABI model 377 DNA sequencer. Additional details are provided in Example 1, below.

FIG. 1 compares the incorporation with THERMINATOR™ DNA polymerase of nucleotides disclosed herein with natural nucleotides. For example, compound 3p065 (5-(α-isopropyl-2-nitrobenzyloxymethyl-2'-dCTP) reaches 50% incorporation at a lower concentration than its natural analog ($IC_{50}$=1.1±0.1 nM versus 3.0±0.6 nM). Compounds labeled with dye also incorporate efficiency with THERMINATOR™ DNA polymerase, for example compound 6p038/6p017 5-(α-isopropyl-2-nitrobenzyl-oxy)methyl-2'-dCTP-Cy5 has an $IC_{50}$=5.1±1.4 nM. Table A shows the $IC_{50}$ concentrations for many of the modified nucleotide analogs described herein.

TABLE A

Effects of Substitution at the α-Carbon on Mismatch Discrimination.

| WW# | Chemical Name | Diastereomer | $IC_{50}$ for incorporation |
|---|---|---|---|
| 1p129 | $N^6$-(2-nitrobenzyl)-2'-dATP | | 2.5 ± 0.3 nM |
| 2p043 | 5-(α-methyl-nitrobenzyl-oxymethyl)-2'-dUTP | mixture | 1.7 ± 0.2 nM |
| 2p108 | $O^6$-(2-nitrobenzyl)-2'-dGTP | | 4.0 ± 0.7 nM |
| 2p143 | $O^6$-(α-methyl-2-nitrobenzyl)-2'-dGTP | mixture | 10 ± 0.0 nM |
| 2p148 | 5-(α-isopropyl-nitrobenzyl-oxymethyl)-2'-dUTP | mixture | 2.3 ± 0.1 nM |
| 3p006 | $N^6$-(α-methyl-2-nitrobenzyl)-2'-dATP | mixture | 8.5 ± 1.8 nM |
| 3p063 | 5-(α-isopropyl-2-nitrobenzyl-oxymethyl)-2'-dUTP | single | 2.0 nM |
| 3p065 | 5-(α-isopropyl-2-nitrobenzyl-oxymethyl)-2'-dCTP | single | 1.1 ± 0.1 nM |
| 3p075 | 5-(α-tert-butyl-2-nitrobenzyl-oxymethyl)-2'-dUTP | single | 3.0 nM |
| 3p085 | 5-(α-tert-butyl-2-nitrobenzyl-oxymethyl)-2'-dCTP | single | 2.0 nM |
| 5p085 | $C^7$-(2-nitrobenzyl-oxymethyl)-2'-dATP | | 3.6 ± 0.3 nM |
| 5p098-ds1 | $C^7$-(α-isopropyl-2-nitrobenzyl-oxymethyl)-2'-dATP (ds1) | single | 6.7 ± 0.8 nM |
| 5p098-ds2 | $C^7$-(α-isopropyl-2-nitrobenzyl-oxymethyl)-2'-dATP (ds2) | single | 5.7 ± 1.1 nM |
| 5p107 | $C^7$-(2-nitrobenzyl-oxymethyl)-2'-dGTP | | 1.5 ± 0.3 nM |
| 5p111 | 5-(α-isopropyl-benzyl-oxymethyl)-2'-dUTP | mixture | 0.8 nM |
| 5p127 | $C^7$-(α-isopropyl-2-nitrobenzyl-oxymethyl)-2'-dATP-6-FAM | single | 6.4 ± 1.0 nM |
| 5p130-LP2 | $C^7$-(α-isopropyl-2-nitrobenzyl-oxymethyl)-2'-dATP-6-CR110 | single | 15 ± 3 nM |
| 5p143-ds1 | $C^7$-(α-isopropyl-2-nitrobenzyl-oxymethyl)-2'-dGTP (ds1) | single | 1.2 ± 0.2 nM |
| 5p143-ds2 | $C^7$-(α-isopropyl-2-nitrobenzyl-oxymethyl)-2'-dGTP (ds2) | single | 1.3 ± 0.3 nM |
| 5p145 | 5-benzyl-oxymethyl-2'-dUTP | | 1.4 nM |
| 5p147 | 5-(2-methyl-benzyl-oxymethyl)-2'-dUTP | | 1.4 nM |
| 5p149 | 5-(2-isopropyl-benzyl-oxymethyl)-2'-dUTP | | 1.4 nM |
| 6p005 | 5-(α-isopropyl-2-nitrobenzyl-oxymethyl)-2'-dUTP-5-R6G | single | 15 ± 1 nM |
| 6p008 | 5-(α-isopropyl-2-nitrobenzyl-oxymethyl)-2'-dUTP-6-JOE | single | 9.0 ± 1.4 nM |
| 6p010 | 5-(2-phenyl-benzyl-oxymethyl)-2'-dUTP | | 1.4 nM |
| 6p015 | 5-(2,6-dimethyl-benzyl-oxymethyl)-2'-dUTP | | 1.4 nM |
| 6p017 | 5-(α-isopropyl-2-nitrobenzyl-oxymethyl)-2'-dCTP-Cy5 | single | 4.8 ± 1.9 nM |
| 6p024 | 5-(2-tert-butyl-benzyl-oxymethyl)-2'-dUTP | | 0.7 nM |
| 6p028/5p127 | $C^7$-(α-isopropyl-2-nitrobenzyl-oxymethyl)-2'-dATP-6-FAM | single | 6.4 ± 1.0 nM |
| 6p034 | $C^7$-(α-isopropyl-2-nitrobenzyl-oxymethyl)-2'-dGTP-6-ROX | single | 7.4 ± 0.1 nM |
| 6p038/6p017 | 5-(α-isopropyl-2-nitrobenzyl-oxymethyl)-2'-dCTP-Cy5 | single | 5.1 ± 1.4 nM |
| 6p044 | 5-(α-isopropyl-2-nitrobenzyl-oxymethyl)-2'-dUTP-6-ROX | single | 18 ± 1 nM |
| 6p057-ds1 | $C^7$-(α-isopropyl-2,6-di-nitrobenzyl-oxymethyl)-2'-dATP (ds1) | single | 5.2 ± 0.2 nM |
| 6p057-ds2 | $C^7$-(α-isopropyl-2,6-di-nitrobenzyl-oxymethyl)-2'-dATP (ds2) | single | 5.8 ± 1.1 nM |
| 6p063 | $N^6$-(α-isopropyl-2-nitrobenzyl)-2'-dATP | single | 12 ± 1 nM |
| 6p075/6p008 | 5-(α-isopropyl-2-nitrobenzyl-oxymethyl)-2'-dUTP-6-JOE | single | 9.0 ± 1.4 nM |
| 6p087-ds1 | $C^7$-(α-isopropyl-4-methoxy-2-nitrobenzyl-oxymethyl)-2'-dATP (ds1) | single | 15 ± 1 nM |
| 6p087-ds2 | $C^7$-(α-isopropyl-4-methoxy-2-nitrobenzyl-oxymethyl)-2'-dATP (ds2) | single | 18 ± 3 nM |
| 6p094 | 5-(α-isopropyl-2-nitrobenzyl-oxymethyl)-2'-dUTP-6-FAM | single | 8.1 ± 0.2 nM |

C. Mismatch Discrimination

It has been reported that substitution at the α-carbon of the 2-nitrobenzyl group can increase the rate of the cleavage reaction (Reichmanis et al., 1985; Cameron and Frechet, 1991; Hasan et al., 1997, which are incorporated herein by reference). Without being bound by theory, the results presented herein suggest that substitution at the α-carbon of the 2-nitrobenzyl group can also affect the termination of DNA synthesis for 3'-unblocked nucleotide triphosphates and improve discrimination against mismatch incorporation. Furthermore, and based on the results discussed in greater detail below, it was found that the stereochemistry of the substitution of α-carbon of the 2-nitrobenzyl group can have a significant impact on the extent of mismatch discrimination and the rate of the cleavage reaction.

Table 1 shows a comparison between the two diastereomers "ds1" and "ds2" of the α-substituted carbon and their precursors. The mismatch/match ratios represent the ability of the polymerase to distinguish between correctly incorporating against a matched template base and a mismatch one. Discrimination is considered sufficient when the mismatch/match ratio is greater than or equal to 100 (two orders of magnitude). Table 1 shows the discrimination of natural dGTP and $C^7$-hydroxymethyl-dGTP analogs 5p107, 5p143-ds1 and 5p143-ds2. Both natural dGTP and $C^7$-(2-nitrobenzyloxy)methyl-2'-dGTP (5p107) show mismatch/match ratios ranging from 10 to 360, and 10 to 250, respectively, two of which are below the 100-fold threshold. Substitution of the α-methylene carbon with an isopropyl group, however, results in a significantly higher discrimination ratio for all mismatch template bases. 5p143-ds1 exhibits a high mismatch discrimination ratio compared with 5p143-ds2. These data provide evidence that the stereochemistry of the α-isopropyl group can affect the degree of discrimination against mismatch incorporation. A similar trend is observed for the $C^7$-hydroxymethyl-dATP analogs. For the compounds shown in Table 1, substitution at the α-carbon of the 2-nitrobenzyl group increases mismatch discrimination in a stereo-specific manner.

TABLE 1

Effects of Substitution at the α-Carbon on Mismatch Discrimination.

| Complement | Mismatch/match ratio ($10^2$) | | | |
|---|---|---|---|---|
| Base | dGTP | 5p107 | 5p143-ds1 | 5p143-ds2 |
| "C" | N/A | N/A | N/A | N/A |
| "T" | 0.1 | 0.1 | 5 | 2.5 |
| "A" | 3.6 | 2.5 | >830 | >770 |
| "G" | 0.2 | 0.4 | >21 | >7.7 | dGTP = natural dGTP
5p107 = $C^7$-(2-nitrobenzyloxy)methyl-2'-dGTP
5p143 = $C^7$-(α-isopropyl-2-nitrobenzyloxy)methyl-2'-dGTP

D. Termination

Without being bound by theory, at least two factors were found to typically influence termination of DNA synthesis after a single incorporation: a) substitution at the α-carbon of the 2-nitrobenzyl group, and b) substitution at the 2-position of the benzyl ring. Table 2 shows the influence of various substitutions using a "weighted sum" analysis, which is determined by quantifying primer extension products using automated gel electrophoresis. A weighted sum of 1.0 represents complete termination after a single incorporation, while a value greater than 1.0 indicates incorporation beyond the +1 position (e.g. nucleotide read through). To standardize the termination assay, a concentration of 25× the $IC_{50}$ value of a given compound is used. The assay is performed as described above for the polymerase end-point assay, except that the template used is a homopolymer repeat, thereby allowing for multiple incorporations of a given nucleotide compound. In this example, modified dUTP analogs are compared to natural dTTP, which at 25× its $IC_{50}$ value extends the entire length of the homopolymer repeat template and misincorporates the $11^{th}$ base (weighted sum=11). Compound 3p085 (2-nitrobenzyloxymethyl-2'-dUTP) shows a degree of termination with a weighted sum of 3.7±0.1. Substitution of the α-carbon with a methyl group (2p043) further improves termination, reducing the weighted sum value to 1.7±0.1. Complete termination is achieved with an α-isopropyl substitution (2p148), showing a weighted sum value of 1.0. The $IC_{50}$ value for the complement base, however, does not increase, indicating that the larger isopropyl substitution has a beneficial effect on termination, but does not compromise incorporation efficiency.

TABLE 2

Both substitutions at the α-carbon of the 2-nitrobenzyl ring, and substitution at the 2-position of the benzyl ring influence termination properties of the compound

| Compound name | Substitution | Adj $IC_{50}$ Conc (nM) | Average Weighted Sum ± SD | | |
|---|---|---|---|---|---|
| | | | 1x $IC_{50}$ | 5x $IC_{50}$ | 25x $IC_{50}$ |
| dTTP | (natural dTTP) | 2.1 | 0.68 | 3.0 | 12.2 |
| 2p043 | α-methyl-5-(2-nitrobenzyl) | 1.7 | 0.53 ± 0.06 | 1.1 ± 0.0 | 1.7 ± 0.1 |
| 2p148 | α-isopropyl-5-(2-nitrobenzyl) | 2.1 | 0.59 ± 0.02 | 0.99 ± 0.01 | 1.0 ± 0.01 |
| 5p111 | α-isopropyl-5-benzyl | 0.8 | 0.44 ± 0.02 | 0.96 ± 0.01 | 1.1 ± 0.03 |
| 5p145 | 5-benzyl | 1.4 | 0.43 ± 0.1 | 1.3 ± 0.3 | 2.9 ± 0.4 |
| 5p147 | 5-(2-methyl benzyl) | 1.4 | 0.51 ± 0.1 | 1.5 ± 0.3 | 2.6 ± 0.4 |
| 5p149 | 5-(2-isopropyl benzyl) | 1.4 | 0.53 ± 0.1 | 1.3 ± 0.1 | 2.2 ± 0.2 |
| 6p010 | 5-(2-phenyl benzyl) | 1.4 | 0.46 ± 0.1 | 1.1 ± 0.1 | 1.7 ± 0.3 |
| 6p015 | 5-(2,6-dimethyl benzyl) | 1.4 | 0.56 ± 0.1 | 1.5 ± 0.1 | 2.2 ± 0.1 |
| 6p024 | 5-(2-tertbutyl benzyl) | 0.7 | 0.44 ± 0.1 | 1.2 ± 0.1 | 1.9 ± 0.1 |

The substitution of the 2-position on the benzyl ring can also influence the termination properties of these modified nucleotides. For example, removing the nitro group from this position (compound 5p111) increases the weighted sum value to 1.1 for an α-isopropyl substitution analog. A number of dUTP analogs were synthesized with various substituents on the 2-position and characterized for termination in the absence of the isopropyl group at the α-carbon. Table 2 shows a general trend of increasing substituent size and shape and improved termination properties, compare 5p145 (WS=2.9) and 6p010 (WS=1.7) at 25×$IC_{50}$ concentrations.

E. UV-Cleavage Rates

Cleavage of the terminating substituted 2-nitrobenzyl group when analogs are incorporated into the primer strand with 365 nm UV light allows for the next cycle of incorporation to resume. Without being bound by theory, at least two factors were found typically influence UV-cleavage rates of incorporated nucleotide analogs: a) stereo-chemistry of the α-carbon substitution of the 2-nitrobenzyl group, and b) substitution on the benzyl ring. Incorporation on a matched template is performed as described above using 1 μM concentration to extend the primer strand. Ten identical tubes are used for each incorporation experiment, after which $NaN_3$ is added to a final concentration of 50 mM. Extended primer reactions are exposed to 365 nm light for various time points using the UV deprotector device described by Wu et al. (2007, which is incorporated herein by reference) and analyzed using an AB model 377 DNA sequencer. The quantitative data are plotted linearly as product formation versus exposure time, and the time point at which half the nucleotide analog is cleaved is calculated, as a $DT_{50}$ value. As shown in Table 3, the stereochemistry affects the rate of UV-cleavage for $C^7$-hydroxymethyl-dATP analogs 5p098-ds1 and -ds2, 6p057-ds1 and -ds2, and 6p087-ds1 and -ds2. For example, based on these examples, the ds2 analogs show faster cleavage rates (e.g., lower $DT_{50}$ values) compared with ds1 analogs. Furthermore, substitution of a methoxy group at the 4 position on the benzyl ring further increases the rate of UV-cleavage, albeit for ds2 analogs only (e.g., the $DT_{50}$ value for 5p098-ds2 is 3.3 sec versus that of 1.9 sec for 6p087-ds2). Based on the examples summarized in Table 3, substitution at the α-carbon of the 2-nitrobenzyl ring increases UV-cleavage in a stereospecific manner.

TABLE 3

Table 3. UV-Cleavage Rates of 2-Nitrobenzyl Ring Derivatives.

| Compound | Substitution | $DT_{50}$ (seconds) |
|---|---|---|
| 5p098-ds1 | α-isopropyl-2-nitrobenzyl | 7.5 ± 0.8 |
| 5p098-ds2 |  | 3.3 ± 0.2 |
| 6p057-ds1 | α-isopropyl-2,6-nitrobenzyl | 7.3 ± 1.2 |
| 6p057-ds2 |  | 4.8 ± 0.5 |
| 6p087-ds1 | α-isopropyl-2-nitrobenzyl-4-methoxy | 8.8 ± 0.6 |
| 6p087-ds2 |  | 1.9 ± 0.1 |

F. Chemical cleavage

In one aspect, the present invention is directed towards the use of chemically cleavable reversible terminators. For example, the benzyl protecting group has been widely used in organic synthesis as a result of its stability and ease of mild and selective deprotection by catalytic hydrogenolysis (Green and Wuts, 1999, which is incorporated herein by reference). Hydrogenolysis, which can be conducted under neutral conditions, is advantageous when working with nucleosides containing phosphoanhydride bonds, since nucleoside diphosphates, and especially nucleoside triphosphates, degrade under acidic conditions (Wu et al., 2004; Johnson et al., 2004, which are incorporated herein by reference). Removal of a benzyl protecting group from solid-supported compounds by hydrogenolysis using palladium nano-particles (Kanie et al., 2000, which is incorporated herein by reference) and hydrogenation conducted on microfluidic device with immobilized palladium catalyst (Kobayashi et al. 2004, which is incorporated herein by reference) have also been reported beside hydrogenolysis using conventional palladium catalyst. Examples of chemically reversible cleavage results, including cleavage of 5-benzyloxymethyl-dU analogs using catalytic hydrogenolysis, are provided in Example 10 below.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods and Materials

Polymerase Assays. Natural and modified nucleotides were tested for incorporation efficiency using the "polymerase end point assay" (Wu et al., 2007, which is incorporated herein by reference). This assay examines incorporation efficiency on matched and mismatched template bases. Incorporation efficiency is measured by determining the concentration at which the compound incorporates on half the primer-template complexes ($IC_{50}$). Titrations of increasing compound concentration were performed to generate curves from which the $IC_{50}$ can be determined.

The assay is performed by first annealing 5 nM of BODIPY-FL labeled primer with 40 nM template DNA in 1× Thermopol Buffer (20 mM Tris-HCl, pH 8.8; 10 mM $(NH_4)_2SO_4$; 10 mM KCl; 2 mM $MgSO_4$; 0.1% Triton X-100, New England BioLabs).

The temperature cycle to complete primer annealing is 80° C. for 30 seconds, 57° C. for 30 seconds, then cooling to 4° C. The sequence of the template DNA is selected depending on which compound will be tested. For example, the first interrogation base after the primer in the template sequence is the complement base of the compound when measuring incorporation efficiency, and one of three mismatched bases when measuring mismatch discrimination properties.

To the annealed reaction, a DNA polymerase (e.g., THERMINATOR™ DNA polymerase, 0.25 units per reaction, New England Biolabs), 1× Thermopol Buffer, and a known concentration of either natural or modified nucleotide are added to each 10 μL reaction and incubated at 75° C. for 10 minutes, cooled on ice, and quenched with 10 μL of stop solution (98% formamide: 10 mM $Na_2EDTA$, pH=8.0, 25 mg/ml Blue Dextran). Stopped reactions are heated to 75° C. for 30 seconds to denature the DNA, and then placed on ice. The extension products are analyzed on a 10% Long Ranger (Lonza) polyacrylamide gel using an ABI model 377 DNA sequencer. The quantitative data are displayed as a linear-log plot of product formation versus compound concentration, and the $IC_{50}$ is calculated using KaleidaGraph software (Synergy Software).

Example 2

Synthesis of α-Substituted 2-Nitrobenzyl Alcohols

Synthesis of (RS)-1-(2-nitrophenyl)ethanol

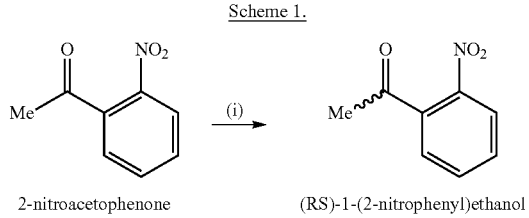

2-nitroacetophenone     (RS)-1-(2-nitrophenyl)ethanol (i) $NaBH_4$, MeOH, 1,4-dioxane, room temperature, 100%.

(RS)-1-(2-Nitrophenyl)ethanol: Sodium borohydride (0.69 g, 18.16 mmol) was added to a solution of a 2-nitroacetophenone (1.0 g, 6.06 mmol) in methanol (9 mL) and 1,4-dioxane (6 mL) in small portions (Dong et al., 2005, which is incorporated herein by reference). The mixture was stirred at room temperature for 30 minutes, then concentrated in vacuo. The residue was diluted with acetyl acetate (50 mL), washed with water (10 mL) and brine (10 mL). The organic phase was dried over $Na_2SO_4$ and concentrated in vacuo to yield racemic (RS)-1-(2-nitrophenyl)ethanol (1.02 g, 100%). $^1$H NMR (400 MHz, $CDCl_3$): δ 7.90 (m, 1 H, Ph-H), 7.84 (m, 1 H, Ph-H), 7.66 (m, 1 H, Ph-H), 7.44 (m, 1 H, Ph-H), 5.42 (m, 1 H, Ph-CH), 2.33 (d, 1 H, J=3.5 Hz, OH) 1.58 (d, 3 H, J=5.1 Hz, $CH_3$).

Synthesis of (RS)-1-(4-iodo-2-nitrophenyl)ethanol

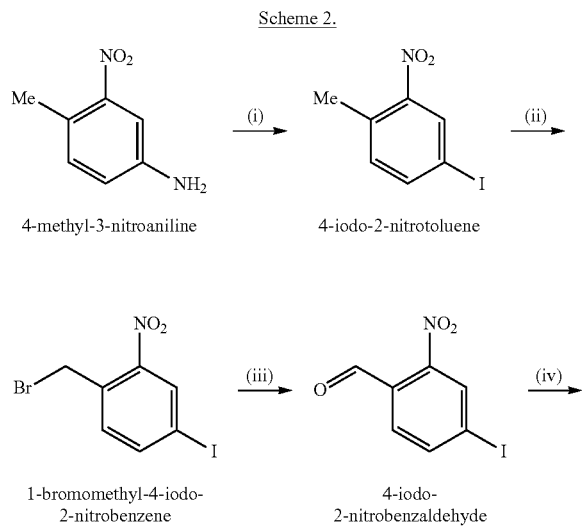

Scheme 2.

4-methyl-3-nitroaniline     4-iodo-2-nitrotoluene 1-bromomethyl-4-iodo-2-nitrobenzene     4-iodo-2-nitrobenzaldehyde

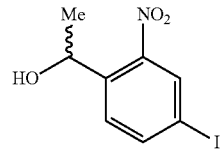

(RS)-1-(4-Iodo-2-nitrophenyl)ethanol

Synthesis of (RS)-1-(4-iodo-2-nitrophenyl)ethanol: (i) $NaNO_2$, $H_2SO_4$, minus 2° C.; then NaI, 100° C., 82%; (ii) NBS, benzoyl peroxide, $CCl_4$, reflux, 45%; (iii) DMSO, $NaHCO_3$, 86° C., 61%; (iv) $Me_2Zn$, $Ti(Oi-Pr)_4$, $CH_2Cl_2$, toluene, 0° C., 48%.

4-Iodo-2-nitrotoluene: To a suspension of 4-methyl-3-nitroaniline (4.30 g, 28.26 mmol) in water (40 mL) cooled in ice-water bath, 98% sulfuric acid (1.89 mL) was added cautiously (Herm et al., 2002, which is incorporated herein by reference). Sodium chloride was added into the ice-water bath to lower the temperature to minus 2° C., and a solution of $NaNO_2$ (2.15 g, 31.10 mmol) in water (10 mL) was added at a rate that the reaction temperature did not exceed 0° C. Upon completion of the addition, the mixture was stirred at minus 2° C. for 45 minutes. This solution of the diazo compound was then carefully added (in small portions) to a boiling solution of NaI (12.89 g, 86 mmol) (CAUTION: vigorous gas evolution). Upon completion of the addition, the reaction mixture was cooled down to room temperature and extracted with methylene chloride (50 mL) four times. The combined organic phase was washed with saturated $NaHCO_3$ (40 mL) and water (40 mL), dried over $Na_2SO_4$, concentrated in vacuo. The residue was purified by silica gel chromatography to yield 4-iodo-2-nitrotoluene (6.07 g, 82%). $^1$H NMR (400 MHz, $CDCl_3$): δ 8.28 (d, 1 H, J=1.8 Hz, Ph-H), 7.81 (dd, 1 H, J=2.2 and 8.1 Hz, Ph-H), 7.09 (d, 1 H, J=8.1 Hz, Ph-H), 2.55 (s, 3 H, $CH_3$).

1-Bromomethyl-4-iodo-2-nitrobenzene: NBS (5.45 g, 30.62 mmol) and benzoyl peroxide (75% aq, 200 mg, 0.85 mmol) were added to a solution of 4-iodo-2-nitrotoluene (4.63 g, 17.60 mmol) in $CCl_4$ (60 mL). The mixture was heated to reflux overnight, then cooled to room temperature, concentrated in vacuo, and purified by column chromatography to yield 1-bromomethyl-4-iodo-2-nitrobenzene (2.71 g, 45%). $^1$H NMR (400 MHz, $CDCl_3$): δ 8.35 (d, 1 H, J=1.8 Hz, Ph-H), 7.93 (dd, 1 H, J=1.8 and 8.1 Hz, Ph-H), 7.30 (d, 1 H, J=8.1 Hz, Ph-H), 4.76 (s, 2 H, $PhCH_2$).

4-Iodo-2-nitrobenzaldehyde: $NaHCO_3$ (3.32 g, 39.48 mmol) was added to a solution of 1-bromomethyl-4-iodo-2-nitrobenzene (2.25 g, 6.58 mmol) in anhydrous DMSO (150 mL). The mixture was stirred at 86° C. for 19 hours under a nitrogen atmosphere, then cooled down to room temperature, diluted with water (300 mL), and extracted with methylene chloride four times (250 mL). The combined organic phase was dried over $Na_2SO_4$, concentrated in vacuo, and purified by silica gel chromatography to yield 4-iodo-2-nitrobenzaldehyde (1.11 g, 61%). $^1$H NMR (400 MHz, $CDCl_3$): δ 10.38 (d, 1 H, J=1.6 Hz, CHO), 8.45 (d, 1 H, J=1.5 Hz, Ph-H), 8.15 (dd, 1 H, J=1.5 and 8.0 Hz, Ph-H), 7.67 (d, 1 H, J=8.1 Hz, Ph-H); $^{13}$C NMR (100 MHz, $CDCl_3$): δ 187.28 (CH), 143.18 (CH), 133.29 (CH), 130.67 (CH), 130.28 (C), 109.60 (C), 99.78 (C).

(RS)-1-(4-Iodo-2-nitrophenyl)ethanol: Titanium(IV) isopropoxide (1.2 mL, 4.04 mmol) was dissolved in anhydrous dichloromethane (8 mL) under a nitrogen atmosphere. The solution was cooled to 0° C. and dimethylzinc (2 M in toluene, 8.67 mL, 17.34 mmol) was added dropwise. The mixture was stirred at 0° C. for 45 minutes followed by addition of 4-iodo-2-nitrobenzaldehyde (800 mg, 2.89 mmol). The mixture was stirred at 0° C. for 36 hours, then quenched by 1 M HCl (CAUTION: vigorous gas evolution!) and extracted with ethyl either (50 mL) three times. The combined organic phase was washed with water (50 mL), saturated NaHCO$_3$ solution (50 mL) and brine (50 mL), dried over Na$_2$SO$_4$, concentrated in vacuo, and purified by column chromatography to yield racemic (RS)-1-(4-Iodo-2-nitrophenyl)ethanol (408 mg, 48%). $^1$H NMR (400 MHz, CDCl$_3$): δ 8.21 (dd, 1 H, J=1.8 and 5.3 Hz, Ph-H), 7.96 (m, 1 H, Ph-H), 7.58 (d, 1 H, J=8.3 Hz, Ph-H), 5.38 (q, 1 H, J=6.1 Hz, Ph-CH), 2.34 (br s, 1 H, OH), 1.54 (d, 3 H, J=6.1 Hz, CH$_3$); $^{13}$C NMR (100 MHz, CDCl$_3$): δ 147.98 (C), 142.49 (CH), 140.68 (C), 132.77 (CH), 131.31 (CH), 91.60 (C), 65.40 (CH), 24.28 (CH$_3$).

Synthesis of (RS)-1-(2-nitrophenyl)-2-methyl-1-propanol and (S)-1-(2-nitrophenyl)-2-methyl-1-propanol Scheme 3.

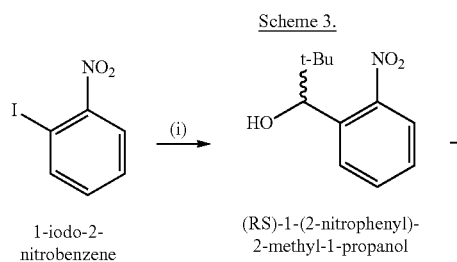

1-iodo-2-nitrobenzene (RS)-1-(2-nitrophenyl)-2-methyl-1-propanol

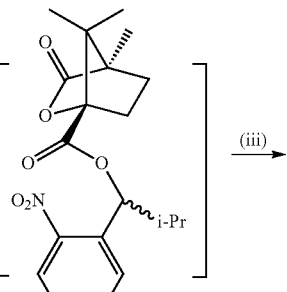

(RS)-1-(2-nitrophenyl)-2-methyl-propyl (1S)-camphanate

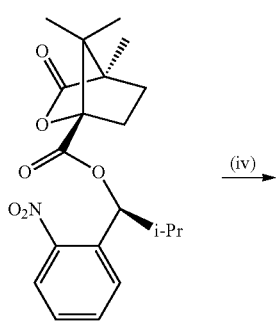

(S)-1-(2-nitrophenyl)-2-methyl-propyl (1S)-camphanate

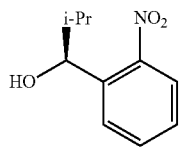

(S)-1-(2-nitrophenyl)-2-methyl-propanol

Synthesis of (RS)-1-(2-nitrophenyl)-2-methyl-1-propanol and (S)-1-(2-nitrophenyl)-2-methyl-1-propanol. (i) PhMgCl, i-PrCHO, THF (anhydrous), minus 40° C. to room temperature, 99% (ii) (1S)-camphanic acid chloride, pyridine (anhydrous), room temperature; (iii) recrystallization from methanol; (iv) K$_2$CO$_3$/MeOH, reflux, 97%.

(RS)-1-(2-Nitrophenyl)-2-methyl-propanol: To a solution of 1-iodo-2-nitrobenzene (1.12 g, 4.5 mmol) in anhydrous THF (15 mL) cooled to minus 40° C. under nitrogen atmosphere, a solution of phenylmagnesium chloride (2 M in THF, 2.4 mL, 4.8 mmol) was added dropwise at a rate that the temperature would not exceed minus 35° C. Upon completion of the addition the mixture was stirred for five minutes at minus 40° C., followed by addition of isobutyraldehyde (0.545 mL, 6.0 mmol). The mixture was gradually warmed up to room temperature, quenched with saturated ammonium chloride (6 mL), poured into water (80 mL), and extracted with ethyl acetate three times (100 mL). Combined organic phase was washed with brine (80 mL), dried over Na$_2$SO$_4$, and concentrated in vacuo. The residue was purified by silica gel column chromatography to yield racemic (RS)-1-(2-nitrophenyl)-2-methyl-propanol (0.876 g, 99%) as a light yellow oil. $^1$H NMR (400 MHz, CDCl$_3$): δ 7.84 (dd, 1 H, J=1.2 and 8.2 Hz, Ph-H), 7.73 (dd, 1 H, J=1.4 and 7.9 Hz, Ph-H), 7.61 (m, 1 H, Ph-H), 7.39 (m, 1 H, Ph-H), 5.03 (dd, 1 H, J=4.5 and 5.8 Hz, Ph-CH), 2.42 (d, 1 H, J=4.5 Hz, OH), 2.02 (m, 1 H, CH), 0.95 (d, 3 H, J=6.7 Hz, CH$_3$), 0.89 (d, 3 H, J=6.8 Hz, CH$_3$); $^{13}$C NMR (100 MHz, CDCl$_3$): δ 148.48 (C), 138.91 (C), 132.95 (CH), 128.85 (CH), 127.95 (CH), 124.21 (CH), 73.79 (CH), 34.30 (CH), 19.66 (CH$_3$), 17.01 (CH$_3$).

(S)-1-(2-Nitrophenyl)-2-methyl-propyl (1S)-camphanate: To a solution of (RS)-1-(2-nitrophenyl)-2-methyl-propanol (2.18 g, 11.2 mmol) in anhydrous pyridine (10 mL) (1S)-camphanic acid chloride (2.63 g, 12.2 mmol) was added. The mixture was stirred for 18 hours at room temperature under nitrogen atmosphere, then concentrated in vacuo to afford crude (RS)-1-(2-nitrophenyl)-2-methyl-propyl (1S)-camphanate (1:1 mixture of diastereomers). The camphanate was dissolved in boiling methanol (100 mL) and the solution was allowed to cool to room temperature and left overnight. Crystals formed were collected by filtration and were redissolved in boiling methanol (80 mL) and the solution was allowed to cool to room temperature and left overnight. Crystals formed were collected by filtration to afford of pure (S)-1-(2-nitrophenyl)-2-methyl-propyl (1S)-camphanate (0.76 g, 36%). $^1$H NMR (400 MHz, CDCl$_3$): δ 7.99 (dd, 1 H, J=1.8 and 7.8 Hz, Ph-H), 7.63 (m, 2 H, Ph-H), 7.45 (m, 1 H, Ph-H), 6.33 (d, 1 H, J=6.0 Hz, Ph-CH), 2.32 (m, 2 H), 1.91 (m, 2 H), 1.67 (m, 1 H), 1.12 (s, 3H, CH$_3$), 1.05 (s, 3 H, CH$_3$), 1.03 (d, 3 H, J=6.8 Hz, CH$_3$), 1.00 (s, 3 H, CH$_3$), 0.99 (d, 3 H, J=6.8 Hz, CH$_3$).

Figure 2:
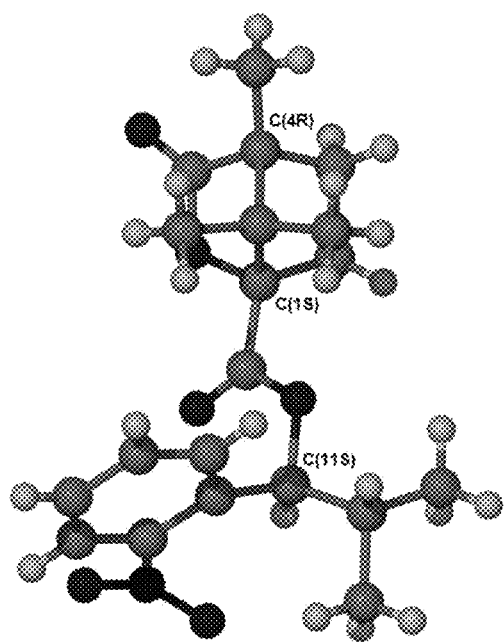
FIG. 2. X-ray Crystallography data of (S)-1-(2-nitrophenyl)-2-methyl-1-propyl (1S)-camphanate: $C_{20}H_{25}NO_6$, M=375.41, colorless plate, 0.26×0.24×0.10 mm$^3$, orthorhombic, space group $P2_12_12_1$ (No. 19), a=11.9268(15), b=11.9812(14), c=13.5488(16) Å, V=1936.1(4) Å$^3$, Z=4, $D_c$=1.288 g/cm$^3$, $F_{000}$=800, MWPC area detector, CuKα radiation, λ=1.54178 Å, T=110(2)K, $2\theta_{max}$=120.0°, 22896 reflections collected, 2665 unique ($R_{int}$=0.0462). Final GooF=1.009, R1=0.0219, wR2=0.0554, R indices based on 2629 reflections with I>2sigma(I) (refinement on F$^2$), 245 parameters, 0 restraints. Lp and absorption corrections applied, μ=0.787 mm$^{-1}$. Absolute structure parameter=0.09 (5).

X-ray Crystallography data of (S)-1-(2-nitrophenyl)-2-methyl-propyl (1S)-camphanate: C$_{20}$H$_{25}$NO$_6$, M=375.41, colorless plate, 0.26×0.24×0.10 mm$^3$, orthorhombic, space group P2$_1$2$_1$2$_1$ (No. 19), a=11.9268(15), b=11.9812(14), c=13.5488(16) Å, V=1936.1(4) Å$^3$, Z=4, D$_c$=1.288 g/cm$^3$, F$_{000}$=800, MWPC area detector, CuKα radiation, λ=1.54178 Å, T=110(2)K, 2θ$_{max}$=120.0°, 22896 reflections collected, 2665 unique (R$_{int}$=0.0462). Final GooF=1.009, R1=0.0219, wR2=0.0554, R indices based on 2629 reflections with I>2sigma(I) (refinement on F$^2$), 245 parameters, 0 restraints. Lp and absorption corrections applied μ=0.787 mm$^{-1}$. Absolute structure parameter=0.09(5) (Flack, 1983, which is incorporated herein by reference). See FIG. 2.

(S)-1-(2-Nitrophenyl)-2-methyl-propanol: (S)-1-(2-Nitrophenyl)-2-methyl-propyl (1S)-camphanate (0.717 g, 1.90 mmol) was dissolved in hot methanol (40 mL) and K$_2$CO$_3$ (0.380 g, 2.74 mmol) was added. The mixture was heated to reflux for one hour, then cooled down, concentrated in vacuo, and diluted with diethyl ether (100 mL). The organic phase was washed with water (20 mL), dried over anhydrous Na$_2$SO$_4$, and purified by silica gel column chromatography to yield (S)-1-(2-nitrophenyl)-2-methyl-propanol (0.360 g, 97%) as a light yellow oil. $^1$H NMR was identical to that of the racemic alcohol.

Synthesis of (RS)-1-(4-Iodo-2-nitrophenyl)-2-methyl-1-propanol, (R)-1-(4-Iodo-2-nitrophenyl)-2-methyl-1-propanol and (S)-1-(4-Iodo-2-nitrophenyl)-2-methyl-1-propanol

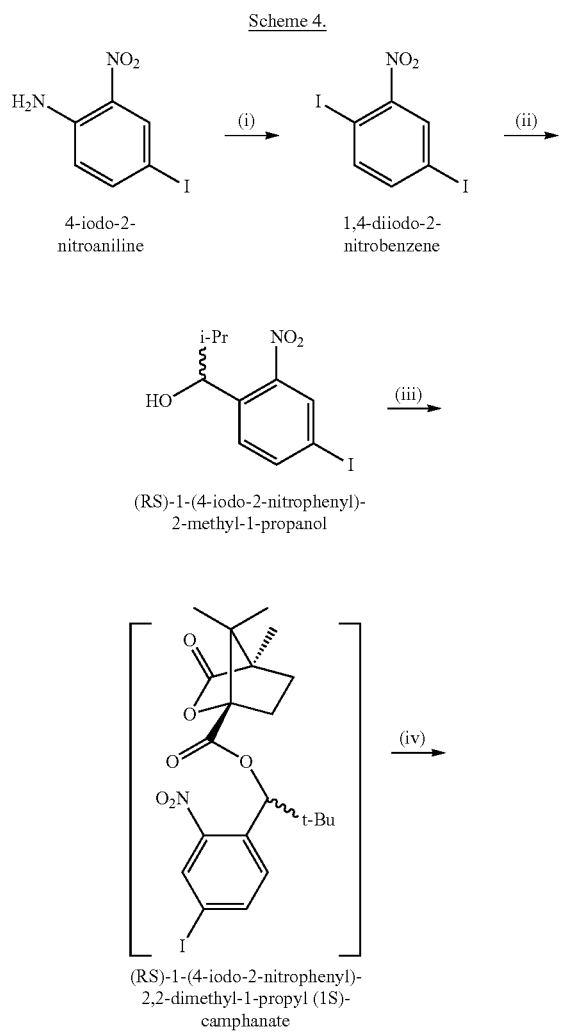

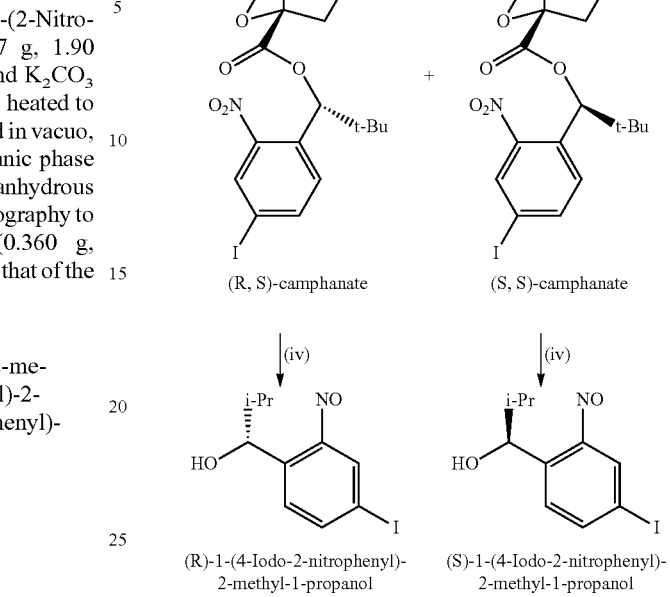

Synthesis of (RS)-1-(4-Iodo-2-nitrophenyl)-2-methyl-1-propanol, (R)-1-(4-Iodo-2-nitrophenyl)-2-methyl-1-propanol and (S)-1-(4-Iodo-2-nitrophenyl)-2-methyl-1-propanol. (i) NaNo$_2$, AcOH, H$_2$SO$_4$, minus 5-0° C.; NaI, 100° C., 99%; (ii) PhMgCl, i-PrCHO, THF (anhydrous), minus 40° C. to room temperature, 80%; (iii) (1S)-camphanic acid chloride, DMAP, CH$_2$Cl$_2$ (anhydrous), room temperature, 84%; (iv) recrystallization from methanol or isopropanol; (v) K$_2$CO$_3$, MeOH, reflux, 100%.

1,4-Diiodo-2-nitrobenzene 4-Iodo-2-nitroaniline (6.60 g, 0.025 mol) was suspended in water (19 mL) and glacial acetic acid (17.5 mL) (Sapountzis et al., 2005, which is incorporated herein by reference). The mixture was cooled to 0° C. Sulfuric acid (17.5 mL, 0.328 mol) was added cautiously. The mixture was cooled to minus 5° C., and a solution of NaNO$_2$ (1.90 g, 0.028 mol) in water (7.5 mL) was added dropwise at a rate that the temperature would not exceed 0° C. Upon completion of the addition the mixture was stirred for 30 minutes and was added in small portions to a boiling solution of sodium iodide (22.33 g, 0.149 mol) in water (7.5 mL) (CAUTION: vigorous nitrogen evolution!). The resulting mixture was kept at 60° C. for one hour, then cooled down to room temperature, followed by addition of diethyl ether (500 mL). The ether solution was separated, washed twice with water (150 mL) and once saturated NaHCO$_3$ (150 mL). The solution was dried over Na$_2$SO$_4$ and concentrated in vacuo to a solid, which was recrystallized from ethanol to yield 1,4-diiodo-2-nitrobenzene (9.30 g, 99%). $^1$H NMR (400 MHz, CDCl$_3$): δ 8.15 (d, 1H, J=2.0 Hz), 7.75 (d, 1 H, J=8.3 Hz), 7.56 (dd, 1 H, J=8.3 and 2.0 Hz).

(RS)-1-(4-Iodo-2-nitrophenyl)-2-methyl-1-propanol: To a solution of 1,4-diiodo-2-nitrobenzene (2.24 g, 6.0 mmol) in anhydrous THF (20 mL) at minus 40° C. under a nitrogen atmosphere, phenylmagnesium bromide (2 M in THF, 3.2 mL, 6.4 mmol) was added dropwise at a rate that the temperature would not exceed minus 35° C. Upon completion of the addition the mixture was stirred for 5 minutes, followed by addition of isobutyraldehyde (0.726 mL, 8.0 mmol). The mixture was gradually warmed up to room temperature, quenched with saturated NH$_4$Cl (8 mL), then poured into water (100 mL). The mixture was extracted three times with ethyl acetate (150 mL), and the combined organic phase was washed with brine (100 mL), dried over Na₂SO₄, concentrated in vacuo and purified by silica gel column chromatography to yield racemic (RS)-1-(4-Iodo-2-nitrophenyl)-2-methyl-1-propanol (1.54 g, 80%) as a light yellow oil. $^1$H NMR (400 MHz, CDCl₃): δ 8.18 (d, 1 H, J=1.7 Hz, Ph-H), 7.93 (dd, 1 H, J=1.7 and 8.3 Hz, Ph-H), 7.50 (d, 1 H, J=8.3 Hz, Ph-H), 5.04 (m, 1 H, Ph-CH), 2.17 (d, 1 H, J=4.4 Hz, OH), 1.98 (m, 1 H, CH), 0.93 (d, 3 H, J=4.4 Hz, CH₃), 0.92 (d, 3 H, J=4.4 Hz, CH₃); $^{13}$C NMR (100 MHz, CDCl₃): δ 148.62 (C), 141.81 (CH), 138.57 (C), 132.72 (CH), 130.49 (CH), 91.51 (C), 73.48 (CH), 34.22 (CH), 19.62 (CH₃), 16.71 (CH₃).

(R)- and (S)-1-(4-iodo-2-nitrophenyl)-2-methyl-propyl (1S)-camphanate: Under a nitrogen atmosphere (1S)-camphanic acid chloride (0.89 g, 4.09 mmol) was added to a solution of (RS)-1-(4-Iodo-2-nitrophenyl)-2-methyl-1-propanol (1.10 g, 3.41 mmol) and DMAP (0.50 g, 4.09 mmol) in anhydrous dichloromethane (30 mL). The mixture was stirred for 1.5 hours at room temperature and then concentrated in vacuo. The residue was purified by silica gel column chromatography to yield (RS)-1-(4-Iodo-2-nitrophenyl)-2-methyl-1-propyl (1S)-camphanates (1.44 g, 84%, 1:1 mixture of diastereomers) as a solid, which was dissolved in boiling methanol (70 mL) and left at room temperature overnight. Crystals formed were filtered to yield pure (R)-1-(4-iodo-2-nitrophenyl)-2-methyl-1-propyl (1S)-camphanate (0.465 g, 65%). The mother liquor was evaporated, and the residue was dissolved in boiling isopropanol (40 mL) and left at room temperature overnight. Crystals formed were filtered and recrystallized from boiling isopropanol (20 mL) to yield pure (S)-1-(4-iodo-2-nitrophenyl)-2-methyl-1-propyl (1S)-camphanate (0.288 g, 40%). $^1$H NMR (400 MHz, CDCl₃) for (R,S)-camphanate: δ 8.30 (d, 1 H, J=1.8 Hz, Ph-H), 7.92 (dd, 1 H, J=1.8 and 8.3 Hz, Ph-H), 7.56 (d, 1 H, J=8.3 Hz, Ph-H), 6.27 (d, 1 H, J=6.8 Hz, Ph-CH), 2.40 (m, 1 H), 2.23 (m, 1 H), 2.06 (m, 1 H), 1.92 (m, 1 H), 1.72 (m, 1 H), 1.11 (s, 3 H, CH₃), 1.03 (d, J=6.8 Hz, 3 H, CH₃), 1.02 (s, 1 H, CH₃), 0.98 (d, J=6.8 Hz, 3 H, CH₃), 0.82 (s, 3 H, CH₃); $^{13}$C NMR (100 MHz, CDCl₃) for (R,S)-camphanate: δ 178.21 (C), 166.92 (C), 148.67 (C), 142.07 (CH), 134.80 (C), 133.34 (CH), 129.73 (CH), 92.59 (C), 90.75 (C), 76.07 (CH), 54.79 (C), 54.34 (C), 33.27 (CH), 31.03 (CH₂), 28.88 (CH₂), 19.07 (CH₃), 17.40 (CH₃), 16.70 (CH₃), 16.66 (CH₃), 9.61 (CH₃).

$^1$H NMR (400 MHz, CDCl₃)) for (S,S)-camphanate: δ 8.30 (d, 1 H, J=1.8 Hz, Ph-H), 7.94 (dd, 1 H, J=1.8 and 8.3 Hz, Ph-H), 7.35 (d, 1 H, J=8.3 Hz, Ph-H), 6.23 (d, 1 H, J=6.1 Hz, Ph-CH), 2.34 (m, 1 H), 2.24 (m, 1 H), 1.91 (m, 2 H), 1.67 (m, 1 H), 1.13 (s, 3 H, CH₃), 1.04 (s, 3 H, CH₃), 1.02 (d, 3 H, J=5.2 Hz, CH₃), 1.00 (s, 3 H, CH₃), 0.98 (d, 3 H, J=5.6 Hz, CH₃); $^{13}$C NMR (100 MHz, CDCl₃) (S,S)-camphanate: δ 178.28 (C), 167.03 (C), 148.67 (C), 142.27 (CH), 134.90 (C), 133.28 (CH), 129.59 (CH), 91.60 (C), 91.06 (C), 76.21 (CH), 54.91 (C), 54.40 (C), 33.16 (CH), 30.75 (CH₂), 28.83 (CH₂), 19.14 (CH₃), 17.41 (CH₃), 16.97 (CH₃), 16.65 (CH₃), 9.70 (CH₃).

Figure 3:
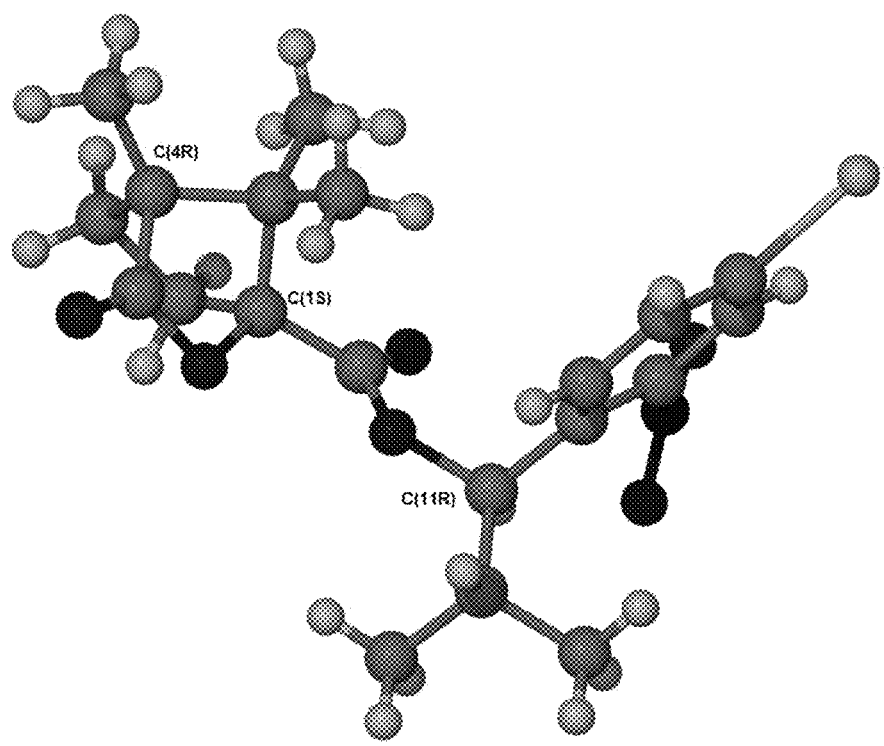
FIG. 3. X-ray crystallography data for (R)-1-(4-iodo-2-nitrophenyl)-2-methyl-1-propyl (1S)-camphanate: Crystal data for $lg_{01}a$: $C_{20}H_{24}INO_6$, M=501.30, colorless plate, 0.30×0.20×0.20 mm$^3$, monoclinic, space group $P2_1$ (No. 4), a=7.5810(15), b=12.446(3), c=11.722(3) Å, β=107.613 (10)°, V=1054.2(4) Å$^3$, Z=2, $D_c$=1.579 g/cm$^3$, $F_{000}$=504, CCD area detector, MoKα radiation, λ=0.71073 Å, T=110 (2)K, $2\theta_{max}$=50.0°, 24239 reflections collected, 3558 unique ($R_{int}$=0.0302). Final GooF=1.010, $R_1$=0.0123, wR2=0.0316, R indices based on 3520 reflections with I>2sigma(I) (refinement on F$^2$), 253 parameters, 3 restraints. Lp and absorption corrections applied, μ=1.554 mm$^{-1}$. Absolute structure parameter=0.020(9).

X-ray crystallography data for (R)-1-(4-iodo-2-nitrophenyl)-2-methyl-1-propyl (1S)-camphanate: Crystal data for lg₀₁a: C₂₀H₂₄INO₆, M=501.30, colorless plate, 0.30×0.20×0.20 mm³, monoclinic, space group P2₁ (No. 4), a=7.5810(15), b=12.446(3), c=11.722(3) Å, β=107.613(10)°, V=1054.2(4) Å³, Z=2, D_c=1.579 g/cm³, F₀₀₀=504, CCD area detector, MoKα radiation, λ=0.71073 Å, T=110(2)K, 2θ_{max}=50.0°, 24239 reflections collected, 3558 unique (R_{int}=0.0302). Final GooF=1.010, R1=0.0123, wR2=0.0316, R indices based on 3520 reflections with I>2sigma(I) (refinement on F²), 253 parameters, 3 restraints. Lp and absorption corrections applied, μ=1.554 mm¹. Absolute structure parameter=0.020(9) (Flack, 1983, which is incorporated herein by reference). See FIG. 3.

(R)-1-(4-Iodo-2-nitrophenyl)-2-methyl-1-propanol: (R)-1-(4-Iodo-2-nitrophenyl)-2-methyl-1-propyl (1S)-camphanate (0.41 g, 0.82 mmol) was dissolved in hot methanol (60 mL) and K₂CO₃ (0.22 g, 1.58 mmol) was added. The mixture was heated to reflux for one hour, cooled to room temperature and concentrated in vacuo. The residue was purified by silica gel column chromatography to yield (R)-1-(4-Iodo-2-nitrophenyl)-2-methyl-1-propanol (0.262 g, 100%) as a light yellow oil. $^1$H NMR was identical to that of the racemic alcohol.

(S)-1-(4-Iodo-2-nitrophenyl)-2-methyl-1-propanol: (S)-1-(4-Iodo-2-nitrophenyl)-2-methyl-1-propyl (1S)-camphanate (0.288 g, 0.57 mmol) was dissolved in hot methanol (40 mL) and K₂CO₃ (0.15 g, 1.1 mmol) was added. The mixture was heated to reflux for one hour, cooled to room temperature and concentrated in vacuo. The residue was purified by silica gel column chromatography to yield (S)-1-(4-Iodo-2-nitrophenyl)-2-methyl-1-propanol (0.184 g, 100%) as a light yellow oil. $^1$H NMR was identical to that of the racemic alcohol.

Synthesis of (RS)-1-(2-nitrophenyl)-2,2-dimethyl-1-propanol and (R or S)-1-(2-nitrophenyl)-2,2-dimethyl-1-propanol

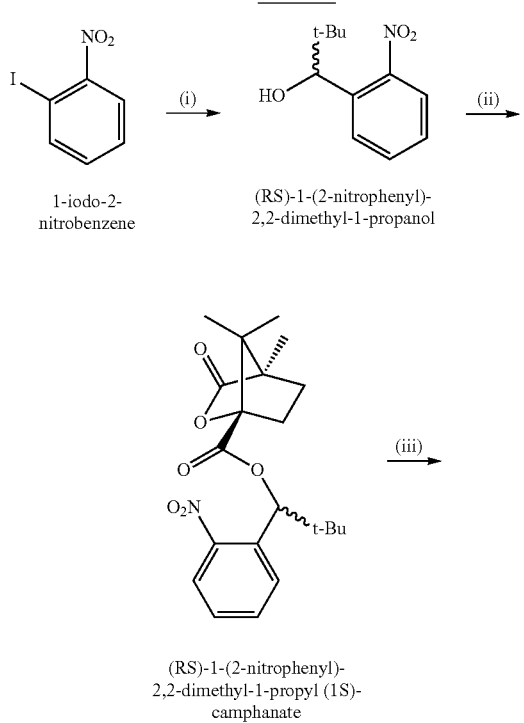

Scheme 5.

1-iodo-2-nitrobenzene (RS)-1-(2-nitrophenyl)-2,2-dimethyl-1-propanol (RS)-1-(2-nitrophenyl)-2,2-dimethyl-1-propyl (1S)-camphanate

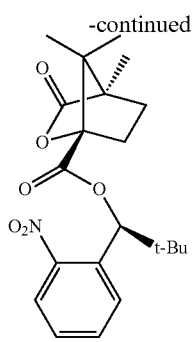

(R or S)-1-(2-nitrophenyl)-2,2-
dimethyl-1-propyl (1S)-
camphanate single diastereomer, absolute
configuration not determined,
drawing is representative

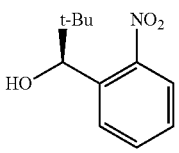

(R or S)-1-(2-nitrophenyl)-
2,2-dimethyl-1-propanol single enantiomer, absolute
configuration not determined,
drawing is representative Synthesis of (RS)-1-(2-nitrophenyl)-2,2-dimethyl-1-propanol
and (R or S)-1-(2-nitrophenyl)-2,2-dimethyl-1-propanol. (i) PhMgCl,
t-BuCHO, THF (anhydrous), minus 40° C. to room temperature, 72%;
(ii) (1S)-camphanic acid chloride, pyridine (anh.), room temperature, 81%;
(iii) recrystallization from methanol; (iv) $K_2CO_3$, MeOH, reflux, 92%.

(RS)-1-(2-Nitrophenyl)-2,2-dimethyl-1-propanol: Under a nitrogen atmosphere, a solution of 1-iodo-2-nitrobenzene (3.0 g, 12 mmol) in anhydrous THF (30 mL) was cooled to minus 40° C., and then phenylmagnesium chloride (2 M in THF, 7.2 mL, 14.5 mmol) was added dropwise at a rate that the temperature would not exceed minus 35° C. After the mixture was stirred for 20 minutes at minus 40° C., trimethylacetaldehyde (1.85 mL, 16.8 mmol) was added dropwise and the mixture was stirred for another 30 minutes at minus 40° C. The mixture was gradually warmed up to room temperature, quenched with saturated ammonium chloride (60 mL), poured into water (60 mL), and extracted with ethyl acetate three times (60 mL each). The combined organic phase was dried over $Na_2SO_4$, and concentrated in vacuo. The residue was purified by silica gel column chromatography to yield (RS)-1-(2-nitrophenyl)-2,2-dimethyl-1-propanol (1.82 g, 72%) as a yellow solid. $^1$H NMR (400 MHz, $CDCl_3$): δ 7.82 (d, 1 H, J=6.4 Hz, Ph-H), 7.76 (d, 1 H, J=6.4 Hz, Ph-H), 7.61 (t, 1 H, J=6.4 Hz, Ph-H), 7.39 (t, 1 H, J=6.4 Hz, Ph-H), 5.39 (d, 1 H, J=2.8 Hz, Ph-CH), 2.14 (d, 1 H, J=3.2 Hz, OH), 0.89 (s, 9 H, $C(CH_3)_3$).

(RS)-1-(2-Nitrophenyl)-2,2-dimethyl-1-propyl (1S)-camphanate: Under a nitrogen atmosphere, (1S)-camphanic acid chloride (3.37 g, 15.6 mmol) was added to a solution of (RS)-1-(2-nitrophenyl)-2,2-dimethyl-1-propanol (2.71 g, 13 mmol) and DMAP (80 mg, 0.65 mmol) in anhydrous pyridine (50 mL). The mixture was stirred for 24 hours at room temperature. Solvent was removed in vacuo, and the residue was dissolved in ethyl acetate (50 mL), washed with 0.5 M HCl (20 mL) twice followed with saturated $NaHCO_3$ solution (20 mL). The organic phase was dried over $Na_2SO_4$, concentrated in vacuo and purified by silica gel column chromatography to yield (RS)-1-(2-nitrophenyl)-2,2-dimethyl-1-propyl (1S)-camphanate (4.11 g, 81%, 1:1 mixture of diastereomers) as a yellow solid. $^1$H NMR (400 MHz, $CDCl_3$) for diastereomers: δ 7.91 (m, 1 H, Ph-H), 7.62 (m, 2 H, Ph-H), 7.46 (m, 1 H, Ph-H), 6.66 and 6.62 (2 s, 1 H, Ph-CH), 2.38 (m, 1 H), 2.10-1.9 (m, 2 H), 1.71 (m, 1 H), 1.13, 1.11, 1.08, 1.04, 1.03, 0.87 (6 s, 9 H, $CH_3\times3$), 0.97 (s, 9 H, $(CH_3)_3C$).

(R or S)-1-(2-Nitrophenyl)-2,2-dimethyl-1-propyl (1S)-amphanate: Pure single diastereomer (R or S)-1-(2-nitrophenyl)-2,2-dimethyl-1-propyl (1S)-camphanate (0.79 g, 35%) was obtained after repeated crystallization of (RS)-1-(2-Nitrophenyl)-2,2-dimethyl-1-propyl (1S)-camphanate (4.57 g) from methanol. The absolute configuration of the single diastereomer camphanate is not determined. $^1$H NMR (400 MHz, $CDCl_3$): δ 7.91 (dd, 1 H, J=0.8 and 8.0 Hz, Ph-H), 7.61 (m, 2 H, Ph-H), 7.46 (m, 1 H, Ph-H), 6.62 (s, 1 H, Ph-CH), 2.35 (m, 1 H), 1.93 (m, 2 H), 1.69 (m, 1 H), 1.13, 1.08 and 1.02 (3 s, 9 H, $CH_3\times3$), 0.96 (s, 9 H, $(CH_3)_3C$).

(R or S)-1-(2-Nitrophenyl)-2,2-dimethyl-1-propanol: A mixture of single diastereomer (R or S)-1-(2-nitrophenyl)-2,2-dimethyl-1-propyl (1S)-camphanate (658 mg, 1.68 mmol) and $K_2CO_3$ (241 mg, 1.74 mmol) in methanol (23 mL) was heated to reflux for 30 minutes. Water (5 mL) was added and the solution was neutralized to pH 7 with 1 M HCl. Solvent was removed in vacuo and the residue was taken into a mixture of ethyl acetate (20 mL) and water (10 mL). The organic phase was separated, dried over anhydrous $Na_2SO_4$, concentrated in vacuo and purified by silica gel column chromatography to yield single enantiomer (R or S)-1-(2-nitrophenyl)-2,2-dimethyl-1-propanol (325 mg, 92%) as a light yellow oil. $^1$H NMR was identical to that of the racemic alcohol. The absolute configuration of the single enantiomer alcohol is not determined.

Synthesis of (RS)-1-(4-Iodo-2-nitrophenyl)-2,2-dimethyl-1-propanol and (R or S)-1-(4-Iodo-2-nitrophenyl)-2,2-dimethyl-1-propanol

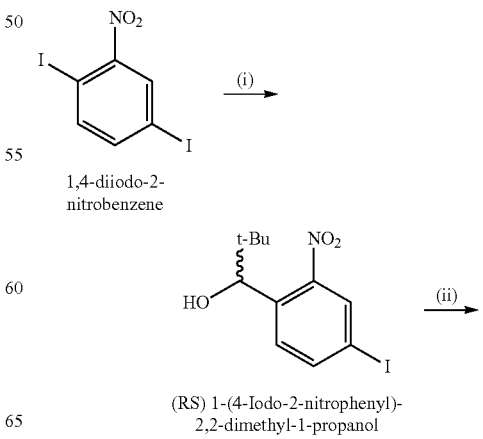

Scheme 6.

1,4-diiodo-2-nitrobenzene (RS) 1-(4-Iodo-2-nitrophenyl)-
2,2-dimethyl-1-propanol

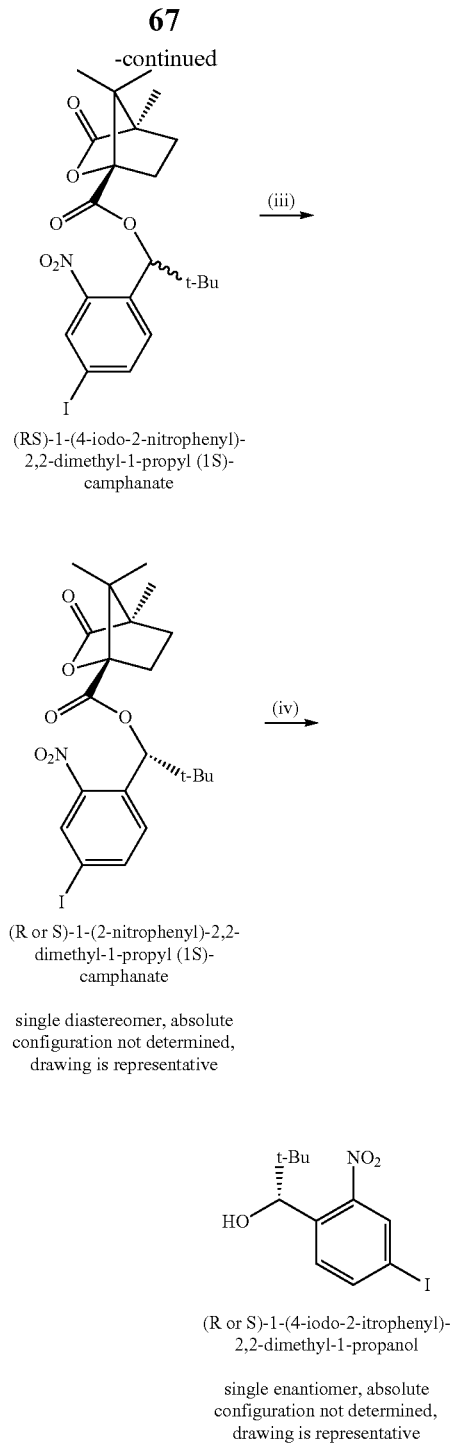

(RS)-1-(4-iodo-2-nitrophenyl)-
2,2-dimethyl-1-propyl (1S)-
camphanate (R or S)-1-(2-nitrophenyl)-2,2-
dimethyl-1-propyl (1S)-
camphanate single diastereomer, absolute
configuration not determined,
drawing is representative (R or S)-1-(4-iodo-2-itrophenyl)-
2,2-dimethyl-1-propanol single enantiomer, absolute
configuration not determined,
drawing is representative Synthesis of (RS)-1-(4-Iodo-2-nitrophenyl)-2,2-dimethyl-1-propanol and (R or S)-1-(4-Iodo-2-nitrophenyl)-2,2-dimethyl-1-propanol. (i) PhMgCl, t-BuCHO, THF (anhydrous), minus 40° C. to room temperature, 81%; (ii) (1S)-camphanic acid chloride, DMAP, CH$_2$Cl$_2$ (anhydrous), room temperature, 88%; (iii) recrystallization from methanol; (iv) K$_2$CO$_3$, MeOH, reflux, 98%.

(RS)-1-(4-Iodo-2-nitrophenyl)-2,2-dimethyl-1-propanol: Under a nitrogen atmosphere a solution of 1,4-diiodo-2-nitrobenzene (3.0 g, 8.0 mmol) in anhydrous THF (20 mL) was cooled to minus 40° C., and then a solution of phenylmagnesium chloride (2 M in THF, 4.8 mL, 9.6 mmol) was added dropwise at a rate that the temperature would not exceed minus 35° C. Upon completion of the addition the mixture was stirred for ten minutes, followed by addition of trimethylacetaldehyde (1.2 mL, 11.2 mmol), and the mixture was stirred for 30 minutes at minus 40° C. The mixture was gradually warmed up to room temperature, quenched with saturated ammonium chloride (60 mL), poured into water (120 mL), and extracted with ethyl acetate twice (60 mL each). The combined organic phase was washed with water (60 mL), dried over Na$_2$SO$_4$, and concentrated in vacuo. The residue was purified by silica gel column chromatography to yield racemic (RS)-1-(4-iodo-2-nitrophenyl)-2,2-dimethyl-1-propanol (2.17 g, 81%) as a brown oil. $^1$H NMR (400 MHz, CDCl$_3$): δ 8.04 (d, 1 H, J=1.6 Hz, Ph-H), 7.88 (dd, 1 H, J=1.6 and 8.4 Hz, Ph-H), 7.51 (d, 1 H, J=8.4 Hz, Ph-H), 5.28 (d, 1 H, J=3.6 Hz, Ph-CH), 2.29 (d, 1 H, J=3.6 Hz, OH), 0.85 (s, 9 H, C(CH$_3$)$_3$). $^{13}$C NMR (100 MHz, CDCl$_3$): δ 149.87 (C), 141.0 (CH), 136.2 (C), 132.3 (CH), 131.63 (CH), 91.85 (C), 74.33 (CH), 36.81 (C), 25.6 (CH$_3$).

(RS)-1-(4-Iodo-2-nitrophenyl)-2,2-dimethyl-1-propyl (1S)-camphanates: Under a nitrogen atmosphere, (1S)-camphanic acid chloride (1.68 g, 7.77 mmol) was added to a solution of (RS)-1-(4-iodo-2-nitrophenyl)-2,2-dimethyl-1-propanol (2.17 g, 6.47 mmol) and DMAP (1.18 g, 9.7 mmol) in anhydrous dichloromethane (50 mL). The mixture was stirred overnight at room temperature and then washed with saturated NaHCO$_3$ solution (60 mL) and water (60 mL). The organic phase was dried over Na$_2$SO$_4$, concentrated in vacuo and purified by silica gel column chromatography to yield (RS)-1-(4-iodo-2-nitrophenyl)-2,2-dimethyl-1-propyl (1S)-camphanate (2.94 g, 88%, 1:1 mixture of diastereomers) as a white solid. $^1$H NMR (400 MHz, CDCl$_3$) for diastereomers: δ 8.23 (m, 1 H, Ph-H), 7.90 (m, 1 H, Ph-H), 7.31 (m, 1 H, Ph-H), 6.56 and 6.51 (2 s, 1 H, Ph-CH), 2.38 (m, 1 H), 2.07-1.9 (m, 2 H), 1.69 (m, 1 H), 1.13, 1.11, 1.07, 1.04, 1.02, 0.87 (6 s, 9 H, CH$_3$×3), 0.96 (s, 9 H, (CH$_3$)$_3$C).

(R or S)-1-(4-Iodo-2-nitrophenyl)-2,2-dimethyl-1-propyl (1S)-camphanate: (RS)-1-(4-Iodo-2-nitrophenyl)-2,2-dimethyl-1-propyl (1S)-camphanate (2.07 g) was dissolved in boiling methanol (100 mL) and left at room temperature for two days. Crystals formed were filtered to yield pure single diastereomer (R or S)-1-(4-iodo-2-nitrophenyl)-2-methyl-1-propyl (1S)-camphanate (0.409 g, 39%). The absolute configuration of the single diastereomer camphanate is not determined. $^1$H NMR (400 MHz, CDCl$_3$): δ 8.23 (d, 1 H, J=2.0 Hz, Ph-H), 7.89 (dd, 2 H, J=2.0 and 8.4 Hz, Ph-H), 7.30 (d, 1 H, J=8.4 Hz, Ph-H), 6.56 (s, 1 H, Ph-CH), 2.42 (m, 1 H), 2.07 (m, 1 H), 1.94 (m, 1 H), 1.73 (m, 1 H), 1.11, 1.04 and 0.87 (3 s, 9 H, CH$_3$ 3), 0.95 (s, 9 H, (CH$_3$)$_3$C).

(R or S)-1-(4-Iodo-2-nitrophenyl)-2,2-dimethyl-1-propanol: A mixture of single diastereomer (R or S)-1-(4-iodo-2-nitrophenyl)-2,2-dimethyl-1-propyl (1S)-camphanate (409 mg, 0.79 mmol) and K$_2$CO$_3$ (110 mg, 0.8 mmol) in methanol (15 mL) was heated to reflux for 30 minutes. Water (5 mL) was added and the solution was neutralized to pH 7 with 1 M HCl. Solvent was removed in vacuo and the residue was taken into a mixture of ethyl acetate (30 mL) and water (10 mL). The organic phase was separated, dried over anhydrous Na$_2$SO$_4$, concentrated in vacuo, and purified by silica gel column chromatography to yield single enantiomer (R or S)-1-(4-iodo-2-nitrophenyl)-2,2-dimethyl-1-propanol (260 mg, 98%) as a light yellow oil. $^1$H NMR was identical to that of the racemic alcohol. The absolute configuration of the single enantiomer alcohol is not determined.

Synthesis of (±)-1-(2,6-dinitrophenyl)-2-methyl-1-propanol

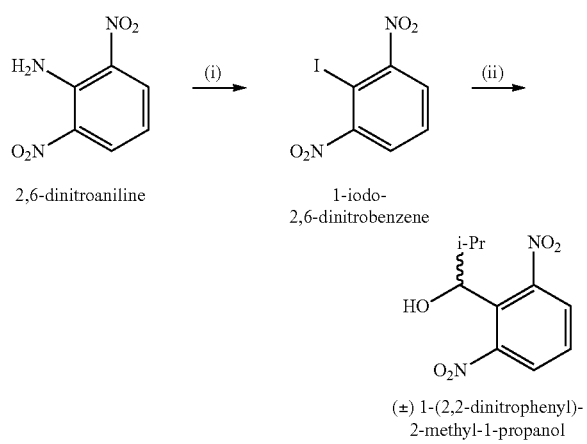

Scheme 7.

2,6-dinitroaniline 1-iodo-2,6-dinitrobenzene (±) 1-(2,2-dinitrophenyl)-2-methyl-1-propanol Synthesis of racemic 1-(2,6-dinitrophenyl)-2-methyl-1-propanol. (i) Isoamyl nitrite, diiodomethane, 105° C., 52%; (ii) PhMgBr, anhydrous THF, minus 45° C.; then i-PrCHO, work up, 30%.

1-Iodo-2,2-dinitrobenzene: To a dispersion of 2,6-dinitroaniline (4.00 g, 0.021 mol) in diiodomethane (24 mL, 0.297 mol) isoamylnitrite (15 mL, 0.112 mol) was added (Smith et al., 1990, which is incorporated herein by reference). The mixture was stirred at room temperature for one hour, and then heated at 105° C. for eight hours. The excess of diiodomethane was removed in high vacuo. The residue was diluted with acetyl acetate (10 mL). Silica (ca 30 mL, mesh 230-400 Å) was added; the mixture was concentrated in vacuo and purified by column chromatography to yield 1-iodo-2,6-dinitrobenzene (3.21 g, 52%). $^1$H NMR (400 MHz, CDCl$_3$): δ 7.84 (d, 2 H, J=8.0 Hz), 7.67 (t, 1 H, J=8.0 Hz).

(±)-1-(2,2-dinitrophenyl)-2-methyl-1-propanol: To a solution of 1-iodo-2,6-dinitrobenzene (1.55 g, 5.27 mmol) in anhydrous tetrahydrofuran (18 mL) cooled at minus 53° C. (dry ice-isopropanol bath) under nitrogen atmosphere, phenylmagnesium bromide (2 M in THF, 3.16 mL, 6.32 mmol) was added at a rate to keep the temperature at or below minus 45° C. Upon completion of the addition the mixture was stirred for five minutes, then isobutyraldehyde (0.957 mL, 10.54 mmol) was added. The mixture was allowed to gradually warm up to room temperature, then quenched with saturated NH$_4$Cl (5 mL) and poured into water (50 mL)/dichloromethane (100 mL). The organic layer was separated; aqueous layer was extracted three times with dichloromethane (50 mL each). Combined organic extract was washed with water (20 mL), dried over anhydrous Na$_2$SO$_4$, concentrated under reduced pressure, and purified by silica gel column chromatography to yield racemic (RS)-1-(2,6-dinitrophenyl)-2-methyl-1-propanol (0.375 g, 30%) as a light yellow oil. $^1$H NMR (400 MHz, CDCl$_3$): δ 7.82 (d, 2 H, J=8.0 Hz, Ph-H), 7.59 (t, 1 H, J=8.0 Hz, Ph-H), 4.84 (dd, 1 H, J=7.6 and 9.2 Hz, Ph-CH), 2.87 (d, 1 H, J=7.6 Hz, OH), 2.18 (m, 1 H, CHCH(CH$_3$)$_2$), 1.12 (d, 3 H, J=6.4 Hz, CH$_3$), 0.77 (d, 3 H, J=6.8 Hz, CH$_3$); $^{13}$C NMR (100 MHz, CDCl$_3$): δ 150.82 (C), 130.62 (C), 129.31 (CH), 127.30 (CH), 74.52 (CH), 34.19 (CH), 19.84 (CH$_3$), 19.14 (CH$_3$).

Synthesis of (±)-1-(4-methoxy-2-nitrophenyl)-2-methyl-1-propanol

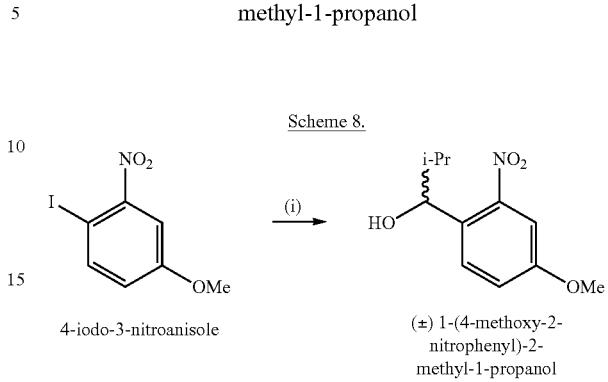

Scheme 8.

4-iodo-3-nitroanisole (±) 1-(4-methoxy-2-nitrophenyl)-2-methyl-1-propanol

Synthesis of 1-(4-methoxy-2-nitrophenyl)-2-methyl-1-propanol. (i) PhMgCl, anhydrous THF, minus 40° C.; then i-PrCHO, work up, 67%.

(±)-1-(4-Methoxy-2-nitrophenyl)-2-methyl-1-propanol: To a solution of 4-iodo-2-nitroanisole (2.79 g, 10.00 mmol) in anhydrous tetrahydrofuran (20 mL) cooled at minus 45° C. (dry ice-isopropanol bath) under nitrogen atmosphere, phenylmagnesium chloride (2 M in THF, 6 mL, 6.32 mmol) was added at a rate to keep the temperature at or below minus 40° C. Upon completion of the addition the mixture was stirred for five minutes, then isobutyraldehyde (1.816 mL, 20.00 mmol) was added. The mixture was allowed to gradually warm up to room temperature, then quenched with saturated NH$_4$Cl (5 mL) and poured into water (30 mL)/dichloromethane (100 mL). The organic layer was separated; aqueous layer was extracted three times with dichloromethane (50 mL each). Combined organic extract was dried over anhydrous Na$_2$SO$_4$, concentrated under reduced pressure, and purified by silica gel column chromatography to yield racemic (RS)-1-(4-methoxy-2-nitrophenyl)-2-methyl-1-propanol (1.502 g, 30%) as a yellow oil. $^1$H NMR (400 MHz, CDCl$_3$): δ 7.62 (AB d, 1 H, J=8.8 Hz, Ph-H), 7.34 (d, 1 H, J=2.6 Hz, Ph-H), 7.15 (dd, 1 H, J=2.6 and 8.8 Hz, Ph-H), 4.91 (m, 1 H, Ph-CH), 3.86 (s, 3H, MeO), 2.45 (br s, 1 H, OH), 2.00 (m, 1 H, CHCH(CH$_3$)$_2$), 0.97 (d, 3 H, J=6.7 Hz, CH$_3$), 0.86 (d, 3 H, J=6.9 Hz, CH$_3$); $^{13}$C NMR (100 MHz, CDCl$_3$): δ 158.76 (C), 149.07 (C), 130.79 (C), 129.88 (CH), 119.62 (CH), 108.66 (CH), 73.75 (CH), 55.81 (CH$_3$), 34.27 (CH), 19.59 (CH$_3$), 17.36 (CH$_3$).

Synthesis (±)-1-(5-cyano-2-nitrophenyl)-2-methyl-1-propanol

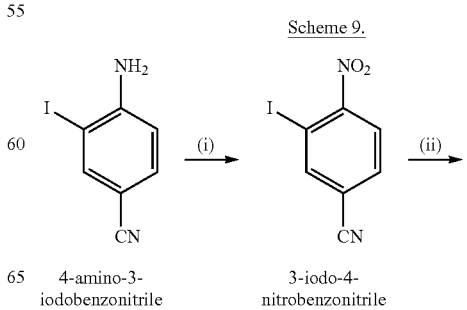

Scheme 9.

4-amino-3-iodobenzonitrile 3-iodo-4-nitrobenzonitrile

71
-continued

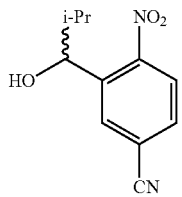

(±) 1-(5-cyano-2-nitrophenyl)-
2-methyl-1-propanol

Synthesis of racemic 1-(5-cyano-2-nitrophenyl)-2-methyl-1-propanol. (i) NaNO$_2$/H$_2$SO$_4$, 0° C., 1 hour, then NaNO$_2$/CuSO$_4$, 100° C., 35%; (ii) PhMgCl, anhydrous THF, minus 40° C.; then i-PrCHO, work up, 30%.

3-iodo-4-nitrobenzonitrile: To a suspension of 4-amino-3-iodobenzene (2.44 g, 10.00 mmol) in aqueous sulfuric acid (2 M, 50 mL) chilled to 0° C. (ice-water-NaCl bath) a solution of sodium nitrite (1.656 g, 24.00 mol) in water (6 mL) was added at such rate that the temperature of the reaction mixture did not exceed 0° C. Upon completion of the addition the mixture was stirred for one hour (or until cleared), then it was transferred in portions to a hot solution of sodium nitrite (13.8 g, 200 mmol) and CuSO$_4$.5H$_2$O (0.12 g, 0.05 mmol). (CAUTION: vigorous gas evolution!) Upon completion of transfer, the mixture was stirred at reflux for 30 minutes, then cooled down to room temperature, and extracted three times with dichloromethane (100 mL each). Combined extracts were dried over Na$_2$SO$_4$, concentrated under reduced pressure, mixed with silica (ca 30 mL, mesh 230-400 Å), and purified by column chromatography to yield 3-iodo-4-nitrobenzonitrile (0.95 g, 35%). $^1$H NMR (400 MHz, CDCl$_3$): δ 8.10 (d, 1 H, J=1.9 Hz), 7.99 (d, 1 H, J=8.2 Hz), 7.29 (dd, 1 H, 8.2 and 1.9 Hz, 1 H); $^{13}$C NMR (100 MHz, CDCl$_3$): δ 141.76 (CH), 139.93 (CH), 131.66 (CH), 116.65 (C), 114.78 (CN), 113.15 (C), 108.62 (C).

(±)-1-(5-cyano-2-nitrophenyl)-2-methyl-1-propanol: To a solution of 3-iodo-4-nitrobenzonitrile (314 mg, 1.14 mmol) in anhydrous tetrahydrofuran (5.5 mL) cooled at minus 45° C. (dry ice-isopropanol bath) under nitrogen atmosphere, phenylmagnesium bromide (2 M in THF, 3.16 mL, 6.32 mmol) was added at a rate to keep the temperature at or below minus 40° C. Upon completion of the addition the mixture was stirred for five minutes, then isobutyraldehyde (0.957 mL, 10.54 mmol) was added. The mixture was allowed to gradually warm up to room temperature, then quenched with saturated NH$_4$Cl (2 mL) and poured into water (50 mL)/dichloromethane (50 mL). The organic layer was separated; aqueous layer was extracted three times with dichloromethane (25 mL each). Combined organic extract was dried over anhydrous Na$_2$SO$_4$, concentrated under reduced pressure, and purified by silica gel column chromatography to yield racemic (RS)-1-(5-cyano-2-nitrophenyl)-2-methyl-1-propanol (57 mg, 23%) as a light yellow oil. $^1$H NMR (400 MHz, CDCl$_3$): δ 7.93 (d, 1 H, J=8.1 Hz, Ph-H), 7.74 (s, 1 H, Ph-H), 7.21 (d, 1 H, J=8.1 Hz, Ph-H), 4.72 (d, 1 H, J=3.6 Hz, Ph-CH), 2.33 (br. s, 1 H, OH), 2.03 (m, 1 H, CHC$\underline{H}$(CH$_3$)$_2$), 1.04 (d, 3 H, J=6.8 Hz, CH$_3$), 0.89 (d, 3 H, J=6.6 Hz, CH$_3$); $^{13}$C NMR (100 MHz, CDCl$_3$): δ 147.78 (C), 140.25 (CH), 131.40 (CH), 131.24 (CH), 118.36 (C), 112.27 (CN), 103.82 (C), 80.80 (CH), 33.56 (CH), 19.70 (CH$_3$), 15.62 (CH$_3$).

72
Example 3

Synthesis of Deoxyuridine and Deoxycytidine Analogs with α-Isopropyl Groups

Synthesis 5-[(S)-1-(2-nitrophenyl)-2-methyl-propyloxy]methyl-2'-deoxyuridine-5'-triphosphate Scheme 10.

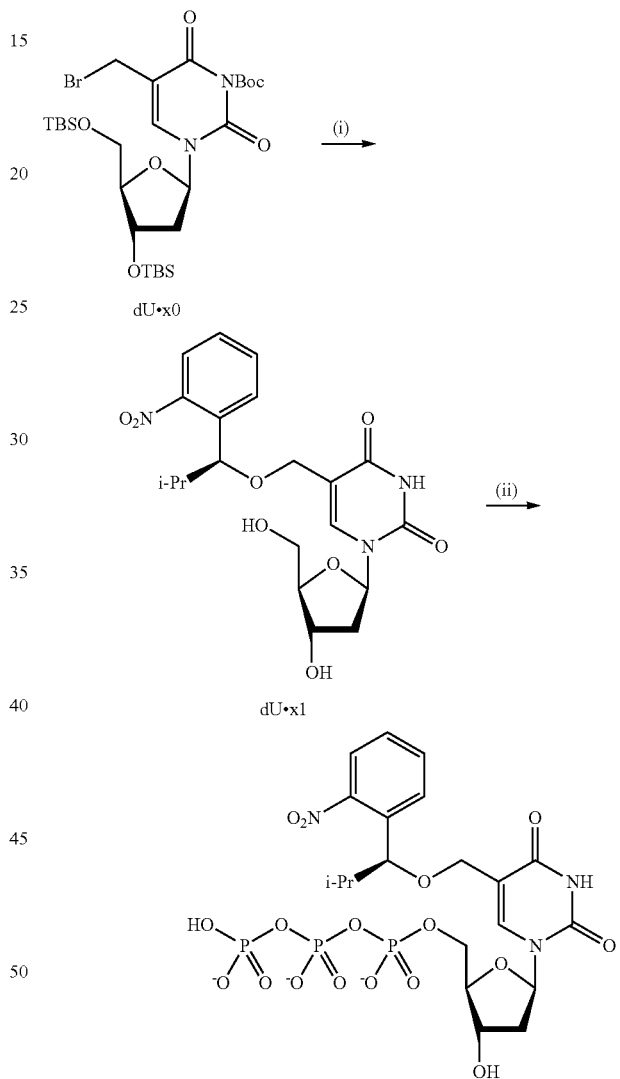

Synthesis of 5-[(S)-1-(2-nitrophenyl)-2-methyl-propyloxy]methyl-2'-deoxyuridine-5'-triphosphate. (i) (S)-1-(2-nitrophenyl)-2-methyl-propanol, neat, 108-112° C., 4%; (ii) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

5-[(S)-1-(2-Nitrophenyl)-2-methyl-propyloxy]methyl-2'-deoxyuridine (dU.x1): Compound dU.x0 (250 mg, 0.385 mmol) and (S)-1-(2-nitrophenyl)-2-methyl-propanol (300 mg, 1.54 mmol) were heated neat at 105-110° C. for 30 minutes under a nitrogen atmosphere. The mixture was cooled down to room temperature, dissolved in minimum amount of ethyl acetate, and purified by silica gel chromatography to yield 5-[(S)-1-(2-nitrophenyl)-2-methyl-propyloxy]methyl-2'-deoxyuridine dU.x1 (6 mg, 4%). (3' or 5)-O-(tert-butyldimethylsilyl)-5-[(S)-1-(2-nitrophenyl)-2-methyl-propyloxy]methyl-2'-deoxyuridine (39 mg, 18%) and 3',5'-O-bis-(tert-butyldimethylsilyl)-5-[(S)-1-(2-nitrophenyl)-2-methyl-propyloxy]methyl-2'-deoxyuridine (36 mg, 14%) were also obtained from the reaction. $^1$H NMR (100 MHz, CD$_3$OD) for dU.x1: δ 7.96 (s, 1 H, H-6), 7.88 (d, 1 H, J=8.3 Hz, Ph-H), 7.74 (dd, 1 H, J=1.5 and 7.6 Hz, Ph-H), 7.68 (m, 1 H, Ph-H), 7.49 (m, 1 H, Ph-H), 6.25 (dd, 1 H, J=6.4 and 7.8 Hz, H-1'), 4.77 (d, 1 H, J=6.0 Hz, Ph-CH), 4.39 (m, 1 H, H-3'), 4.17 (AB d, 1 H, J=12.3 Hz, 5-CH$_2$a), 4.07 (AB d, 1 H, J=12.3 Hz, 5-CH$_2$b), 3.92 (m, 1 H, H-4'), 3.77 (AB dd, 1 H, J=3.4 and 12.1 Hz, H-5'a), 3.71 (AB dd, 1 H, J=3.8 and 12.1 Hz, H-5'b), 2.24 (m, 2 H, H-2'), 1.95 (m, 1 H, CH), 0.94 (d, 3 H, J=6.7 Hz, CH$_3$), 0.85 (d, 3 H, J=6.9 Hz, CH$_3$).

5-[(S)-1-(2-Nitrophenyl)-2-methyl-propyloxy]methyl-2'-deoxyuridine-5'-triphosphate (WW3p063): POCl$_3$ (4 μL, 0.045 mmol) was added to a solution of compound dU.x1 (14 mg, 0.03 mmol) and proton sponge (13 mg, 0.06 mmol) in trimethylphosphate (0.3 mL) at 0° C. and stirred for one hour. Additional POCl$_3$ (4 μL, 0.045 mmol) was added and the mixture was stirred for another three hours. A solution of tri-n-butylammonium pyrophosphate (72 mg, 0.15 mmol) and tri-n-butylamine (30 μL) in anhydrous DMF (0.3 mL) was added. After five minutes of stirring, triethylammonium bicarbonate buffer (1 M, pH 7.5; 5 mL) was added. The reaction was stirred at room temperature for one hour and then lyophilized to dryness. The residue was dissolved in water (5 mL), filtered, and purified by anion exchange chromatography on a Q Sepharose FF column (2.5×20 cm) with a linear gradient of NH$_4$HCO$_3$ (50 mM to 500 mM in 240 minutes) at a flow rate of 4.5 mL/min. The fractions containing triphosphate were combined and lyophilized to give 5-[(S)-1-(2-nitrophenyl)-2-methyl-propyloxy]methyl-2'-deoxyuridine-5'-triphosphate WW3p063 (10 mg, 46%) as a white fluffy solid. $^1$H NMR (400 MHz, D$_2$O): δ 7.88 (dd, 1 H, J=1.2 and 6.4 Hz, Ph-H), 7.66 (m, 1 H, Ph-H), 7.58 (dd, 1 H, J=1.2 and 6.4 Hz, Ph-H), 7.56 (s, 1 H, H-6), 7.46 (dt, 1 H, J=1.2 and 6.4 Hz, Ph-H), 6.09 (t, 1 H, J=5.6 Hz, H-1'), 4.46 (m, 1 H, H-3'), 4.39 (AB d, 1 H, J=10 Hz, 5-CH$_2$a), 4.23 (AB d, 1 H, J=10 Hz, 5-CH$_2$b), 4.20-4.12 (m, 3 H, H-4' and H-5'), 2.29 (m, 1 H, H-2'a), 2.2 (m, 1 H, H-2'b), 1.94 (m, 1 H, CH), 0.97 (d, 3 H, J=5.6 Hz, CH$_3$), 0.74 (d, 3 H, J=5.6 Hz, CH$_3$). $^{31}$P NMR (162 MHz, D$_2$O): δ −5.06 (d, J=16.2 Hz), −10.55 (d, J=16.2 Hz), −20.9 (t, J=16.2 Hz).

Synthesis 5-[(S)-1-(2-nitrophenyl)-2-methyl-propyloxy]methyl-2'-deoxycytidine-5'-triphosphate Scheme 11. Synthesis of 5-[(S)-1-(2-nitrophenyl)-2-methyl-propyloxy]methyl-2'-deoxycytidine-5'-triphosphate.

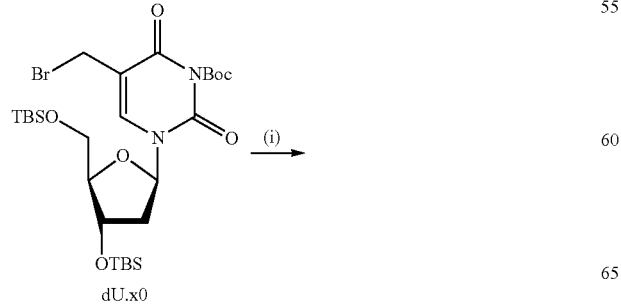
dU.x0

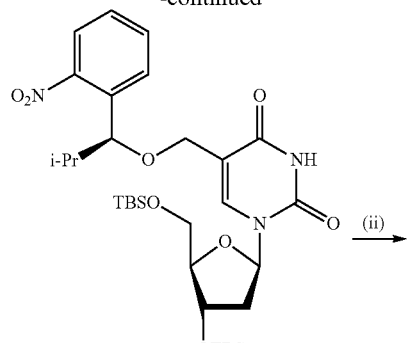
dU.x2

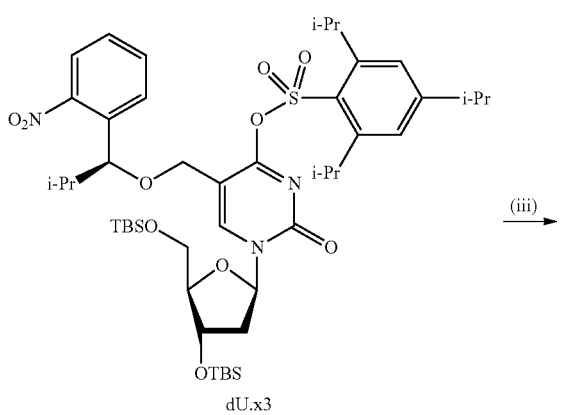
dU.x3

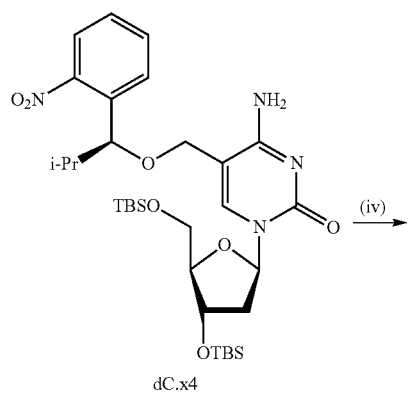
dC.x4

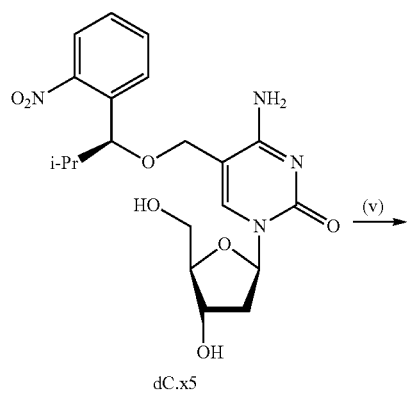
dC.x5

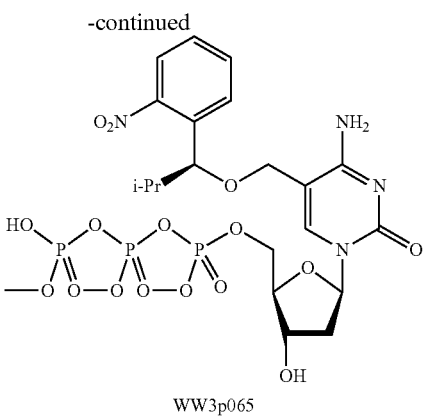

WW3p065

(i) (S)-1-(2-nitrophenyl)-2-methyl-propanol, neat, 108-112° C., 14%;
(ii) 2,4,6-triisopropylbenzenesulfonyl chloride, DAMP, Et₃N, CH₂Cl₂ (anhydrous), room temperature, 42%;
(iii) NH₃ (0.5 M in 1,4-dioxane), 85-90° C., 61%;
(iv) n-Bu₄NF, THF, room temperature, 96%;
(v) POCl₃, proton sponge, (MeO)₃PO, 0° C.; (n-Bu₃NH)₂H₂P₂O₇, n-Bu₃N, DMF; 1 M HNEt₃HCO₃

3',5'-O-Bis-(tert-butyldimethylsilyl)-5-[(S)-1-(2-nitrophenyl)-2-methyl-propyloxy]methyl-2'-deoxyuridine (dU.x2): Compound dU.x0 (250 mg, 0.385 mmol) and (S)-1-(2-nitrophenyl)-2-methyl-propanol (300 mg, 1.54 mmol) were heated neat at 105-110° C. for 30 minutes under a nitrogen atmosphere. The mixture was cooled down to room temperature, dissolved in minimum amount of ethyl acetate, and purified by silica gel chromatography to yield 3',5'-O-bis-(tert-butyldimethylsilyl)-5-[(S)-1-(2-nitrophenyl)-2-methyl-propyloxy]methyl-2'-deoxyuridine dU.x2 (36 mg, 14%). (3' or 5')—O-(tert-butyldimethylsilyl)-5-[(S)-1-(2-nitrophenyl)-2-methyl-propyloxy]methyl-2'-deoxyuridine (39 mg, 18%) and 5-[(S)-1-(2-nitrophenyl)-2-methyl-propyloxy]methyl-2'-deoxyuridine (6 mg, 4%) were also obtained from the reaction. $^1$H NMR (400 MHz, CDCl₃) for dU.x2: δ 8.76 (s, 1 H, NH), 7.84 (dd, 1 H, J=1.1 and 8.1 Hz, Ph-H), 7.73 (dd, 1 H, J=1.3 and 7.9 Hz, Ph-H), 7.66 (m, 1 H, Ph-H), 7.59 (s, 1 H, H-6), 7.42 (m, 1 H, Ph-H), 6.29 (dd, 1 H, J=5.9 and 7.8 Hz, H-1'), 4.78 (d, 1 H, J=6.2 Hz, Ph-CH), 4.42 (m, 1 H, H-3'), 4.18 (AB d, 1 H, J=12.0 Hz, 5-CH₂a), 4.04 (AB d, 1 H, J=12.0 Hz, 5-CH₂b), 3.94 (m, 1 H, H-4'), 3.77 (m, 2 H, H-5'), 2.30 (m, 1 H, H-2'a), 2.05 (m, 1 H, H-2'b), 1.96 (m, 1 H, CH), 0.92 (d, 3 H, J=6.7 Hz, CH₃), 0.90 (s, 9 H, (CH₃)₃CSi), 0.89 (s, 9 H, (CH₃)₃CSi), 0.84 (d, 3 H, J=6.9 Hz, CH₃), 0.10 (s, 3 H, CH₃Si), 0.09 (s, 3 H, CH₃Si), 0.08 (s, 3 H, CH₃Si), 0.07 (s, 3 H, CH₃Si); $^{13}$C NMR (100 MHz, CDCl₃) for dU.x2: δ 162.39 (C), 150.01 (C), 149.47 (C), 138.33 (CH), 136.78 (C), 132.88 (CH), 129.24 (CH), 124.08 (CH), 111.48 (C), 87.84 (CH), 85.16 (CH), 81.33 (CH), 72.35 (CH), 64.50 (CH₂), 63.09 (CH₂), 40.95 (CH₂), 34.91 (CH), 25.94 (C(CH₃)₃), 25.76 (C(CH₃)₃), 19.28 (CH₃), 18.41 (C), 18.02 (C), 17.90 (CH₃), −4.66 (CH₃), −4.82 (CH₃), −5.32 (CH₃), −5.41 (CH₃).

3',5'-O-Bis-(tert-butyldimethylsilyl)-5-[(S)-1-(2-nitrophenyl)-2-methyl-propyloxy]methyl-O⁴-(2,4,6-triisopropylbenzenesulfonyl)-2'-deoxyuridine (dU.x3): To a solution of compound dU.x2 (90 mg, 0.136 mmol), DMAP (17 mg, 0.140 mmol), and triethylamine (0.172 mL, 1.224 mmol) in anhydrous dichloromethane (6 mL) 2,4,6-triisopropylbenzenesulfonyl chloride (1.57 g, 5.19 mmol) was added. The mixture was stirred at room temperature for 17 hours under nitrogen atmosphere, then concentrated in vacuo and purified by column chromatography to afford 3',5'-O-bis-(tert-butyldimethylsilyl)-5-[(S)-1-(2-nitrophenyl)-2-methyl-propy-loxy]methyl-4-O-(2,4,6-triisopropylbenzenesulfonyl)-2'-deoxyuridine dU.x3 (54 mg, 42%). $^1$H NMR (400 MHz, CDCl₃): δ 8.07 (s, 1 H, H-6), 7.86 (m, 1 H, Ph-H), 7.71 (m, 1 H, Ph-H), 7.46 (m, 1 H, Ph-H), 7.16 (s, 2 H, Ph-H), 6.09 (t, 1 H, J=6.4 Hz, H-1'), 4.79 (d, 1 H, J=6.2 Hz, Ph-CH), 4.34 (m, 1 H, H-3'), 4.12 (m, 4 H), 3.97 (m, 1 H, H-4'), 3.80 (AB dd, 1 H, J=3.4 and 11.2 Hz, H-5'a), 3.80 (AB dd, 1 H, J=3.6 and 11.2 Hz, H-5'b), 2.89 (m, 1 H, CH), 2.51 (m, 1 H, H-2'a), 1.96 (m, 2 H), 1.29 and 1.21 (d, 12 H, J=6.7 Hz, CH₃×4), 1.25 (d, 6 H, J=7.0 Hz, CH₃×2), 0.99 (d, 3 H, J=6.7 Hz, CH₃), 0.87 (2 s, 18 H, (CH₃)₃CSi), 0.84 (d, 3 H, J=6.9 Hz, CH₃), 0.07 (s, 6 H, (CH₃)₂Si), 0.06 (s, 6 H, (CH₃)₂Si).

3',5'-O-Bis-(tert-butyldimethylsilyl)-5-[(S)-1-(2-nitrophenyl)-2-methyl-propoxy]methyl-2'-deoxcytidine (dC.x4): To a solution of compound dU.x3 (47 mg, 0.051 mmol) in anhydrous 1,4-dioxane (3 mL) a solution of ammonia (3 mL, 0.5 M in dioxane, 1.50 mmol) was added. The mixture was transferred into a sealed tube and heated at 85-90° C. for 1.5 hours. The mixture was cooled down to room temperature, concentrated in vacuo and purified by silica gel column chromatography to yield 3',5'-O-bis-(tert-butyldimethylsilyl)-5-[(S)-1-(2-nitrophenyl)-2-methyl-propoxy]methyl-2'-deoxcytidine dC.x4 (20 mg, 61%) as a waxy solid. $^1$H NMR (400 MHz, CDCl₃) δ 7.81 (d, 1 H, J=8.1 Hz, Ph-H), 7.66 (m, 2 H, Ph-H), 7.51 (s, 1 H, H-6), 7.45 (m, 1 H, Ph-H), 6.64 and 5.81 (2 br. s, 2 H, NH₂), 6.28 (t, 1 H, J=6.5 Hz, H-1'), 4.70 (d, 1 H, J=6.8 Hz, Ph-CH), 4.32 (m, 1 H, H-3'), 4.20 (AB d, 1 H, J=12.6 Hz, 5-CH₂a), 4.07 (AB d, 1 H, J=12.6 Hz, 5-CH₂b), 3.89 (m, 1 H, H-4'), 3.77 (AB dd, 1H, J=3.5 and 11.2 Hz, H-5'a), 3.69 (AB dd, 1 H, J=3.4 and 11.2 Hz, H-5'b), 2.42 (m, 1 H, H-2'a), 1.99 (m, 2 H, H-2'b and CH), 0.98 (d, 3 H, J=6.6 Hz, CH₃), 0.88 (s, 9 H, (CH₃)₃CSi), 0.80 (s, 9 H, (CH₃)₃CSi), 0.78 (d, 3 H, J=7.0 Hz, CH₃), 0.07 (s, 3 H, CH₃Si), 0.06 (s, 3 H, CH₃Si), −0.01 (s, 3 H, CH₃Si), −0.04 (s, 3 H, CH₃Si).

5-[(S)-1-(2-nitrophenyl)-2-methyl-propyloxy]methyl-2'-deoxcytidine (dC.x5): To a solution of compound dC.x4 (16 mg, 0.024 mmol) in THF (1 mL) a solution of tetra-n-butylammonium fluoride trihydrate (31 mg, 0.096 mmol) in THF (2 mL) was added. The mixture was stirred at room temperature for 30 minutes, concentrated in vacuo and purified by silica gel column chromatography to give 5-[(S)-1-(2-nitrophenyl)-2-methyl-propyloxy]methyl-2'-deoxycytidine dC.x5 (10 mg, 96%) as a waxy solid. $^1$H NMR (400 MHz, DMSO-d₆) δ 7.95 (m, 1 H, Ph-H), 7.76 (m, 1 H, Ph-H), 7.64 (m, 1 H, Ph-H), 7.63 (s, 1 H, H-6), 7.56 (d, 1 H, J=8.3 Hz, Ph-H), 7.39 and 6.66 (2 br. s, 2 H, D₂O exchangeable, NH₂), 6.13 (m, 1 H, H-1'), 5.20 (d, 1 H, J=4.1 Hz, D₂O exchangeable, 3'-OH), 4.85 (t, 1 H, J=5.4 Hz, D₂O exchangeable, 5'-OH), 4.67 (d, 1 H, J=6.0 Hz, Ph-CH), 4.17 (m, 1 H, H-3'), 4.10 (AB d, 1 H, J=12.2 Hz, 5-CH₂a), 3.99 (AB d, 1 H, J=12.2 Hz, 5-CH₂b), 3.74 (m, 1 H, H-4'), 3.49 (m, 2 H, H-5'), 2.08 (m, 1 H, H-2'a), 1.91 (m, 2 H, H-2'b and CH), 0.88 (d, 3 H, J=6.7 Hz, CH₃), 0.77 (d, 3 H, J=6.9 Hz, CH₃); $^{13}$C NMR (100 MHz, CD₃OD): δ 166.57 (C), 158.14 (C), 151.46 (C), 142.74 (CH), 137.30 (C), 134.29 (CH), 130.28 (CH), 129.91 (CH), 125.32 (CH), 104.64 (C), 89.00 (CH), 87.57 (CH), 81.04 (CH), 72.13 (CH), 66.42 (CH₂), 62.87 (CH₂), 42.22 (CH₂), 36.30 (CH), 19.64 (CH₃), 18.56 (CH₃).

5-[(S)-1-(2-nitrophenyl)-2-methyl-propyloxy]methyl-2'-deoxycytidine-5'-phosphate (WW3p065) POCl₃ (3 μL, 0.034 mmol) was added to a solution of compound dU.x5 (10 mg, 0.023 mmol) and proton sponge (10 mg, 0.046 mmol) in trimethylphosphate (0.3 mL) at 0° C. and stirred for two hour. Additional POCl₃ (3 μL, 0.034 mmol) was added and the mixture was stirred for another one hour. A solution of tri-n-butylammonium pyrophosphate (55 mg, 0.115 mmol) and tri-n-butylamine (30 μL) in anhydrous DMF (0.25 mL) was added. After five minutes of stirring, triethylammonium bicarbonate buffer (1 M, pH 7.5; 5 mL) was added. The reaction was stirred at room temperature for one hour and then lyophilized to dryness. The residue was dissolved in water (5 mL), filtered, and purified by anion exchange chromatography on a Q Sepharose FF column (2.5×20 cm) with a linear gradient of $NH_4HCO_3$ (50 mM to 500 mM in 240 minutes) at a flow rate of 4.5 mL/min. The fractions containing triphosphate were combined and lyophilized to give 5-[(S)-1-(2-nitrophenyl)-2-methyl-propyloxy]methyl-2'-deoxycytidine-5'-triphosphate WW3p065 (16 mg, 96%) as a white fluffy solid. $^1$H NMR (400 MHz, $D_2O$): δ 7.85 (dd, 1 H, J=1.2 and 8.4 Hz, Ph-H), 7.65 (m, 3 H, Ph-H and H6), 7.49 (dt, 1 H, J=1.6 and 8.4 Hz, Ph-H), 6.05 (t, J=6.4 Hz, 1 H, H-1'), 4.54 (AB d, 1 H, J=13.6 Hz, 5-$CH_2$a), 4.46 (m, 1 H, H-3'), 4.44 (AB d, 1 H, J=13.6 Hz, 5-$CH_2$b), 4.18 (m, 3 H, H-4' and H-5'), 2.39 (m, 1 H, H-2'a), 2.2 (m, 1 H, H-2'b), 2.01 (m, 1 H, CH), 1.06 (d, 3 H, J=6.4 Hz, $CH_3$), 0.73 (d, 3 H, J=7.2 Hz, $CH_3$); $^{31}$P NMR (162 MHz, $D_2O$) for diastereomers: 6-5.25 (d, J=21.0 Hz), -10.79 (d, J=19.44 Hz), -21.14 (t, J=21.0 Hz).

Example 4

Synthesis of Deoxyuridine and Deoxycytidine Analogs with α-tert-Butyl Groups

Synthesis 5-[(R or S)-1-(2-nitrophenyl)-2,2-dimethyl-1-propyloxy]methyl-2'-deoxyuridine-5'-triphosphate Scheme 12.

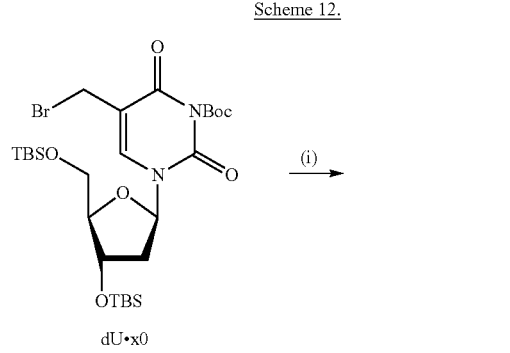

dU•x0

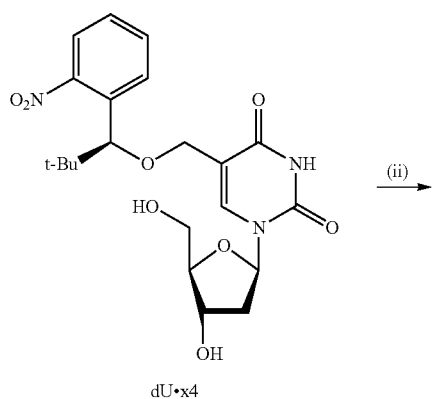

dU•x4

-continued

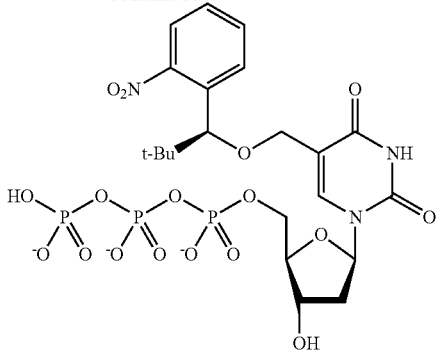

WW3p075

Synthesis of 5-[(R or S)-1-(2-nitrophenyl)-2,2-dimethyl-1-propyloxy]methyl-2'-deoxyuridine-5'-triphosphate. (i) (R or S)-1-(2-nitrophenyl)-2,2-dimethyl-1-propanol, neat, 108-115° C., 4%; (ii) $POCl_3$, proton sponge, $(MeO)_3PO$, 0° C.; (n-$Bu_3NH)_2H_2P_2O_7$, n-$Bu_3N$, DMF; 1M $HNEt_3HCO_3$.

5-[(R or S)-1-(2-nitrophenyl)-2,2-dimethyl-1-propyloxy]methyl-2'-deoxyuridine (dU.x4): Compound dU.x0 (520 mg, 0.802 mmol) and enantio-pure (R or S)-1-(2-nitrophenyl)-2,2-dimethyl-1-propanol (580 mg, 2.77 mmol) were heated neat at 108-115° C. for one hour under a nitrogen atmosphere. The mixture was cooled down to room temperature, dissolved in minimum amount of ethyl acetate, and purified by silica gel chromatography to yield 5-[(R or S)-1-(2-nitrophenyl)-2,2-dimethyl-1-propyloxy]methyl-2'-deoxyuridine (dU.x4) (16 mg, 4%). (3' or 5')-O-(tert-butylsimethylsilyl)-5-[(R or S)-1-(2-nitrophenyl)-2,2-dimethyl-1-propyloxy]methyl-2'-deoxyuridine (78 mg, 17%), and 3',5'-O-bis-(tert-butylsimethylsilyl)-5-[(R or S)-1-(2-nitrophenyl)-2,2-dimethyl-1-propyloxy]methyl-2'-deoxyuridine (115 mg, 21%) were also obtained from the reaction. $^1$H NMR (100 MHz, $CD_3OD$) for dU.x4: δ 7.84 (s, 1 H, H-6), 7.68 (dd, 1 H, J=1.2 and 8.1 Hz, Ph-H), 7.64 (dd, 1 H, J=1.4 and 7.9 Hz, Ph-H), 7.53 (m, 1 H, Ph-H), 7.36 (m, 1 H, Ph-H), 6.13 (t, 1 H, J=7.2 Hz, H-1'), 4.84 (s, 1 H, Ph-CH), 4.26 (m, 1 H, H-3'), 4.13 (AB d, 1 H, J=12.4 Hz, 5-$CH_2$a), 3.96 (AB d, 1 H, J=12.4 Hz, 5-$CH_2$b), 3.78 (m, 1 H, H-4'), 3.60 (m, 2 H, H-5'), 2.12 (m, 2 H, H-2'), 0.69 (s, 9H, $(CH_3)_3C$).

5-[(R or S)-1-(2-nitrophenyl)-2,2-dimethyl-1-propyloxy]methyl-2'-deoxyuridine-5'-triphosphate (WW3p075): $POCl_3$ (5 μL, 0.053 mmol) was added to a solution of compound dU.x4 (16 mg, 0.035 mmol) and proton sponge (15 mg, 0.07 mmol) in trimethylphosphate (0.3 mL) at 0° C. and stirred for two hours. Additional $POCl_3$ (3 μL, 0.032 mmol) was added and the mixture was stirred for another one hour. A solution of tri-n-butylammonium pyrophosphate (83 mg, 0.175 mmol) and tri-n-butylamine (35 μL) in anhydrous DMF (0.35 mL) was added. After five minutes of stirring, triethylammonium bicarbonate buffer (1 M, pH 7.5; 5 mL) was added. The reaction was stirred at room temperature for one hour and then lyophilized to dryness. The residue was dissolved in water (5 mL), filtered, and purified by anion exchange chromatography on a Q Sepharose FF column (2.5×20 cm) with a linear gradient of $NH_4HCO_3$ (50 mM to 500 mM in 240 minutes) at a flow rate of 4.5 mL/min. The fractions containing triphosphate were combined and lyophilized to give 5-[(R or S)-1-(2-nitrophenyl)-2,2-dimethyl-1-propyloxy]methyl-2'-deoxyuridine-5'-triphosphate WW3p075 (14 mg, 53%) as a white fluffy solid. $^1$H NMR (400 MHz, $D_2O$): δ 7.83 (d, 1 H, J=8.8 Hz, Ph-H), 7.63 (m, 3 H, Ph-H and H-6), 7.47 (m, 1 H, Ph-H), 6.08 (t, 1 H, J=6.8 Hz, H-1'), 4.46 (m, 1 H, H-3'), 4.41 (AB d, 1 H, J=8.4 Hz, 5-$CH_2$a), 4.32 (AB d, 1 H, J=8.8 Hz, 5-CH₂b), 4.20-4.11 (m, 3 H, H-4' and H-5'), 2.24 (m, 2 H, H-2'), 0.79 (s, 9 H, (CH₃)₃C); ³¹P NMR (162 MHz, D₂O): 6-5.11 (d, J=19.4 Hz), −10.55 (d, J=19.4 Hz), −20.9 (t, J=19.4 Hz).

Synthesis 5-[(R or S)-1-(2-nitrophenyl)-2,2-dimethyl-1-propyloxy]methyl-2'-deoxycytidine-5'-triphosphate

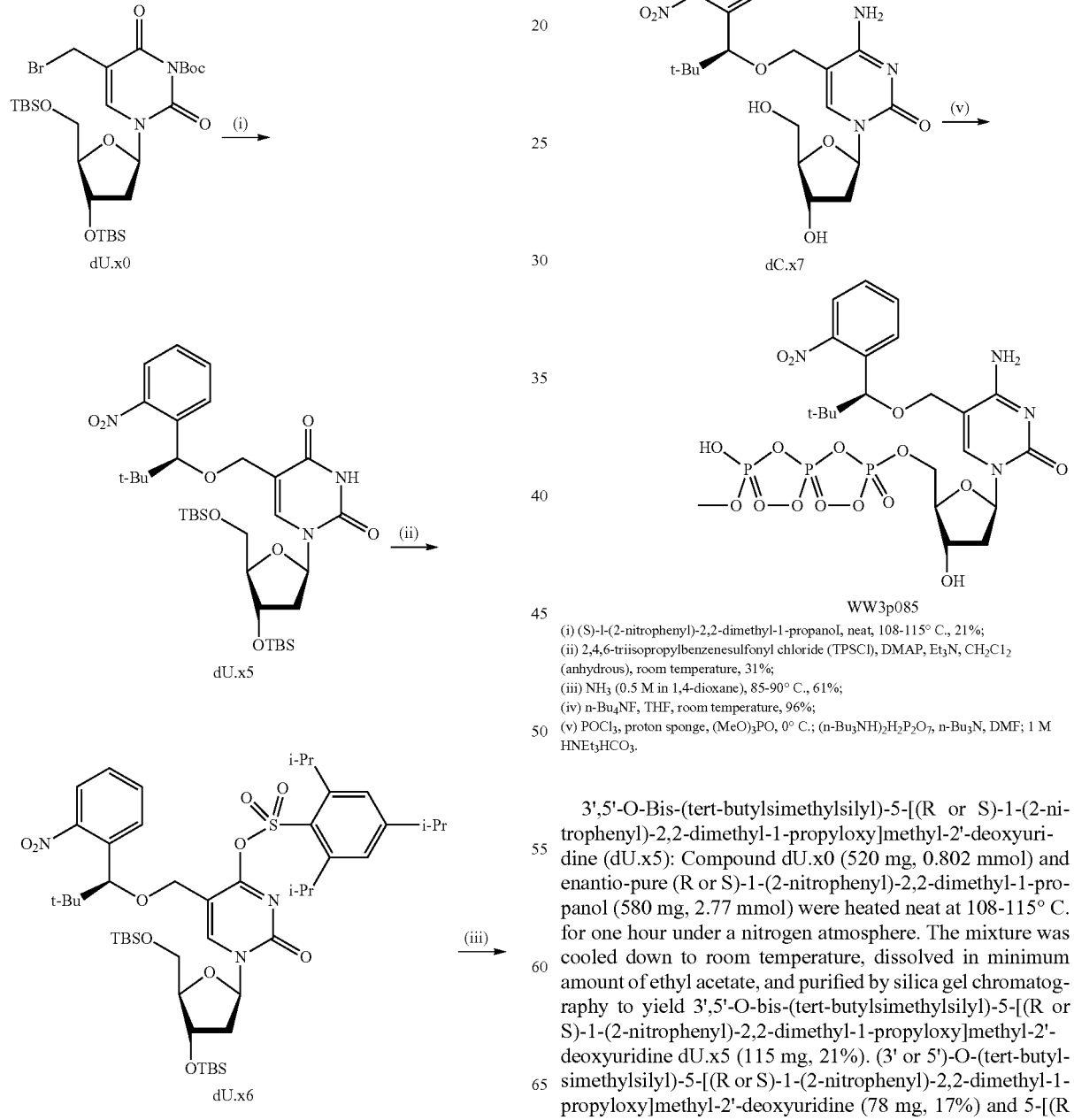

Scheme 13. Synthesis of 5-[(R or S)-1-(2-nitrophenyl)-2,2-dimethyl-propyloxy]methyl-2'-deoxycytidine-5'-triphosphate.

(i) (S)-1-(2-nitrophenyl)-2,2-dimethyl-1-propanol, neat, 108-115° C., 21%;
(ii) 2,4,6-triisopropylbenzenesulfonyl chloride (TPSCl), DMAP, Et₃N, CH₂Cl₂ (anhydrous), room temperature, 31%;
(iii) NH₃ (0.5 M in 1,4-dioxane), 85-90° C., 61%;
(iv) n-Bu₄NF, THF, room temperature, 96%;
(v) POCl₃, proton sponge, (MeO)₃PO, 0° C.; (n-Bu₃NH)₂H₂P₂O₇, n-Bu₃N, DMF; 1 M HNEt₃HCO₃.

3',5'-O-Bis-(tert-butylsimethylsilyl)-5-[(R or S)-1-(2-nitrophenyl)-2,2-dimethyl-1-propyloxy]methyl-2'-deoxyuridine (dU.x5): Compound dU.x0 (520 mg, 0.802 mmol) and enantio-pure (R or S)-1-(2-nitrophenyl)-2,2-dimethyl-1-propanol (580 mg, 2.77 mmol) were heated neat at 108-115° C. for one hour under a nitrogen atmosphere. The mixture was cooled down to room temperature, dissolved in minimum amount of ethyl acetate, and purified by silica gel chromatography to yield 3',5'-O-bis-(tert-butylsimethylsilyl)-5-[(R or S)-1-(2-nitrophenyl)-2,2-dimethyl-1-propyloxy]methyl-2'-deoxyuridine dU.x5 (115 mg, 21%). (3' or 5')-O-(tert-butylsimethylsilyl)-5-[(R or S)-1-(2-nitrophenyl)-2,2-dimethyl-1-propyloxy]methyl-2'-deoxyuridine (78 mg, 17%) and 5-[(R or S)-1-(2-nitrophenyl)-2,2-dimethyl-1-propyloxy]methyl- 2'-deoxyuridine (16 mg, 4%) was also obtained from the reaction. $^1$H NMR (400 MHz, CDCl$_3$) for dU.x5: δ 8.97 (s, 1 H, NH), 7.76 (d, 2 H, J=8.0 Hz, Ph-H), 7.60 (m, 2 H, Ph-H and H-6), 7.41 (s, 1 H, Ph-H), 6.29 (dd, 1 H, J=6.0 and 7.6 Hz, H-1'), 4.97 (s 1 H, Ph-CH), 4.42 (m, 1 H, H-3'), 4.28 (AB d, 1 H, J=12.0 Hz, 5-CH$_2$a), 4.06 (AB d, 1 H, J=12.0 Hz, 5-CH$_2$b), 3.92 (m, 1 H, H-4'), 3.76 (m, 2 H, H-5'), 2.30 (m, 1 H, H-2'a), 2.05 (m, 1 H, H-2'b), 0.95 (s, 9 H, (CH$_3$)$_3$CSi), 0.90 (s, 9 H, (CH$_3$)$_3$CSi), 0.83 (s, 9 H, (CH$_3$)$_3$C), 0.12 (s, 3 H, CH$_3$Si), 0.09 (s, 3 H, CH$_3$Si), 0.07 (s, 3 H, CH$_3$Si), 0.06 (s, 3H, CH$_3$Si); $^{13}$C NMR (100 MHz, CDCl$_3$) for dU.x5: δ 162.52 (C), 150.82 (C), 150.15 (C), 138.50 (CH), 134.19 (C), 132.01 (CH), 130.11 (CH), 128.14 (CH), 123.81 (CH), 111.45 (C), 87.70 (CH), 84.98 (CH), 81.44 (CH), 72.19 (CH), 64.60 (CH$_2$), 62.95 (CH$_2$), 40.85 (CH$_2$), 36.51 (C), 25.94 ((CH$_3$)$_3$C), 25.91 ((CH$_3$)$_3$C), 25.78 (C(CH$_3$)$_3$), 18.39 (C), 18.00 (C), −4.66 (CH$_3$), −4.84 (CH$_3$), −5.35 (CH$_3$), −5.42 (CH$_3$).

3',5'-O-Bis-(tert-butylsimethylsilyl)-5-[(R or S)-1-(2-nitrophenyl)-2,2-dimethyl-1-propyloxy]methyl-O$^4$-(2,4,6-triisopropylbenzenesulfonyl)-2'-deoxyuridine (dU.x6): To a solution of dU.x5 (110 mg, 0.16 mmol), DMAP (20 mg, 0.17 mmol), and triethylamine (63 μL, 0.45 mmol) in anhydrous dichloromethane (3 mL) 2,4,6-triisopropyl benzenesulfonyl chloride (61 mg, 0.20 mmol) was added. The mixture was stirred at room temperature for 36 hours under a nitrogen atmosphere, then concentrated in vacuo and purified by silica gel column chromatography to give 3',5'-O-bis-(tert-butylsimethylsilyl)-5-[(R or S)-1-(2-nitrophenyl)-2,2-dimethyl-1-propyloxy]methyl-O$^4$-(2,4,6-triisopropylbenzenesulfonyl)-2'-deoxyuridine dU.x6 (47 mg, 31%). $^1$H NMR (500 MHz, CDCl$_3$): δ 8.08 (s, 1 H, H-6), 7.80 (dd, 1 H, J=1.2 and 8.0 Hz, Ph-H), 7.78 (dd, 1 H, J=1.6 and 8.0 Hz, Ph-H), 7.67 (m, 1 H, Ph-H), 7.46 (m, 1 H, Ph-H), 7.20 (s, 2 H, Ph-H), 6.09 (t, 1 H, J=6.4 Hz, H-1'), 4.98 (s, 1 H, Ph-CH), 4.35 (m, 1 H, H-3'), 4.25 (AB d, 1 H, J=11.6 Hz, 5-CH$_2$a), 4.11 (AB d, 1 H, J=11.6 Hz, 5-CH$_2$b), 3.97 (m, 1 H, H-4'), 3.79 (dd, 1 H, J=3.6 and 11.6 Hz, H-5'a), 3.74 (dd, 1 H, J=11.6 and 3.6 Hz, H-5'b), 2.90 (m, 1 H, CH), 2.50 (m, 2 H, H-2'), 1.98 (m, 2 H, CH), 1.31-1.22 (m, 18 H, (CH$_3$)$_2$CH×3), 0.88 (2 s, 18 H, (CH$_3$)$_3$CSi×2), 0.87 (s, 9 H, (CH$_3$)$_3$C), 0.07 (s, 6 H, (CH$_3$)$_2$Si), 0.06 (s, 6 H, (CH$_3$)$_2$Si); $^{13}$C NMR (100 MHz, CDCl$_3$): δ 166.03 (C), 154.39 (C), 153.52 (C), 151.09 (C), 150.94 (C), 144.77 (CH), 133.60 (C), 132.43 (CH), 131.07 (CH), 130.12 (CH), 128.24 (CH), 123.05 (CH), 123.81 (CH), 104.64 (C), 88.39 (CH), 87.42 (CH), 82.45 (CH), 71.93 (CH), 64.41 (CH$_2$), 62.78 (CH$_2$), 42.09 (CH$_2$), 36.54 (C), 34.26 (CH), 29.60 (CH), 25.92 ((CH$_3$)$_3$C), 25.82 ((CH$_3$)$_3$C), 25.74 ((CH$_3$)$_3$C), 24.62 (CH$_3$), 24.34 (CH$_3$), 23.48 (CH$_3$), 18.40 (C), 17.99 (C), −4.62 (CH$_3$), −4.92 (CH$_3$), −5.37 (CH$_3$), −5.34 (CH$_3$).

3',5'-O-Bis-(tert-butyldimethylsilyl)-5-[(R or S)-1-(2-nitrophenyl)-2,2-dimethyl-1-propyloxy]methyl-2'-deoxycytidine (dC.x6): To a solution of compound dU.x6 (47 mg, 0.050 mmol) in anhydrous 1,4-dioxane (2 mL) a solution of ammonia (2 mL, 0.5 M in dioxane) was added. The mixture was transferred into a sealable tube and was heated at 92° C. for 10 hours. The mixture was cooled down to room temperature, concentrated in vacuo and purified by silica gel column chromatography to yield 3',5'-O-bis-(tert-butyldimethylsilyl)-5-[(R or S)-1-(2-nitrophenyl)-2,2-dimethyl-1-propyloxy]methyl-2'-deoxycytidine dC.x6 (31 mg, 91%). $^1$H NMR (400 MHz, CDCl$_3$) δ 7.67 (m, 3 H, Ph-H), 7.53 (s, 1 H, H-6), 7.45 (m, 1 H, Ph-H), 6.30 (t, 1 H, J=6.6 Hz, H-1'), 5.72 (br s, 2 H, NH$_2$), 4.88 (s, 1 H, Ph-CH), 4.32 (m, 1 H, H-3'), 4.28 (AB d, 1 H, J=12.8 Hz, 5-CH$_2$a), 4.08 (AB d, 1 H, J=12.8 Hz, 5-CH$_2$b), 3.87 (m, 1 H, H-4'), 3.74 (dd, 1 H, J=3.6 and 14.8 Hz, H-5'a), 3.66 (dd, 1 H, J=3.6 and 11.3 Hz, H-5'b), 2.41 (m, 1 H, H-2'a), 2.03 (m, 1 H, H-2'b), 0.90 (s, 9 H, (CH$_3$)$_3$CSi), 0.87 (s, 9 H, (CH$_3$)$_3$CSi), 0.83 (s, 9 H, (CH$_3$)$_3$C), 0.09 (2 s, 6 H, (CH$_3$)$_2$Si), 0.06 (2 s, 6 H, (CH$_3$)$_2$Si); $^{13}$C NMR (100 MHz, CDCl$_3$): δ 165.16 (C), 155.52 (C), 151.31 (C), 140.63 (CH), 133.31 (C), 132.04 (CH), 129.53 (CH), 128.56 (CH), 123.76 (CH), 101.89 (C), 87.39 (CH), 85.72 (CH), 81.24 (CH), 71.59 (CH), 66.55 (CH$_2$), 62.68 (CH$_2$), 41.65 (CH$_2$), 36.20 (C), 25.92 ((CH$_3$)$_3$C), 25.82 ((CH$_3$)$_3$C), 25.75 ((CH$_3$)$_3$C), 18.23 (C), 17.97 (C), −4.64 (CH$_3$), −4.94 (CH$_3$), −5.47 (CH$_3$), −5.53 (CH$_3$).

5-[(R or S)-1-(2-nitrophenyl)-2,2-dimethyl-1-propyloxy]methyl-2'-deoxycytidine (dC.x7): A solution of tetra-n-butylammonium fluoride trihydrate (28 mg, 0.09 mmol) in THF (1 mL) was added to a solution of compound dC.x6 (20 mg, 0.03 mmol) in THF (2 mL). The mixture was stirred at room temperature for 30 minutes, then concentrated in vacuo and purified by silica gel column chromatography to yield 5-[(R or S)-1-(2-nitrophenyl)-2,2-dimethyl-1-propyloxy]methyl-2'-deoxcytidine dC.x7 (11 mg, 82%). $^1$H NMR (400 MHz, CD$_3$OD) δ 7.87 (s, 1 H, H-6), 7.82 (dd, 1 H, J=1.2 and 8.4 Hz, Ph-H), 7.76 (dd, 1 H, J=1.6 and 8.0 Hz, Ph-H), 7.68 (m, 1 H, Ph-H), 7.51 (m, 1 H, Ph-H), 6.23 (t, 1 H, J=6.6 Hz, H-1'), 4.94 (s, 1 H, Ph-CH), 4.44 (AB d, 1 H, J=13.2 Hz, 5-CH$_2$a), 4.34 (m, 1 H, H-3'), 4.11 (AB d, 1 H, J=13.2 Hz, 5-CH$_2$b), 3.88 (m, 1 H, H-4'), 3.71 (dd, 1 H, J=3.2 and 12.0 Hz, H-5'a), 3.63 (dd, 1 H, J=4.0 and 12.0 Hz, H-5'b), 2.35 (m, 1 H, H-2'a), 2.14 (m, 1 H, H-2'b), 0.80 (s, 9 H, (CH$_3$)$_3$C); $^{13}$C NMR (100 MHz, CD$_3$OD): δ 166.65 (C), 158.22 (C), 152.66 (C), 143.25 (CH), 134.69 (C), 133.42 (CH), 131.19 (CH), 129.96 (CH), 125.30 (CH), 104.49 (C), 88.94 (CH), 87.46 (CH), 81.44 (CH), 72.20 (CH), 66.33 (CH$_2$), 62.88 (CH$_2$), 42.11 (CH$_2$), 37.34 (C), 26.44 ((CH$_3$)$_3$C).

5-[(R or S)-1-(2-nitrophenyl)-2,2-dimethyl-1-propyloxy]methyl-2'-deoxycytidine-5'triphosphate (WW3p085): POCl$_3$ (3.5 μL, 0.038 mmol) was added to a solution of compound dU.x7 (11 mg, 0.025 mmol) and proton sponge (10.5 mg, 0.049 mmol) in trimethylphosphate (0.3 mL) at 0° C. and stirred for two hour. Additional POCl$_3$ (3.5 μL, 0.038 mmol) was added and the mixture was stirred for another one hour. A solution of tri-n-butylammonium pyrophosphate (59 mg, 0.125 mmol) and tri-n-butylamine (30 μL) in anhydrous DMF (0.25 mL) was added. After five minutes of stirring, triethylammonium bicarbonate buffer (1 M, pH 7.5; 5 mL) was added. The reaction was stirred at room temperature for one hour and then lyophilized to dryness. The residue was dissolved in water (5 mL), filtered, and purified by anion exchange chromatography on a Q Sepharose FF column (2.5×20 cm) with a linear gradient of NH$_4$HCO$_3$ (50 mM to 500 mM in 240 minutes) at a flow rate of 4.5 mL/min. The fractions containing triphosphate were combined and lyophilized to give 5-[(R or S)-1-(2-nitrophenyl)-2,2-dimethyl-1-propyloxy]methyl-2'-deoxycytidine-5'-triphosphate WW3p085 (12 mg, 65%) as a white fluffy solid. $^1$H NMR (400 MHz, CD$_3$OD) δ 7.81 (d, 1 H, J=8.0 Hz, Ph-H), 7.65 (m, 3 H, Ph-H and H-6), 7.45 (t, 1 H, J=8.0 Hz, Ph-H), 6.03 (t, 1 H, J=6.4 Hz, H-1'), 4.52 (AB d, 1 H, J=13.6 Hz, 5-CH$_2$a), 4.46 (d, 1 H, J=13.6 Hz, 5-CH$_2$b), 4.41 (m, 1 H, H-3'), 4.12 (m, 3 H, H-4' and H-5'), 2.35 (m, 1 H, H-2'a), 2.17 (m, 1 H, H-2'b), 0.82 (s, 9 H, (CH$_3$)$_3$C); $^{31}$P NMR (162 MHz, D$_2$O) for diastereomers: 6-5.15 (d, J=21.0 Hz), −10.64 (d, J=19.44 Hz), −21.0 (t, J=21.0 Hz).

Example 5

Synthesis of Dye-Attached Deoxyuridine and Deoxycytidine Analogs with α-Isopropyl Groups

Synthesis of 6-JOE labeled 5-{(R)-1-[4-(3-amino-1-propynyl)-2-nitrophenyl]-2-methyl-propyloxy}methyl-2'-deoxyuridine-5'-triphosphate

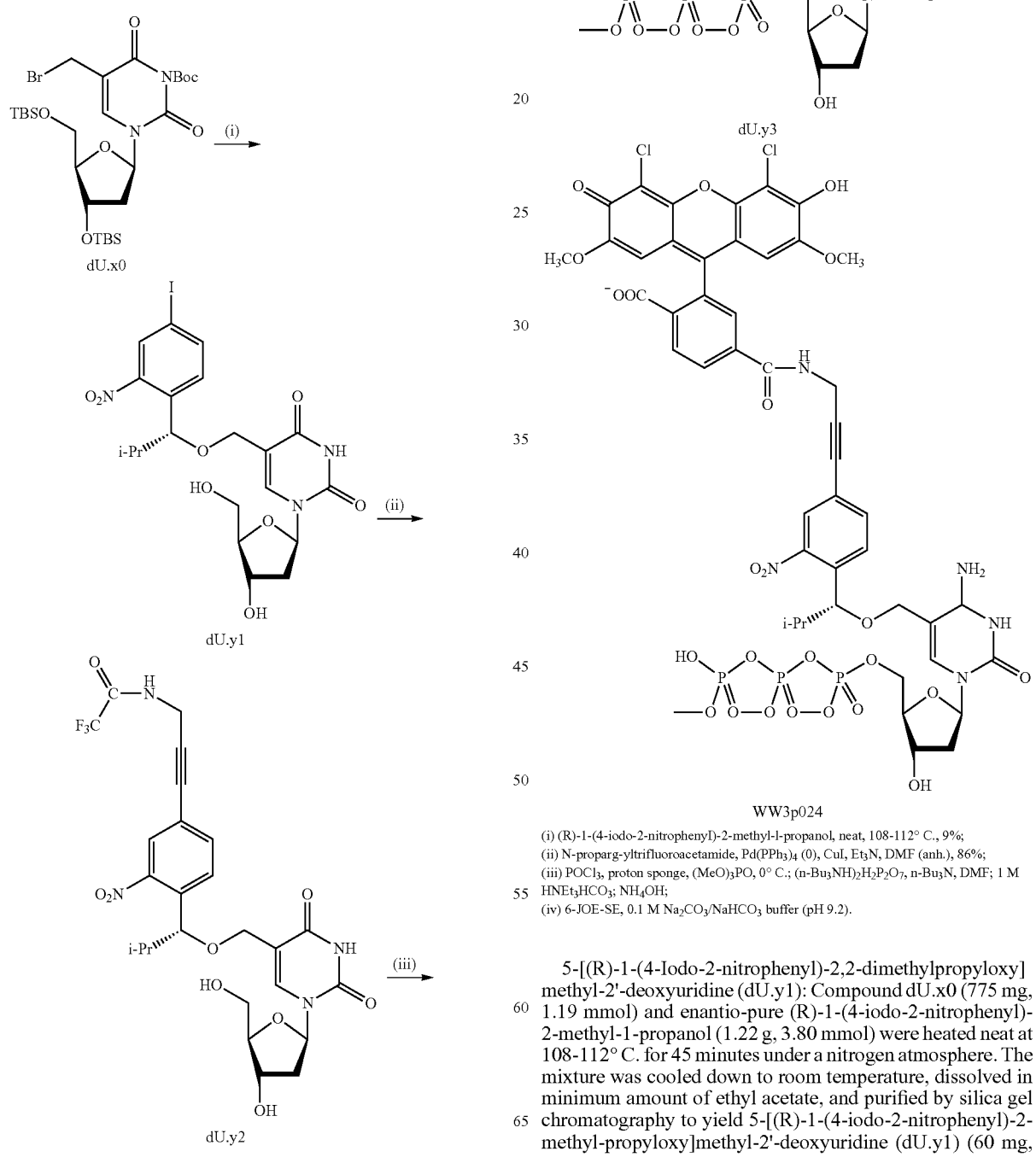

Scheme 14. Synthesis of 6-JOE labeled 5-{(R)-1-[4-(3-amino-1-propynyl)-2-nitrophenyl]-2-methyl-propyloxy}methyl-2'-deoxyuridine-5'-triphosphate.

(i) (R)-1-(4-iodo-2-nitrophenyl)-2-methyl-1-propanol, neat, 108-112° C., 9%;
(ii) N-proparg-yltrifluoroacetamide, Pd(PPh$_3$)$_4$ (0), CuI, Et$_3$N, DMF (anh.), 86%;
(iii) POCl$_3$, proton sponge, (MeO)$_3$PO, 0° C.; (n-Bu$_3$NH)$_2$H$_2$P$_2$O$_7$, n-Bu$_3$N, DMF; 1 M HNEt$_3$HCO$_3$; NH$_4$OH;
(iv) 6-JOE-SE, 0.1 M Na$_2$CO$_3$/NaHCO$_3$ buffer (pH 9.2).

5-[(R)-1-(4-Iodo-2-nitrophenyl)-2,2-dimethylpropyloxy] methyl-2'-deoxyuridine (dU.y1): Compound dU.x0 (775 mg, 1.19 mmol) and enantio-pure (R)-1-(4-iodo-2-nitrophenyl)-2-methyl-1-propanol (1.22 g, 3.80 mmol) were heated neat at 108-112° C. for 45 minutes under a nitrogen atmosphere. The mixture was cooled down to room temperature, dissolved in minimum amount of ethyl acetate, and purified by silica gel chromatography to yield 5-[(R)-1-(4-iodo-2-nitrophenyl)-2-methyl-propyloxy]methyl-2'-deoxyuridine (dU.y1) (60 mg, 9%). (3' or 5')-O-(tert-butylsimethylsilyl)-5-[(R)-1-(4-iodo- 2-nitrophenyl)-2-methyl-propyloxy]methyl-2'-deoxyuridine (90 mg, 11%) and 3',5'-O-bis-(tert-butylsimethylsilyl)-5-[(R)-1-(4-iodo-2-nitrophenyl)-2-methyl-propyl-oxy]methyl-2'-deoxyuridine (194 mg, 21%) were also obtained from the reaction. $^1$H NMR (400 MHz, CD$_3$CD) for dU.y1: δ 8.23 (d, 1 H, J=1.7 Hz, Ph-H), 8.03 (dd, J=8.4 and 1.7 Hz, 1 H, Ph-H), 8.00 (s, 1 H, H-6), 7.50 (d, 1 H, J=8.4 Hz, Ph-H), 6.26 (t, 1 H, J=6.8 Hz, H-1'), 4.69 (d, 1 H, J=5.8 Hz, PhCH), 4.40 (m, 1 H, H-3'), 4.13 (AB d, J=11.8 Hz, 1 H, 5-CH$_2$a), 4.08 (AB d, J=11.8 Hz, 1 H, 5-CH$_2$b), 3.93 (m, 1 H, H-4'), 3.79 (dd, J=12.0 and 3.3 Hz, 1 H, H-5'a), 3.73 (dd, J=12.0 and 3.6 Hz, 1 H, H-5'b), 2.26 (m, 1 H, H-2'a), 2.19 (m, 1 H, H-2'b), 1.93 (m, 1 H, CH(CH$_3$)$_3$), 0.93 (d, J=6.4 Hz, 3H, CH$_3$), 0.87 (d, J=6.8 Hz, 3 H, CH$_3$).

5-{(R)-1-[4-(3-Trifluoroacetamido-1-propynyl)-2-nitrophenyl]-2-methyl-propyloxy}methyl-2'-deoxyuridine (dU.y2): A solution of compound dU.y1 (60 mg, 0.11 mmol), N-propargyltrifluoroacetylamide (48 mg, 0.32 mmol), tetrakis(triphenyl-phosphine)-palladium(0) (12 mg, 0.01 mmol), CuI (4 mg, 0.02 mmol), and Et$_3$N (30 μL, 0.21 mmol) in anhydrous DMF (5 mL) was stirred at room temperature for 4.5 hours. Methanol (4 mL) and methylene chloride (4 mL) were added, followed by sodium bicarbonate (49 mg, 0.58 mmol). The mixture was stirred for another hour, then concentrated in vacuo and purified by silica gel column chromatography to yield 5-{(R)-1-[4-(3-trifluoroacetamido-1-propynyl)-2-nitrophenyl]-2-methyl-propyloxy}methyl-2'-deoxyuridine dU.y2 (54 mg, 86%). $^1$H NMR (400 MHz, DMSO-d$_6$): δ 11.33 (s, 1 H, D$_2$O exchangeable, 3-NH), 10.12 (br t, J=4.8 Hz, 1H, D$_2$O exchangeable, CH$_2$NHTFA), 7.98 (d, 1 H, J=1.5 Hz, Ph-H), 7.85 (s, 1 H, H-6), 7.74 (dd, J=8.2 and 1.5 Hz, 1 H, Ph-H), 7.64 (d, 1 H, J=8.2 Hz, Ph-H), 6.13 (t, 1 H, J=6.8 Hz, H-1'), 5.24 (d, J=4.2 Hz, 1 H, D$_2$O exchangeable, 3'-OH), 4.96 (t, J=5.2 Hz, 1H, D$_2$O exchangeable, 5'-OH), 4.61 (d, 1 H, J=5.5 Hz, PhCH), 4.30 (d, 2 H, J=4.8 Hz, CH$_2$NHTFA), 4.22 (m, 1 H, H-3'), 3.97 (s, 2 H, 5-CH$_2$a and 5-CH$_2$b), 3.76 (m, 1 H, H-4'), 3.56 (m, 2 H, H-5'a and H-5'b), 2.06 (m, 2 H, H-2'a and H-2'b), 1.88 (m, 1 H, CH(CH$_3$)$_3$), 0.83 (d, J=6.7 Hz, 3 H, CH$_3$), 0.80 (d, J=6.8 Hz, 3 H, CH$_3$); $^{13}$C NMR (100 MHz, CD$_3$OD): δ 163.59 (C), 157.22 (C), 150.67 (C), 149.23 (C), 139.78 (CH), 137.05 (C), 135.21 (CH), 129.48 (CH), 126.63 (CH), 122.76 (C), 110.89 (C), 87.60 (CH), 85.70 (C), 85.14 (CH), 87.96 (CH), 80.27 (C), 70.86 (CH), 64.34 (CH$_2$), 61.44 (CH$_2$), 39.96 (CH$_2$), 34.62 (CH), 29.07 (CH$_2$), 18.30 (CH$_3$), 16.44 (CH$_3$).

5-{(R)-1-[4-(3-Amino-1-propynyl)-2-nitrophenyl]-2-methyl-propyloxy}methyl-2'-deoxyuridine-5'-triphosphate (dU.y3): POCl$_3$ (6 μL, 0.06 mmol) was added to a solution of compound dU.y2 (18 mg, 0.03 mmol) and proton sponge (13 mg, 0.06 mmol) in trimethylphosphate (0.3 mL) at 0° C. and stirred for two hours. A solution of bis-tri-n-butylammonium pyrophosphate (73 mg, 0.15 mmol) and tri-n-butylamine (30 μL) in anhydrous DMF (0.3 mL) was added. After five minutes of stirring, triethylammonium bicarbonate buffer (1 M, pH 7.5; 5 mL) was added. The reaction was stirred for one hour at room temperature and then lyophilized to dryness. The residue was dissolved in water (5 mL), filtered, and part of the solution was purified with reverse-phase HPLC using a Perkin Elmer OD-300 C$_{18}$ column (4.6×250 mm) to yield 5-{(R)-1-[4-(3-trifluoroacetamido-1-propynyl)-2-nitrophenyl]-2-methyl-propyloxy}methyl-2'-deoxy-uridine-5'-triphosphate. Mobile phase: A, 100 mM triethylammonium acetate (TEAA) in water (pH 7.0); B, 100 mM TEAA in water/CH$_3$CN (30:70). The purified triphosphate was then treated with concentrated ammonium hydroxide (27%) at room temperature for two hours to yield 5-{(R)-1-[4-(3-amino-1-propynyl)-2-nitrophenyl]-2-methyl-propyloxy}methyl-2'-deoxyuridine-5'-triphosphate dU.y3. $^1$H NMR (400 MHz, D$_2$O): δ 8.01 (s, 1 H, Ph-H), 7.76 (d, 1 H, J=6.9 Hz, Ph-H), 7.62 (m, 2 H, H-6 and Ph-H), 6.17 (t, 1 H, J=6.4 Hz, H-1'), 4.55 (m, 1 H, H-3'), 4.39 and 4.29 (2 d, 2 H, J=6.4 Hz, CH$_2$), 4.17 (m, 3 H, H-4' and H-5'), 3.74 (s, 2 H, CH$_2$), 2.28 (m, 2 H, H-2'), 2.00 (m, 1 H, CH), 0.79 (m, 3 H, CH$_3$); $^{31}$P NMR (162 MHz, D$_2$O): 6-5.40 (d, J=19.4 Hz), −10.75 (d, J=19.4 Hz), −21.23 (t, J=19.4 Hz).

6-JOE labeled 5-{(R)-1-[4-(3-amino-1-propynyl)-2-nitrophenyl]-2-methyl-propyloxy}methyl-2'-deoxyuridine-5'-triphosphate (WW3p024): A solution of 6-JOE-SE (0.625 mg, 1 μmol) in anhydrous DMSO (25 μL) was added to a solution of triphosphate dU.y3 (0.31 μmol) in Na$_2$CO$_3$/NaHCO$_3$ buffer (0.1 M, pH 9.2; 180 μL) and incubated at room temperature for one hour. The reaction was purified by reverse-phase HPLC using a Perkin Elmer OD-300 C$_{18}$ column (4.6×250 mm) to yield the 6-JOE labeled triphosphate WW3p024. Mobile phase: A, 100 mM TEAA in water (pH 7.0); B, 100 mM TEAA in water/CH$_3$CN (30:70). WW3p024 was characterized by its incorporation by DNA polymerase and photo deprotection.

Synthesis of Cy5 labeled 5-{(R)-1-[4-(3-amino-1-propynyl)-2-nitrophenyl]-2-methyl-propyloxy}methyl-2'-deoxycytidine-5'-triphosphate Scheme 15.

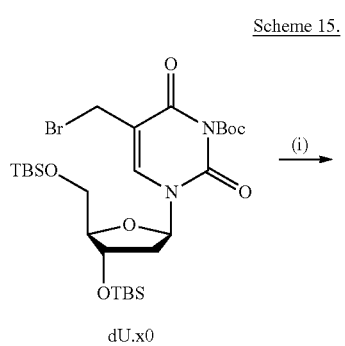

dU.x0

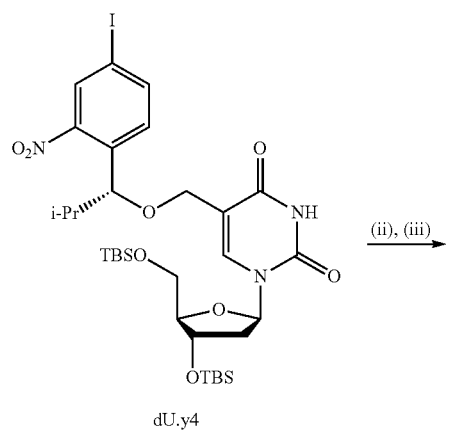

dU.y4

87
-continued

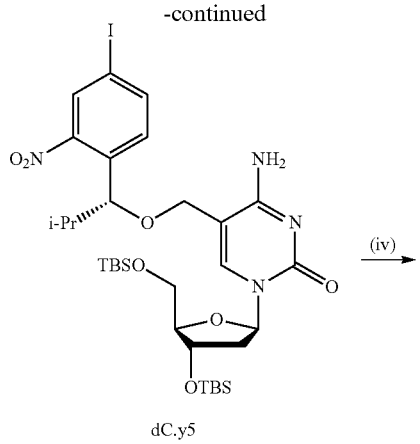

dC.y5

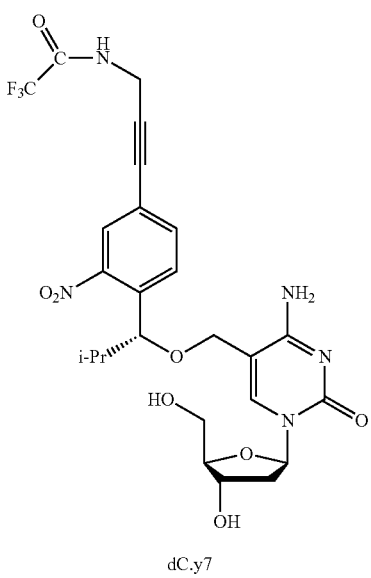

dC.y6 dC.y7

Synthesis of Cy5 labeled 5-{(R)-1-[4-(3-amino-1-propynyl)-2-nitrophenyl]-2-methyl-propyloxy}methyl-2′-deoxycytidine-5′-triphosphate (i) (R)-1-(4-iodo-2-nitrophenyl)-2-methyl-1-propanol, neat, 108-112° C., 21%; (ii) TPSCl, DMAP, Et₃N, CH₂Cl₂ (anhydrous), room temperature; (iii) NH₃, 1,4-dioxane, 92-94° C., 76% for two steps; (iv) n-Bu₄NF, THF, room temperature, 80%; (v) N-propargyltrifluoroacetamide, Pd(PPh₃)₄(0), CuI, Et₃N, DMF(anhydrous), 99%; (vi) POCl₃, proton sponge, (MeO)₃PO, 0° C.; (n-Bu₃NH)₂H₂P₂O₇, n-Bu₃N, DMF; 1M HNEt₃HCO₃; NH₄OH;

88

Scheme 16.

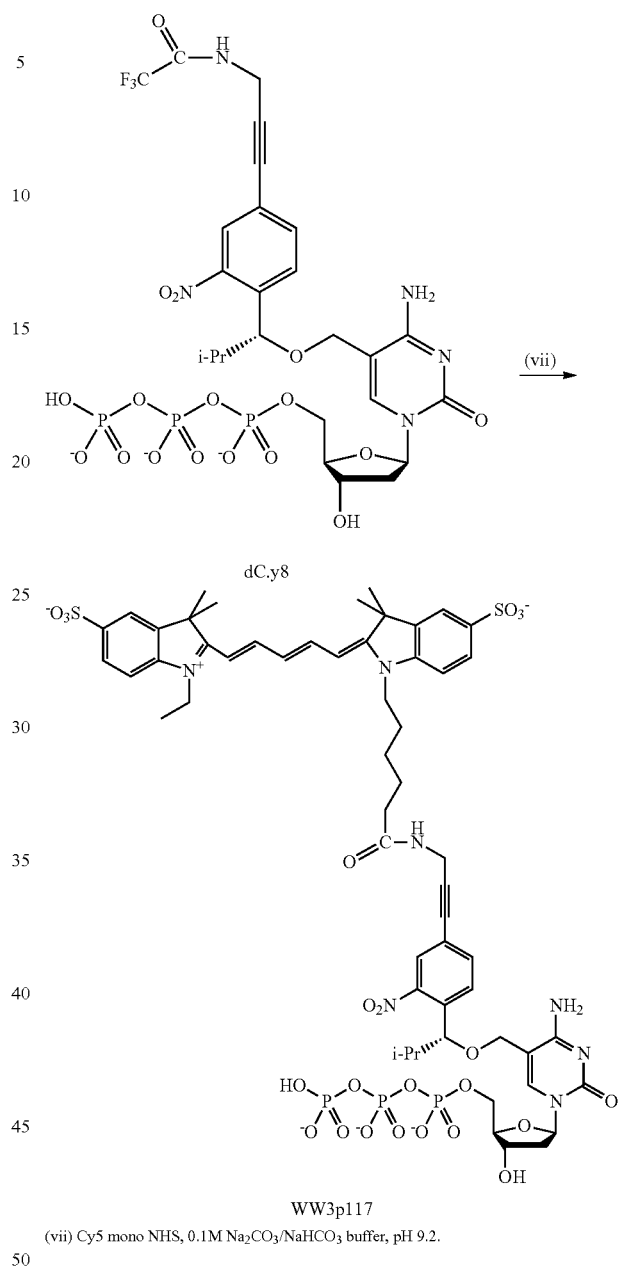

dC.y8

WW3p117

(vii) Cy5 mono NHS, 0.1M Na₂CO₃/NaHCO₃ buffer, pH 9.2.

3′,5′-O-Bis-(tert-butyldimethylsilyl)-5-[(R)-1-(4-iodo-2-nitrophenyl)-2-methyl-propyloxy]methyl-2′-deoxyuridine (dU.y4): Compound dU.x0 (775 mg, 1.19 mmol) and enantio-pure (R)-1-(4-iodo-2-nitrophenyl)-2-methyl-1-propanol (1.22 g, 3.80 mmol) were heated neat at 108-112° C. for 45 minutes under a nitrogen atmosphere. The mixture was cooled down to room temperature, dissolved in minimum amount of ethyl acetate, and purified by silica gel chromatography to yield 3′,5′-O-bis-(tert-butyldimethylsilyl)-5-[(R)-1-(4-iodo-2-nitrophenyl)-2-methyl-propyloxy]methyl-2′-deoxyuridine dU.y4 (194 mg, 21%). (3′ or 5′)-O-(tert-butyldimethylsilyl)-5-[(R)-1-(4-iodo-2-nitrophenyl)-2-methyl-propyloxy]methyl-2′-deoxyuridine (90 mg, 11%) and 5-[(R)-1-(4-iodo-2-nitrophenyl)-2-methyl-propyloxy]methyl-2′-deoxyuridine (60 mg, 9%) were also obtained from the reaction. ¹H NMR (400 MHz, CDCl₃) for dU.y4: δ 8.43

(s, 1 H, 3-NH), 8.18 (d, 1 H, J=1.6 Hz, Ph-H), 7.96 (dd, J=8.3 and 1.6 Hz, 1 H, Ph-H), 7.65 (s, 1 H, H-6), 7.47 (d, 1 H, J=8.3 Hz, Ph-H), 6.29 (dd, 1 H, J=7.8 and 5.8 Hz, H-1'), 4.74 (d, 1 H, J=5.8 Hz, PhCH), 4.39 (m, 1 H, H-3'), 4.14 (AB d, J=11.6 Hz, 1 H, 5-CH$_2$a), 3.98 (AB d, J=11.6 Hz, 1 H, 5-CH$_2$b), 3.97 (m, 1 H, H-4'), 3.78 (m, 2 H, H-5'a and H-5'b), 2.31 (m, 1 H, H-2'a), 1.99 (m, 1 H, H-2'b), 1.91 (m, 1 H, C$\underline{H}$(CH$_3$)$_3$), 0.92 (d, J=6.7 Hz, 3 H, CH$_3$), 0.90 (s, 9 H, (CH$_3$)$_3$CSi), 0.98 (s, 9 H, (CH$_3$)$_3$CSi), 0.86 (d, J=6.9 Hz, 3H, CH$_3$), 0.09 (s, 3 H, CH$_3$Si), 0.08 (s, 3 H, CH$_3$Si), 0.07 (s, 3 H, CH$_3$Si), 0.04 (s, 3 H, CH$_3$Si); $^{13}$C NMR (100 MHz, CDCl$_3$) for dU.y4: δ 162.20 (C), 149.83 (C), 149.69 (C), 141.89 (CH), 138.68 (CH), 136.56 (C), 132.63 (CH), 130.94 (CH), 111.19 (C), 91.84 (C), 88.00 (CH), 85.41 (CH), 80.99 (CH), 72.40 (CH), 64.46 (CH$_2$), 63.18 (CH$_2$), 41.22 (CH$_2$), 34.74 (CH), 25.93 (C(CH$_3$)$_3$), 25.75 (C(CH$_3$)$_3$), 19.29 (CH$_3$), 18.40 (C), 18.00 (C), 17.49 (CH$_3$), −4.64 (CH$_3$), −4.81 (CH$_3$), −5.37 (2 CH$_3$).

3',5-O-Bis-(tert-butyldimethylsilyl)-5-[(R)-1-(4-iodo-2-nitrophenyl)-2-methyl-propyloxy]methyl-2'-deoxycytidine (dC.y5): To a solution of compound dU.y4 (0.256 g, 0.32 mmol), DMAP (23 mg, 0.21 mmol) and triethylamine (1.138 mL, 8.10 mmol) in anhydrous dichloromethane (14 mL), 2,4,6-triisopropyl benzenesulfonyl chloride (1.57 g, 5.19 mmol) was added. The mixture was stirred at room temperature for 16 hours under a nitrogen atmosphere, and then concentrated in vacuo. Ammonia (0.5 M in dioxane, 24 mL, 12.0 mmol) was added and the mixture was transferred into a sealed tube, and heated at 92-94° C. for four hours. The mixture was concentrated under reduced pressure and purified by silica gel column chromatography to yield 3',5'-O-bis-(tert-butyldimethylsilyl)-5-[(R)-1-(4-iodo-2-nitrophenyl)-2-methyl-propyloxy]methyl-2'-deoxycytidine dC.y5 (192 mg, 76%). $^1$H NMR (400 MHz, CDCl$_3$) δ 8.13 (d, 1 H, J=1.6 Hz, Ph-H), 7.95 (dd, J=8.3 and 1.6 Hz, 1 H, Ph-H), 7.59 (s, 1 H, H-6), 7.38 (d, 1 H, J=8.3 Hz, Ph-H), 6.28 (t, 1 H, J=6.5 Hz, H-1'), 6.02 (br, 2 H, 4-NH$_2$), 4.63 (d, 1 H, J=6.6 Hz, PhCH), 4.32 (m, 1 H, H-3'), 4.19 (AB d, J=12.5 Hz, 1H, 5-CH$_2$a), 4.04 (AB d, J=12.5 Hz, 1 H, 5-CH$_2$b), 3.93 (m, 1 H, H-4'), 3.81 (AB dd, J=11.3 and 3.0 Hz, 1 H, H-5'a), 3.72 (AB dd, J=11.3 and 2.8 Hz, 1 H, H-5'b), 2.43 (m, 1 H, H-2'a), 1.92 (m, 2 H, H-2'b and C$\underline{H}$(CH$_3$)$_3$), 0.96 (d, J=6.6 Hz, 3H, CH$_3$), 0.82 (d, J=6.9 Hz, 3H, CH$_3$), 0.89 (s, 9 H, (CH$_3$)$_3$CSi), 0.80 (s, 9 H, (CH$_3$)$_3$CSi), 0.06 (s, 3 H, CH$_3$Si), 0.05 (s, 3 H, CH$_3$Si), −0.02 (s, 3 H, CH$_3$Si), −0.04 (s, 3 H, CH$_3$Si); $^{13}$C NMR (100 MHz, CDCl$_3$): δ 165.02 (C), 152.93 (C), 150.09 (C), 141.92 (CH), 140.37 (CH), 135.53 (C), 132.55 (CH), 130.35 (CH), 101.50 (C), 92.35 (C), 87.76 (CH), 86.26 (CH), 80.33 (CH), 71.98 (CH), 66.92 (CH$_2$), 62.84 (CH$_2$), 42.14 (CH$_2$), 34.75 (CH), 25.89 (C(CH$_3$)$_3$), 25.77 (C(CH$_3$)$_3$), 19.01 (CH$_3$), 18.30 (C), 18.15 (CH$_3$), 18.00 (C), −4.57 (CH$_3$), −4.87 (CH$_3$), −5.43 (CH$_3$), −5.49 (CH$_3$).

5-[(R)-1-(4-Iodo-2-nitrophenyl)-2-methyl-propyloxy]methyl-2'-deoxycytidine dC.y6: A solution of tetra-n-butylammonium fluoride trihydrate (112 mg, 0.36 mmol) in THF (2 mL) was added to a solution of compound dC.y5 (192 mg, 0.24 mmol) in THF (8 mL). The mixture was stirred at room temperature for 45 minutes, then concentrated in vacuo and purified by silica gel column chromatography to yield 5-[(R)-1-(4-iodo-2-nitrophenyl)-2-methyl-propyloxy]methyl-2'-deoxycytidine dC.y6 (110 mg, 80%). $^1$H NMR (400 MHz, DMSO-d$_6$) δ 8.26 (d, 1 H, J=1.7 Hz, Ph-H), 8.07 (dd, J=8.3 and 1.7 Hz, 1 H, Ph-H), 7.70 (s, 1 H, H-6), 7.38 (d, 1 H, J=8.3 Hz, Ph-H), 7.32 and 6.59 (2 br. s, 2 H, D$_2$O exchangeable, 4-NH$_2$), 6.11 (dd, 1 H, J=7.2 and 6.1 Hz, H-1'), 5.19 (d, J=4.2 Hz, 1 H, D$_2$O exchangeable, 3'-OH), 4.88 (t, J=5.4 Hz, 1 H, D$_2$O exchangeable, 5'-OH), 4.58 (d, 1 H, J=6.0 Hz, PhCH), 4.19 (m, 1 H, H-3'), 4.07 (AB d, J=12.2 Hz, 1 H, 5-CH$_2$a), 4.02 (AB d, J=12.2 Hz, 1 H, 5-CH$_2$b), 3.75 (m, 1 H, H-4'), 3.51 (m, 2 H, H-5'a and H-5'b), 2.09 (m, 1 H, H-2'a), 1.90 (m, 2 H, H-2'b and C$\underline{H}$(CH$_3$)$_3$), 0.87 (d, J=6.7 Hz, 3 H, CH$_3$), 0.78 (d, J=6.8 Hz, 3 H, CH$_3$); $^{13}$C NMR (100 MHz, CD$_3$OD): δ 166.48 (C), 158.09 (C), 151.27 (C), 143.22 (CH), 142.77 (CH), 137.32 (C), 133.80 (CH), 132.20 (CH), 104.72 (C), 93.10 (C), 89.08 (CH), 87.73 (CH), 81.82 (CH), 72.05 (CH), 67.22 (CH$_2$), 62.82 (CH$_2$), 42.21 (CH$_2$), 36.20 (CH), 19.62 (CH$_3$), 18.41 (CH$_3$).

5-{(R)-1-[4-(3-Trifluoroacetamido-1-propynyl)-2-nitrophenyl]-2-methyl-propyloxy}methyl-2'-deoxycytidine (dC.y7): A solution of compound dC.y6 (110 mg, 0.20 mmol), N-propargyltrifluoroacetylamide (88 mg, 0.59 mmol), tetra-kis(triphenylphosphine)-palladium(0) (23 mg, 0.02 mmol), CuI (7 mg, 0.04 mmol), and Et$_3$N (0.11 mL, 0.78 mmol) in anhydrous DMF (4 mL) was stirred at room temperature for 4.5 hours. Methanol (4 mL) and methylene chloride (4 mL) were added, followed by sodium bicarbonate (90 mg, 1.07 mmol). The mixture stirred for another one hour, then concentrated in vacuo and purified by silica gel column chromatography to yield 5-{(R)-1-[4-(3-trifluoroacetamido-1-propynyl)-2-nitrophenyl]-2-methyl-propyloxy}methyl-2'-deoxycytidine dC.y7 (112 mg, 99%). $^1$H NMR (400 MHz, DMSO-d$_6$): δ 10.12 (br t, 1 H, D$_2$O exchangeable, CH$_2$N$\underline{H}$TFA), 7.98 (d, 1 H, J=1.6 Hz, Ph-H), 7.76 (dd, J=8.2 and 1.7 Hz, 1 H, Ph-H), 7.73 (s, 1 H, H-6), 7.62 (d, 1 H, J=8.2 Hz, Ph-H), 7.33 and 6.60 (2 br. s, 2 H, D$_2$O exchangeable, 4-NH$_2$), 6.11 (t, 1 H, J=6.8 Hz, H-1'), 5.19 (d, J=4.2 Hz, 1 H, D$_2$O exchangeable, 3'-OH), 4.89 (t, J=5.4 Hz, 1 H, D$_2$O exchangeable, 5'-OH), 4.64 (d, 1 H, J=5.9 Hz, PhCH), 4.31 (d, 2 H, J=5.2 Hz, C$\underline{H_2}$NHTFA), 4.19 (m, 1 H, H-3'), 4.09 (AB d, J=12.1 Hz, 1 H, 5-CH$_2$a), 4.03 (AB d, J=12.1 Hz, 1 H, 5-CH$_2$b), 3.75 (m, 1 H, H-4'), 3.52 (m, 2 H, H-5'a and H-5'b), 2.08 (m, 1 H, H-2'a), 1.91 (m, 2 H, H-2' b and C$\underline{H}$(CH$_3$)$_3$), 0.87 (d, J=6.7 Hz, 3 H, CH$_3$), 0.79 (d, J=6.8 Hz, 3 H, CH$_3$): $^{13}$C NMR (100 MHz, CD$_3$OD): δ 164.83 (C), 157.51 (C), 157.14 (C), 156.45 (C), 149.25 (C), 141.23 (CH), 136.46 (C), 135.39 (CH), 129.39 (C), 126.64 (CH), 122.98 (C), 117.43 (C), 114.58 (C), 87.54 (CH), 86.22 (CH), 86.02 (C), 80.34 (C), 80.27 (CH), 70.53 (CH), 65.75 (CH$_2$), 61.28 (CH$_2$), 40.60 (CH$_2$), 34.73 (CH), 29.16 (CH$_2$), 18.15 (CH$_3$), 16.96 (CH$_3$). HRMS: for C$_{25}$H$_{29}$F$_3$N$_5$O$_8$ [MH$^+$]: clcd 584.1968 found 584.1926

5-{(R)-1-[4-(3-Amino-1-propynyl)-2-nitrophenyl]-2-methyl-propyloxy}methyl-2'-deoxycytidine-5'-triphosphate (dC.y8): POCl$_3$ (6 μL, 0.06 mmol) was added to a solution of compound dC.y7 (19 mg, 0.03 mmol) and proton sponge (14 mg, 0.06 mmol) in trimethylphosphate (0.3 mL) at 0° C. and stirred for two hours. A solution of bis-tri-n-butylammonium pyrophosphate (76 mg, 0.16 mmol) and tri-n-butylamine (32 μL) in anhydrous DMF (0.32 mL) was added. After five minutes of stirring, triethylammonium bicarbonate buffer (1 M, pH 7.5; 5 mL) was added. The reaction was stirred for one hour at room temperature and then concentrated in vacuo at 25° C. The residue was dissolved in water (2 mL), filtered, and purified with reverse-phase HPLC using a Perkin Elmer OD-300 C$_{18}$ column (4.6×250 mm) to yield 5-{(R)-1-[4-(3-trifluoroacetamido-1-propynyl)-2-nitrophenyl]-2-methyl-propyloxy}methyl-2'-deoxycytidine-5'-triphosphate. Mobile phase: A, 100 mM triethylammonium acetate (TEAA) in water (pH 7.0); B, 100 mM TEAA in water/CH$_3$CN (30:70). The purified triphosphate was then treated with concentrated ammonium hydroxide (27%) at room temperature for two hours to yield 5-{(R)-1-[4-(3-amino-1-propynyl)-2-nitrophenyl]-2-methyl-propyloxy}methyl-2'-deoxycytidine-5'-triphosphate dC.y8.

Cy5 labeled 5-{(R)-1-[4-(3-amino-1-propynyl)-2-nitrophenyl]-2-methyl-propyl-oxy}methyl-2'-deoxycytidine-5'-triphosphate (WW3p117): A solution of Cy5 mono NHS (1 mg, 1.26 μmol) in anhydrous DMSO (40 μL) was added to a solution of triphosphate dC.y8 (0.31 μmol) in $Na_2CO_3$/ $NaHCO_3$ buffer (0.1 M, pH 9.2; 100 μL) and left at room temperature for one hour. The reaction was purified by reverse-phase HPLC using a Perkin Elmer OD-300 $C_{18}$ column (4.6×250 mm) to yield the Cy5 labeled triphosphate WW3p117. Mobile phase: A, 100 mM TEAA in water (pH 7.0); B, 100 mM TEAA in water/$CH_3CN$ (30:70).

Example 6

Synthesis of Dye-Attached Deoxyuridine and Deoxycytidine Analogs with α-tert-Butyl Groups Synthesis of 6-TAMRA labeled 5-{(R or S)-1-[4-(3-amino-1-propynyl)-2-nitrophenyl]-2,2-dimethyl-propoxy}methyl-2'-deoxycytidine-5'-triphosphate Scheme 17. Synthesis of 6-TAMRA labeled 5-{(R or S)-1-[4-(3-amino-1-propynyl)-2-nitrophenyl]-2,2-dimethyl-propoxy}methyl-2'-deoxycytidine-5'-triphosphate.

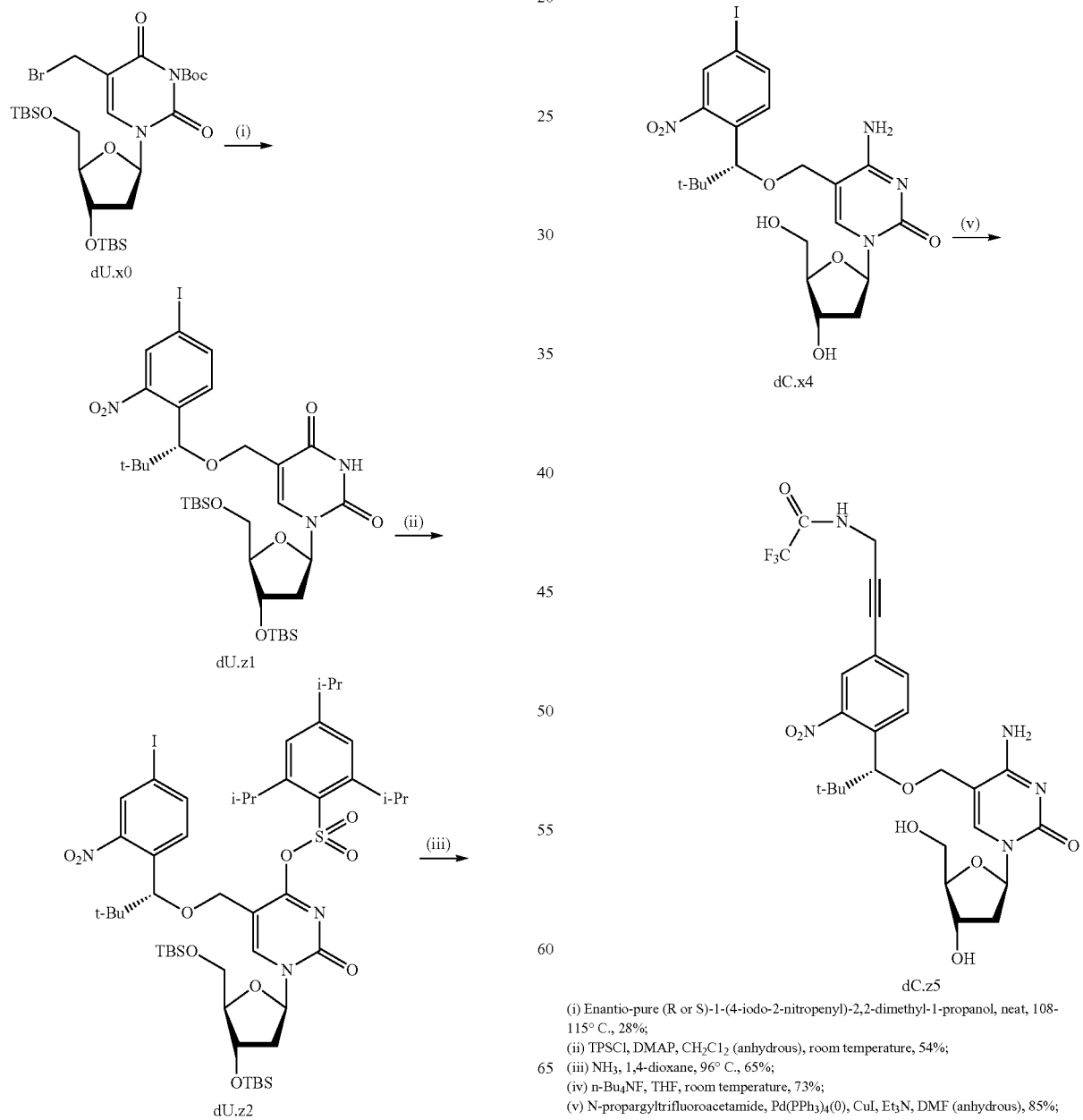

(i) Enantio-pure (R or S)-1-(4-iodo-2-nitropenyl)-2,2-dimethyl-1-propanol, neat, 108-115° C., 28%;
(ii) TPSCl, DMAP, $CH_2Cl_2$ (anhydrous), room temperature, 54%;
(iii) $NH_3$, 1,4-dioxane, 96° C., 65%;
(iv) n-$Bu_4NF$, THF, room temperature, 73%;
(v) N-propargyltrifluoroacetamide, Pd($PPh_3$)$_4$(0), CuI, $Et_3N$, DMF (anhydrous), 85%;

Scheme 18.

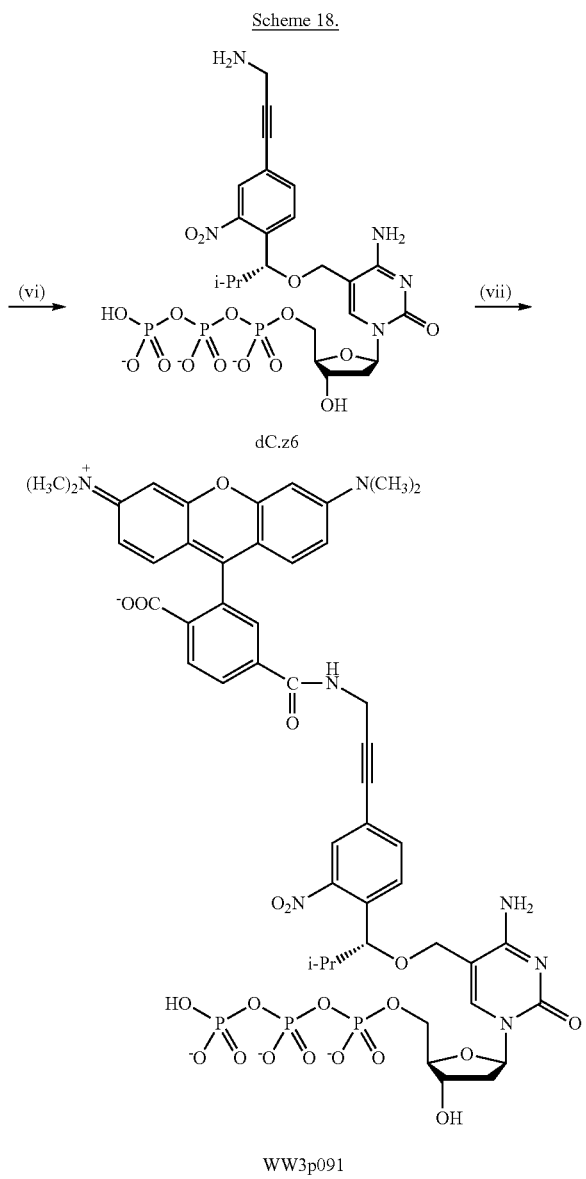

WW3p091
(vi) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$; NH$_4$OH; (vii) 6-TAMRA-SE, 0.1M Na$_2$CO$_3$/NaHCO$_3$ buffer, pH 9.2.

3',5'-O-Bis-(tert-butyldimethylsilyl)-5-[(R or S)-1-(4-iodo-2-nitrophenyl)-2,2-dimethyl-propyloxy]methyl-2'-deoxyuridine (dU.z1): Compound dU.x0 (688 mg, 1.06 mmol) and enantio-pure (R or S)-1-(4-iodo-2-nitrophenyl)-2,2-dimethyl-1-propanol (889 mg, 2.65 mmol) were heated neat at 108-115° C. for one hour under a nitrogen atmosphere. The mixture was cooled down to room temperature, dissolved in minimum amount of ethyl acetate, and purified by silica gel chromatography to yield 3',5'-O-bis-(tert-butyldimethylsilyl)-5-[(R or S)-1-(4-iodo-2-nitrophenyl)-2,2-dimethyl-propyloxy]-methyl-2'-deoxyuridine dU.z1 (236 mg, 28%). (3' or 5')-O-(tert-butyldimethylsilyl)-5-[(R or S)-1-(4-Iodo-2-nitrophenyl)-2,2-dimethyl-propyloxy]methyl-2'-deoxyuridine (20 mg, 3%) and 5-[(R or S)-1-(4-iodo-2-nitrophenyl)-2,2-dimethyl-propyloxy]methyl-2'-deoxyuridine (49 mg, 8%) were also obtained from the reaction. $^1$H NMR (400 MHz, CDCl$_3$) for dU.z1: δ 8.86 (s, 1 H, 3-NH), 8.08 (d, 1 H, J=1.8 Hz, Ph-H), 7.94 (dd, J=8.4 and 1.7 Hz, 1 H, Ph-H), 7.68 (s, 1 H, H-6), 7.47 (d, 1 H, J=8.4 Hz, Ph-H), 6.29 (dd, 1 H, J=7.8 and 5.8 Hz, H-1'), 4.91 (s, 1 H, PhCH), 4.39 (m, 1 H, H-3'), 4.23 (AB d, J=11.8 Hz, 1 H, 5-CH$_2$a), 4.01 (AB d, J=11.8 Hz, 1 H, 5-CH$_2$b), 3.98 (m, 1 H, H-4'), 3.78 (m, 2 H, H-5'a and H-5'b), 2.31 (m, 1 H, H-2'a), 1.99 (m, 1 H, H-2'b), 1.91 (m, 1 H, CH(CH$_3$)$_3$), 0.90 (s, 9 H, (CH$_3$)$_3$CSi), 0.89 (s, 9 H, (CH$_3$)$_3$CSi), 0.82 (s, 9 H, (CH$_3$)$_3$CC), 0.09 (2 s, 6 H, (CH$_3$)$_2$Si), 0.08 (s, 3 H, CH$_3$Si), 0.06 (s, 3 H, CH$_3$Si); $^{13}$C NMR (100 MHz, CDCl$_3$) for dU.z1: δ 162.41 (C), 150.98 (C), 150.00 (C), 141.60 (CH), 138.58 (CH), 133.83 (C), 132.26 (CH), 131.89 (CH), 111.16 (C), 92.05 (C), 88.03 (CH), 85.49 (CH), 81.62 (CH), 72.46 (CH), 64.64 (CH$_2$), 63.22 (CH$_2$), 41.22 (CH$_2$), 36.55 (C), 25.92 (C(CH$_3$)$_3$), 25.75 (C(CH$_3$)$_3$), 25.70 (C(CH$_3$)$_3$), 18.38 (C), 18.00 (C), −4.64 (CH$_3$Si), −4.81 (CH$_3$Si), −5.39 (2 (CH$_3$)$_2$Si).

3',5'-O-Bis-(tert-butyldimethylsilyl)-5-[(R or S)-1-(4-iodo-2-nitrophenyl)-2,2-di-methyl-propyloxy]methyl-O$^4$-(2,4,6-triisopropylbenzenesulfonyl)-2'-deoxyuridine (dU.z2): 2,4,6-Triisopropyl benzenesulfonyl chloride (1.57 g, 5.19 mmol) was added to a solution of compound dU.z1 (0.236 g, 0.29 mmol), DMAP (38 mg, 0.32 mmol) and tri-ethylamine (0.465 mL, 3.31 mmol) in anhydrous dichloromethane (10 mL). The mixture was stirred at room temperature for 24 hours under a nitrogen atmosphere, then concentrated in vacuo and purified by silica gel column chromatography to give 3',5'-β-bis-(tert-butyldimethylsilyl)-5-[(R or S)-1-(4-iodo-2-nitrophenyl)-2,2-dimethyl-propyloxy]methyl-O$^4$-(2,4,6-triisopropylbenzenesulfonyl)-2'-deoxyuridine dU.z2 (169 mg, 54%). $^1$H NMR (500 MHz, CDCl$_3$): δ 8.18 (s, 1 H, H-6), 8.10 (d, J=1.8 Hz, 1 H, Ph-H), 7.98 (dd, J=8.3 and 1.8 Hz, 1 H, Ph-H), 7.63 (d, J=8.3 Hz, 1 H, Ph-H), 7.20 (s, 2 H, OSO$_2$Ph-H), 6.10 (t, J=6.3 Hz, 1 H, H-1'), 4.91 (s, 1 H, PhCH(t-Bu)O), 4.30 (m, 1 H, H-3'), 4.23 (m 3 H, 5-CH$_2$a and OSO$_2$Ph(o-CH(CH$_3$)$_2$)$_2$), 4.01 (m, 2 H, H-4' and 5-CH$_2$b), 3.85 (AB dd, J=11.4 and 3.3 Hz, 1 H, H-5'a), 3.74 (AB dd, J=11.4 and 2.8 Hz, 1 H, H-5'b), 2.90 (sep, J=6.9 Hz, 1 H, OSO$_2$Ph(p-CH(CH$_3$)$_2$)), 2.53 (m, 1 H, H-2'a), 1.94 (m, 1 H, H-2'b), 1.29 (d, J=6.9 Hz, 6 H, OSO$_2$Ph (p-CH(CH$_3$)$_2$)), 1.26 (d, J=7.2 Hz, 12 H, OSO$_2$Ph(o-CH (CH$_3$)$_2$)$_2$), 0.87 (s, 18 H, (CH$_3$)$_3$CSi), 0.85 (s, 9 H, (CH$_3$)$_3$CC), 0.06 and 0.05 (2 s, 12 H, 2 (CH$_3$)$_2$Si); $^{13}$C NMR (100 MHz, CDCl$_3$): δ 166.01 (C), 154.43 (C), 153.54 (C), 151.21 (C), 151.08 (C), 145.07 (CH), 141.49 (CH), 133.16 (C), 132.32 (CH), 131.76 (CH), 131.15 (C), 124.08 (CH), 104.64 (C), 92.25 (C), 88.60 (CH), 87.83 (CH), 82.48 (CH), 71.83 (CH), 64.33 (CH$_2$), 62.75 (CH$_2$), 42.31 (CH$_2$), 36.51 (C), 34.26 (CH), 29.68 (CH), 25.91 (C(CH$_3$)$_3$), 25.73 (C(CH$_3$)$_3$), 24.51 (C(CH$_3$)$_3$), 23.52 (CH$_3$), 23.45 (CH$_3$), 18.37 (C), 17.98 (C), −4.57 (CH$_3$), −4.91 (CH$_3$), −5.34 (CH$_3$), −5.39 (CH$_3$).

3',5'-O-Bis-(tert-butyldimethylsilyl)-5-[(R or S)-1-(4-iodo-2-nitrophenyl)-2,2-dimethyl-propyloxy]methyl-2'-deoxcytidine (dC.z3): Ammonia (0.5 M in dioxane, 4 mL, 2.0 mmol) was added to compound dU.z2 (169 mg, 0.158 mmol) and the mixture was transferred into a sealed tube, and heated at 96° C. for 16 hours. After cooled to room temperature, the mixture was concentrated under reduced pressure and purified by silica gel column chromatography to afford 3',5'-O-bis-(tert-butyldimethylsilyl)-5-[(R or S)-1-(4-iodo-2-nitrophenyl)-2,2-dimethyl-propyloxy]methyl-2'-deoxcytidine dC.z3 (83 mg, 65%). $^1$H NMR (400 MHz, CDCl$_3$) δ 8.04 (d, 1 H, J=1.6 Hz, Ph-H), 7.92 (dd, J=8.3 and 1.6 Hz, 1 H, Ph-H), 7.66 (s, 1 H, H-6), 7.42 (d, 1 H, J=8.3 Hz, Ph-H), 6.29 (t, 1 H, J=6.7 Hz, H-1'), 4.81 (s, 1 H, PhCH), 4.32 (m, 1 H, H-3'), 4.28 (AB d, J=12.9 Hz, 1 H, 5-CH$_2$a), 4.04 (AB d, J=12.9 Hz, 1 H, 5-CH$_2$b), 3.96 (m, 1 H, H-4'), 3.79 (AB dd, J=11.2 and 3.2 Hz, 1 H, H-5'a), 3.72 (AB dd, J=11.2 and 2.8 Hz, 1 H, H-5'b), 2.42 (m, 1 H, H-2'a), 1.90 (m, 1 H, H-2'b), 0.88 (s, 9 H, (CH$_3$)$_3$ CSi), 0.81 (s, 9 H, (CH$_3$)$_3$CSi), 0.80 (s, 9 H, (CH$_3$)$_3$CC), 0.07 (s, 3 H, CH$_3$Si), 0.06 (s, 3 H, CH$_3$Si), −0.05 (s, 6 H, (CH$_3$)$_2$Si); $^{13}$C NMR (100 MHz, CDCl$_3$): δ 165.23 (C), 155.63 (C), 151.24 (C), 141.01 (CH), 140.65 (CH), 133.29 (C), 132.26 (CH), 131.35 (CH), 101.59 (C), 92.38 (C), 87.80 (CH), 86.29 (CH), 81.00 (CH), 72.17 (CH), 66.80 (CH$_2$), 62.92 (CH$_2$), 42.10 (CH$_2$), 36.27 (C), 25.82 (C(CH$_3$)$_3$), 25.80 (C(CH$_3$)$_3$), 25.77 (C(CH$_3$)$_3$), 18.27 (C), 17.99 (C), −4.58 (CH$_3$), −4.85 (CH$_3$), −5.47 (CH$_3$), −5.53 (CH$_3$).

5-[(R or S)-1-(4-Iodo-2-nitrophenyl)-2,2-dimethyl-propyloxy]methyl-2'-deoxy-cytidine (dC.z4): A solution of tetra-n-butylammonium fluoride trihydrate (81 mg, 0.26 mmol) in THF (2 mL) was added to a solution of compound dC.z3 (82 mg, 0.10 mmol) in THF (3 mL). The mixture was stirred at room temperature for 1 hour, then concentrated in vacuo and purified by silica gel column chromatography to give 5-[(R or S)-1-(4-iodo-2-nitrophenyl)-2,2-dimethyl-propyloxy]methyl-2'-deoxycytidine dC.z4 (43 mg, 73%). $^1$H NMR (400 MHz, DMSO-d$_6$) δ 8.23 (d, 1 H, J=1.6 Hz, Ph-H), 8.06 (dd, J=8.4 and 1.6 Hz, 1 H, Ph-H), 7.73 (s, 1 H, H-6), 7.38 (d, 1 H, J=8.4 Hz, Ph-H), 7.37 and 6.64 (2 br. s, 2 H, D$_2$O exchangeable, 4-NH$_2$), 6.10 (t, 1 H, J=6.8 Hz, H-1'), 5.20 (d, J=4.0 Hz, 1 H, D$_2$O exchangeable, 3'-OH), 4.88 (t, J=5.2 Hz, 1 H, D$_2$O exchangeable, 5'-OH), 4.76 (s, 1 H, PhCH), 4.19 (m, 1 H, H-3'), 4.10 (s, 1 H, 5-CH$_2$a and 5-CH$_2$b), 3.75 (m, 1 H, H-4'), 3.51 (m, 2 H, H-5'a and H-5'b), 2.08 (m, 1 H, H-2'a), 1.93 (m, 1 H, H-2'b), 0.76 (s, 9 H, (CH$_3$)$_3$C).

5-[(R or S)-1-(4-{3-Trifluoroacetamido-1-propynyl}-2-nitrophenyl)-2,2-dimethyl-propyloxy]methyl-2'-deoxycytidine (dC.z5): A mixture of compound dC.z4 (40 mg, 0.069 mmol), N-propargyltrifluoroacetylamide (32 mg, 0.208 mmol), CuI (3 mg, 0.014 mmol), Et$_3$N (0.01 mL, 0.138 mmol) and tetrakis(triphenylphosphine)palladium(0) (8 mg, 0.007 mmol) in anhydrous DMF (3 mL) was stirred at room temperature for 4.5 hours. Methanol (3 mL) and methylene chloride (3 mL) were added, followed by sodium bicarbonate (32 mg, 0.380 mmol). The mixture was stirred for 15 minutes, then concentrated in vacuo and purified by silica gel column chromatography to yield 5-[(R or S)-1-(4-{3-trifluoroacetamido-1-propynyl}-2-nitrophenyl)-2,2-dimethyl-propyl-oxy]methyl-2'-deoxycytidine dC.z5 (35 mg, 85%). $^1$H NMR (400 MHz, DMSO-d$_6$): δ 10.13 (br t, 1 H, D$_2$O exchangeable, NHTFA), 7.94 (d, 1 H, J=1.6 Hz, Ph-H), 7.75 (m, 2 H, Ph-H and H-6), 7.63 (d, 1 H, J=8.2 Hz, Ph-H), 7.34 and 6.66 (2 br. s, 2 H, D$_2$O exchangeable, 4-NH$_2$), 6.10 (t, 1 H, J=6.8 Hz, H-1'), 5.20 (d, J=4.2 Hz, 1 H, D$_2$O exchangeable, 3'-OH), 4.89 (t, J=5.4 Hz, 1 H, D$_2$O exchangeable, 5'-OH), 4.82 (s, 1 H, PhCH), 4.31 (d, 2 H, J=5.4 Hz, CH$_2$NHTFA), 4.19 (m, 1 H, H-3'), 4.14 (AB d, J=12.5 Hz, 1 H, 5-CH$_2$a), 4.10 (AB d, J=12.5 Hz, 1 H, 5-CH$_2$b), 3.75 (m, 1 H, H-4'), 3.51 (m, 2 H, H-5'a and H-5'b), 2.08 (m, 1 H, H-2'a), 1.93 (m, 1 H, H-2'b), 0.76 (s, 9 H, (CH$_3$)$_3$C); $^{13}$C NMR (100 MHz, CD$_3$OD): δ 164.83 (C), 157.51 (C), 157.14 (C), 156.45 (C), 150.34 (C), 141.65 (CH), 134.48 (CH), 133.91 (C), 130.26 (CH), 126.50 (CH), 123.01 (C), 87.55 (CH), 86.28 (C), 86.08 (C), 80.77 (CH), 80.17 (C), 70.623 (CH), 65.74 (CH$_2$), 61.33 (CH$_2$), 40.51 (CH$_2$), 36.19 (C), 29.09 (CH$_2$), 24.83 (CH$_3$)$_3$C).

5-[(R or S)-1-(4-{3-Amino-1-propynyl}-2-nitrophenyl)-2,2-dimethyl-propyl-oxy]methyl-2'-deoxycytidine-5'-triphosphate (dC.z6): POCl$_3$ (2.5 µL, 0.027 mmol) was added to a solution of compound dC.z5 (11 mg, 0.018 mmol) and proton sponge (8 mg, 0.036 mmol) in trimethylphosphate (0.3 mL) at 0° C. and stirred for two hours. Additional POCl$_3$ (2.5 µL, 0.027 mmol) was added twice in one hour interval. A solution of bis-tri-n-butylammonium pyrophosphate (43 mg, 0.09 mmol) and tri-n-butylamine (20 µL) in anhydrous DMF (0.2 mL) was added. After five minutes of stirring, triethylammonium bicarbonate buffer (1 M, pH 7.5; 5 mL) was added. The reaction was stirred for one hour at room temperature and then concentrated in vacuo at 25° C. The residue was dissolved in water (5 mL), filtered, and part of the mixture was purified with reverse-phase HPLC using a Perkin Elmer OD-300 C$_{18}$ column (4.6×250 mm) to yield 5-{(R or S)-1-[4-(3-trifluoroacetamido-1-propynyl)-2-nitrophenyl]-2,2-dimethyl-propyloxy}methyl-2'-deoxy-cytidine-5'-trihosphate. Mobile phase: A, 100 mM triethylammonium acetate (TEAA) in water (pH 7.0); B, 100 mM TEAA in water/CH$_3$CN (30:70). The purified triphosphate was then treated with concentrated ammonium hydroxide (27%) at room temperature for two hours to yield 5-{(R or S)-1-[4-(3-amino-1-propynyl)-2-nitrophenyl]-2,2-dimethyl-propyloxy}methyl-2'-deoxycytidine-5'-trihosphate dC.z6. $^1$H NMR (400 MHz, CD$_3$OD) δ 8.01 (s, 1 H, H-6), 7.84 (d, 1 H, J=8.0 Hz, Ph-H), 7.67 (d, 1 H, J=8.0 Hz, Ph-H), 7.51 (m, 1 H, Ph-H), 6.11 (t, 1 H, J=6.4 Hz, H-1'), 4.54 (AB d, 1 H, J=13.6 Hz, 5-CH$_2$a), 4.49 (m, 1 H, H-3'), 4.35 (d, 1 H, J=13.6 Hz, 5-CH$_2$b), 4.15-3.81 (m, 4 H, H-4', H-5' and CH$_2$), 2.31 (m, 1 H, H-2'a), 2.12 (m, 1 H, H-2'b), 0.81 (s, 9 H, (CH$_3$)$_3$C); $^{31}$P NMR (162 MHz, D$_2$O) for diastereomers: 6-5.20 (d, J=19.4 Hz), −10.77 (d, J=19.4 Hz), −20.96 (t, J=19.4 Hz).

6-TAMRA labeled 5-[(R or S)-1-(4-{3-amino-1-propynyl}-2-nitrophenyl)-2,2-dimethyl-propyloxy]methyl-2'-deoxcytidine-5'-triphosphate (WW3p091): A solution of Cy5 mono NHS (0.65 mg, 1.23 µmol) in anhydrous DMSO (26 µL) was added to a solution of triphosphate dC.z6 (0.386 µmol) in Na$_2$CO$_3$/NaHCO$_3$ buffer (0.1 M, pH 9.2; 200 µL) and left at room temperature for one hour. The reaction was purified by reverse-phase HPLC using a Perkin Elmer OD-300 C$_{18}$ column (4.6×250 mm) to yield the 6-TAMRA labeled triphosphate WW3p091. Mobile phase: A, 100 mM TEAA in water (pH 7.0); B, 100 mM TEAA in water/CH$_3$CN (30:70).

Example 7

Synthesis of 7-Deazaguanosine Analogs

Synthesis of 7-(2-nitrobenzyloxy)methyl-7-deaza-2'-deoxyguanosine-5'-triphosphate

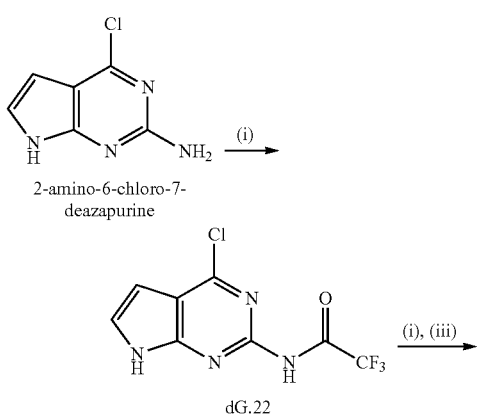

Scheme 19. Synthesis of 7-(2-nitrobenzyloxy)methyl-7-deaza-2'-deoxyguanosine-5'-triphosphate.

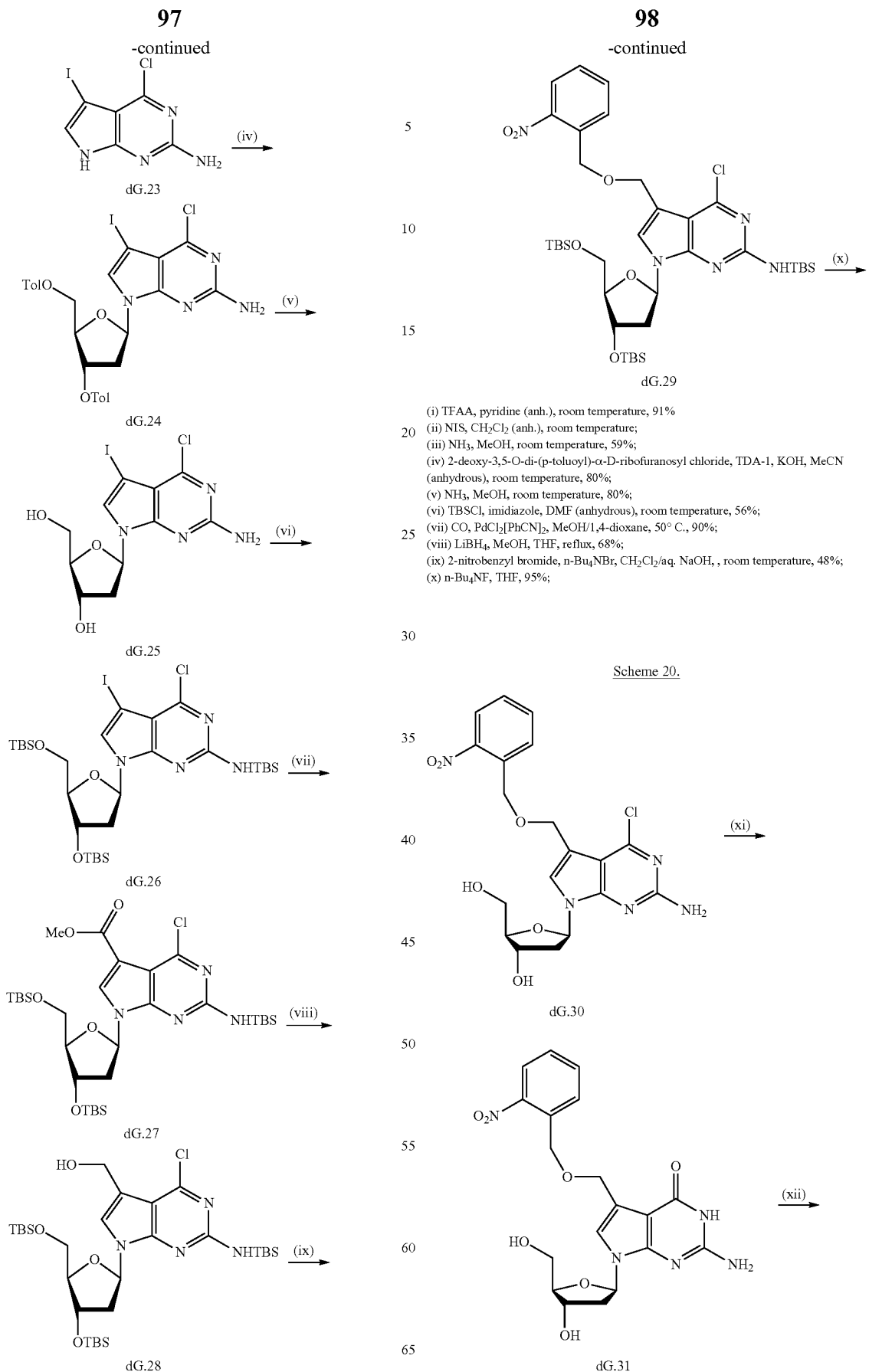

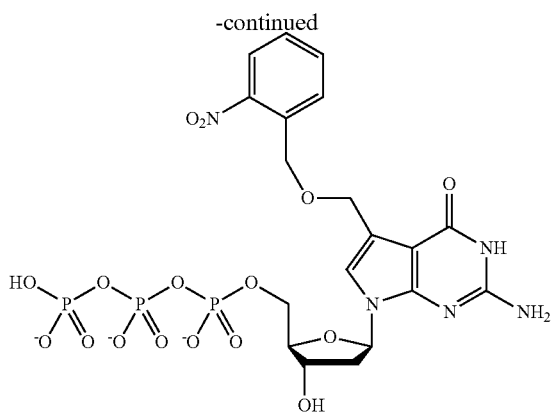

WW5p107

(xi) DABCO, H₃O, reflux, 30%; (xii) POCl₃, proton sponge, (MeO)₃PO, 0° C.; (n-Bu₃NH)₂H₂P₂O₇, n-Bu₃N, DMF; 1M HNEt₃HCO₃.

6-Chloro-2-(trifluoroacetyl)amino-7-deazapurine (dG.22): Compound dG.22 was synthesized according to the procedure described by Seela and Peng (2006, which is incorporated herein by reference). To a solution of 2-amino-6-chloro-7-deazapurine (2.00 g, 11.86 mmol) in anhydrous pyridine (15 mL) was added trifluoroacetic anhydride (2.18 mL, 15.54 mmol) over fifteen minutes. The solution was stirred at room temperature for three hours and concentrated in vacuo and co-evaporated with water (2 mL) two times. The material was then filtered, washed with cold water, and dried over KOH under vacuum to yield 6-choloro-2-(trifluoroacetyl)amino-7-deazapurine dG.22 (2.86 g, 91%) as an amber solid.

2-Amino-6-chloro-7-iodo-7-deazapurine (dG.23): Compound dG.23 was synthesized according to the procedure described by Seela and Peng (2006, which is incorporated herein by reference). To a suspension of compound dG.22 (2.86 g, 10.81 mmol) in anhydrous CH₂Cl₂ (51 mL) was added N-iodosuccinimide (2.68 g, 11.89 mmol). The mixture was protected from light while stirring at room temperature for two hours. The reaction was then diluted with 322 mL CH₂Cl₂ and filtered; the precipitate was then dissolved in 7N NH₃ in methanol solution (41 mL) and stirred at room temperature for three hours. The resulting solid was filtered and dried in vacuo to yield 2-amino-6-chloro-7-iodo-7-deazapurine dG.23 (1.86 g, 59%) as an amber solid.

2-Amino-6-chloro-9-[β-D-3',5'-O-di-(p-toluoyl)-2'-deoxyribofuranosyl]-7-iodo-7-deazapurine (dG.24): To a suspension of KOH (1.38 g, 22.16 mmol) and tris(3,6-dioxaheptyl)amine (0.26 mL, 0.80 mmol) in anhydrous acetonitrile (76 mL) was added compound dG.23 (1.86 g, 6.33 mmol). After stirring the mixture for five minutes, 2-deoxy-3,5-di-O-(p-toluoyl)-α-D-ribofuranosyl chloride (3.20 g, 8.23 mmol) was added over 15 minutes. The reaction was stirred at room temperature for 30 minutes then filtered, and the precipitate was washed with acetonitrile (75 mL). The combined filtrated was concentrated in vacuo and purified by silica gel chromatography to yield 2-amino-6-chloro-9-[β-D-3',5'-O-di-(p-toluoyl)-2'-deoxyribofuranosyl]-7-iodo-7-deazapurine dG.24 (3.29 g, 80%) as a white foam. ¹H NMR (400 MHz, CDCl₃): δ 8.05 (m, 4 H, Ph-H), 7.39 (s, 1 H, H-8), 7.37 (m, 4 H, Ph-H), 6.66 (dd, 1 H, J=8.0 and 6.0 Hz, H-1'), 5.83 (m, 1 H, H-3'), 5.24 (bs, 2 H, 2-NH₂), 4.85 (dd, 1 H, H-5'a), 4.74 (dd, 1 H, H-5'b), 4.68 (m, 1 H, H-4'), 2.88 (m, 1 H, H-2'a), 2.76 (m, 1 H, H-2'b), 2.54 (s, 3 H, Ph-CH₃), 2.53 (s, 3 H, Ph-CH₃).

2-Amino-6-chloro-9-(β-D-2'-deoxyribofuranosyl)-7-iodo-7-deazapurine (dG.25): Compound dG.24 (3.29 g, 5.09 mmol) was dissolved in 7N NH₃ in methanol solution (153 mL) and stirred at room temperature for 32 hours. The mixture was concentrated in vacuo and purified by silica gel chromatography to yield 2-amino-6-chloro-9-(β-D-2'-deoxyribofuranosyl)-7-iodo-7-deazapurine dG.25 (1.66 g, 80% yield) as a white foam. ¹H NMR (400 MHz, DMSO-d₆): δ 7.60 (s, 1 H, H-8), 6.87 (bs, 2 H, 2-NH₂), 6.40 (dd, 1 H, J=8.0 and 6.0 Hz, H-1'), 5.25 (d, 1 H, 3'-OH), 4.93 (t, 1 H, 5'-OH), 4.30 (m, 1 H, H-3'), 3.78 (m, 1 H, H-4'), 3.51 (m, 2 H, H-5'a and H-5'b), 2.40 (m, 1 H, H-2'a), 2.13 (m, 1 H, H-2'b).

9-[β-D-3',5'-O-Bis-(tert-butyldimethylsilyl)-2'-deoxyribofuranosyl]-2-(tert-butyldimethylsilyl)amino-6-chloro-7-iodo-7-deazapurine (dG.26): Compound dG.25 (0.29 g, 0.70 mmol) was evaporated from anhydrous pyridine three times (3 mL each) and then dissolved in anhydrous DMF (5 mL). tert-Butyldimethylsilyl chloride (1.27 g, 8.43 mmol) and imidazole (1.15 g, 16.86 mmol) were added, and the mixture was stirred at 40° C. for 42 hours (additional tert-butyldimethylsilyl chloride (0.64 g, 4.22 mmol) and imidazole (0.57 g, 8.43 mmol were added every six hours). The reaction was concentrated in vacuo and purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-iodo-7-deazapurine dG.26 (0.30 g, 56% yield) as a white foam. ¹H NMR (400 MHz, CDCl₃): δ 7.35 (s, 1 H, H-8), 6.53 (t, 1 H, J=6.0 Hz, H-1'), 4.70 (s, 1 H, 2-NH), 4.47 (m, 1 H, H-3'), 3.97 (m, 1 H, H-4'), 3.78 (m, 2 H, H-5'a and H-5'b), 2.23 (m, 2 H, H-2'a and H-2'b), 0.98 (s, 9 H, (CH₃)₃CSi), 0.95 (s, 9 H, (CH₃)₃CSi), 0.90 (s, 9 H, (CH₃)₃CSi), 0.29 (2 s, 6 H, (CH₃)₂Si), 0.13 (2 s, 6 H, CH₃)₂Si), 0.09 (s, 6 H, CH₃)₂Si).

9-[β-D-3',5'-O-Bis-(tert-butyldimethylsilyl)-2'-deoxyribofuranosyl]-2-(tert-butyl-dimethylsilyl)amino-6-chloro-7-methoxycarbonyl-7-deazapurine (dG.27): A solution of dG.26 (105 mg, 0.139 mmol) was dissolved in anhydrous 1,4-dioxane (6 mL). Anhydrous methanol (6 mL) and triethylamine (0.04 mL) were added, and the mixture was stirred for ten minutes under carbon monoxide atmosphere, followed by addition of bis(benzonitrile)dichloropalladium(II). The reaction was stirred at 50° C. for 48 hours under CO atmosphere, and then concentrated in vacuo. The residue was purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-methoxycarbonyl-7-deazapurine dG.27 (112 mg, 90%) as a viscous oil. ¹H NMR (400 MHz, CDCl₃): δ 7.92 (s, 1 H, H-8), 6.57 (dd, 1 H, J=8.0 and 6.0 Hz, H-1'), 4.78 (s, 1 H, 2-NH), 4.49 (m, 1 H, H-3'), 4.02 (m, 1 H, H-4'), 3.85 (s, 3 H, CH₃), 3.81 (m, 2 H, H-5'a and H-5'b), 2.25 (m, 2 H, H-2'a and H-2'b), 0.98 (s, 9 H, (CH₃)₃CSi), 0.93 (s, 9 H, (CH₃)₃CSi), 0.92 (s, 9 H, (CH₃)₃CSi), 0.31 (s, 6 H, (CH₃)₂Si), 0.13 (2 s, 6 H, (CH₃)₂Si), 0.11 (s, 6 H, (CH₃)₂Si); ¹³C NMR (100 MHz, CDCl₃): δ 163.04 (C), 160.06 (C), 154.46 (C), 153.04 (C), 129.81 (CH), 107.79 (C), 107.51 (C), 87.86 (CH), 84.05 (CH), 72.73 (CH), 63.21 (CH₂), 51.26 (CH₃), 42.21 (CH₂), 26.48 (CH₃), 25.96 (CH₃), 25.72 (CH₃), 18.42 (C), 18.03 (C), 17.59 (C), −4.73 (CH₃), −4.80 (CH₃), −5.49 (CH₃), −5.57 (CH₃).

9-[β-D-3',5'-O-Bis-(tert-butyldimethylsilyl)-2'-deoxyribofuranosyl]-2-(tert-butyldimethylsilyl)amino-6-chloro-7-hydroxymethyl-7-deazapurine (dG.28): To a solution of dG.27 (52 mg, 0.076 mmol) in anhydrous THF (3 mL) lithium borohydride (0.007 g, 0.305 mmol) was added, followed by methanol (0.05 mL). The reaction mixture was heated at reflux for one hour. Upon cooling down, the reaction mixture was diluted with dichloromethane (100 mL), quenched with water (10 mL); the organic layer was separated, washed two times with brine (10 mL each), dried over anhydrous sodium sulfate, and concentrated in vacuo. The residue was purified by silica gel chromatography to yield 9-[β-D-3',5'-O-bis-(tert-butyldimethylsilyl)-2'-deoxyribo-furanosyl]-2-(tert-butyldimethylsilyl)amino-6-chloro-7-hydroxymethyl-7-deazapurine dG.28 (0.12 g, 45%) as a viscous oil. $^1$H NMR (400 MHz, CDCl$_3$): δ 7.16 (s, 1 H, H-8), 6.56 (t, 1 H, J=6.4 Hz, H-1'), 4.79 (AB d, J=13.6 Hz, 7-CH$_2$a), 4.75 (AB d, J=13.6 Hz, 7-CH$_2$b), 4.70 (s, 1 H, 2-NH), 4.50 (m, 1 H, H-3'), 3.96 (m, 1 H, H-4'), 3.76 (m, 2 H, H-5'a and H-5'b), 2.23 (m, 2 H, H-2'a and H-2'b), 0.98 (s, 9 H, (CH$_3$)$_3$CSi), 0.94 (s, 9 H, (CH$_3$)$_3$CSi), 0.92 (s, 9 H, (CH$_3$)$_3$CSi), 0.30 (s, 3 H, (CH$_3$)$_2$Si), 0.29 (s, 3 H, (CH$_3$)$_2$Si), 0.11 (s, 6 H, (CH$_3$)$_2$Si), 0.10 (s, 6 H, (CH$_3$)$_2$Si); $^{13}$C NMR (100 MHz, CDCl$_3$): δ 160.07 (C), 154.29 (C), 151.23 (C), 120.92 (CH), 115.65 (C), 108.44 (C), 87.26 (CH), 83.21 (CH), 72.50 (CH), 63.28 (CH$_2$), 57.15 (CH$_2$), 42.33 (CH$_2$), 26.55 (CH$_3$), 25.97 (CH$_3$), 25.73 (CH$_3$), 18.42 (C), 17.93 (C), 17.61 (C), −4.71 (CH$_3$), −4.75 (CH$_3$), −5.34 (CH$_3$), −5.47 (CH$_3$).

9-[β-D-3',5'-O-Bis-(tert-butyldimethylsilyl)-2'-deoxyribofuranosyl]-2-(tert-butyl-dimethylsilyl)amino-6-chloro-7-(2-nitrobenzyloxy)methyl-7-deazapurine (dG.29): To a solution of compound dG.28 (150 mg, 0.23 mmol) in CH$_2$Cl$_2$ (3 mL) were added n-Bu$_4$NBr (37 mg, 0.12 mmol), 2-nitrobenzyl bromide (148 mg, 0.68 mmol) and 1 M NaOH solution (3 mL). The reaction mixture was stirred vigorously at room temperature for two days in the dark. The organic layer was separated, dried over Na$_2$SO$_4$, concentrated in vacuo, and purified by silica gel chromatography to yield 9-[β-D-3',5'-O-bis-(tert-butyldimethylsilyl)-2'-deoxyribofuranosyl]-2-(tert-butyldimethylsilyl)amino-6-chloro-7-(2-nitrobenzyloxy)methyl-7-deazapurine dG.29 (87 mg, 48%) as a viscous oil. $^1$H NMR (400 MHz, CDCl$_3$): δ 8.06 (dd, 1 H, J=8.0 and 1.2 Hz, Ph-H), 7.87 (d, 1 H, J=7.2 Hz, Ph-H), 7.61 (dt, 1 H, J=7.6 and 1.2 Hz, Ph-H), 7.43 (m, 1 H, Ph-H), 7.20 (s, 1 H, H-8), 6.56 (dd, 1 H, J=7.6 and 6.0 Hz, H-1'), 4.99 (s, 2 H, PhCH$_2$), 4.83 (AB d, 1 H, J=11.4 Hz, 7-CH$_2$a), 4.75 (AB d, 1 H, J=11.4 Hz, 7-CH$_2$b), 4.67 (s, 1 H, 2-NH), 4.50 (m, 1 H, H-3'), 3.96 (m, 1 H, H-4'), 3.77 (m, 2 H, H-5'a and H-5'b), 2.25 (m, 2 H, H-2'a and H-2'b), 0.98 (s, 9 H, (CH$_3$)$_3$CSi), 0.92 (s, 18 H, (CH$_3$)$_3$CSi), 0.30 (s, 3 H, (CH$_3$)$_2$Si), 0.29 (s, 3 H, (CH$_3$)$_2$Si), 0.09 (m, 12 H, (CH$_3$)$_2$Si); $^{13}$C NMR (100 MHz, CDCl$_3$): δ 159.94 (C), 154.18 (C), 151.78 (C), 147.16 (C), 135.23 (C), 133.6 (CH), 129.0 (CH), 127.75 (CH), 124.49 (CH), 121.85 (CH), 112.17 (C), 108.74 (C), 87.24 (CH), 83.22 (CH), 72.50 (CH), 68.48 (CH$_2$), 65.04 (CH$_2$), 63.27 (CH$_2$), 41.31 (CH$_2$), 26.52 (CH$_3$), 25.93 (CH$_3$), 25.7 (CH$_3$), 18.36 (C), 17.89 (C), 17.56 (C), −4.75 (CH$_3$), −4.81 (CH$_3$), −5.39 (CH$_3$), −5.52 (CH$_3$).

2-Amino-6-chloro-9-[β-D-2'-deoxyribofuranosyl]-7-(2-nitrobenzyloxy)methyl-7-deazapurine (dG.30): A solution of n-Bu$_4$NF (123 mg, 0.39 mmol) in THF (2 mL) was added dropwise to a solution of compound dG.29 (105 mg, 0.13 mmol) in THF (3 mL) at 0° C. The reaction mixture was stirred at 0° C. for one hour and then at room temperature for two hours. The reaction was concentrated in vacuo and purified by silica gel chromatography to yield 2-amino-6-chloro-9-[β-D-2'-deoxyribofuranosyl]-7-(2-nitrobenzyloxy)methyl-7-deazapurine dG.30 (57 mg, 95%) as a yellow foam. $^1$H NMR (400 MHz, DMSO-d$_6$): 6, 8.02 (m, 1 H, Ph-H), 7.74 (m, 2 H, Ph-H), 7.55 (m, 1 H, Ph-H), 7.41 (s, 1 H, H-8), 6.73 (s, 2 H, D$_2$O exchangeable, NH$_2$), 6.41 (dd, 1 H, J=8.4 and 6.0 Hz, H-1'), 5.26 (d, 1 H, D$_2$O exchangeable, 3'-OH), 4.91 (t, 1 H, D$_2$O exchangeable, 5'-OH), 4.88 (s, 2 H, Ph-CH$_2$), 4.66 (dd, 2 H, J=11.6 Hz, 7-CH$_2$), 4.31 (m, 1 H, H-3'), 3.78 (m, 1 H, H-4'), 3.50 (m, 2 H, H-5'), 2.38 (m, 1 H, H-2'a), 2.15 (m, 1 H, H-2'b).

7-(2-Nitrobenzyloxy)methyl-7-deaza-2'-deoxyguanosine (dG.31): A mixture of dG.29 (38 mg, 0.084 mmol) and 1,4-diazabicyclo[2.2.2]octane (11 mg, 0.1 mmol) in water (4 mL) was heated to reflux under a nitrogen atmosphere for 4 hours. Water was removed in vacuo, and the residue was evaporated from methanol three times (3 mL each), and purified by silica gel chromatography to yield 7-(2-nitrobenzyloxy)methyl-7-deaza-2'-deoxyguanosine dG.31 (11 mg, 30%). $^1$H NMR (400 MHz, DMSO-d$_6$): δ 10.4 (s, 1 H, D$_2$O exchangeable, N—H), 8.03 (dd, 1 H, J=8.4 and 0.8 Hz, Ph-H), 7.83 (d, 1 H, J=7.6 Hz, Ph-H), 7.73 (m, 1 H, Ph-H), 7.55 (m, 1 H, Ph-H), 6.92 (s, 1 H, H-8), 6.28 (m, 1 H, H-1'), 6.26 (bs, 2 H, D$_2$O exchangeable, NH$_2$), 5.21 (d, 1 H, D$_2$O exchangeable, 3'-OH), 4.89 (t, 1 H, D$_2$O exchangeable, 5'-OH), 4.88 (s, 2 H, Ph-CH$_2$), 4.60 (dd, 2 H, 7-CH$_2$), 4.28 (m, 1 H, H-3'), 3.74 (m, 1 H, H-4'), 3.48 (m, 2 H, H-5'), 2.32 (m, 1 H, H-2'a), 2.08 (m, 1 H, H-2'b).

7-(2-Nitrobenzyloxy)methyl-7-deaza-2'-deoxyguanosine-5'-triphosphate (WW5p107): POCl$_3$ (5 μL, 0.05 mmol) was added to a solution of compound dG.31 (11 mg, 0.025 mmol) in trimethylphosphate (0.3 mL), and the reaction was stirred at 0° C. under a nitrogen atmosphere for two hours. A solution of bis-tri-n-butylammonium pyrophosphate (118 mg, 0.25 mmol) and tri-n-butylamine (50 μL) in anhydrous DMF (0.5 mL) was added. After 30 minutes of stirring, triethylammonium bicarbonate buffer (1 M, pH 7.5; 5 mL) was added. The reaction was stirred for one hour at room temperature and then concentrated in vacuo. The residue was dissolved in water (10 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to give 7-(2-nitrobenzyloxy)methyl-7-deaza-2'-deoxyguanosine-5'-triphosphate WW5p107 which was further purified by reverse phase HPLC on a Perkin Elmer Aquapore OD-300 column (7 μm, 250×4.6 mm). Mobile phase: A, 100 mM triethylammonium acetate (TEAA) in water; B, 100 mM TEAA in water/CH$_3$CN (30:70).

Synthesis of 7-[1-(2-nitrophenyl)-2-methyl-propyloxy]methyl-7-deaza-2'-deoxyguanosine-5'-triphosphate Scheme 21.

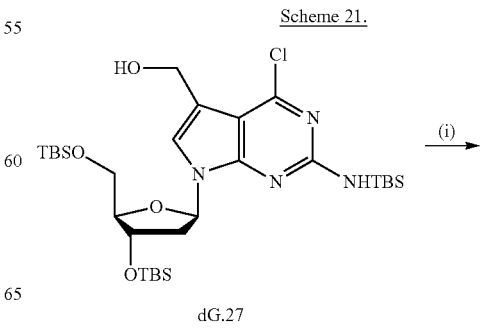

dG.27

103

-continued

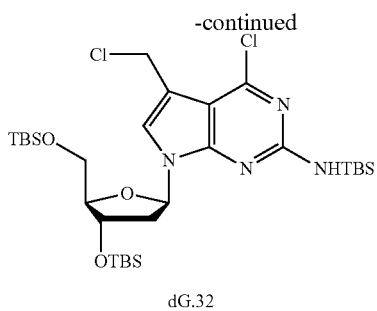

dG.32

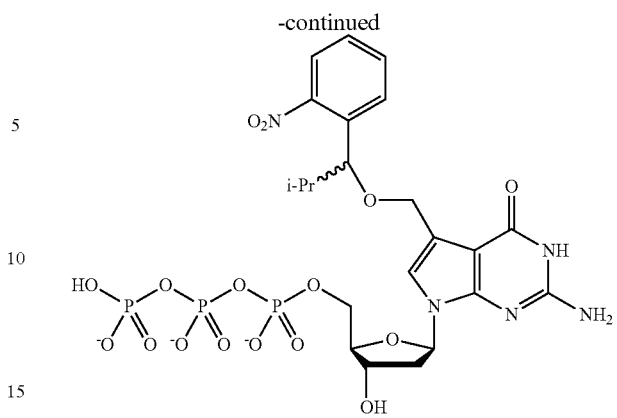

dG.33 dG.34

104

-continued

WW5p143 ds1 & ds2

Synthesis of 7-[1-(2-nitrophenyl)-2-methyl-propyloxy]methyl-7-deaza-2'-deoxyguanosine-5'-triphosphate.
(i) PPh$_3$/CH$_2$Cl$_2$ (anhydrous), K$_2$CO$_3$, reflux, 46%;
(ii) 1-(2-nitrophenyl)-2-methyl-propanol (racemic), neat, vacuum, 124° C.; (iii) n-Bu$_4$NF, THF, 7% for two steps; (iv) DABCO, H$_2$O, reflux, 29%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

9-[β-D-3',5'-O-Bis-(tert-butyldimethylsilyl)-2'-deoxyribofuranosyl]-2-(tert-butyldimethylsilyl)amino-6-chloro-7-chloromethyl-7-deazapurine (dG.32): To a solution of dG.27 (1.22 g, 1.84 mmol) in carbon tetrachloride (24 mL, freshly distilled from CaH$_2$) were added potassium carbonate (1.00 g, 7.36 mmol) and triphenyl phosphine (1.20 g, 4.60 mmol). The reaction was stirred at reflux for 24 hours. The mixture was concentrated in vacuo and purified by silica gel chromatography to yield 9-[β-D-3',5'-β-bis-(tert-butyldimethylsilyl)-2'-deoxyribofuranosyl]-2-(tert-butyldimethylsilyl) amino-6-chloro-7-chloromethyl-7-deazapurine dG.32 (0.54 g, 43%) as foam. $^1$H NMR (400 MHz, CDCl$_3$): δ 7.16 (s, 1 H, H-8), 6.54 (dd, 1 H, J=8.0 and 6.0 Hz, H-1'), 4.78 (AB d, J=11.4 Hz, 7-CH$_2$a), 4.68 (AB d, J=11.4 Hz, 7-CH$_2$b), 4.64 (s, 1 H, 2-NH), 4.47 (m, 1 H, H-3'), 3.94 (m, 1 H, H-4'), 3.73 (m, 2 H, H-5'a and H-5'b), 2.20 (m, 2 H, H-2'a and H-2'b), 0.98 (s, 9 H, (CH$_3$)$_3$CSi), 0.91 (s, 9 H, (CH$_3$)$_3$CSi), 0.90 (s, 9 H, (CH$_3$)$_3$CSi), 0.28 (2 s, 6 H, (CH$_3$)$_2$Si), 0.09 (2 s, 6 H, (CH$_3$)$_2$Si), 0.07 (2 s, 6 H, (CH$_3$)$_2$Si); $^{13}$C NMR (100 MHz, CDCl$_3$): δ 159.85 (C), 154.16 (C), 151.82 (C), 121.86 (CH), 112.80 (C), 108.94 (C), 87.23 (CH), 83.17 (CH), 72.58 (CH), 63.35 (CH$_2$), 41.24 (CH$_2$), 29.72 (CH$_2$), 26.57 (CH$_3$), 25.97 (CH$_3$), 25.74 (CH$_3$), 18.38 (C), 17.93 (C), 17.62 (C), −4.71 (CH$_3$), −4.74 (CH$_3$), −4.76 (CH$_3$), −5.37 (CH$_3$), −5.49 (CH$_3$).

2-Amino-6-chloro-9-[β-D-2'-deoxyribofuranosyl]-7-[1-(2-nitrophenyl)-2-methyl-propyl-oxy]methyl-7-deazapurine (dG.33): Compound dG.32 (0.82 g, 1.21 mmol) and 1-(2-nitrophenyl)-2-methyl-propanol (2.36 g, 12.10 mmol) were dissolved in anhydrous dichloromethane (10 mL). The solvent was removed in vacuo, and the residue was heated in vacuo at 124° C. for 22 hours, then dissolved in ethyl acetate and purified by silica gel chromatography to yield crude 9-[β-D-3',5'-O-bis-(tert-butyldimethylsilyl)-2'-deoxyribofuranosyl]-2-amino-6-chloro-7-[1-(2-nitrophenyl)-2-methyl-propyloxy]methyl-7-deazapurine. This intermediate was then dissolved in tetrahydrofuran (14 mL) and treated with tetra-n-butylammonium fluoride trihydrate (0.954 g, 3.03 mmol). After 30 minutes, the mixture was evaporated and purified by column chromatography to yield 9-[β-D-2'-deoxyribofuranosyl]-2-amino-6-chloro-7-[1-(2-nitrophenyl)-2-methyl-propyl-oxy]methyl-7-deazapurine dG.33 (41 mg, 7%, 1:1 mixture of diastereomers). $^1$H NMR (400 MHz, CD₃OD) for diastereomers: δ 7.82 and 7.79 (2 dd, J=8.0 and 1.2 Hz, 1 H, Ph-H), 7.72 (dt, J=8.0 and 1.6 Hz, 1 H, Ph-H), 7.60 (m, 1 H, Ph-H), 7.41 (m, 1 H, Ph-H), 7.17 and 7.14 (2 s, 1 H, H-8), 6.41 (m, 1 H, H-1'), 4.71 (t, 1 H, J=6.8 Hz Ph-CH), 4.48 (m, 2 H, 7-CH₂ and H-3'), 3.94 (m, 1 H, H-4'), 3.71 (m, 2 H, H-5'), 2.53 (m, 1 H, H-2'a), 2.27 (m, 1 H, H-2'b), 1.92 (oct, J=6.8 Hz, 1 H, CHCH(CH₃)₂), 0.96 and 0.94 (2 d, J=6.8 Hz, 3 H, CH₃), 0.80 and 0.76 (2 d, J=6.8 Hz, 3 H, CH₃); ¹³C NMR (100 MHz, CD₃OD) for diastereomers: δ 160.65 (C), 155.83 and 155.78 (C), 153.54 and 153.45 (C), 151.39 and 151.12 (C), 138.42 and 138.27 (C), 133.89 and 133.77 (CH), 130.66 and 130.56 (CH), 129.44 and 129.36 (CH), 125.66 and 125.29 (CH), 124.97 and 124.88 (CH), 113.67 and 113.39 (C), 110.08 (C), 88.81 and 88.78 (CH), 85.52 and 85.27 (CH), 81.60 and 81.87 (CH), 73.08 (CH), 64.71 and 64.18 (CH₂), 63.84 and 63.78 (CH₂), 41.00 and 40.86 (CH₂), 36.31 and 36.28 (CH), 19.77 and 19.73 (CH₃), 18.58 and 18.52 (CH₃).

7-[1-(2-nitrophenyl)-2-methyl-propyloxy]methyl-7-deaza-2'-deoxyguanosine (dG.34): A mixture of dG.33 (54 mg, 0.11 mmol) and 1,4-diazabicyclo[2.2.2]octane (25 mg, 0.22 mmol) in water (5 mL) was heated to reflux under a nitrogen atmosphere for three hours. Water was removed in vacuo, and the residue was evaporated from methanol three times (5 mL each), and purified by silica gel chromatography to yield 7-[1-(2-nitrophenyl)-2-methyl-propyloxy]methyl-7-deaza-2'-deoxyguanosine dG.34 (15 mg, 29%, 1:1 mixture of diastereomers). ¹H NMR (400 MHz, CD₃OD) for diastereomers: δ 7.82 (m, 1 H, Ph-H), 7.76 (m, 1 H, Ph-H), 7.60 (m, 1 H, Ph-H), 7.42 (m, 1 H, Ph-H), 6.81 and 6.78 (2 s, 1 H, H-8), 6.28 (m, 1 H, H-1'), 4.79 (m, 1 H, Ph-CH), 4.50 (m, 3 H, 7-CH₂ and H-3'), 3.92 (m, 1 H, H-4'), 3.71 (m, 2 H, H-5'), 2.48 (m, 1 H, H-2'a), 2.22 (m, 1 H, H-2'b), 1.92 (m, 1 H, CH), 0.93 (m, 3 H, CH₃), 0.83 (m, 3 H, CH₃).

7-[1-(2-Nitrophenyl)-2-methyl-propyloxy]methyl-7-deaza-2'-deoxyguanosine-5'-triphosphate (WW5p143 ds1 & ds2): POCl₃ (6 µL, 0.064 mmol) was added to a solution of compound dG.34 (15 mg, 0.032 mmol) in trimethylphosphate (0.4 mL) and the reaction was stirred at 0° C. under a nitrogen atmosphere for five hours. A solution of bis-tri-n-butylammonium pyrophosphate (285 mg, 0.6 mmol) and tri-n-butylamine (120 µL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to give 7-[1-(2-nitrophenyl)-2-methyl-propyloxy]methyl-7-deaza-2'-deoxyguanosine-5'-triphosphate WW5p143 as mixture of two diastereomers, which were separated by reverse phase HPLC on a Perkin Elmer Aquapore OD-300 column (7 µm, 250×4.6 mm) to yield the single diastereomer WW5p143_ds1 (fast eluting) and WW5p143_ds2 (slow eluting). Mobile phase: A, 100 mM triethylammonium acetate (TEAA) in water; B, 100 mM TEAA in water/CH₃CN (30:70).

Synthesis of 6-ROX labeled 7-{(R)-1-[4-(3-amino-1-propynyl)-2-nitrophenyl]-2-methyl-propyloxy}methyl-7-deaza-2'-deoxyguanosine-5'-triphosphate Scheme 22.

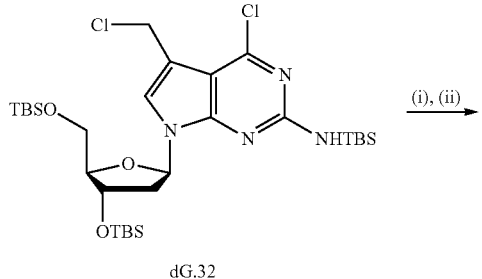

dG.32

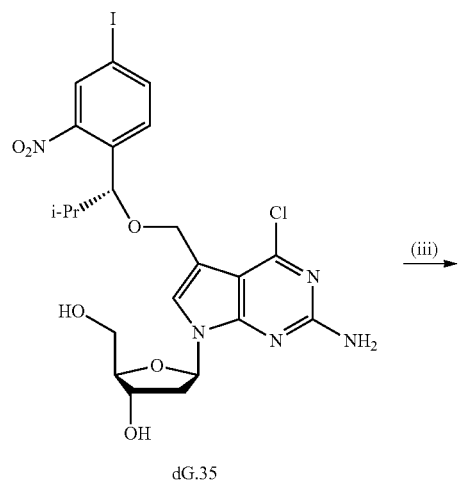

dG.35

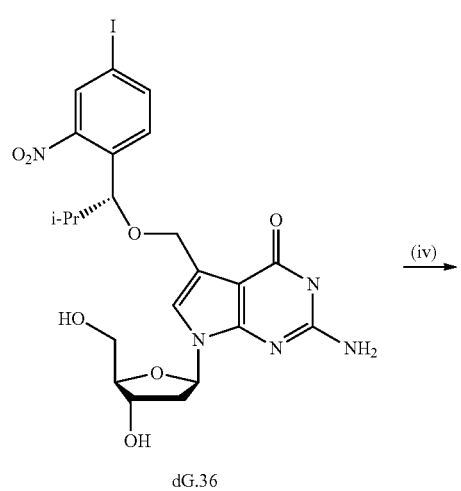

dG.36

107
-continued

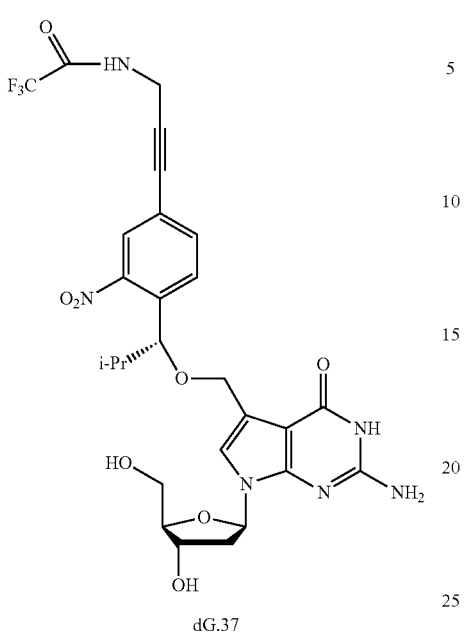
dG.37

Synthesis of 6-ROX labeled 7-{(R)-1-[4-(3-amino-1-propynyl)-2-nitrophenyl]-2-methyl-propyloxy}methyl-7-deaza-2'-deoxyguanosine-5'-triphosphate (i) (R)-1-(4-iodo-2-nitrophenyl)-2-methyl-propanol, neat, vacuum, 124° C.; (ii) n-Bu₄NF, THF, 13% for two steps; (iii) DABCO, H₂O, reflux, four hours, 23%; (iv) N-propargyltrifluoroacetamide, Pd(PPh₃)₄ (0), CuI, Et₃N, anhydrous DMF (anhydrous), four hours, 50%;

Scheme 23.

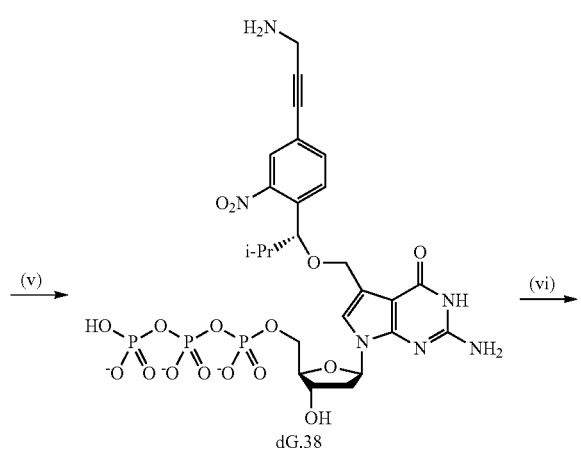
dG.38

108
-continued

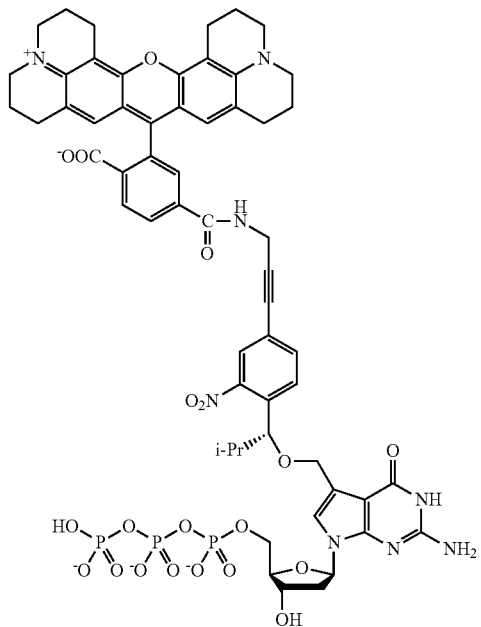
WW6p034

(v) POCl₃, proton sponge, (MeO)₃PO, 0° C.; (n-Bu₃NH)₂H₂P₂O₇, n-Bu₃N, DMF; 1M HNEt₃HCO₃; (vi) 6-ROX-SE, 0.1M Na₂CO₃/NaHCO₃ buffer (pH 9.2), one hour.

2-Amino-6-chloro-9-[β-D-2'-deoxyribofuranosyl]-7-[(R)-1-(4-iodo-2-nitro-phenyl)-2-methyl-propyloxy]methyl-7-deazapurine (dG.35): Compound dG.32 (0.62 g, 0.914 mmol) and (R)-1-(4-iodo-2-nitrophenyl)-2-methyl-propanol (3.52 g, 10.97 mmol) were dissolved in anhydrous dichloromethane (10 mL). The solvent was removed in vacuo, and the residue was heated in vacuo at 122° C. for 16 hours, then dissolved in ethyl acetate and purified by silica gel chromatography to yield crude 2-amino-6-chloro-9-[β-D-3',5'-O-bis-(tert-butyldimethylsilyl)-2'-deoxyribofuranosyl]-7-[(R)-1-(4-iodo-2-nitro-phenyl)-2-methyl-propyloxy]methyl-7-deazapurine that was dissolved in tetrahydrofuran (15 mL). The intermediate was treated with tetra-n-butylammonium fluoride trihydrate (0.72 g, 2.28 mmol). After 30 minutes, the mixture was evaporated and purified by column chromatography to yield 2-amino-6-chloro-9-[β-D-2'-deoxyribofuranosyl]-7-[(R)-1-(4-iodo-2-nitrophenyl)-2-methyl-propyloxy]methyl-7-deazapurine dG.35 (74 mg, 13%). ¹H NMR (400 MHz, CD₃OD): δ 8.09 (d, J=1.2 Hz, 1 H, Ph-H), 7.86 (dd, J=8.0 and 1.2 Hz, 1 H, Ph-H), 7.43 (d, J=8.0 Hz, 1 H, Ph-H), 7.14 (s, 1 H, H-8), 6.38 (dd, J=8.0 and 6.0 Hz, 1 H, H-1'), 4.65 (d, J=6.4 Hz, 1H, Ph-CH), 4.57 (AB d, J=12.4, 1 H, 7-CH₂a), 4.48 (m, 1 H, H-3'), 4.47 (AB d, J=12.4, 1 H, 7-CH₂b), 3.95 (m, 1 H, H-4'), 3.76 (AB dd, J=12.0 and 3.6 Hz, 1 H, H-5'a), 3.70 (AB dd, J=12.0 and 3.6 Hz, 1 H, H-5'b), 2.52 (m, 1 H, H-2'a), 2.26 (m, 1 H, H-2'b), 1.89 (oct, J=6.8 Hz, 1 H, CHCH(CH₃)₂), 0.94 (d, J=6.8 Hz, 3 H, CH₃), 0.79 (2 d, J=6.8 Hz, 3 H, CH₃); ¹³C NMR (100 MHz, CD₃OD): δ 159.09 (C), 151.52 (C), 151.95 (C), 149.53 (C), 141.20 (CH), 136.91 (C), 131.91 (CH), 130.96 (CH), 124.03 (CH), 111.96 (C), 108.59 (C), 90.84 (C), 87.29 (CH), 83.97 (CH), 79.92 (CH), 71.62 (CH), 63.44 (CH₂), 62.36 (CH₂), 39.31 (CH₂), 34.63 (CH), 18.22 (CH₃), 16.95 (CH₃).

7-[(R)-1-(4-iodo-2-nitrophenyl)-2-methyl-propyloxy]methyl-7-deaza-2'-deoxy-guanosine (dG.36): Compound dG.35 (72 mg, 0.12 mmol) and 1,4-diazabicyclo[2.2.2]octane (52 mg, 0.46 mmol) in water (5 mL) was heated to reflux under a nitrogen atmosphere for four hours. Water was removed in vacuo, and the residue was evaporated from methanol three times (5 mL each), and purified by silica gel chromatography to yield 7-[(R)-1-(4-iodo-2-nitrophenyl)-2-methyl-propyloxy]methyl-7-deaza-2'-deoxyguanosine dG.36 (16 mg, 23%). $^1$H NMR (400 MHz, CD$_3$OD): δ 8.12 (d, J=1.6 Hz, 1 H, Ph-H), 7.86 (dd, J=8.4 and 1.6 Hz, 1 H, Ph-H), 7.50 (d, J=8.4 Hz, 1 H, Ph-H), 6.80 (s, 1 H, H-8), 6.28 (dd, J=8.0 and 6.0 Hz, 1 H, H-1'), 4.74 (d, J=5.6 Hz, 1 H, Ph-CH), 4.55 (AB d, J=12.0, 1 H, 7-CH$_2$a), 4.48 (AB d, J=12.0, 1 H, 7-CH$_2$b), 4.44 (m, 1 H, H-3'), 3.92 (m, 1 H, H-4'), 3.75 (AB dd, J=12.0 and 4.0 Hz, 1 H, H-5'a), 3.69 (AB dd, J=12.0 and 4.0 Hz, 1 H, H-5'b), 2.46 (m, 1 H, H-2'a), 2.23 (m, 1 H, H-2'b), 1.91 (m, 1 H, CH), 0.93 (d, J=6.8 Hz, 3 H, CH$_3$), 0.86 (2 d, J=6.8 Hz, 3 H, CH$_3$).

7-{(R)-1-[4-(3-Trifluoroacetamido-1-propynyl)-2-nitrophenyl]-2-methyl-propyloxy}methyl-7-deaza-2'-deoxyguanosine (dG.37): A solution of compound dG.36 (15 mg, 0.025 mmol), N-propargyltrifluoroacetylamide (11 mg, 0.075 mmol), tetrakis(triphenylphosphine)-palladium(0) (3 mg, 0.0025 mmol), CuI (1 mg, 0.005 mmol), and Et$_3$N (7 μL, 0.050 mmol) in anhydrous DMF (1.5 mL) was stirred at room temperature for four hours. The mixture was concentrated in vacuo and purified by silica gel column chromatography to yield 7-{(R)-1-[4-(3-trifluoroacetamido-1-propynyl)-2-nitrophenyl]-2-methyl-propyloxy}methyl-7-deaza-2'-deoxyguanosine dG.37 (15 mg, 99%) as a waxy solid. $^1$H NMR (400 MHz, CD$_3$OD): δ 7.88 (d, J=1.6 Hz, 1 H, Ph-H), 7.75 (d, J=8.0 Hz, 1 H, Ph-H), 7.45 (dd, J=8.0 and 1.6 Hz, 1 H, Ph-H), 6.83 (s, 1 H, H-8), 6.30 (dd, J=8.4 and 6.4 Hz, 1 H, H-1'), 4.80 (d, J=6.4 Hz, 1 H, Ph-CH), 4.56 (AB d, J=12.0, 1 H, 7-CH$_2$a), 4.50 (AB d, J=12.0, 1 H, 7-CH$_2$b), 4.47 (m, 1 H, H-3'), 4.35 (s, 1 H, CH$_2$N), 3.94 (m, 1 H, H-4'), 3.77 (AB dd, J=12.0 and 4.0 Hz, 1 H, H-5'a), 3.71 (AB dd, J=12.0 and 4.0 Hz, 1 H, H-5'b), 2.49 (m, 1 H, H-2'a), 2.23 (m, 1 H, H-2'b), 1.93 (m, 1 H, CH), 0.95 (d, J=6.4 Hz, 3 H, CH$_3$), 0.87 (d, J=6.4 Hz, 3 H, CH$_3$); $^{13}$C NMR (100 MHz, CD$_3$OD): δ 161.61 (C), 154.02 (C), 152.67 (C), 150.49 (C), 142.69 (C), 139.77 (C), 136.37 (CH), 131.37 (CH), 127.90 (CH), 123.71 (C), 119.34 (CH), 117.19 (C), 116.42 (C), 88.69 (CH), 86.89 (C), 85.58 (CH), 81.93 (C), 81.42 (CH), 71.19 (CH), 65.42 (CH$_2$), 63.97 (CH$_2$), 41.12 (CH$_2$), 36.16 (CH), 30.63 (CH$_2$), 19.93 (CH$_3$), 18.00 (CH$_3$).

7-{(R)-1-[4-(3-Amino-1-propynyl)-2-nitrophenyl]-2-methyl-propyloxy}methyl-7-deaza-2'-deoxyguanosine-5'-triphosphate (dG.38): POCl$_3$ (7 μL, 0.076 mmol) was added to a solution of compound dG.37 (12 mg, 0.019 mmol) and proton sponge (8 mg, 0.038 mmol) in trimethylphosphate (0.3 mL), and the reaction was stirred at 0° C. under a nitrogen atmosphere for four hours. A solution of bis-tri-n-butylammonium pyrophosphate (237 mg, 0.5 mmol) and tri-n-butylamine (100 μL) in anhydrous DMF (1 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to dryness. The residue was dissolved in water (5 mL) and treated with concentrated ammonium hydroxide (2 mL, 27%) at room temperature for one hour to give 7-{(R)-1-[4-(3-amino-1-propynyl)-2-nitrophenyl]-2-methyl-propyloxy}methyl-7-deaza-2'-deoxyguanosine-5'-triphosphate dG.38 which was purified by reverse phase HPLC on a Perkin Elmer Aquapore OD-300 column (7 μm, 250×4.6 mm). Mobile phase: A, 100 mM triethylammonium acetate (TEAA) in water; B, 100 mM TEAA in water/CH$_3$CN (30:70).

6-ROX labeled 7-{(R)-1-[4-(3-amino-1-propynyl)-2-nitrophenyl]-2-methyl-propyloxy}methyl-7-deaza-2'-deoxyguanosine-5'-triphosphate (WW6p034): A solution of 6-ROX-SE (3.5 mg, 5.54 μmol) in anhydrous DMSO (280 μL) was added to a solution of triphosphate dG.38 (0.85 μmol) in Na$_2$CO$_3$/NaHCO$_3$ buffer (0.1 M, pH 9.2, 800 μL). The mixture was left at room temperature for one hour. The dye labeled triphosphate was first purified by anion exchange HPLC using a Perkin Elmer AX-300 column (7 μm, 250×4.6 mm). Mobile phase: A, 25% CH$_3$CN/75% 0.1 M TEAB; B, 25% CH$_3$CN/75% 1.5 M TEAB. The product was further purified by reverse-phase HPLC using a Perkin Elmer OD-300 column (7 μm, 4.6×250 mm) to yield 6-ROX labeled triphosphate WW6p034. Mobile phase: A, 100 mM triethylammonium acetate (TEAA) in water (pH 7.0); B, 100 mM TEAA in water/CH$_3$CN (30:70).

Example 8

Synthesis of 7-Deazaadenosine Analogs

Synthesis of 7-(2-nitrobenzyloxy)methyl-7-deaza-2'-deoxyadenosine-5'-triphosphate Scheme 24. Synthesis of 7-(2-nitrobenzyloxy)methyl-7-deaza-2'-deoxyadenosine-5'-triphosphate.

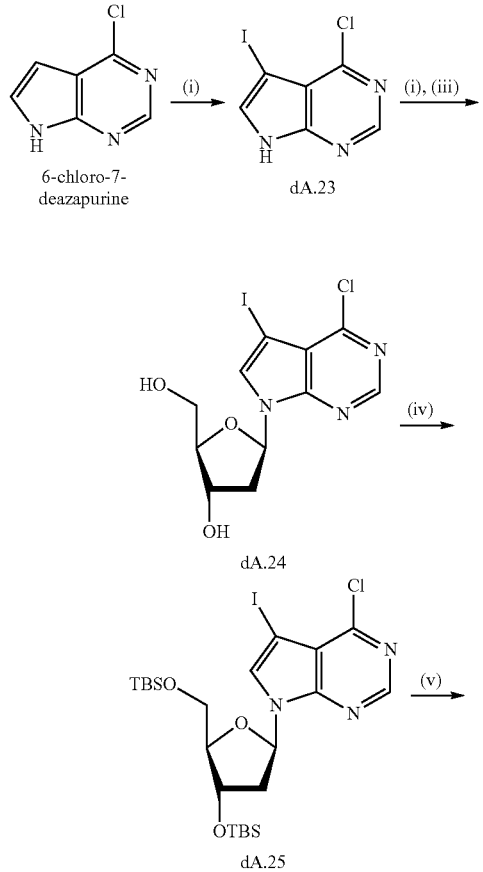

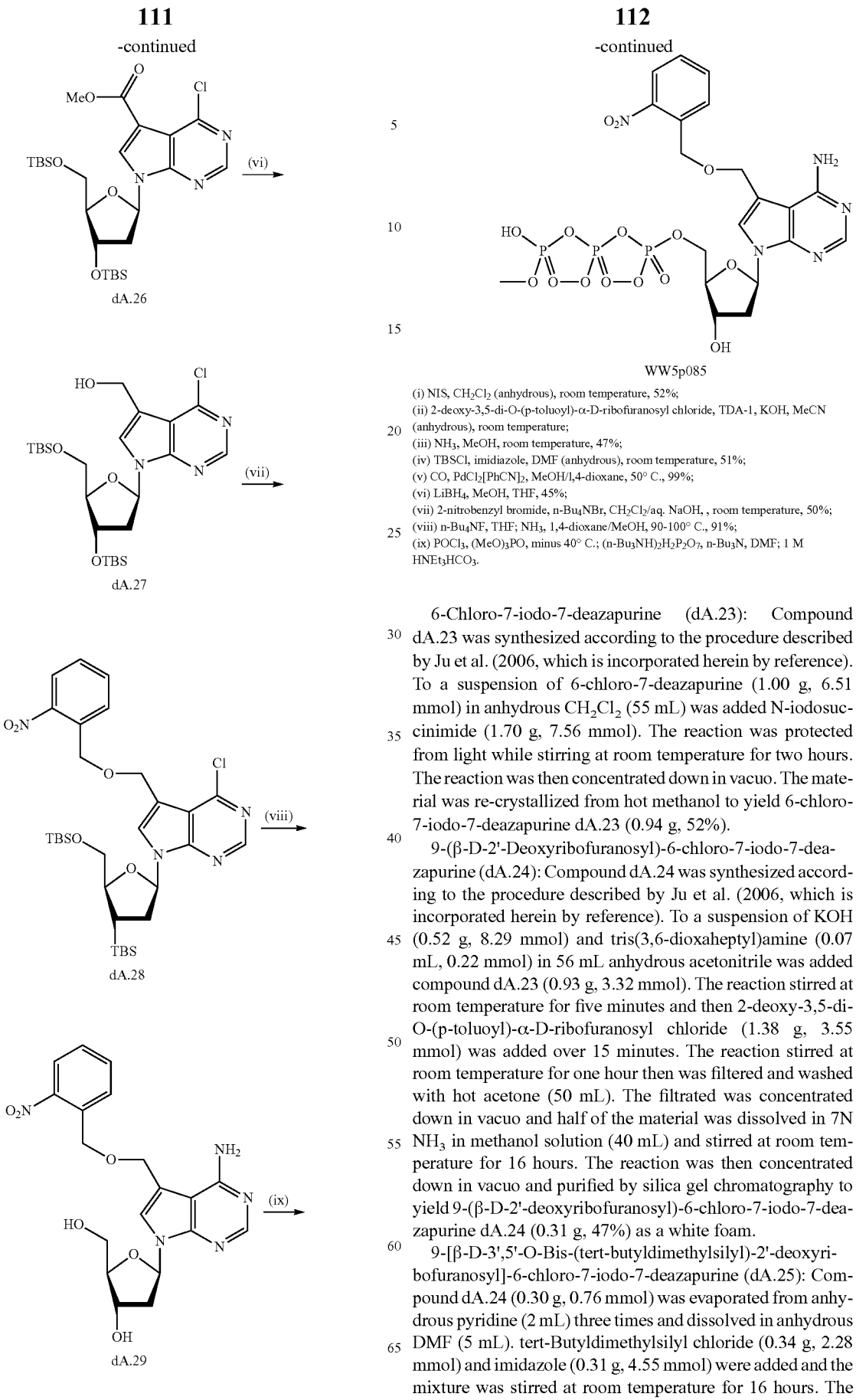

(i) NIS, CH₂Cl₂ (anhydrous), room temperature, 52%;
(ii) 2-deoxy-3,5-di-O-(p-toluoyl)-α-D-ribofuranosyl chloride, TDA-1, KOH, MeCN (anhydrous), room temperature;
(iii) NH₃, MeOH, room temperature, 47%;
(iv) TBSCl, imidiazole, DMF (anhydrous), room temperature, 51%;
(v) CO, PdCl₂[PhCN]₂, MeOH/1,4-dioxane, 50° C., 99%;
(vi) LiBH₄, MeOH, THF, 45%;
(vii) 2-nitrobenzyl bromide, n-Bu₄NBr, CH₂Cl₂/aq. NaOH, , room temperature, 50%;
(viii) n-Bu₄NF, THF; NH₃, 1,4-dioxane/MeOH, 90-100° C., 91%;
(ix) POCl₃, (MeO)₃PO, minus 40° C.; (n-Bu₃NH)₂H₂P₂O₇, n-Bu₃N, DMF; 1 M HNEt₃HCO₃.

6-Chloro-7-iodo-7-deazapurine (dA.23): Compound dA.23 was synthesized according to the procedure described by Ju et al. (2006, which is incorporated herein by reference). To a suspension of 6-chloro-7-deazapurine (1.00 g, 6.51 mmol) in anhydrous CH₂Cl₂ (55 mL) was added N-iodosuccinimide (1.70 g, 7.56 mmol). The reaction was protected from light while stirring at room temperature for two hours. The reaction was then concentrated down in vacuo. The material was re-crystallized from hot methanol to yield 6-chloro-7-iodo-7-deazapurine dA.23 (0.94 g, 52%).

9-(β-D-2'-Deoxyribofuranosyl)-6-chloro-7-iodo-7-deazapurine (dA.24): Compound dA.24 was synthesized according to the procedure described by Ju et al. (2006, which is incorporated herein by reference). To a suspension of KOH (0.52 g, 8.29 mmol) and tris(3,6-dioxaheptyl)amine (0.07 mL, 0.22 mmol) in 56 mL anhydrous acetonitrile was added compound dA.23 (0.93 g, 3.32 mmol). The reaction stirred at room temperature for five minutes and then 2-deoxy-3,5-di-O-(p-toluoyl)-α-D-ribofuranosyl chloride (1.38 g, 3.55 mmol) was added over 15 minutes. The reaction stirred at room temperature for one hour then was filtered and washed with hot acetone (50 mL). The filtrated was concentrated down in vacuo and half of the material was dissolved in 7N NH₃ in methanol solution (40 mL) and stirred at room temperature for 16 hours. The reaction was then concentrated down in vacuo and purified by silica gel chromatography to yield 9-(β-D-2'-deoxyribofuranosyl)-6-chloro-7-iodo-7-deazapurine dA.24 (0.31 g, 47%) as a white foam.

9-[β-D-3',5'-O-Bis-(tert-butyldimethylsilyl)-2'-deoxyribofuranosyl]-6-chloro-7-iodo-7-deazapurine (dA.25): Compound dA.24 (0.30 g, 0.76 mmol) was evaporated from anhydrous pyridine (2 mL) three times and dissolved in anhydrous DMF (5 mL). tert-Butyldimethylsilyl chloride (0.34 g, 2.28 mmol) and imidazole (0.31 g, 4.55 mmol) were added and the mixture was stirred at room temperature for 16 hours. The reaction was concentrated in vacuo and purified by silica gel chromatography to yield 9-[β-D-3',5'-β-bis-(tert-butyldimethylsilyl)-2'-deoxyribofuranosyl]-6-chloro-7-iodo-7-deazapurine dA.25 (0.24 g, 51%) as a white foam. $^1$H NMR (400 MHz, CDCl$_3$): δ 8.61 (s, 1 H, H-2), 7.81 (s, 1 H, H-8), 6.74 (t, 1 H, J=6.4 Hz, H-1'), 4.56 (m, 1 H, H-4'), 4.01 (m, 1 H, H-3'), 3.87 (dd, 1 H, H-5'a), 3.79 (dd, 1 H, H-5'b), 2.39 (m, 2 H, H-2'a and H-2'b), 0.96 (s, 9 H, (CH$_3$)$_3$CSi), 0.91 (s, 9 H, (CH$_3$)$_3$CSi), 0.18 (2s, 6 H, (CH$_3$)$_2$Si), 0.15 (s, 6 H, (CH$_3$)$_2$Si); $^{13}$C NMR (100 MHz, CDCl$_3$): δ 152.50 (C), 150.80 (CH), 150.48 (C), 131.94 (CH), 117.33 (C), 87.92 (CH), 84.16 (CH), 72.20 (CH), 63.01 (CH$_2$), 51.98 (C), 42.08 (CH$_2$), 26.07 (CH$_3$), 25.77 (CH$_3$), 18.51 (C), 18.05 (C), −4.63 (CH$_3$), −4.78 (CH$_3$), −5.25 (CH$_3$), −5.39 (CH$_3$).

9-[β-D-3',5'-O-Bis-(tert-butyldimethylsilyl)-2'-deoxyribofuranosyl]-6-chloro-7-methoxycarbonyl-7-deazapurine (dA.26): To a solution of dA.25 (1.3 g, 2.1 mmol) in anhydrous 1,4-dioxane (30 mL) and anhydrous methanol (25 mL) was added triethylamine (0.58 mL). After stirring for ten minutes under CO atmosphere, bis(benzonitrile)dichloropalladium(II) was added. The reaction was stirred at 50° C. for 48 hours under CO atmosphere, and then concentrated in vacuo. The residue was purified by silica gel chromatography to give 9-[β-D-3',5'-O-bis-(tert-butyldimethylsilyl)-2'-deoxyribofuranosyl]-6-chloro-7-methoxycarbonyl-7-deazapurine dA.26 (1.15 g, 99%) as a viscous oil. $^1$H NMR (400 MHz, CDCl$_3$): δ 8.69 (s, 1 H, H-2), 8.31 (s, 1 H, H-8), 6.77 (t, 1 H, J=6.8 Hz, H-1'), 4.58 (m, 1 H, H-4'), 4.06 (m, 1 H, H-3'), 3.90 (s, 3 H, CH$_3$O), 3.87 (dd, 1 H, H-5'a), 3.81 (dd, 1 H, H-5'b), 2.42 (m, 2 H, H-2'a and H-2'b), 0.93 (s, 18 H, (CH$_3$)$_3$CSi), 0.13 (s, 6 H, (CH$_3$)$_2$Si), 0.12 (s, 6 H, (CH$_3$)$_2$Si); $^{13}$C NMR (100 MHz, CDCl$_3$): δ 162.46 (C), 153.12 (C), 152.07 (C), 151.35 (CH), 133.27 (CH), 115.27 (C), 107.65 (C), 88.23 (CH), 84.52 (CH), 72.46 (CH), 63.06 (CH$_2$), 51.55 (CH$_3$), 42.15 (CH$_2$), 25.99 (CH$_3$), 25.77 (CH$_3$), 18.45 (C), 18.03 (C), −4.64 (CH$_3$), −4.78 (CH$_3$), −5.49 (CH$_3$), −5.55 (CH$_3$).

9-[β-D-3',5'-O-Bis-(tert-butyldimethylsilyl)-2'-deoxyribofuranosyl]-6-chloro-7-hydroxymethyl-7-deazapurine (dA.27): To a solution of dA.26 (0.28 g, 0.50 mmol) in anhydrous THF (4 mL) lithium borohydride (0.044 g, 2.01 mmol) was added, followed by methanol (0.1 mL). The reaction mixture was stirred at room temperature for ten minutes and then heated at reflux for 45 minutes. Upon cooling down, the reaction mixture was diluted with dichloromethane (20 ml) and quenched with water (2 mL). The organic layer was separated, washed with brine two times (5 mL each), dried over anhydrous sodium sulfate, and concentrated in vacuo. The residue was purified by silica gel chromatography to yield 9-[β-D-3',5'-O-bis-(tert-butyldimethylsilyl)-2'-deoxyribofuranosyl]-6-chloro-7-hydroxymethyl-7-deazapurine dA.27 (0.12 g, 45%) as a white foam. $^1$H NMR (400 MHz, CDCl$_3$): δ 8.62 (s, 1 H, H-8), 7.61 (s, 1 H, H-2), 6.75 (dd, 1 H, J=6.0 and 7.2 Hz, H-1'), 4.96 (AB d, 1 H, J=11.6 Hz, 7-CH$_2$a), 4.91 (AB d, 1 H, J=11.6 Hz, 7-CH$_2$b), 4.57 (m, 1 H, H-4'), 4.00 (m, 1 H, H-3'), 3.80 (m, 2 H, H-5'a and H-5'b), 2.44 (m, 1 H, H-2'a), 2.04 (m, 1 H, H-2'b), 0.91 (2 s, 18 H, (CH$_3$)$_3$CSi), 0.11 (2 s, 12 H, (CH$_3$)$_2$Si); $^{13}$C NMR (100 MHz, CDCl$_3$): δ 151.84 (C), 151.37 (C), 150.98 (CH), 125.33 (CH), 115.97 (C), 115.48 (C), 87.67 (CH), 83.73 (CH), 72.28 (CH), 63.07 (CH$_2$), 56.89 (CH$_2$), 41.42 (CH$_2$), 25.98 (CH$_3$), 25.79 (CH$_3$), 18.45 (C), 18.03 (C), −4.64 (CH$_3$), −4.76 (CH$_3$), −5.35 (CH$_3$), −5.47 (CH$_3$).

9-[β-D-3',5'-O-Bis-(tert-butyldimethylsilyl)-2'-deoxyribofuranosyl]-6-chloro-7-(2-nitrobenzyloxy)methyl-7-deazapurine (dA.28): To a solution of dA.27 (30 mg, 0.057 mmol) in CH$_2$Cl$_2$ (2 mL) were added n-Bu$_4$NBr (9 mg, 0.029 mmol), 2-nitrobenzyl bromide (37 mg, 0.17 mmol) and 1 M NaOH solution (2 mL). The reaction mixture was stirred vigorously at room temperature for 48 hours in the dark. The organic layer was separated, dried over Na$_2$SO$_4$, concentrated in vacuo, and purified by silica gel chromatography to yield 9-[β-D-3',5'-O-bis-(tert-butyldimethylsilyl)-2'-deoxyribofuranosyl]-6-chloro-7-(2-nitrobenzyloxy)methyl-7-deazapurine dA.28 (19 mg, 50%) as a viscous oil. $^1$H NMR (400 MHz, CDCl$_3$): δ 8.63 (s, 1 H, H-2), 8.06 (dd, 1 H, J=8.4 and 1.2 Hz, Ph-H), 7.84 (d, 1 H, J=7.6 Hz, Ph-H), 7.64 (s, 1 H, H-8), 7.62 (m, 1 H, Ph-H), 7.43 (t, 1 H, Ph-H), 6.75 (dd, 1 H, J=7.2 and 6.0 Hz, H-1'), 5.03 (s, 2 H, PhCH$_2$), 4.95 (AB d, 1 H, J=12.0 Hz, 7-CH$_2$a), 4.88 (AB d, 1 H, J=12.0 Hz, 7-CH$_2$b), 4.59 (m, 1 H, H-4'), 4.00 (m, 1 H, H-3'), 3.80 (m, 2 H, H-5'a and H-5'b), 2.48 (m, 1 H, H-2'a), 2.37 (m, 1 H, H-2'b), 0.92 (2 s, 18 H, (CH$_3$)$_3$CSi), 0.11 (s, 6 H, (CH$_3$)$_2$Si), 0.10 (s, 6 H, (CH$_3$)$_2$Si).

7-(2-Nitrobenzyloxy)methyl-7-deaza-2'-deoxyadenosine (dA.29): A solution of n-Bu$_4$NF (17 mg, 0.054 mmol) in THF (1 mL) was added to a solution of dA.28 (18 mg, 0.027 mmol) in THF (1 mL) at 0° C. The reaction mixture was gradually warmed to room temperature and stirred for two hours. The mixture was concentrated in vacuo, and then the residue was dissolved in 1,4-dioxane (2 mL) followed by addition of 7N NH$_3$ in methanol (4 mL). The mixture was transferred to a sealed tube and stirred at 90-100° C. for 16 hours, then cooled down, concentrated in vacuo, and the residue was purified by silica gel chromatography to yield 7-(2-nitrobenzyloxy)methyl-7-deaza-2'-deoxyadenosine dA.29 (10 mg, 91%) as a white foam. $^1$H NMR (400 MHz, DMSO-d$_6$): δ 8.08 (s, 1 H, H-2), 8.06 (m, 1 H, Ph-H), 7.75 (m, 2 H, Ph-H), 7.58 (m, 1 H, Ph-H), 7.42 (s, 1 H, H-8), 6.64 (bs, 2 H, D$_2$O exchangeable, 6-NH$_2$), 6.48 (dd, 1 H, J=2.0 and 6.0 Hz, H-1'), 5.25 (d, 1 H, J=4.0 Hz, D$_2$O exchangeable, 3'-OH), 5.08 (t, 1 H, J=5.6 Hz, D$_2$O exchangeable, 5'-OH), 4.90 (s, 2 H, PhCH$_2$), 4.75 (AB dd, 2 H, 7-CH$_2$), 4.33 (m, 1 H, H-3'), 3.81 (m, 1 H, H-4'), 3.54 (m, 2 H, H-5'a and H-5'b), 2.47 (m, 1 H, H-2'a), 2.15 (m, 1 H, H-2'b).

7-(2-Nitrobenzyloxy)methyl-7-deaza-2'-deoxyadenosine-5'-triphosphate (WW5p085)

POCl$_3$ (2.6 μL, 0.028 mmol) was added to a solution of dA.29 (6 mg, 0.014 mmol) and proton sponge (6 mg, 0.028 mmol) in trimethylphosphate (0.25 mL) at minus 40° C. and stirred for four hours. A solution of bis-tri-n-butylammonium pyrophosphate (66 mg, 0.14 mmol) and tri-n-butylamine (28 μL) in anhydrous DMF (0.28 mL) was added. After 30 minutes of stirring, triethylammonium bicarbonate buffer (1 M, pH 7.5; 1 mL) was added. The reaction was stirred at room temperature for one hour and then concentrated in vacuo. The residue was dissolved in water (2 mL), filtered, and purified with reverse-phase HPLC using a Perkin Elmer OD-300 C$_{18}$ column (7 μm, 4.6×250 mm) to yield 7-(2-nitrobenzyloxy) methyl-7-deaza-2'-deoxyadenosine-5'-triphosphate WW5p085. Mobile phase: A, 100 mM triethylammonium acetate (TEAA) in water (pH 7.0); B, 100 mM TEAA in water/CH$_3$CN (30:70).

Synthesis of 7-[1-(2-nitrophenyl)-2-methyl-propyloxy]methyl-7-deaza-2'-deoxyadenosine-5'-triphosphate

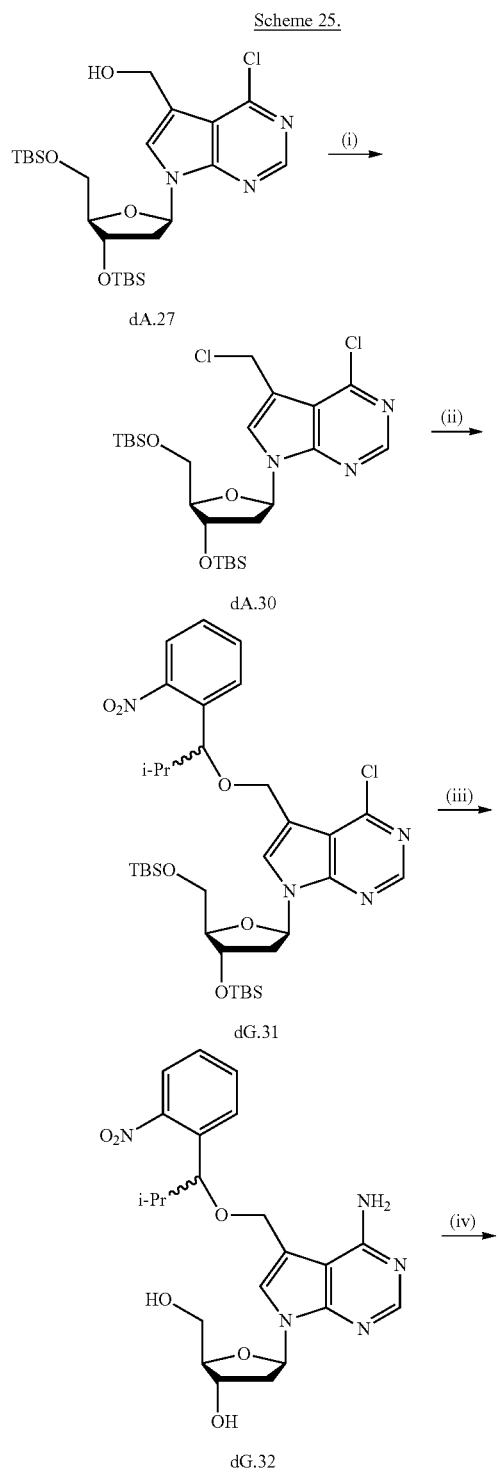

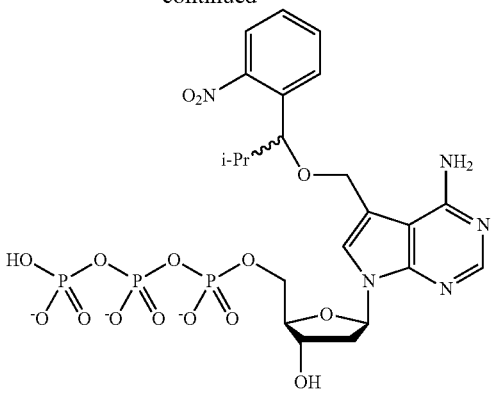

WW5p098 ds1 & ds2
Synthesis of 7-[1-(2-nitrophenyl)-2-methyl-propyloxy]methyl-7-deaza-2'-deoxyadenosine-5'-triphosphate.
(i) TsCl, DMAP, CH$_2$Cl$_2$ (anhydrous), room temperature, 39%;
(ii) 1-(2-nitrophenyl)-2-methyl-propanol (racemic), neat, vacuum, 105° C., 54%; (iii) n-Bu$_4$NF, THF; NH$_3$, 1,4-dioxane/MeOH, 90-100° C., 76%; (iv) POCl$_3$, (MeO)$_3$PO, minus 40° C. to 0° C.; (n-Bu$_3$NH)$_2$H$_2$P$_2$O$_7$, n-Bu$_3$N, DMF; 1M HNEt$_3$HCO$_3$.

9-[β-D-3',5'-O-Bis-(tert-butyldimethylsilyl)-2'-deoxyribofuranosyl]-6-chloro-7-chloromethyl-7-deazapurine (dA.30): To a solution of dA.27 (0.257 g, 0.485 mmol) in dichloromethane (12 mL, freshly distilled from CaH$_2$) were added 4-N,N-dimethylaminopyridine (0.148 g, 1.213 mmol) and tosyl chloride (0.111 g, 0.583 mmol). The reaction mixture was stirred at room temperature for 18 hours, and then concentrated in vacuo. The residue was purified by silica gel chromatography to yield 9-[β-D-3',5'-O-bis-(tert-butyldimethylsilyl)-2'-deoxyribofuranosyl]-6-chloro-7-chloromethyl-7-deazapurine dA.30 (0.103 g, 26%) as a viscous oil. $^1$H NMR (400 MHz, CDCl$_3$): δ 8.64 (s, 1 H, H-2), 7.72 (s, 1 H, H-8), 6.73 (t, 1 H, J=6.8 Hz, H-1'), 4.95 (AB d, J=12.4 Hz, 7-CH$_2$a), 4.91 (AB d, J=12.0 Hz, 7-CH$_2$b), 4.58 (m, 1 H, H-3'), 4.00 (m, 1 H, H-4'), 3.82 (m, 2 H, H-5'a and H-5'b), 2.41 (m, 2 H, H-2'a and H-2'b), 0.95 (s, 9 H, (CH$_3$)$_3$CSi), 0.93 (s, 9 H, (CH$_3$)$_3$CSi), 0.12 (s, 6 H, (CH$_3$)$_2$Si), 0.11 (s, 6 H, (CH$_3$)$_2$Si); $^{13}$C NMR (100 MHz, CDCl$_3$): δ 151.78 (C), 151.56 (C), 151.26 (CH), 126.68 (CH), 112.15 (C), 115.54 (C), 87.78 (CH), 83.97 (CH), 72.17 (CH), 62.98 (CH$_2$), 41.72 (CH$_2$), 37.56 (CH$_2$), 25.99 (CH$_3$), 25.78 (CH$_3$), 18.45 (C), 18.03 (C), −4.63 (CH$_3$), −4.78 (CH$_3$), −5.35 (CH$_3$), −5.45 (CH$_3$).

9-[β-D-3',5'-O-Bis-(tert-butyldimethylsilyl)-2'-deoxyribofuranosyl]-6-chloro-7-[1-(2-nitrophenyl)-2-methyl-propyloxy]methyl-7-deazapurine (dA.31): Compound dA.30 (54 mg, 0.1 mmol) and 1-(2-nitrophenyl)-2-methyl-propanol (191 mg, 0.978 mmol) were dissolved in anhydrous dichloromethane (10 mL). The solvent was removed in vacuo and the residue was heated in vacuo for one hour, then dissolved in ethyl acetate and purified by silica gel chromatography to yield 9-[β-D-3',5'-O-bis-(tert-butyldimethylsilyl)-2'-deoxyribofuranosyl]-6-chloro-7-[1-(2-nitrophenyl)-2-methyl-propyloxy]methyl-7-deazapurine dA.31 (38 mg, 54%, 1:1 mixture of diastereomers). $^1$H NMR (400 MHz, CDCl$_3$) for diastereomers: δ 8.60 and 8.59 (2 s, 1 H, H-2), 7.83 (m, 1 H, Ph-H), 7.79 (m, 1 H, Ph-H), 7.56 (m, 1 H, Ph-H), 7.48 and 7.47 (2 s, 1 H, H-8), 7.38 (m, 1 H, Ph-H), 6.70 (m, 1 H, H-1'), 4.81 (m, 1 H, Ph-CH), 4.70 (m, 1 H, 7-CH$_2$a), 4.58 (m, 2 H, 7-CH$_2$b and H-3'), 3.99 (m, 1 H, H-4'), 3.78 (m, 2 H, H-5'a and H-5'b), 2.48 (m, 1 H, H-2'a), 2.35 (m, 1 H, H-2'b), 1.96 (m, 1 H, CH), 0.98 and 0.96 (2 d, 3 H, CH$_3$), 0.93 (2 s, 9 H, (CH$_3$)$_3$CSi), 0.89 (2 s, 9 H, (CH$_3$)$_3$CSi), 0.82 and 0.78 (2 d, 3 H, CH$_3$), 0.12 (2 s, 6 H, (CH$_3$)$_2$Si), 0.08 and 0.07 (2 s, 3 H, (CH$_3$)$_2$Si), 0.06 and 0.05 (2 s, 3 H, (CH$_3$)$_2$Si); $^{13}$C NMR (100 MHz, CDCl$_3$) for diastereomers: δ 152.60 and 152.47 (C), 150.84 (CH), 150.28 and 150.21 (C), 149.56 and 149.47 (C), 148.01 (C), 137.22 and 137.08 (C), 132.70 and 132.68 (CH), 129.15 and 129.13 (CH), 127.97 (CH), 126.65 and 126.29 (CH), 123.85 and 123.79 (CH), 112.36 and 112.07 (C), 87.63 and 87.59 (CH), 83.71 and 83.68 (CH), 81.92 and 81.08 (CH), 72.40 and 72.28 (CH), 63.50 (CH$_2$), 63.15 and 63.03 (CH$_2$), 41.07 and 41.00 (CH$_2$), 35.08 and 35.05 (CH), 19.20 and 19.11 (CH$_3$), 18.42 and 18.40 (C), 18.18 and 18.05 (CH$_3$), −4.67 and −4.76 (CH$_3$Si), −4.78 (CH$_3$Si), −5.35 (CH$_3$Si), −5.47 and −5.51 (CH$_3$Si).

7-[1-(2-Nitrophenyl)-2-methyl-propyloxy]methyl-7-deaza-2'-deoxyadenosine (dA.32): A solution of n-Bu$_4$NF (44 mg, 0.140 mmol) in THF (2 mL) was added to a solution of dA.31 (38 mg, 0.053 mmol) in THF (2 mL) at 0° C. The reaction was gradually warmed to room temperature and stirred for two hours. The mixture was concentrated in vacuo, dissolved in 1,4-dioxane (4 mL), followed by addition of 7N NH$_3$ in methanol solution (8 mL). The mixture was transferred to a sealed tube and stirred at 90-100° C. for 24 hours, then cooled down, concentrated in vacuo, and the residue was purified by silica gel chromatography to yield 7-[1-(2-nitrophenyl)-2-methyl-propyloxy]methyl-7-deaza-2'-deoxyadenosine dA.32 (19 mg, 76%, 1:1 mixture of diastereomers) as a viscous oil. $^1$H NMR (400 MHz, DMSO-d$_6$) for diastereomers: δ 8.06 and 8.04 (2 s, 1 H, H-2), 7.90 (m, 1 H, Ph-H), 7.67 (m, 2 H, Ph-H), 7.56 (m, 2 H, Ph-H), 7.19 and 7.16 (2 s, 1 H, H-8), 6.63 (bs, 2 H, D$_2$O exchangeable, 6-NH$_2$), 6.39 (m, 1 H, H-1'), 5.23 (m, 1 H, D$_2$O exchangeable, 3'-OH), 5.00 (m, 1 H, D$_2$O exchangeable, 5'-OH), 4.72 (2 d, 1 H, Ph-CH), 4.45 (s, 2 H, 7-CH$_2$), 4.30 (m, 1 H, H-3'), 3.77 (m, 1 H, H-4'), 3.49 (m, 2 H, H-5'a and H-5'b), 2.40 (m, 1 H, H-2'a), 2.12 (m, 1 H, H-2'b), 1.94 (m, 1 H, CH), 0.87 (m, 3 H, CH$_3$), 0.74 (m, 3 H, CH$_3$); $^{13}$C NMR (100 MHz, CD$_3$OD) for diastereomers: δ 157.76 (C), 151.08 (CH), 149.92 and 149.57 (C), 148.01 (C), 135.99 and 135.92 (C), 132.51 and 132.41 (CH), 128.89 (CH), 128.20 and 128.15 (CH), 123.49 and 123.43 (CH), 122.32 and 121.97 (CH), 111.86 (C), 103.02 (C), 87.65 and 87.59 (CH), 85.25 and 85.00 (CH), 80.29 and 79.60 (CH), 71.73 (CH), 63.97 and 69.92 (CH$_2$), 63.49 and 62.41 (CH$_2$), 39.95 and 39.77 (CH$_2$), 34.55 and 34.51 (CH), 18.09 (CH$_3$), 17.16 (CH$_3$).

7-[1-(2-Nitrophenyl)-2-methyl-propyloxy]methyl-7-deaza-2'-deoxyadenosine-5'-triphosphate (WW5p098 ds1 & ds2): POCl$_3$ (8 μL, 0.083 mmol) was added to a solution of compound dA.32 (19 mg, 0.041 mmol) in trimethylphosphate (0.4 mL), and the reaction was stirred at minus 40° C. under a nitrogen atmosphere for two hours. Additional POCl$_3$ (8 μL, 0.083 mmol) was added, and the reaction was stirred at 0° C. for additional three hours. A solution of bis-tri-n-butylammonium pyrophosphate (97 mg, 0.2 mmol) and tri-n-butylamine (40 μL) in anhydrous DMF (0.4 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (5 mL), filtered, and purified by anion exchange chromatography using a Q Sepharose FF column (2.5×10 cm) with a linear gradient of 25% acetonitrile/75% 0.1M triethylammonium bicarbonate (TEAB) to 25% acetonitrile/75% 1.5 M TEAB over 240 min at 4.5 ml/min. The fractions containing triphosphate were combined and lyophilized to yield 7-[1-(2-nitrophenyl)-2-methyl-propyloxy]methyl-7-deaza-2'-deoxyadenosine-5'-triphosphate WW5p098 as mixture of two diastereomers, which were separated by reverse phase HPLC on a Perkin Elmer Aquapore OD-300 column (7 μm, 250×4.6 mm) to yield the single diastereomer WW5p098 ds1 (fast eluting) and WW5p098 ds2 (slow eluting). Mobile phase: A, 100 mM triethylammonium acetate (TEAA) in water; B, 100 mM TEAA in water/CH$_3$CN (30:70).

Synthesis of 6-FAM labeled 7-{(R)-1-[4-(3-amino-1-propynyl)-2-nitrophenyl]-2-methyl-propyloxy}methyl-7-deaza-2'-deoxyadenosine-5'-triphosphate Scheme 26. Synthesis of 6-FAM labeled 7-{(R)-1-[4-(3-amino-1-propynyl)-2-nitrophenyl]-2-methyl-propyloxy}methyl-7-deaza-2'-deoxyadenosine-5'-triphosphate

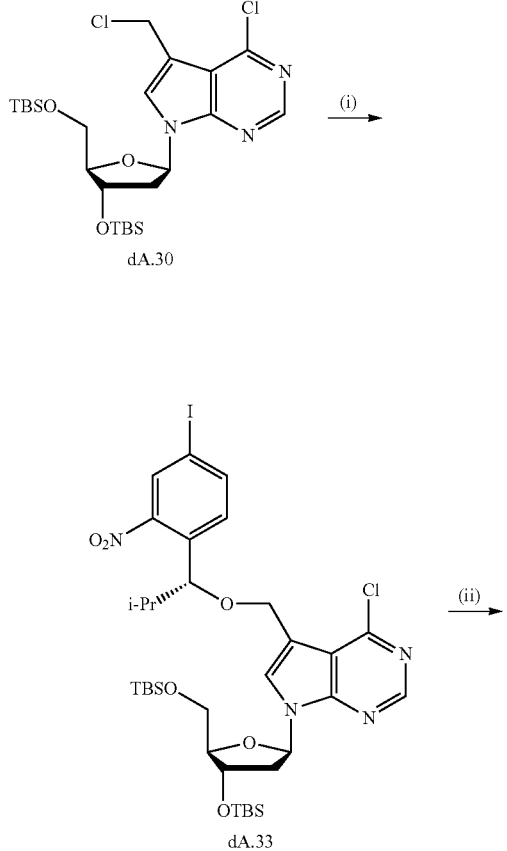

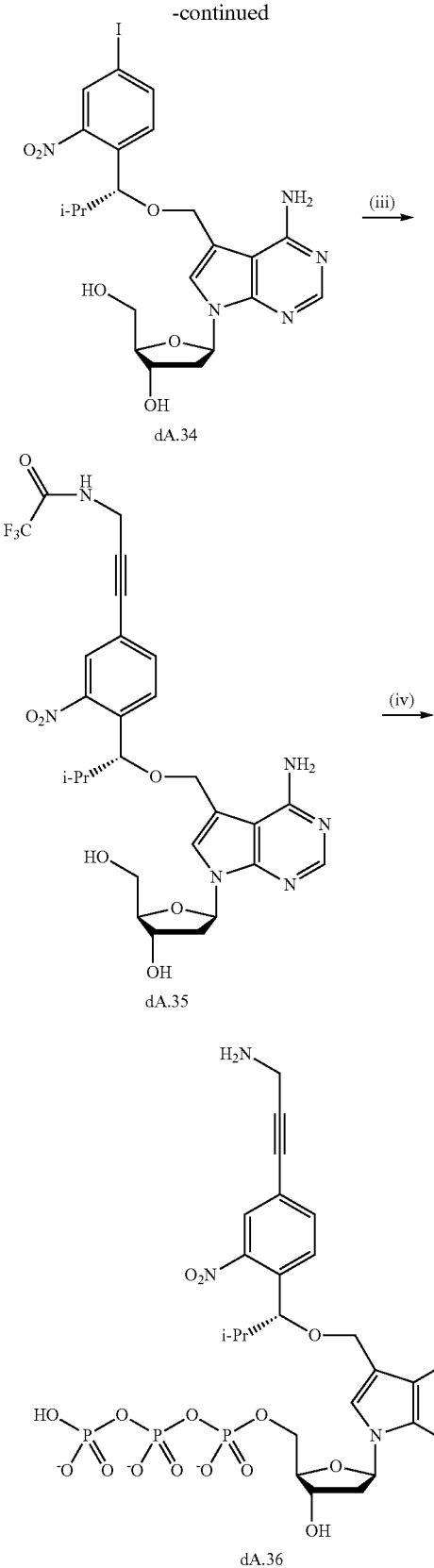

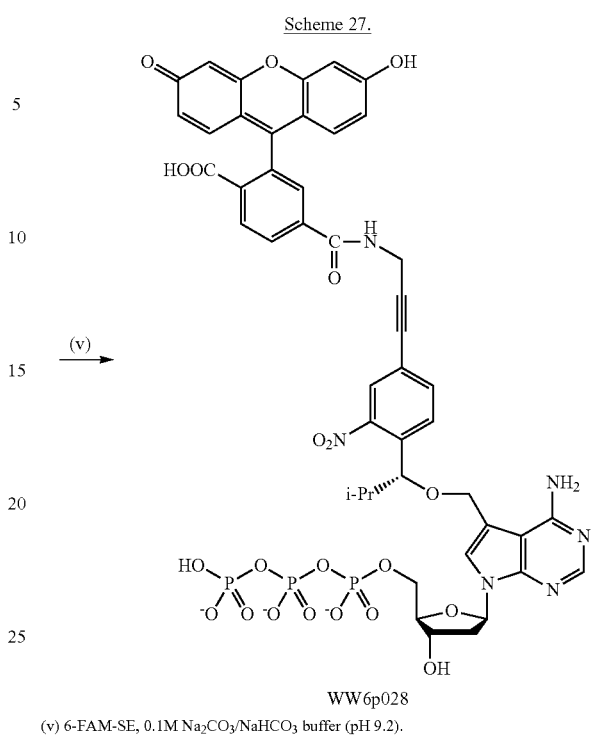

Scheme 27.

(v) 6-FAM-SE, 0.1M Na₂CO₃/NaHCO₃ buffer (pH 9.2).

9-[β-D-3',5'-O-Bis-(tert-butyldimethylsilyl)-2'-deoxyribofuranosyl]-6-chloro-7-[(R)-1-(4-iodo-2-nitrophenyl)-2-methyl-propyloxy]methyl-7-deazapurine (dA.33): Compound dA.30 (80 mg, 0.147 mmol) and enantio-pure (R)-1-(4-iodo-2-nitrophenyl)-2-methyl-propanol (518 mg, 1.163 mmol) were dissolved in anhydrous dichloromethane (10 mL). The solvent was removed in vacuo, and the residue was heated in vacuo for one hour, then dissolved in ethyl acetate and purified by silica gel chromatography to yield 9-[β-D-3', 5'-O-bis-(tert-butyldimethylsilyl)-2'-deoxyribofuranosyl]-6-chloro-7-[(R)-1-(4-iodo-2-nitrophenyl)-2-methyl-propyloxy]methyl-7-deazapurine dA.33 (57 mg, 47%). $^1$H NMR (400 MHz, CDCl$_3$): δ 8.60 (s, 1 H, H-2), 8.12 (d, J=2.0 Hz, 1 H, Ph-H), 7.87 (dd, J=8.4 and 1.6 Hz, 1 H, Ph-H), 7.47 (d, J=8.0 Hz, 1 H, Ph-H), 7.47 (s, 1 H, H-8), 6.71 (dd, J=7.6 and 6.0 Hz, 1 H, H-1'), 4.76 (d, J=6.4 Hz, 1 H, Ph-CH), 4.70 (AD d, J=11.6 Hz, 1 H, 7-CH$_2$a), 4.58 (m, 2 H, 7-CH$_2$b and H-3'), 4.00 (m, 1 H, H-4'), 3.79 (m, 2 H, H-5'a and H-5'b), 2.45 (m, 1 H, H-2'a), 2.36 (m, 1 H, H-2'b), 1.93 (sep, J=6.8 Hz, 1 H, CHCH(CH$_3$)$_2$), 0.98 (d, J=6.4 Hz, 3 H, CH$_3$), 0.93 (s, 9 H, (CH$_3$)$_3$CSi), 0.91 (s, 9 H, (CH$_3$)$_3$CSi), 0.82 (d, J=6.8 Hz, 3 H, CH$_3$), 0.126 (s, 6 H, (CH$_3$)$_2$Si), 0.123 (s, 3 H, (CH$_3$)$_2$Si), 0.09 (s, 3 H, (CH$_3$)$_2$Si), 0.06 (s, 3 H, (CH$_3$)$_2$Si); $^{13}$C NMR (100 MHz, CDCl$_3$): δ 151.81 (C), 151.76 (C), 150.93 (CH), 149.79 (C), 141.63 (CH), 137.04 (C), 132.34 (CH), 130.85 (CH), 126.41 (CH), 116.17 (C), 112.06 (C), 91.57 (C), 87.65 (CH), 83.77 (CH), 80.68 (CH), 72.41 (CH), 63.58 (CH$_2$), 63.15 (CH$_2$), 41.07 (CH$_2$), 34.95 (CH), 25.96 (C(CH$_3$)$_3$), 25.80 (C(CH$_3$)$_3$), 19.13 (CH$_3$), 18.42 (C), 18.05 (CH$_3$), −4.63 (CH$_3$), −4.78 (CH$_3$), −5.35 (CH$_3$), −5.45 (CH$_3$).

7-[(R)-1-(4-Iodo-2-nitrophenyl)-2-methyl-propyloxy] methyl-7-deaza-2'-deoxyadenosine (dA.34): A solution of n-Bu$_4$NF (58 mg, 0.182 mmol) in THF (2 mL) was added to a solution of dA.33 (57 mg, 0.069 mmol) in THF (2 mL) at 0° C. The reaction was gradually warmed to room temperature and stirred for two hours. The mixture was concentrated in vacuo, dissolved in 1,4-dioxane (5 mL), followed by addition of 7N $NH_3$ in methanol solution (16 mL). The mixture was transferred to a sealed tube and stirred at 90-100° C. for 24 hours, then cooled down, concentrated in vacuo, and the residue was purified by silica gel chromatography to yield 7-[(R)-1-(4-iodo-2-nitrophenyl)-2-methyl-propyloxy]methyl-7-deaza-2'-deoxyadenosine dA.34 (33 mg, 82%). $^1$H NMR (400 MHz, DMSO-$d_6$): δ 8.22 (d, J=1.6 Hz, 1 H, Ph-H), 8.04 (s, 1 H, H-2), 8.00 (dd, J=8.4 and 1.6 Hz, 1 H, Ph-H), 7.39 (d, J=8.4 Hz, 2 H, Ph-H), 7.19 (s, 1 H, H-8), 6.60 (bs, 2 H, $D_2O$ exchangeable, 6-$NH_2$), 6.40 (dd, J=8.4 and 6.0 Hz, 1 H, H-1'), 5.24 (d, J=4.0 Hz, 1 H, $D_2O$ exchangeable, 3'-OH), 5.00 (d, J=5.2 Hz, 1 H, $D_2O$ exchangeable, 5'-OH), 4.64 (d, J=6.0 Hz, 1 H, Ph-CH), 4.45 (AB dd, 2H, 7-$CH_2$), 4.29 (m, 1 H, H-3'), 3.78 (m, 1 H, H-4'), 3.47 (m, 2 H, H-5'a and H-5'b), 2.40 (m, 1 H, H-2'a), 2.11 (m, 1 H, H-2'b), 1.92 (m, 1 H, CH), 0.87 (d, J=6.4 Hz, 3 H, $CH_3$), 0.76 (d, J=6.8 Hz, 3 H, $CH_3$); $^{13}$C NMR (100 MHz, $CD_3OD$): δ 164.68 (C), 151.12 (CH), 150.12 (C), 149.84 (C), 141.38 (CH), 136.09 (C), 131.94 (CH), 130.66 (CH), 122.15 (CH), 111.79 (C), 103.09 (C), 91.16 (C), 87.63 (CH), 85.12 (CH), 80.31 (CH), 71.80 (CH), 63.36 ($CH_2$), 62.53 ($CH_2$), 39.76 ($CH_2$), 34.41 (CH), 18.00 ($CH_3$), 17.20 ($CH_3$).

7-{(R)-1-[4-(3-Trifluoroacetamido-1-propynyl)-2-nitrophenyl]-2-methyl-propyloxy}methyl-7-deaza-2'-deoxyadenosine (dA.35): A solution of compound dA.34 (33 mg, 0.056 mmol), N-propargyltrifluoroacetylamide (25 mg, 0.168 mmol), tetrakis(triphenylphosphine)-palladium(0) (7 mg, 0.0065 mmol), CuI (2 mg, 0.0112 mmol), and $Et_3N$ (16 µL, 0.050 mmol) in anhydrous DMF (3 mL) was stirred at room temperature for four hours. The mixture was concentrated in vacuo and purified by silica gel column chromatography to yield 7-{(R)-1-[4-(3-trifluoroacetamido-1-propynyl)-2-nitrophenyl]-2-methyl-propyloxy}methyl-7-deaza-2'-deoxyadenosine dA.35 (34 mg, 99%) as a waxy solid. $^1$H NMR (400 MHz, DMSO-$d_6$): δ 10.11 (br t, 1 H, $D_2O$ exchangeable, NHTFA), 8.12 (br s, 1 H, H-2), 7.94 (d, J=1.6 Hz, 1 H, Ph-H), 7.71 (AB dd, J=8.0 and 1.6 Hz, 1 H, Ph-H), 7.62 (AB d, J=8.4 Hz, 2 H, Ph-H), 7.28 (s, 1 H, H-8), 6.95 (bs, 2 H, $D_2O$ exchangeable, 6-$NH_2$), 6.42 (dd, J=8.0 and 6.0 Hz, 1 H, H-1'), 5.25 (br s, 1 H, $D_2O$ exchangeable, 3'-OH), 4.98 (br s, 1 H, $D_2O$ exchangeable, 5'-OH), 4.60 (d, J=6.0 Hz, 1 H, Ph-C$\underline{H}$), 4.51 (AB dd, J=12.8 Hz, 1 H, 7-$CH_2$a), 4.45 (AB dd, J=12.4 Hz, 1 H, 7-$CH_2$b), 4.30 (m, 3 H, $C\underline{H}_2$NH and H-3'), 3.78 (m, 1 H, H-4'), 3.47 (m, 2 H, H-5'a and H-5'b), 2.39 (m, 1 H, H-2'a), 2.14 (m, 1 H, H-2'b), 1.95 (m, 1 H, CH), 0.88 (d, J=6.8 Hz, 3 H, $CH_3$), 0.76 (d, J=6.8 Hz, 3 H, $CH_3$); $^{13}$C NMR (100 MHz, $CD_3OD$): δ 157.62 (C), 151.15 (CH), 150.05 (C), 149.47 (C), 136.64 (C), 135.03 (CH), 129.34 (CH), 126.31 (CH), 122.68 (C), 122.14 (CH), 115.02 (C), 111.84 (C), 87.59 (CH), 85.83 (C), 85.01 (CH), 80.28 (CH), 80.13 (C), 81.42 (CH), 71.74 (CH), 64.28 ($CH_2$), 62.49 ($CH_2$), 39.73 ($CH_2$), 34.50 (CH), 29.07 ($CH_2$), 18.03 ($CH_3$), 17.18 ($CH_3$).

7-{(R)-1-[4-(3-Amino-1-propynyl)-2-nitrophenyl]-2-methyl-propyloxy}methyl-7-deaza-2'-deoxyadenosine-5'-triphosphate (dA.36): $POCl_3$ (8 µL, 0.089 mmol) was added to a solution of compound dA.35 (27 mg, 0.045 mmol) and proton sponge (19 mg, 0.089 mmol) in trimethylphosphate (0.4 mL) and the reaction was stirred at 0° C. under a nitrogen atmosphere for two hours. A solution of bis-tri-n-butylammonium pyrophosphate (285 mg, 0.6 mmol) and tri-n-butylamine (120 µL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (10 mL), filtered, and purified by anion exchange chromatography using a Q Sepharose FF column (2.5×10 cm) with a linear gradient of 25% acetonitrile/75% 0.1 M triethylammonium bicarbonate (TEAB) to 25% acetonitrile/75% 1.5 M TEAB over 240 min at 4.5 ml/min. The fractions containing triphosphate were combined and lyophilized to dryness. The residue was dissolved in water (5 mL) and treated with concentrated ammonium hydroxide (2 mL, 27%) at room temperature for one hour to yield 7-{(R)-1-[4-(3-amino-1-propynyl)-2-nitrophenyl]-2-methyl-propyloxy}methyl-7-deaza-2'-deoxyadenosine-5'-triphosphate dA.36, which was purified by reverse phase HPLC on a Perkin Elmer Aquapore OD-300 column (7 µm, 250×4.6 mm). Mobile phase: A, 100 mM triethylammonium acetate (TEAA) in water; B, 100 mM TEAA in water/$CH_3CN$ (30:70).

6-FAM labeled 7-{(R)-1-[4-(3-amino-1-propynyl)-2-nitrophenyl]-2-methyl-propyloxy}methyl-7-deaza-2'-deoxyadenosine-5'-triphosphate (WW6p028): A solution of 6-FAM-SE (4 mg, 8.4 µmol) in anhydrous DMSO (80 µL) was added to a solution of triphosphate dA.36 (2.6 µmol) in $Na_2CO_3/NaHCO_3$ buffer (0.1 M, pH 9.2, 1.6 mL). The mixture was left at room temperature for one hour. The dye labeled triphosphate was first purified by anion exchange HPLC using a PerkinElmer AX-300 column (7 µm, 250×4.6 mm). Mobile phase: A, 25% $CH_3CN$/75% 0.1 M TEAB; B, 25% $CH_3CN$/75% 1.5 M TEAB. The product was further purified by reverse-phase HPLC using a Perkin Elmer OD-300 column (7 µm, 4.6×250 mm) to yield 6-FAM labeled triphosphate WW6p028. Mobile phase: A, 100 mM triethylammonium acetate (TEAA) in water (pH 7.0); B, 100 mM TEAA in water/$CH_3CN$ (30:70).

Synthesis of 7-[1-(2,6-dinitrophenyl)-2-methyl-propyloxy]methyl-7-deaza-2'-deoxyadenosine-5'-triphosphate Scheme 28.
Synthesis of 7-[1-(2,6-dinitrophenyl)-2-methyl-propyloxy]methyl-7-deaza-2'-deoxyadenosine-5'-triphosphate.

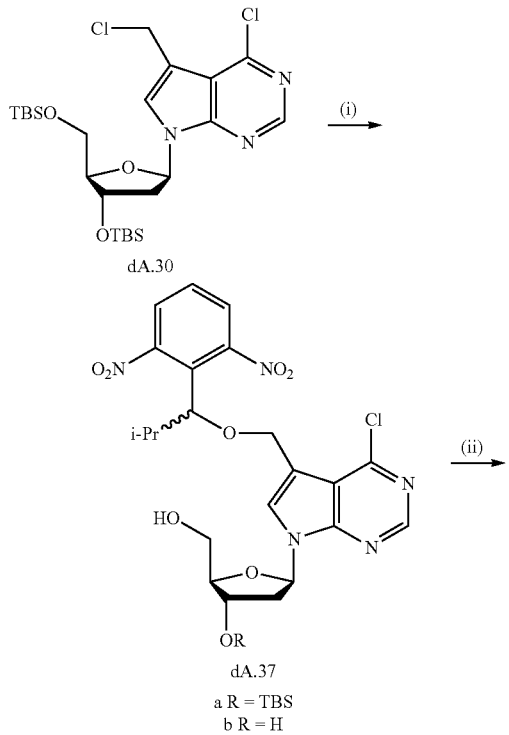

dA.30 dA.37
a R = TBS
b R = H

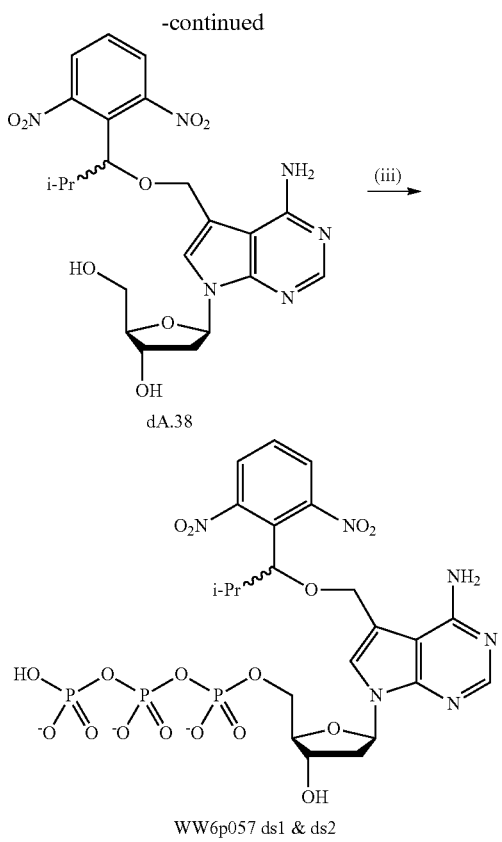

(i) 1-(2,6-dinitrophenyl)-2-methyl-propanol (racemic), neat, vacuum, 108° C., 33% (dA.37a) and 11% (da.37b);
(ii) n-Bu₄NF, THF; NH₃, 1,4-dioxane/MeOH, 90-100° C., 86%;
(iv) POCl₃, (MeO)₃PO, 0° C.; (n-Bu₃NH)₂H₂P₂O₇, n-Bu₃N, DMF; 1M HNEt₃HCO₃.

9-[β-D-3'-O-(tert-Butyldimethylsilyl)-2'-deoxyribofuranosyl]-6-chloro-7-[1-(2,6-dinitrophenyl)-2-methyl-propyloxy]methyl-7-deazapurine (dA.37a) and 9-[β-D-2'-deoxyribofuranosyl]-6-chloro-7-[1-(2,6-dinitrophenyl)-2-methylpropyloxy]methyl-7-deazapurine (dA.37b): Compound dA.30 (109 mg, 0.201 mmol) and 1-(2,6-dinitrophenyl)-2-methyl-propanol (448 mg, 1.863 mmol) were dissolved in anhydrous dichloromethane (10 mL). The solvent was removed in vacuo, and the residue was heated at 108° C. in vacuo for 30 minutes, then dissolved in ethyl acetate and purified by silica gel chromatography to yield 9-[β-D-3'-O-(tert-butyldimethylsilyl)-2'-deoxyribofuranosyl]-6-chloro-7-[1-(2,6-dinitrophenyl)-2-methyl-propyloxy]methyl-7-deazapurine dA.37a (42 mg, 33%, 1:1 mixture of diastereomers) and 9-[β-D-2'-deoxyribofuranosyl]-6-chloro-7-[1-(2,6-dinitrophenyl)-2-methyl-propyloxy]methyl-7-deazapurine dA.37b (13 mg, 11%, 1:1 mixture of diastereomers). $^1$H NMR (400 MHz, CDCl₃) for dA.37a (1:1 mixture of diastereomers): δ 8.59 (s, 1 H, H-2), 7.78 (m, 2 H, Ph-H), 7.63 (m, 1 H, Ph-H), 7.38 (s, 1 H, H-8), 6.39 (m, 1 H, H-1'), 5.01 (2 br s, 1 H, 5'-OH), 4.72 (m, 4 H, Ph-CH, 7-CH₂, and H-3'), 4.11 (m, 1 H, H-4'), 3.91 (AB d, 1 H, H-5'a), 3.85 (m, 1 H, H-5'b), 2.96 (m, 1 H, CH(CH₃)₂), 2.40 (m, 2 H, H-2'), 1.08 (m, 3 H, CH₃), 0.91 (s, 9 H, (CH₃)₃CSi), 0.78 (2 d, J=6.8 Hz, 3 H, CH₃), 0.13 (s, 6 H, (CH₃)₂Si); $^{13}$C NMR (100 MHz, CDCl₃) for dA.37a (1:1 mixture of diastereomers): δ 152.60 and 152.47 (C), 150.92 and 150.66 (C), 150.47 and 150.28 (C), 151.84 (C), 150.28 and 150.21 (C), 129.72 and 129.69 (CH), 129.18 (CH), 128.77 (C), 128.63 and 128.54 (CH), 126.69 (CH), 117.57 and 117.29 (C), 110.84 and 110.59 (C), 89.39 and 89.18 (CH), 88.70 and 88.80 (CH), 82.00 and 81.84 (CH), 73.47 and 73.35 (CH), 64.56 and 64.34 (CH₂), 63.10 and 63.05 (CH₂), 41.12 (CH₂), 34.86 (CH), 25.81 ((CH₃)₃Si), 19.13 (CH₃), 18.36 (CH₃), 18.08 (C), −4.67 (CH₃Si), −4.76 (CH₃Si).
$^1$H NMR (400 MHz, CD₃OD) for dA.37b (1:1 mixture of diastereomers): δ 8.57 and 8.56 (2 s, 1 H, H-2), 7.96 (m, 2 H, Ph-H), 7.45 (m, 2 H, Ph-H and H-8), 6.39 (m, 1 H, H-1'), 4.78 (m, 2 H, Ph-CH, 7-CH₂a), 4.56 (m, 2 H, 7-CH₂b and H-3'), 4.02 (m, 1 H, H-4'), 3.78 (m, 2 H, H-5'), 2.62 (m, 1 H, CH(CH₃)₂), 2.44 (m, 1 H, H-2'a), 2.30 (m, 1 H, H-2'b), 1.02 and 0.95 (2 d, J=6.4 Hz, 3 H, CH₃), 0.71 and 0.69 (2 d, J=7.2 Hz, 3 H, CH₃).

7-[1-(2,6-Dinitrophenyl)-2-methyl-propyloxy]methyl-7-deaza-2'-deoxyadenosine (dA.38): A solution of n-Bu₄NF (44 mg, 0.140 mmol) in THF (2 mL) was added to a solution of dA.37a (42 mg, 0.066 mmol) in THF (5 mL) at 0° C. The reaction was gradually warmed to room temperature and stirred for two hours. The mixture was concentrated in vacuo, and a solution of dA.37b (12 mg, 0.022 mmol) in 1,4-dioxane (4 mL) was added, followed by 7N NH₃ in methanol solution (18 mL). The mixture was transferred to a sealed tube and stirred at 90-100° C. for 36 hours, then cooled down, concentrated in vacuo, and the residue was purified by silica gel chromatography to yield 7-[1-(2,6-dinitrophenyl)-2-methyl-propyloxy]methyl-7-deaza-2'-deoxyadenosine dA.38 (38 mg, 86%, 1:1 mixture of diastereomers) as a viscous oil. $^1$H NMR (400 MHz, DMSO-d₆) for diastereomers: δ 8.17 (m, 1 H, Ph-H), 8.07 and 8.06 (2 s, 1 H, H-2), 7.85 (m, 1 H, Ph-H), 7.69 (m, 1 H, Ph-H), 7.20 and 7.18 (2 s, 1 H, H-8), 6.57 (bs, 2 H, D₂O exchangeable, 6-NH₂), 6.46 (m, 1 H, H-1'), 5.26 (d, J=3.6 Hz, 1 H, D₂O exchangeable, 3'-OH), 5.01 (m, 1 H, D₂O exchangeable, 5'-OH), 4.60 (m, 2 H, Ph-CH and 7-CH₂a), 4.29 (m, 1 H, 7-CH₂b), 4.13 (m, 1 H, H-3'), 3.80 (m, 1 H, H-4'), 3.51 (m, 2 H, H-5'a and H-5'b), 2.49 (m, 1 H, CH(CH₃)₃), 2.16 (m, 1 H, H-2'a and H-2'b), 0.91 (m, 3 H, CH₃), 0.65 (m, 3 H, CH₃); $^{13}$C NMR (100 MHz, CD₃OD) for diastereomers: δ 157.73 (C), 151.33 and 151.18 (CH), 150.39 (C), 150.22 (C), 130.45 and 130.49 (CH), 127.25 and 127.13 (C), 126.90 (CH), 128.20 and 128.15 (CH), 123.45 and 123.32 (CH), 110.32 and 110.23 (CH), 103.03 and 102.75 (C), 87.74 and 87.58 (CH), 85.43 and 84.73 (CH), 79.94 and 79.37 (CH), 71.88 and 71.64 (CH), 64.08 and 63.71 (CH₂), 62.67 and 62.32 (CH₂), 40.95 and 39.82 (CH₂), 34.24 and 34.16 (CH), 19.63 (CH₃), 17.49 (CH₃). ToF-MS (ESI): For the molecular ion C₂₂H₂₇N₆O₈ [M+H]⁺, the calculated mass was 503.1890, and the observed mass was 503.2029.

7-[1-(2,6-Dinitrophenyl)-2-methyl-propyloxy]methyl-7-deaza-2'-deoxyadenosine-5'-triphosphate (WW6p057 ds1 & ds2): POCl₃ (11 μL, 0.12 mmol) was added to a solution of compound dA.38 (30 mg, 0.06 mmol) in trimethylphosphate (0.4 mL) and the reaction was stirred at 0° C. under a nitrogen atmosphere for four hours. A solution of bis-tri-n-butylammonium pyrophosphate (285 mg, 0.6 mmol) and tri-n-butylamine (120 μL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (10 mL), filtered, and purified by anion exchange chromatography using a Q Sepharose FF column (2.5×20 cm) with a linear gradient of 25% acetonitrile/75% 0.1 M triethylammonium bicarbonate (TEAB) to 25% acetonitrile/75% 1.5 M TEAB over 240 min at 4.5 ml/min. The fractions containing triphosphate were combined and lyophilized to yield 7-[1-(2,6-dinitrophenyl)-2-methyl-propyloxy]methyl-7-deaza-2'-deoxyadenosine-5'-triphosphate WW6p057 as mixture of

Synthesis of 7-[1-(4-methoxy-2-nitrophenyl)-2-methyl-propyloxy]methyl-7-deaza-2'-deoxyadenosine-5'-triphosphate two diastereomers which were separated by reverse phase HPLC on a PerkinElmer Aquapore OD-300 column (7 µm, 250×4.6 mm) to yield the single diastereomer WW6p057 ds1 (fast eluting) and WW6p057 ds2 (slow eluting). Mobile phase: A, 100 mM triethylammonium acetate (TEAA) in water; B, 100 mM TEAA in water/CH₃CN (30:70).

Scheme 29. Synthesis of 7-[1-(4-methoxy-2-nitrophenyl)-2-methyl-propyloxy]methyl-7-deaza-2'-deoxyadenosine-5'-triphosphate.

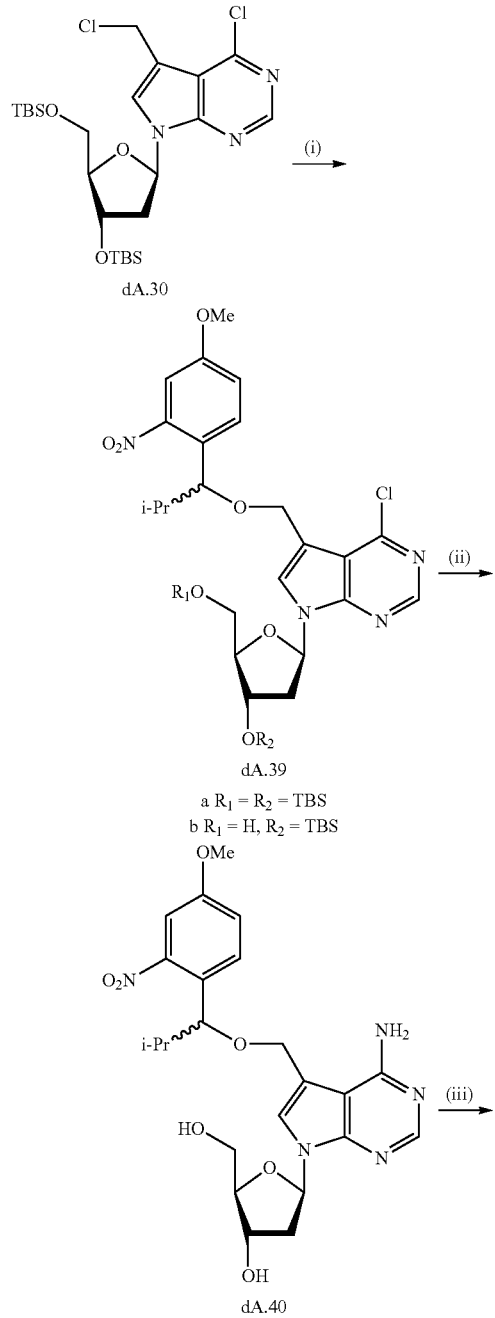

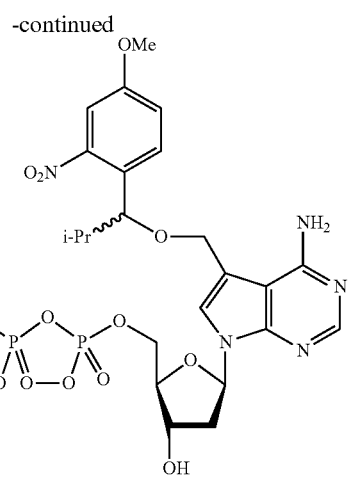

WW6p087 ds1 & ds2

(i) 1-(4-methoxy-2-nitrophenyl)-2-methyl-propanol (racemic), neat, vacuum, 108° C., 33% (dA.39a) and 21% (dA.39b);
(ii) n-Bu₄NF, THF; NH₃, 1,4-dioxane/MeOH, 90-100° C., 61%;
(iv) POCl₃, (MeO)₃PO, 0° C.; (n-Bu₃NH)₂H₂P₂O₇, n-Bu₃N, DMF; 1 M HNEt₃HCO₃.

9-[β-D-3',5'-O-Bis-(tert-butyldimethylsilyl)-2'-deoxyribofuranosyl]-6-chloro-7-[1-(4-methoxy-2-nitrophenyl)-2-methyl-propyloxy]methyl-7-deazapurine (dA.39a) and 9-[β-D-3'-O-(tert-butyldimethylsilyl)-2'-deoxyribofuranosyl]-6-chloro-7-[1-(4-methoxy-2-nitrophenyl)-2-methyl-propyloxy]methyl-7-deazapurine (dA.39b): Compound dA.30 (103 mg, 0.19 mmol) and 1-(4-methoxy-2-nitrophenyl)-2-methyl-propanol (428 mg, 1.90 mmol) were dissolved in anhydrous dichloromethane (3 mL). The solvent was removed in vacuo, and the residue was heated at 108° C. in vacuo for 30 minutes, then dissolved in ethyl acetate and purified by silica gel chromatography to 9-[β-D-3',5'-O-bis-(tert-butyldimethylsilyl)-2'-deoxyribofuranosyl]-6-chloro-7-[1-(4-methoxy-2-nitrophenyl)-2-methyl-propyloxy]methyl-7-deazapurine dA.39a (46 mg, 33%, 1:1 mixture of diastereomers) and 9-[β-D-3'-O-(tert-butyldimethylsilyl)-2'-deoxyribofuranosyl]-6-chloro-7-[1-(4-methoxy-2-nitrophenyl)-2-methyl-propyloxy]methyl-7-deazapurine dA.39b (25 mg, 21%, 1:1 mixture of diastereomers). $^1$H NMR (400 MHz, CDCl₃) for dA.39a (1:1 mixture of diastereomers): δ 8.60 and 8.59 (2 s, 1 H, H-2), 7.64 and 7.62 (2 d, J=6.4 Hz, 1 H, Ph-H), 7.47 and 7.45 (2 s, 1 H, H-8), 7.32 (m, 1 H, Ph-H), 7.12 (m, 1 H, Ph-H), 6.71 (m, 1 H, H-1'), 4.62 (m, 4 H, Ph-CH, 7-CH₂, and H-3'), 3.99 (m, 1 H, H-4'), 3.87 and 3.86 (2 s, 3 H, MeO), 3.70 (AB d, 1 H, H-5'a and H-5'b), 2.50 (m, 1 H, H-2'a), 2.35 (m, 1 H, H-2'a), 1.93 (m, 1 H, CH(CH₃)₂), 1.00 and 0.97 (2 d, J=6.8 Hz, 3 H, CH₃), 0.93 and 0.92 (2 s, 9 H, (CH₃)₃CSi), 0.91 and 0.89 (2 s, 9 H, (CH₃)₃CSi), 0.80 and 0.76 (2 d, J=6.8 Hz, 3 H, CH₃), 0.12 and 0.10 (2 s, 6 H, (CH₃)₂Si), 0.08, 0.07, 0.06 and 0.05 (4 s, 6 H, (CH₃)₂Si); $^{13}$C NMR (100 MHz, CDCl₃) for dA.39a (1:1 mixture of diastereomers): δ 158.82 (C), 151.82 and 151.46 (C), 151.32 and 151.16 (C), 150.85 (CH), 150.27 and 150.08 (C), 130.16 (CH), 128.95 and 129.80 (C), 126.56 and 126.22 (CH), 119.60 (CH), 112.49 and 122.22 (C), 108.21 and 108.14 (CH), 87.64 and 87.58 (CH), 83.69 (CH), 80.68 and 79.98 (CH), 72.42 and 72.27 (CH), 63.26 and 63.17 (CH₂), 63.03 and 62.80 (CH₂), 55.80 (CH₃), 41.04 (CH₂), 35.08 (CH), 25.95 ((CH₃)₃Si), 25.80 ((CH₃)₃Si), 25.66 ((CH₃)₃Si), 19.12 and 19.05 (CH₃), 18.42 (CH₃), 18.05 (C), −3.75 (CH₃Si), −4.66 and −4.76 (CH₃Si), −5.36 (CH₃Si), −5.46 and −5.50 (CH₃Si).

¹H NMR (400 MHz, CDCl₃) for dA.39b (1:1 mixture of diastereomers): δ 8.59 and 8.57 (2 s, 1 H, H-2), 7.62 and 7.60 (2 d, J=6.4 Hz, 1 H, Ph-H), 7.33 and 7.32 (2 d, J=2.4 Hz, 1 H, Ph-H), 7.30 and 7.29 (2 s, 1 H, H-8), 7.14 and 7.10 (2 dd, J=8.8, 2.4 Hz, 1 H, Ph-H), 6.28 (m, 1 H, H-1'), 5.06 (br t, 1 H, 5'-OH), 4.64 (m, 4 H, Ph-CH, 7-CH₂, and H-3'), 4.11 (m, 1 H, H-4'), 3.94 (AB d, J=10.8 Hz, 1 H, H-5'a), 3.87 and 3.85 (2 s, 3 H, MeO), 3.76 (m, 1 H, H-5'b), 2.93 (m, 1 H, H-2'a), 2.25 (m, 1 H, H-2'b), 1.96 (sep, J=6.4 Hz, 1 H, CH(CH₃)₂), 0.95 (m, 3 H, CH₃), 0.94 (s, 9 H, (CH₃)₃CSi), 0.80 (m, 3 H, CH₃), 0.13 (s, 6 H, (CH₃)₂Si).

7-[1-(4-methoxy-2-nitrophenyl)-2-methyl-propyloxy]methyl-7-deaza-2'-deoxyadenosine (dA.40): A solution of n-Bu₄NF (68 mg, 0.217 mmol) in THF (2 mL) was added to a solution of dA.39a (46 mg, 0.063 mmol) and dA.39b (25 mg, 0.040 mmol) in THF (8 mL) at 0° C. The reaction was gradually warmed to room temperature and stirred for 30 minutes. The mixture was concentrated in vacuo, dissolved in 1,4-dioxane (8 mL), followed by addition of 7N NH₃ in methanol (24 mL). The mixture was transferred to a sealed tube and stirred at 90-100° C. for 16 hours, then cooled down, concentrated in vacuo, and the residue was purified by silica gel chromatography to yield 7-[1-(4-methoxy-2-nitrophenyl)-2-methyl-propyloxy]methyl-7-deaza-2'-deoxyadenosine dA.40 (38 mg, 61%, 1:1 mixture of diastereomers) as a viscous oil. ¹H NMR (400 MHz, DMSO-d₆) for diastereomers: δ 8.06 and 8.05 (2 s, 1 H, H-2), 7.57 and 7.54 (2 d, J=8.8 Hz, 1 H, Ph-H), 7.47 and 7.44 (2 d, J=2.6 Hz, 1 H, Ph-H), 7.33 and 7.27 (2 dd, J=8.8, 2.6 Hz, 1 H, Ph-H), 7.18 and 7.15 (2 s, 1 H, H-8), 6.63 (bs, 2 H, D₂O exchangeable, 6-NH₂), 6.43 (m, 1 H, H-1'), 5.24 (m, 1 H, D₂O exchangeable, 3'-OH), 5.03 (m, 1 H, D₂O exchangeable, 5'-OH), 4.55 (m, 2 H, Ph-CH, 7-CH₂a), 4.30 (m, 2 H, 7-CH₂b and H-3'), 3.86 and 3.84 (2 s, 3 H, MeO), 3.78 (m, 1 H, H-4'), 3.48 (m, 2 H, H-5'), 2.45 (m, 1 H, H-2'a), 2.12 (m, 1 H, H-2'b), 1.93 (m, 1 H, CH(CH₃)₂), 0.88 (m, 3 H, CH₃), 0.74 and 0.71 (2 d, J=6.8 Hz, 3 H, CH₃); ¹³C NMR (100 MHz, CD₃OD) for diastereomers: δ 158.46 and 158.40 (C), 158.40 (C), 150.28 and 150.25 (CH), 149.97 and 149.78 (C), 149.28 (C), 129.19 and 129.16 (CH), 126.69 and 126.56 (C), 121.36 and 121.02 (CH), 118.11 and 117.99 (CH), 111.20 and 110.95 (C), 107.27 and 107.20 (CH), 102.40 and 102.36 (C), 86.87 and 86.83 (CH), 84.42 and 84.25 (CH), 79.47 and 78.73 (CH), 70.97 (CH), 63.00 and 62.46 (CH₂), 61.73 and 61.64 (CH₂), 54.30 (CH₃), 39.16 and 38.99 (CH₂), 33.71 and 33.68 (CH), 17.29 (CH₃), 16.71 and 16.66 (CH₃). ToF-MS (ESI): For the molecular ion C₂₃H₃₀N₅O₇ [M+H]⁺, the calculated mass was 488.2145, and the observed mass was 488.2466.

7-[1-(4-Methoxy-2-nitrophenyl)-2-methyl-propyloxy]methyl-7-deaza-2'-deoxyadenosine-5'-triphosphate (WW6p087 ds1 & ds2)

POCl₃ (11 μL, 0.12 mmol) was added to a solution of compound dA.40 (28 mg, 0.06 mmol) in trimethylphosphate (0.35 mL), and the reaction was stirred at 0° C. under a nitrogen atmosphere for two hours. A solution of bis-tri-n-butylammonium pyrophosphate (237 mg, 0.5 mmol) and tri-n-butylamine (100 μL) in anhydrous DMF (1.0 mL) was added. After 10 minutes of stirring, triethylammonium bicarbonate buffer (1 M, pH 7.5; 10 mL) was added. The reaction was stirred for one hour at room temperature and then concentrated in vacuo. The residue was dissolved in water (10 mL), filtered, and purified by anion exchange chromatography using a Q Sepharose FF column (2.5×20 cm) with a linear gradient of 25% acetonitrile/75% 0.1 M triethylammonium bicarbonate (TEAB) to 25% acetonitrile/75% 1.5 M TEAB over 240 min at 4.5 ml/min. The fractions containing triphosphate were combined and lyophilized to yield 7-[1-(4-methoxy-2-nitrophenyl)-2-methyl-propyloxy]methyl-7-deaza-2'-deoxyadenosine-5'-triphosphate WW6p087 as mixture of two diastereomers, which were separated by reverse phase HPLC on a Perkin Elmer Aquapore OD-300 column (7 μm, 250×4.6 mm) to yield the single diastereomer WW6p087 ds1 (fast eluting) and WW6p087 ds2 (slow eluting). Mobile phase: A, 100 mM triethylammonium acetate (TEAA) in water; B, 100 mM TEAA in water/CH₃CN (30:70).

Example 9

Synthesis of Chemically Cleavable Analogs

Synthesis of 5-(benzyloxy)methyl-2'-deoxyuridine-5'-triphosphate

Scheme 30. Synthesis of 5-(benzyloxy)methyl-2'-deoxyuridine-5'-triphosphate.

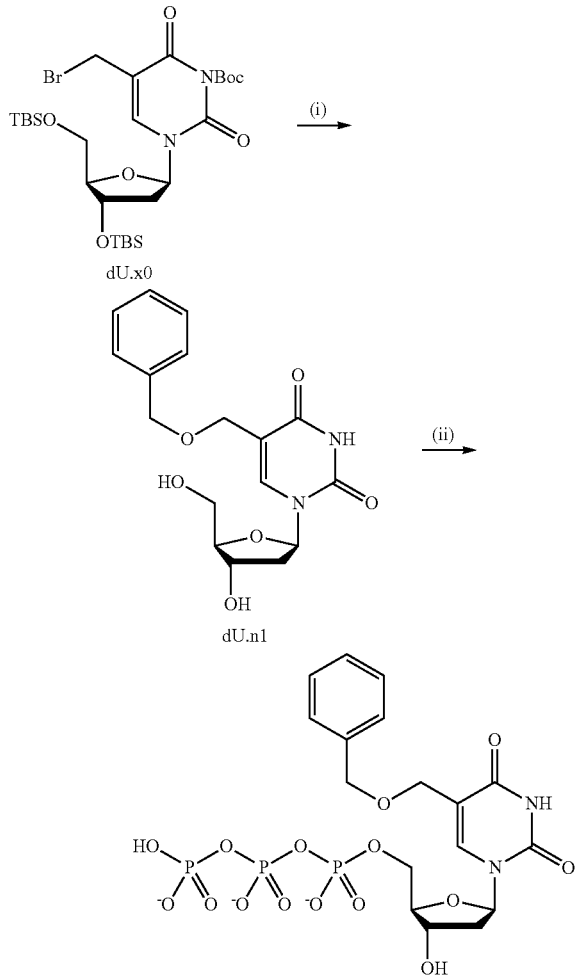

(i) benzyl alcohol, neat, 112° C., 44%;
(ii) POCl₃, proton sponge, (MeO)₃PO, 0° C.; (n-Bu₃NH)₂H₂P₂O₇, n-Bu₃N, DMF, 1M HNEt₃HCO₃.

5-(Benzyloxy)methyl-2'-deoxyuridine (dU.n1): Compound dU.x0 (381 mg, 0.586 mmol) and benzyl alcohol (634 mg, 5.864 mmol) were heated neat at 112° C. for 30 minutes under a nitrogen atmosphere. The mixture was cooled down to room temperature, dissolved in minimum amount of dichloromethane, and purified by silica gel chromatography to yield 5-(benzyloxy)methyl-2'-deoxyuridine dU.n1 (89 mg, 44%). It is noted that dU.n1 is known (e.g., see Mel'nik et al., 1991, which is incorporated herein by reference), but it was obtained in a different way than reported here). $^1$H NMR (400 MHz, DMSO-d$_6$): δ 11.40 (s, 1 H, D$_2$O exchangeable, 3-NH), 7.94 (s, 1 H, H-6), 7.30 (m, 5 H, Ph-H), 6.17 (t, 1 H, J=6.8 Hz, H-1'), 5.26 (d, J=4.2 Hz, 1 H, D$_2$O exchangeable, 3'-OH), 5.04 (t, J=5.2 Hz, 1 H, D$_2$O exchangeable, 5'-OH), 4.49 (s, 2 H, PhCH$_2$), 4.24 (m, 1 H, H-3'), 4.17 (m, 2 H, 5-CH$_2$a and 5-CH$_2$b), 3.79 (m, 1 H, H-4'), 3.57 (m, 2 H, H-5'a and H-5'b), 2.10 (m, 2 H, H-2'a and H-2'b); $^{13}$C NMR (100 MHz, CD$_3$OD): δ 165.29 (C), 152.24 (C), 141.23 (CH), 139.62 (C), 129.52 (CH), 129.05 (CH), 128.84 (CH), 112.44 (C), 89.04 (CH), 86.73 (CH), 73.69 (CH$_2$), 72.27 (CH), 65.95 (CH$_2$), 62.92 (CH$_2$), 41.50 (CH$_2$).

5-(Benzyloxy)methyl-2-deoxyuridine-5'-triphosphate (WW5p145): POCl$_3$ (8 μL, 0.086 mmol) was added to a solution of compound dU.n1 (15 mg, 0.043 mmol) and proton sponge (18 mg, 0.086 mmol) in trimethylphosphate (0.35 mL) and the reaction was stirred at 0° C. under a nitrogen atmosphere for two hours. A solution of bis-tri-n-butylammonium pyrophosphate (237 mg, 0.5 mmol) and tri-n-butylamine (100 μL) in anhydrous DMF (1 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(benzyloxy)methyl-2'-deoxyuridine-5'-triphosphate WW5p145. $^1$H NMR (400 MHz, D$_2$O): δ 7.82 (s, 1 H, H-6), 7.26 (m, 5 H, Ph-H), 6.14 (t, J=6.8 Hz, 1 H, H-1'), 4.51 (m, 1 H, H-3'), 4.5 (s, 2 H, Ph-CH$_2$), 4.31 (2 d, 2 H, 5-CH$_2$), 4.08 (m, 3 H, H-4' and H-5'), 2.21 (m, 2 H, H-2'); $^{31}$P NMR (162 Hz, D$_2$O): 6-9.79 (d, J=19.4 Hz), −11.67 (d, J=21.0 Hz), −23.13 (t, J=21.0 Hz).

Synthesis of 5-(1-phenyl-2-methyl-propyloxy)methyl-2'-deoxyuridine-5'-triphosphate Scheme 31. Synthesis of 5-(1-phenyl-2-methyl-propoxy)methyl-2'-deoxyuridine-5'-triphosphate.

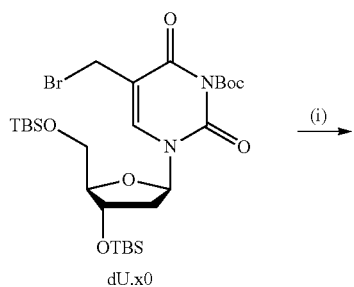

dU.x0

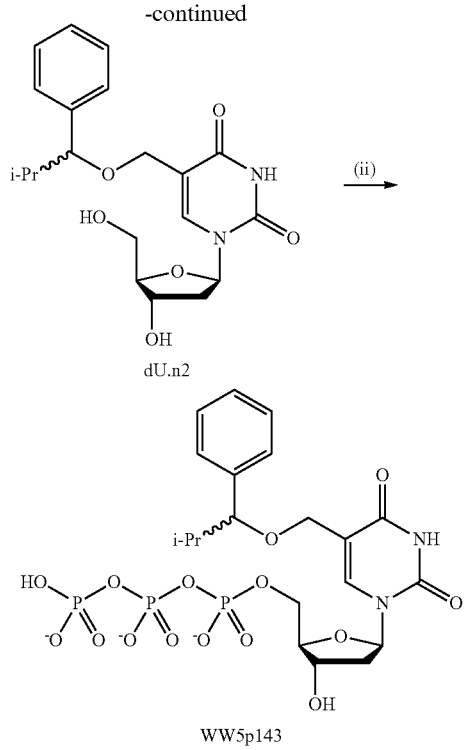

(i) 2-methyl-1-phenyl-1-propanol, neat, 108-114° C., 12%;
(ii) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

5-(1-Phenyl-2-methyl-propyloxy)methyl-2'-deoxyuridine (dU.n2):Compound dU.x0 (0.331 g, 0.51 mmol) and 2-methyl-1-phenyl-1-propanol (1.238 g, 8.24 mmol) were heated neat at 108-114° C. for one hour under a nitrogen atmosphere. The mixture was cooled down to room temperature, dissolved in minimum amount of ethyl acetate, and purified by silica gel chromatography to yield 5-(1-phenyl-2-methyl-propyloxy) methyl-2'-deoxyuridine dU.n2 (26 mg, 12%, 1:1 mixture of diastereomers). 3',5'-O-Bis-(tert-butyldimethylsilyl)-5-(1-phenyl-2-methyl-propyloxy)methyl-2'-deoxy-uridine (77 mg, 24%, 1:1 mixture of diastereomers) and (3' or 5')—O-(tert-butyldimethylsilyl)-5-(1-phenyl-2-methyl-propyloxy) methyl-2'-deoxyuridine (46 mg, 18%, 1:1 mixture of diastereomers) were also obtained from the reaction. $^1$H NMR (400 MHz, DMSO-d$_6$) for dU.n2 (1:1 mixture of diastereomers): δ 11.31 (br s, 1 H, D$_2$O exchangeable, 3-NH), 7.77 (2 s, 1 H, H-6), 7.29 (m, 5 H, Ph-H), 6.14 (m, 1 H, H-1'), 5.25 (d, J=4.4 Hz, 1 H, D$_2$O exchangeable, 3'-OH), 4.98 (m, 1 H, D$_2$O exchangeable, 5'-OH), 4.22 (m, 1 H, H-3'), 4.00 (m, 1 H, PhCH), 3.91 (m, 2 H, 5-CH$_2$a and 5-CH$_2$b), 3.77 (m, 1 H, H-4'), 3.54 (m, 2 H, H-5'a and H-5'b), 2.06 (m, 2 H, H-2'a and H-2'b), 1.83 (m, 2 H, CH(CH$_3$)$_2$), 0.88 (d, J=6.8 Hz, 3 H, CH$_3$), 0.66 (d, J=6.8 Hz, 3 H, CH$_3$).

$^1$H NMR (400 MHz, CDCl$_3$) for 3',5'-O-bis-(tert-butyldimethylsilyl)-5-(1-phenyl-2-methyl-propyloxy)methyl-2'-deoxyuridine (1:1 mixture of diastereomers): δ 9.07 and 9.06 (2 s, 1 H, 3-NH), 7.95 and 7.53 (2 s, 1 H, H-6), 7.29 (m, 5 H, Ph-H), 6.29 (m, 1 H, H-1'), 4.24 (m, 1 H, H-3'), 4.03 (m, 4 H, 5-CH$_2$a, 5-CH$_2$b, PhCH, and H-4'), 3.77 (AB dd, J=11.2 and 3.4 Hz, 1 H, H-5'a), 3.75 (AB dd, J=11.2 and 4.4 Hz, 1 H, H-5'b), 2.29 (m, 1 H, H-2'a), 1.98 (m, 1 H, H-2'b), 1.04 and 1.01 (2 d, J=6.4 and 6.8 Hz, 3 H, CH$_3$), 0.90 (s, 9 H, (CH$_3$)$_3$C), 0.89 and 0.88 (2 s, 9 H, (CH$_3$)$_3$C), 0.74 and 0.73 (2 d, J=6.8 and 6.4 Hz, 3 H, CH$_3$) 0.10 and 0.09 (2 s, 6 H, CH$_3$Si), 0.08 and 0.07 (2 s, 3 H, CH₃Si), 0.06 and 0.05 (2 s, 3 H, (CH₃)₂Si); $^{13}$C NMR (100 MHz, CDCl₃) for 3',5'-O-bis-(tert-butyldimethylsilyl)-5-(1-phenyl-2-methyl-propyloxy)methyl-2'-deoxyuridine (1:1 mixture of diastereomers): δ 162.51 (C), 150.20 and 150.15 (C), 140.83 and 140.79 (C), 137.28 and 137.19 (CH), 128.15 and 128.11 (CH), 127.54 (CH), 127.45 (CH), 112.41 (C), 88.40 and 88.31 (CH), 87.83 and 87.78 (CH), 85.38 and 85.30 (CH), 72.49 and 72.41 (CH), 63.64 and 63.57 (CH₂), 63.22 (CH₂), 40.79 (CH₂), 34.82 and 34.79 (CH), 25.93 and 25.92 (C(CH₃)₃), 25.76 and 25.72 (C(CH₃)₃), 19.20 and 19.17 (CH₃), 19.00 (CH₃), 18.38 (C), 18.00 (C), −4.65 (CH₃), −4.80 (CH₃), −5.35 and −5.38 (CH₃), −5.40 and −5.44 (CH₃).

$^{1}$H NMR (400 MHz, CDCl₃) for (3' or 5')-O-(tert-butyldimethylsilyl)-5-(1-phenyl-2-methyl-propyloxy)methyl-2'-deoxyuridine (1:1 mixture of diastereomers): δ 9.09 (s, 1 H, 3-NH), 7.61 (s, 1 H, H-6), 7.28 (m, 5 H, Ph-H), 6.18 (m, 1 H, H-1'), 4.51 (m, 1 H, H-3'), 4.09 (s, 2 H, 5-CH₂a, 5-CH₂b), 3.98 (d, J=7.2 Hz, 1 H, PhCH), 3.93 (m, 1 H, H-4'), 3.90 (m, 1 H, H-5'a), 3.73 (m, 1 H, H-5'b), 2.50 (br, 1 H, 3'- or 5'-OH), 2.30 (m, 1 H, H-2'a), 1.98 (m, 2 H, H-2'b and CH(CH₃)₂), 1.01 (d, J=6.4 Hz, 3 H, CH₃), 0.91 (s, 9 H, (CH₃)₃C), 0.74 (d, J=6.8 Hz, 3 H, CH₃), 0.10 (s, 3 H, CH₃Si), 0.07 and 0.06 (2 s, 3 H, CH₃Si).

5-(1-Phenyl-2-methyl-propyloxy)methyl-2-deoxyuridine-5'-triphosphate (WW5p143): POCl₃ (6 µL, 0.063 mmol) was added to a solution of compound dU.n2 (15 mg, 0.032 mmol) and proton sponge (14 mg, 0.063 mmol) in trimethylphosphate (0.4 mL) and the reaction was stirred at 0° C. under a nitrogen atmosphere for two hours. Additional POCl₃ (6 µL, 0.063 mmol) was added twice in one hour intervals. A solution of bis-tri-n-butylammonium pyrophosphate (285 mg, 0.6 mmol) and tri-n-butylamine (120 µL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(1-phenyl-2-methyl-propyloxy)methyl-2'-deoxyuridine-5-'triphosphate WW5p143 (1:1 mixture of diastereomers); $^{31}$P NMR (162 Hz, D₂O): δ-10.88 (m), −11.33 (m), −23.08 (m).

Synthesis of 5-(2-methylbenzyloxy)methyl-2'-deoxyuridine-5'-triphosphate

Scheme 32.
Synthesis of 5-(2-methylbenzyloxy)methyl-2'-deoxyuridine-5'-triphosphate.

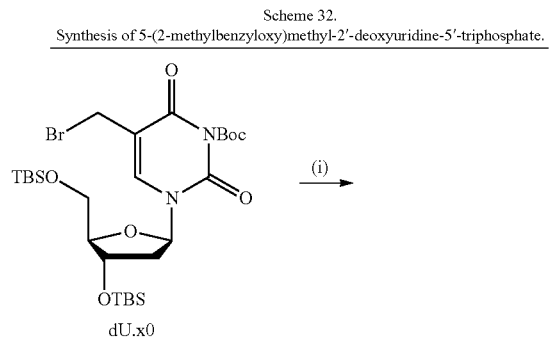

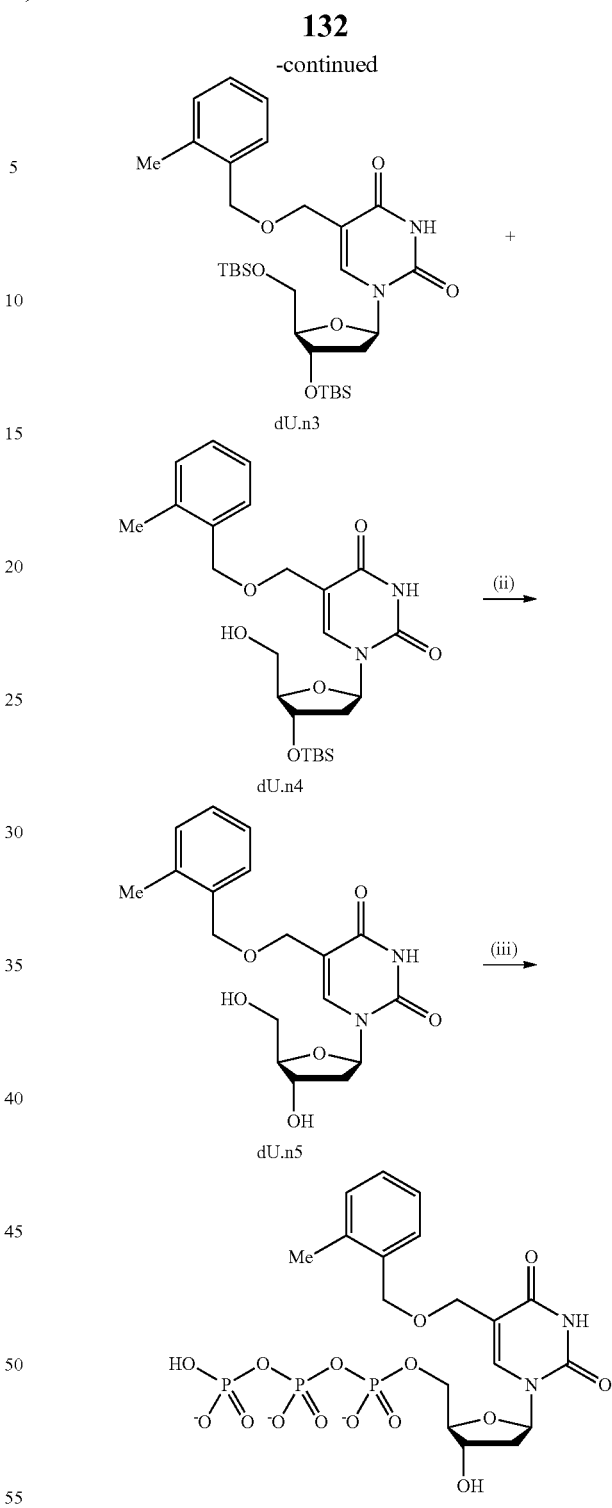

(i) 2-methylbenzyl alcohol, neat, 110° C.;
(ii) n-Bu₄NF, THF, room temperature, 38%;
(iii) POCl₃, proton sponge, (MeO)₃PO, 0° C.; (n-Bu₃NH)₂H₂P₂O₇, n-Bu₃N, DMF; 1M HNEt₃HCO₃.

3',5'-O-Bis-(tert-butyldimethylsilyl)-5-(2-methylbenzyloxy)methyl-2'-deoxyuridine (dU.n3) and (3' or 5')-O-(tert-butyldimethylsilyl)-5-(2-methylbenzyloxy)methyl-2'-deoxyuridine (dU.n4:) Compound dU.x0 (0.438 g, 0.67 mmol) and 2-methylbenzyl alcohol (0.823 g, 6.74 mmol) were heated neat at 110° C. for 45 minutes under a nitrogen atmosphere. The mixture was cooled down to room temperature and purified by silica gel chromatography to yield 3',5'-O-bis-(tert-butyldimethylsilyl)-5-(2-methylbenzyloxy)methyl-2'-deoxyuridine dU.n3 (20 mg, 5%) and (3' or 5')—O-(tert-butyldimethylsilyl)-5-(2-methylbenzyloxy)methyl-2'-deoxyuridine dU.n4 (43 mg, 14%). $^1$H NMR (400 MHz, CDCl$_3$) for dU.n3: δ 8.42 (s, 1 H, NH), 7.66 (s, 1 H, H-6), 7.30 (m, 1 H, Ph-H), 7.18 (m, 3 H, Ph-H), 6.28 (t, 1 H, H-1'), 4.59 (2 d, 2 H, Ph-CH$_2$), 4.38 (m, 1 H, H-3'), 4.27 (2 d, 2 H, 5-CH$_2$), 3.94 (m, 1 H, H-4'), 3.75 (m, 2 H, H-5'), 2.34 (s, 3 H, CH$_3$), 2.26 (m, 1 H, H-2'a), 2.0 (m, 1 H, H-2'b), 0.89 and 0.90 (2 s, 18 H, (CH$_3$)$_3$CSi), 0.09 and 0.08 (2 s, 6 H, (CH$_3$)$_2$Si), 0.07 and 0.06 (2 s, 6 H, (CH$_3$)$_2$Si); $^1$H NMR (400 MHz, CDCl$_3$) for dU.n4: δ 8.67 (s, 1 H, NH), 7.73 (s, 1 H, H-6), 7.33 (m, 1 H, Ph-H), 7.22 (m, 3 H, Ph-H), 6.16 (t, 1 H, J=6.4 Hz, H-1'), 4.6 (s, 2 H, Ph-CH$_2$), 4.46 (m, 1 H, H-3'), 4.34 (2 d, 2 H, 5-CH$_2$), 3.92 (m, 1 H, H-4'), 3.81 (m, 1 H, H-5'a), 3.67 (m, 1 H, H-5'b), 2.35 (s, 3 H, CH$_3$), 2.30 (m, 1 H, H-2'a), 2.24 (m, 1 H, H-2'b), 0.89 (1 s, 9 H, (CH$_3$)$_3$CSi), 0.07 (2 s, 6 H, (CH$_3$)$_2$Si).

5-(2-Methylbenzyloxy)methyl-2'-deoxyuridine (dU.n5): A solution of compound dU.n3 (20 mg, 0.034 mmol) in THF (2 mL) was treated with n-Bu$_4$NF (32 mg, 0.1 mmol) at room temperature for three hours. Separately a solution of compound dU.n4 (43 mg, 0.09 mmol) in THF (4 mL) was also treated with n-Bu$_4$NF (64 mg, 0.2 mmol) at room temperature for three hours. The two reaction mixtures were combined, concentrated in vacuo, and purified by silica gel column chromatography to yield 5-(2-methylbenzyloxy)methyl-2'-deoxyuridine dU.n5 (17 mg, 38%). $^1$H NMR (400 MHz, DMSO-d$_6$): δ 11.38 (s, 1 H, D$_2$O exchangeable, NH), 7.93 (s, 1 H, H-6), 7.29 (m, 1 H, Ph-H), 7.15 (m, 3 H, Ph-H), 6.15 (t, 1 H, J=6.8 Hz, H-1'), 5.24 (d, J=4.4 Hz, 1 H, D$_2$O exchangeable, 3'-OH), 5.02 (t, 1 H, J=5.2 Hz, D$_2$O exchangeable, 5'-OH), 4.46 (s, 2 H, Ph-CH$_2$), 4.22 (m, 1 H, H-3'), 4.16 (2 d, 2 H, 5-CH$_2$), 3.77 (m, 1 H, H-4'), 3.55 (m, 2 H, H-5'), 2.24 (s, 1 H, CH$_3$), 2.08 (m, 2 H, H-2').

5-(2-Methylbenzyloxy)methyl-2'-deoxyuridine-5'-triphosphate (WW147): POCl$_3$ (8 µL, 0.083 mmol) was added to a solution of compound dU.n5 (15 mg, 0.041 mmol) and proton sponge (18 mg, 0.083 mmol) in trimethylphosphate (0.35 mL) and the reaction was stirred at 0° C. under a nitrogen atmosphere for two hours. Additional POCl$_3$ (4 µL, 0.041 mmol) was added and the mixture was stirred for another two hours at 0° C. A solution of bis-tri-n-butylammonium pyrophosphate (237 mg, 0.5 mmol) and tri-n-butylamine (100 µL) in anhydrous DMF (1 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in water (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(2-methylbenzyloxy)methyl-2'-deoxyuridine-5'-triphosphate WW5p147. $^1$H NMR (400 MHz, D$_2$O): δ 7.96 (s, 1 H, H-6), 7.32 (m, 1 H, Ph-H), 7.24 (m, 3 H, Ph-H), 6.28 (t, J=6.8 Hz, 1 H, H-1'), 4.63 (m, 3 H, Ph-CH$_2$ and H-3'), 4.43 (2 d, 2 H, 5-CH$_2$), 4.20 (m, 3 H, H-4' and H-5'), 2.36 (m, 2 H, H-2'), 2.31 (s, 3 H, CH$_3$); $^{31}$P NMR (162 Hz, D$_2$O): δ-7.29 (m), −10.66 (d, J=17.8 Hz), −21.4 (m).

Synthesis of 5-(2-isopropylbenzyloxy)methyl-2'-deoxyuridine-5'-triphosphate

Scheme 33. Synthesis of 5-(2-isopropylbenzyloxy)methyl-2'-deoxyuridine-5'-triphosphate

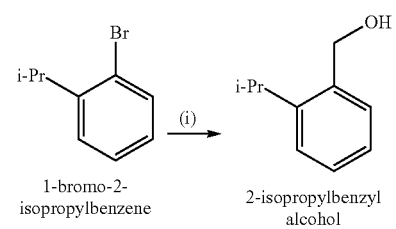

1-bromo-2-isopropylbenzene 2-isopropylbenzyl alcohol

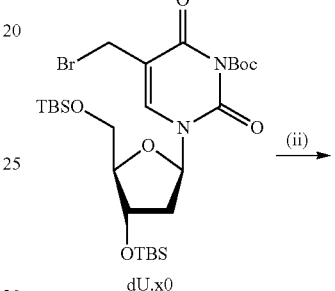

dU.x0

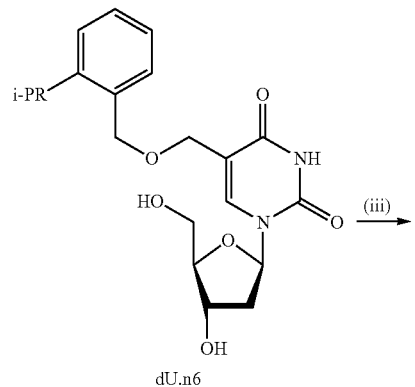

dU.n6

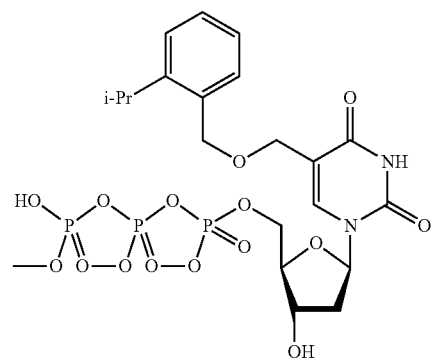

WW5p149

(i) n-BuLi, formaldehyde minus 78° C., 59%;
(ii) 2-isopropylbenzyl alcohol, neat, 110-112° C., 12%;
(iii) POCl$_3$, proton sponge, (MeO)$_3$PO, 0° C.; (n-Bu$_3$NH)$_2$H$_2$P$_2$O$_7$, n-Bu$_3$N, DMF; 1 M HNEt$_3$HCO$_3$.

2-Isopropylbenzyl alcohol: To a solution of 1-bromo-2-isopropylbenzene (2.50 g, 12.56 mmol) in anhydrous THF (40 mL), 2,2'-dipyridyl (ca 2 mg) was added under nitrogen atmosphere (Zhi et al., 2003, which is incorporated herein by reference). The mixture was cooled down minus 78° C., and a solution of n-butyllithium (5.52 mL, 2.5 M in hexanes, 13.82 mmol) was added dropwise via syringe within the period of ten minutes. Upon addition, the mixture was stirred for 30 minutes, then warmed up to minus 30° C., and a flow of formaldehyde (generated from 1.77 g of paraformaldehyde by heating at 160° C.) was passed through the solution until the deep red color disappeared completely. The mixture was quenched with saturated ammonium chloride (5 mL), then poured into brine (15 mL). Organic layer was separated; aqueous layer was extracted twice with dichloromethane (20 mL each); combined extracts were dried over anhydrous $Na_2SO_4$, evaporated, and purified by silica gel chromatography to yield 2-isopropylbenzyl alcohol (1.11 g, 59%) as an oil. $^1$H NMR (400 MHz, $CDCl_3$): δ 7.30 (m, 3 H, Ph-H), 7.18 (m, 3 H, Ph-H), 4.75 (s, 2 H, C$\underline{H}_2$OH), 3.27 (sep, J=6.6 Hz, 1 H, C$\underline{H}$(CH$_3$)$_2$), 1.53 (s, 1 H, CH$_2$O$\underline{H}$), 1.26 (d, J=6.6 Hz, 1 H, CH(C$\underline{H}_3$)$_2$).

5-(2-Isopropylbenzyloxy)methyl-2'-deoxyuridine (dU.n6): Compound dU.x0 (0.331 g, 0.51 mmol) and 2-isopropylbenzyl alcohol (1.238 g, 8.24 mmol) were heated neat at 110-112° C. for 1.5 hours under nitrogen atmosphere. The mixture was cooled down to room temperature, dissolved in ethyl acetate, and purified by silica gel chromatography to yield 5-(2-isopropylbenzyloxy)methyl-2'-deoxyuridine dU.n6 (33 mg, 12%). 3',5'-O-bis-(tert-butyldimethylsilyl)-5-(2-isopropylbenzyloxy)methyl-2'-deoxyuridine (134 mg, 29%) and (3' or 5')-O-(tert-butyldimethylsilyl)-5-(2-isopropylbenzyloxy)methyl-2'-deoxyuridine (98 mg, 26%) were also obtained from the reaction. $^1$H NMR (400 MHz, DMSO-$d_6$) for dU.n6: δ 11.41 (s, 1H, $D_2O$ exchangeable, NH), 7.94 (s, 1 H, H-6), 7.29 (m, 3 H, Ph-H), 7.14 (m, 1 H, Ph-H), 6.16 (t, 1 H, J=6.8 Hz, H-1'), 5.26 (t, J=4.4 Hz, 1 H, $D_2O$ exchangeable, 5'-OH), 5.03 (t, J=5.2 Hz, 1 H, $D_2O$ exchangeable, 5'-OH), 4.51 (s, 2 H, CH$_2$O), 4.24 (m, 1 H, H-3'), 4.18 (AB d, J=12.7 Hz, 1 H, 5-CH$_2$a), 4.15 (AB d, J=12.7 Hz, 1 H, 5-CH$_2$b), 3.78 (m, 1 H, H-4'), 3.56 (m, 2 H, H-5'a and H-5'b), 3.15 (sep, J=6.8 Hz, 1 H, C$\underline{H}$(CH$_3$)$_2$), 2.09 (m, 2 H, H-2'a and H-2'b), 1.15 (d, J=6.8 Hz, 6 H, CH(C$\underline{H}_3$)$_2$); $^{13}$C NMR (100 MHz, $CD_3OD$) for dU.n6: δ 163.77 (C), 150.77 (C), 147.85 (C), 139.85 (CH), 134.29 (C), 129.41 (CH), 128.19 (CH), 125.19 (CH), 125.03 (CH), 110.97 (C), 87.56 (CH), 85.22 (CH), 70.85 (CH), 70.35 (CH$_2$), 64.29 (CH$_2$), 61.47 (CH$_2$), 40.01 (CH$_2$), 28.39 (CH), 23.09 (CH$_3$).

$^1$H NMR (400 MHz, $CDCl_3$) for 3',5'-O-bis-(tert-butyldimethylsilyl)-5-(2-isopropylbenzyloxy)methyl-2'-deoxyuridine: δ 9.60 (s, 1 H, 3-NH), 7.64 (s, 1 H, H-6), 7.28 (m, 3 H, Ph-H), 7.28 (dt, J=7.1 and 1.8 Hz, 1 H, Ph-H), 6.29 (dd, J=7.7 and 5.9 Hz, 1 H, H-1'), 4.64 (s, 2 H, CH$_2$O), 4.38 (m, 1 H, H-3'), 4.31 (AB d, J=12.7 Hz, 1 H, 5-CH$_2$a), 4.27 (AB d, J=12.7 Hz, 1 H, 5-CH$_2$b), 3.93 (m, 1 H, H-4'), 3.74 (m, 2 H, H-5'a and H-5'b), 3.24 (sep, J=6.8 Hz, 1 H, C$\underline{H}$(CH$_3$)$_2$), 2.28 (m, 1 H, H-2'a), 2.00 (m, 1 H, H-2'b), 1.23 (d, J=6.8 Hz, 6 H, CH(C$\underline{H}_3$)$_2$), 0.89 (s, 9 H, (CH$_3$)$_3$C), 0.88 (s, 9 H, (CH$_3$)$_3$C), 0.09 (s, 3 H, CH$_3$Si), 0.07 (s, 3 H, CH$_3$Si), 0.06 (s, 3 H, CH$_3$Si), 0.05 (s, 3 H, CH$_3$Si); $^{13}$C NMR (100 MHz, $CDCl_3$) for 3',5'-O-bis-(tert-butyldimethylsilyl)-5-(2-isopropylbenzyloxy)methyl-2'-deoxyuridine: δ 162.94 (C), 150.29 (C), 147.74 (C), 138.11 (CH), 134.27 (C), 129.41 (CH), 128.40 (CH), 125.54 (CH), 125.38 (CH), 111.90 (C), 87.81 (CH), 85.28 (CH), 72.24 (CH), 71.08 (CH$_2$), 64.44 (CH$_2$), 62.99 (CH$_2$), 41.08 (CH$_2$), 28.63 (CH), 25.92 (C(CH$_3$)$_3$), 25.74 (C(CH$_3$)$_3$), 23.99 (CH$_3$), 18.36 (C), 17.98 (C), −4.67 (CH$_3$), −4.84 (CH$_3$), −5.44 (CH$_3$), −5.52 (CH$_3$).

$^1$H NMR (400 MHz, DMSO-$d_6$) for (3' or 5')-O-(tert-butyldimethylsilyl)-5-(2-isopropylbenzyloxy)methyl-2'-deoxyuridine: δ 11.42 (s, 1 H, $D_2O$ exchangeable, NH), 7.89 (s, 1 H, H-6), 7.28 (m, 3 H, Ph-H), 7.12 (m, 1 H, Ph-H), 6.14 (t, 1 H, J=6.8 Hz, H-1'), 5.07 (t, J=5.2 Hz, 1 H, $D_2O$ exchangeable, 5'-OH), 4.51 (s, 2 H, CH$_2$O), 4.41 (m, 1 H, H-3'), 4.31 (AB d, J=12.7 Hz, 1 H, 5-CH$_2$a), 4.15 (AB d, J=12.7 Hz, 1 H, 5-CH$_2$b), 3.76 (m, 1 H, H-4'), 3.56 (m, 2 H, H-5'a and H-5'b), 3.14 (sep, J=6.8 Hz, 1 H, C$\underline{H}$(CH$_3$)$_2$), 2.16 (m, 1 H, H-2'a), 2.09 (m, 1 H, H-2'b), 1.14 (d, J=6.8 Hz, 6 H, CH(C$\underline{H}_3$)$_2$), 0.86 (s, 9 H, (CH$_3$)$_3$C), 0.06 (s, 6 H, (CH$_3$)$_2$Si); $^{13}$C NMR (100 MHz, $CDCl_3$) for (3' or 5')-O-(tert-butyldimethylsilyl)-5-(2-isopropylbenzyloxy)methyl-2'-deoxy-uridine: δ 162.77 (C), 150.30 (C), 147.76 (C), 138.79 (CH), 134.26 (C), 129.32 (CH), 128.54 (CH), 125.60 (CH), 125.48 (CH), 111.92 (C), 87.77 (CH), 87.14 (CH), 71.72 (CH), 71.03 (CH$_2$), 64.40 (CH$_2$), 61.98 (CH$_2$), 40.68 (CH$_2$), 28.68 (CH), 25.71 (C(CH$_3$)$_3$), 23.99 (CH$_3$), 17.93 (C), −4.73 (CH$_3$), −4.88 (CH$_3$).

Compounds 3',5'-O-bis-(tert-butyldimethylsilyl)-5-(2-isopropylbenzyl-oxy)methyl-2'-deoxyuridine (134 mg, 0.22 mmol) and (3' or 5')-O-(tert-butyldimethylsilyl)-5-(2-isopropylbenzyloxy)methyl-2'-deoxyuridine (98 mg, 0.19 mmol) were dissolved in THF (5 mL), and a solution of tetra-n-butylammonium fluoride trihydrate (323 mg, 1.05 mmol) in THF (2 mL) was added. The mixture was stirred at room temperature for one hour, then concentrated in vacuo and purified by silica gel column chromatography to give 5-(2-isopropylbenzyloxy)methyl-2'-deoxyuridine dU.n6 (108 mg, 67%).

5-(2-Isopropylbenzyloxy)methyl-2'-deoxyuridine-5'triphosphate (WW5p149): $POCl_3$ (15 μL, 0.164 mmol) was added to a solution of compound dU.n6 (32 mg, 0.082 mmol) and proton sponge (35 mg, 0.164 mmol) in trimethylphosphate (0.5 mL) and the reaction was stirred at 0° C. under a nitrogen atmosphere for 2 hours. A solution of bis-tri-n-butylammonium pyrophosphate (356 mg, 0.75 mmol) and tri-n-butylamine (150 μL) in anhydrous DMF (1.5 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in a mixture of water (5 mL) and acetonitrile (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(2-isopropylbenzyloxy)methyl-2'-deoxyuridine-5'-triphosphate WW5p149. $^1$H NMR (400 MHz, $D_2O$): δ 7.98 (s, 1 H, H-6), 7.36 (m, 3 H, Ph-H), 7.21 (m, 1 H, Ph-H), 6.27 (t, J=6.8 Hz, 1 H, H-1'), 4.64 (m, 3 H, Ph-CH$_2$ and H-3'), 4.43 (AB d, 1 H, J=12 Hz, 5-CH$_2$a), 4.39 (AB d, 1 H, J=12 Hz, 5-CH$_2$b), 4.25 (m, 3 H, H-4' and H-5'), 2.34 (m, 2 H, H-2'), 1.15 (d, 3 H, J=6.8 Hz, CH$_3$); $^{31}$P NMR (162 Hz, $D_2O$): 6-5.11 (d, J=21.0 Hz), −10.5 (d, J=19.4 Hz), −20.94 (t, J=21.0 Hz).

Synthesis of 5-(2-tert-butylbenzyloxy)methyl-2'-deoxyuridine-5'-triphosphate

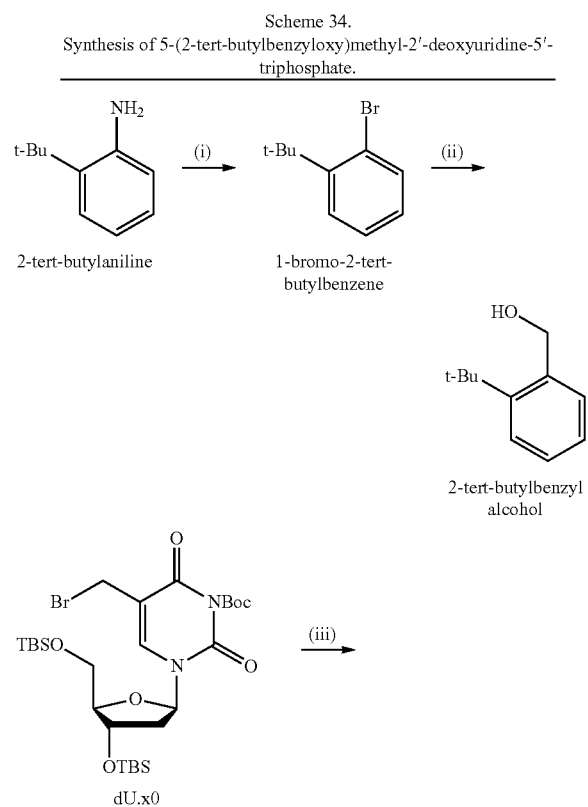

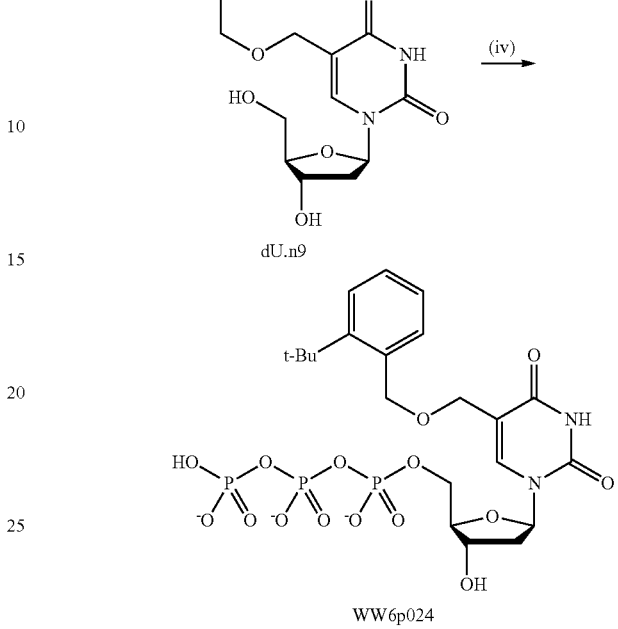

(i) NaNO$_2$, HBr, 5-10° C., then Cu(0), 50° C., 27%;
(ii) n-BuLi, formaldehyde, minus 78° C., 75%;
(iii) 2-tert-butylbenzyl alcohol, neat, 115-118° C.;
(iv) n-Bu$_4$NF, THF, room temperature, 70%; (v) POCl$_3$, proton sponge, (MeO)$_3$PO, 0° C.; (n-Bu$_3$NH)$_2$H$_2$P$_2$O$_7$, n-Bu$_3$N, DMF; 1M HNEt$_3$HCO$_3$.

1-Bromo-2-tert-butylbenzene: To a solution of 2-tert-butylaniline (7.46 g, 50 mmol 15.6 mL) in hydrobromic acid (40% w/w, 15 mL) cooled at <5° C. (ice/salt bath), a solution of 7.55 g (0.11 mol) of sodium nitrite in 10 mL of water was added at a rate that the temperature did not exceed 10° C. (ca two hour addition time). When the diazotization was completed, 0.20 g of copper powder was added. (CAUTION: the solution was refluxed very cautiously because of vigorous gas evolution!). When the vigorous evolution of nitrogen subsided, the system was kept at 50° C. for 30 minutes and was then diluted with 80 mL of water and extracted three times with diethyl ether (100 mL each). The organic layer was washed with 10% solution of KOH; dried over Na$_2$SO$_4$, concentrated in vacuo, and purified by chromatography on silica gel chromatography. The product obtained was further distilled at 85° C. (3 mm Hg) to yield 1-bromo-2-tert-butylbenzene (2.88 g, 27%). $^1$H NMR (400 MHz, CDCl$_3$): δ 7.58 (m, 1 H, Ph-H), 7.45 (m, 1 H, Ph-H), 7.24 (m, 1 H, Ph-H), 7.02 (m, 1 H, Ph-H), 1.51 (s, 9 H, C(CH$_3$)$_3$).

2-tert-Butylbenzyl alcohol: To a solution of 1-bromo-2-tert-butylbenzene (2.88 g, 13.51 mmol) in anhydrous THF (45 mL) 2,2'-dipyridyl (ca 10 mg) was added under a nitrogen atmosphere. The mixture was cooled down minus 78° C., and a solution of n-butyllithium (2.5 M in hexanes, 5.94 mL, 14.86 mmol) was added dropwise via syringe within the period of ten minutes. Upon addition, the mixture was stirred for 30 minutes, then warmed up to minus 30° C., and a flow of formaldehyde (generated from 1.91 g of paraformaldehyde by heating at over 160° C.) was passed through the solution until the deep red color disappeared completely. The mixture was quenched with saturated ammonium chloride solution (5 mL), then poured into a mixture of dichloromethane (100 mL) and water (50 mL). The organic phase was separated and the aqueous phase was extracted with dichloromethane (20 mL) twice. The combined organic phase was dried over anhydrous Na₂SO₄, concentrated in vacuo, and purified by silica gel chromatography to yield 2-tert-butylbenzyl alcohol (1.67 g, 75%) as an oil. ¹H NMR (400 MHz, CDCl₃): δ 7.50 (m, 1 H, Ph-H), 7.41 (m, 1 H, Ph-H), 7.24 (m, 2 H, Ph-H), 4.93 (d, J=4.8 Hz, 2 H, C$\underline{H}_2$OH), 1.54 (br, 1 H, CH₂O$\underline{H}$), 1.43 (s, 1 H, C(CH₃)₃).

3',5'-O-Bis-(tert-butyldimethylsilyl)-5-(2-tert-butylbenzyloxy)methyl-2'-deoxyuridine (dU.n7) and (3' or 5')-O-(tert-butyldimethylsilyl)-5-(2-tert-butylbenzyloxy)methyl-2'-deoxyuridine (dU.n8): Compound dU.x0 (230 mg, 0.36 mmol) and 2-tert-butylbenzyl alcohol (0.49 g, 3.60 mmol) were heated neat at 118-122° C. for one hour under a nitrogen atmosphere. The mixture was cooled down to room temperature, dissolved in minimum amount of ethyl acetate, and purified by silica gel chromatography to yield 3',5'-O-bis-(tert-butyldimethylsilyl)-5-(2-tert-butylbenzyloxy)methyl-2'-deoxyuridine dU.n7 (32 mg, 17%) and (3' or 5')-O-(tert-butyldimethylsilyl)-5-(2-tert-butylbenzyloxy)methyl-2'-deoxyuridine dU.n8 (28 mg, 19%). ¹H NMR (400 MHz, CDCl₃) for dU.n7: δ 9.28 (s, 1 H, 3-NH), 7.77 (s, 1 H, H-6), 7.43 (m, 2 H, Ph-H), 7.25 (m, 2 H, Ph-H), 6.16 (t, J=6.6 Hz, 1 H, H-1'), 4.84 (AB d, J=11.2 Hz, 1 H, 5-CH₂a), 4.81 (AB d, J=11.2 Hz, 1 H, 5-CH₂b), 4.40 (m, 1 H, H-3'), 4.36 (s, 2 H, CH₂O), 3.91 (m, 1 H, H-4'), 3.76 (AB d, J=12.0 Hz, 1 H, H-5'a), 3.64 (AB d, J=12.0 Hz, 1 H, H-5'b), 2.27 (m, 2 H, H-2'a and H-2'b), 1.40 (s, 9 H, C(CH₃)₃), 0.89 (s, 9H, SiC(CH₃)₃), 0.88 (s, 9 H, (CH₃)₃CSi), 0.09 (s, 3 H, CH₃Si), 0.07 (s, 3 H, CH₃Si), 0.06 (s, 3 H, CH₃Si), 0.05 (s, 3 H, CH₃Si); ¹H NMR (400 MHz, DMSO-d₆) for dU.n8: δ 11.42 (s, 1 H, D₂O exchangeable, NH), 7.93 (s, 1 H, H-6), 7.42 (m, 1 H, Ph-H), 7.35 (m, 1 H, Ph-H), 7.18 (m, 2 H, Ph-H), 6.15 (t, 1 H, J=6.8 Hz, H-1'), 5.08 (t, J=5.2 Hz, 1 H, D₂O exchangeable, 5'-OH), 4.66 (s, 2 H, CH₂O), 4.41 (m, 1 H, H-3'), 4.26 (AB d, J=11.6 Hz, 1 H, 5-CH₂a), 4.21 (AB d, J=11.6 Hz, 1 H, 5-CH₂b), 3.78 (m, 1 H, H-4'), 3.56 (m, 2 H, H-5'a and H-5'b), 2.18 (m, 2 H, H-2'a and H-2'b), 1.34 (s, 9 H, (C$\underline{H}_3$)₃C), 0.85 (s, 9 H, (CH₃)₃CSi), 0.07 (s, 6 H, (CH₃)₂Si).

5-(2-tert-butylbenzyloxy)methyl-2'-deoxyuridine (dU.n9): Compounds dU.n7 (32 mg, 0.050 mmol) and dU.n8 (27 mg, 0.052 mmol) were dissolved in THF (4 mL), and a solution of tetra-n-butylammonium fluoride trihydrate (65 mg, 0.204 mmol) in THF (2 mL) was added. The mixture was stirred at room temperature for one hour, then concentrated in vacuo and purified by silica gel column chromatography to give 5-(2-tert-butylbenzyloxy)methyl-2'-deoxyuridine dU.n9 (108 mg, 67%). ¹H NMR (400 MHz, CD₃OD): δ 8.10 (s, 1 H, H-6), 7.46 (m, 1 H, Ph-H), 7.39 (m, 1 H, Ph-H), 7.20 (m, 1 H, Ph-H), 6.28 (t, 1 H, J=6.6 Hz, H-1'), 4.79 (s, 2 H, CH₂O), 4.37 (m, 3 H, 5-CH₂a, 5-CH₂b, and H-3'), 3.92 (m, 1 H, H-4'), 3.76 (AB dd, J=12.4 and 3.2 Hz, 1 H, H-5'a), 3.70 (AB dd, J=12.4 and 3.6 Hz, 1 H, H-5'a, H-5'b), 2.22 (m, 2 H, H-2'a and H-2'b), 1.39 (s, 9 H, C(CH₃)₃).

5-(2-tert-butylbenzyloxy)methyl-2'-deoxyuridine-5'-triphosphate (WW6p024): POCl₃ (10 µL, 0.11 mmol) was added to a solution of compound dU.n9 (30 mg, 0.074 mmol) and proton sponge (32 mg, 0.15 mmol) in trimethylphosphate (0.4 mL) and the reaction was stirred at 0° C. under a nitrogen atmosphere for two hours. A solution of bis-tri-n-butylammonium pyrophosphate (285 mg, 0.6 mmol) and tri-n-butylamine (120 µL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in a mixture of water (5 mL) and acetonitrile (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(2-tert-butylbenzyloxy)methyl-2'-deoxyuridine-5'-triphosphate WW6p024. ¹H NMR (400 MHz, D₂O): δ 7.89 (s, 1 H, H-6), 7.34 (d, 1 H, J=1.6 Hz, Ph-H), 7.32 (d, 1 H, J=2.0 Hz, Ph-H), 7.15 (m, 2 H, Ph-H), 6.17 (t, J=6.8 Hz, 1 H, H-1'), 4.64 (2 d, 2 H, Ph-CH₂), 4.48 (m, 1 H, H-3'), 4.32 (2 d, 2 H, 5-CH₂), 4.04 (m, 3 H, H-4' and H-5'), 2.23 (m, 2 H, H-2'), 1.20 (s, 9 H, C(CH₃)₃); ³¹P NMR (162 Hz, D₂O): δ-11.76 (m), −12.41 (d, J=19.4 Hz), −24.0 (t, J=19.4 Hz).

Synthesis of 5-(2-phenylbenzyloxy)methyl-2'-deoxyuridine-5'-triphosphate

Scheme 35.
Synthesis of 5-(2-phenylbenzyloxy)methyl-2'-deoxyuridine-5'-triphosphate

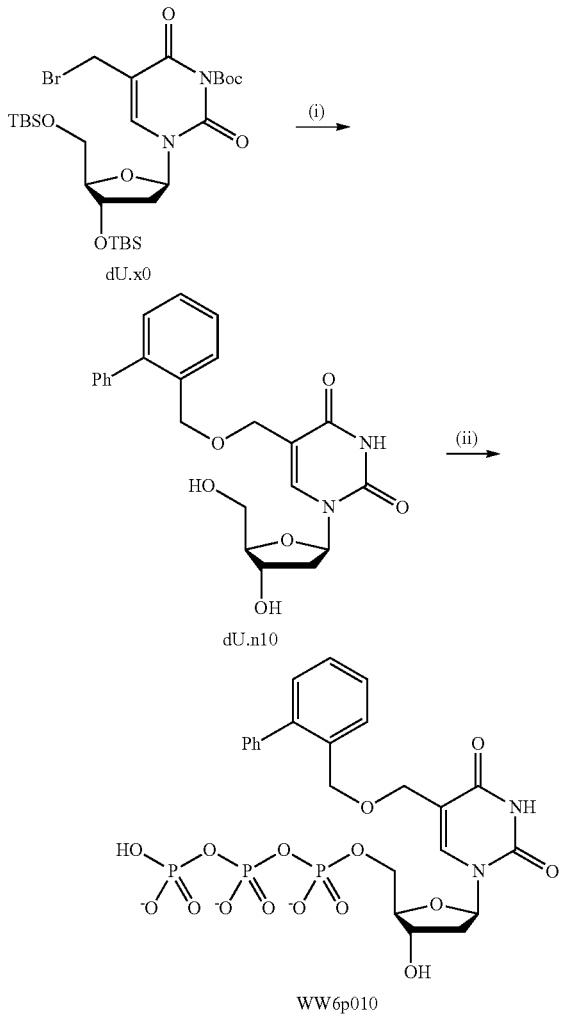

(i) 2-biphenylmethanol, neat, 118-122° C., 15%;
(ii) POCl₃, proton sponge, (MeO)₃PO, 0° C.; (n-Bu₃NH)₂H₂P₂O₇, n-Bu₃N, DMF; 1M HNEt₃HCO₃.

5-(2-Phenylbenzyloxy)methyl-2'-deoxyuridine (dU.n10): Compound dU.x0 (0.916 g, 1.41 mmol) and 2-biphenylmethanol (2.596 g, 14.10 mmol) were heated neat at 118-122° C. for 1.5 hours under a nitrogen atmosphere. The mixture was cooled down to room temperature, dissolved in ethyl acetate, and purified by silica gel chromatography to yield 5-(2-phenylbenzyloxy)methyl-2'-deoxyuridine dU.n10 (87 mg, 15%). 3',5'-O-Bis-(tert-butyldimethylsilyl)-5-(2-phenylbenzyloxy)methyl-2'-deoxyuridine (134 mg, 19%) and (3' or 5')-O-(tert-butyldimethylsilyl)-5-(2-phenylbenzyloxy)methyl-2'-deoxyuridine (263 mg, 36%) were also obtained from the reaction. $^1$H NMR (400 MHz, DMSO-$d_6$) for dU.n10: δ 11.40 (s, 1 H, $D_2O$ exchangeable, NH), 7.91 (s, 1 H, H-6), 7.39 (m, 9 H, Ph-H), 6.14 (t, 1 H, J=6.8 Hz, H-1'), 5.25 (t, J=4.4 Hz, 1 H, $D_2O$ exchangeable, 5'-OH), 5.02 (t, J=5.2 Hz, 1 H, $D_2O$ exchangeable, 5'-OH), 4.33 (s, 2 H, $CH_2O$), 4.21 (m, 1 H, H-3'), 4.15 (AB d, J=11.6 Hz, 1 H, 5-$CH_2$a), 4.08 (AB d, J=12.7 Hz, 1 H, 5-$CH_2$b), 3.78 (m, 1 H, H-4'), 3.55 (m, 2 H, H-5'a and H-5'b), 2.05 (m, 2 H, H-2'a and H-2'b); $^1$H NMR (400 MHz, $CDCl_3$) for 3',5'-O-bis-(tert-butyldimethylsilyl)-5-(2-phenylbenzyloxy)methyl-2'-deoxyuridine: δ 8.75 (s, 1 H, 3-NH), 7.63 (s, 1 H, H-6), 7.37 (m, 9 H, Ph-H), 6.29 (dd, J=7.6 and 6.0 Hz, 1 H, H-1'), 4.49 (s, 2 H, $CH_2O$), 4.39 (m, 1 H, H-3'), 4.24 (AB d, J=12.7 Hz, 1 H, 5-$CH_2$a), 4.19 (AB d, J=12.7 Hz, 1 H, 5-$CH_2$b), 3.96 (m, 1 H, H-4'), 3.76 (m, 2 H, H-5'a and H-5'b), 2.28 (m, 1 H, H-2'a), 2.03 (m, 1 H, H-2'b), 0.91 (s, 9 H, $(CH_3)_3C$), 0.89 (s, 9 H, $(CH_3)_3C$), 0.09 (s, 3 H, $CH_3Si$), 0.06 (s, 3 H, $CH_3Si$), 0.05 (s, 3 H, $CH_3Si$), 0.02 (s, 3 H, $CH_3Si$); $^1$H NMR (400 MHz, DMSO-$d_6$) for (3' or 5')-O-(tert-butyldimethylsilyl)-5-(2-phenylbenzyloxy)methyl-2'-deoxyuridine: δ 11.42 (s, 1 H, $D_2O$ exchangeable, NH), 7.86 (s, 1 H, H-6), 7.39 (m, 9 H, Ph-H), 6.13 (t, 1 H, J=6.8 Hz, H-1'), 5.08 (t, J=5.2 Hz, 1 H, $D_2O$ exchangeable, 5'-OH), 4.39 (m, 1 H, H-3'), 4.33 (s, 2 H, $CH_2O$), 4.15 (AB d, J=11.6 Hz, 1 H, 5-$CH_2$a), 4.09 (AB d, J=11.6 Hz, 1 H, 5-$CH_2$b), 3.77 (m, 1 H, H-4'), 3.54 (m, 2 H, H-5'a and H-5'b), 2.08 (m, 2 H, H-2'a and H-2'b), 0.87 (s, 9 H, $(CH_3)_3C$), 0.07 (2 s, 6 H, $(CH_3)_2Si$).

5-(2-Phenylbenzyloxy)methyl-2'-deoxyuridine-5'-triphosphate (WW6p010): $POCl_3$ (9 µL, 0.1 mmol) was added to a solution of compound dU.n10 (28 mg, 0.066 mmol) and proton sponge (28 mg, 0.13 mmol) in trimethylphosphate (0.4 mL) and the reaction was stirred at 0° C. under a nitrogen atmosphere for two hours. A solution of bis-tri-n-butylammonium pyrophosphate (285 mg, 0.6 mmol) and tri-n-butylamine (120 µL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in a mixture of water (6 mL) and acetonitrile (4 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(2-phenylbenzyloxy)methyl-2'-deoxyuridine-5'-triphosphate WW6p010. $^1$H NMR (400 MHz, $D_2O$): δ 7.77 (s, 1 H, H-6), 7.56 (m, 1 H, Ph-H), 7.44 (m, 2 H, Ph-H), 7.39 (m, 3 H, Ph-H), 7.27 (m, 3 H, Ph-H), 6.25 (t, J=6.8 Hz, 1 H, H-1'), 4.62 (m, 1 H, H-3'), 4.41 (AB d, 1 H, J=11.2 Hz, 5-$CH_2$a), 4.36 (AB d, 1 H, J=12 Hz, 5-$CH_2$b), 4.24 (m, 1 H, H-4'), 4.17 (m, 2 H, H-5'), 2.30 (m, 2 H, H-2'); $^{31}$P NMR (162 Hz, $D_2O$): 6-5.59 (d, J=19.4 Hz), −10.6 (d, J=19.4 Hz), −21.04 (t, J=19.4 Hz).

Synthesis of 5-(2,6-dimethylbenzyloxy)methyl-2'-deoxyuridine-5'-triphosphate

Scheme 36. Synthesis of 5-(2,6-dimethylbenzyloxy)methyl-2'-deoxyuridine-5'-triphosphate:

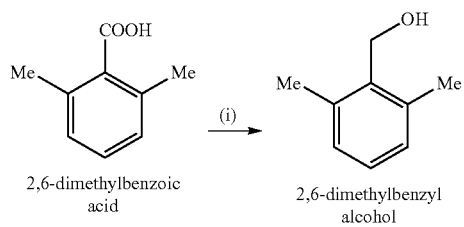

2,6-dimethylbenzoic acid 2,6-dimethylbenzyl alcohol

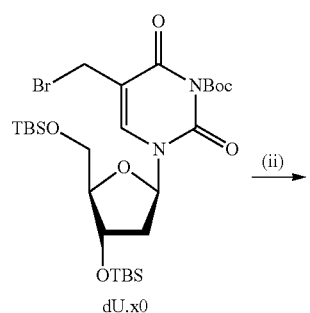

dU.x0

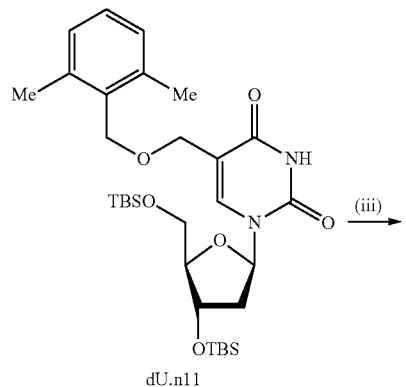

dU.n11

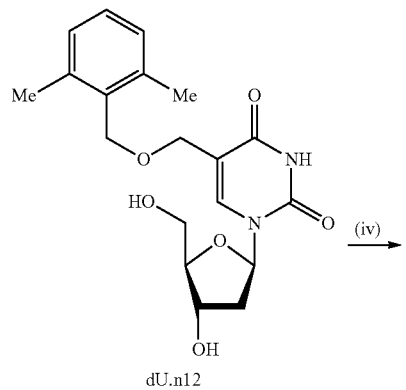

dU.n12

143

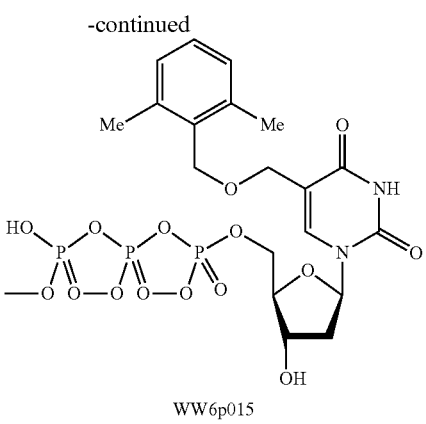

WW6p015

(i) BH₃(SMe₂), THF, reflux, 51%;
(ii) 2,6-dimethylbenzyl alcohol, neat, 118-120° C., 80%;
(iii) n-Bu₄NF, THF, room temperature, 67%;
(iv) POCl₃, proton sponge, (MeO)₃PO, 0° C.; (n-Bu₃NH)₂H₂P₂O₇, n-Bu₃N, DMF; 1 M HNEt₃HCO₃.

2,6-dimethylbenzyl alcohol: 2,6-Dimethylbenzyl alcohol was prepared according to Beaulieu et al. (2000, which is incorporated herein by reference), but was unsuccessful, so a different reducing agent was used. To a suspension of 2,6-dimethylbenzoic acid (1.00 g, 6.65 mmol) in anhydrous THF (10 mL) a solution of BH₃(SMe₂) in THF was cautiously added under nitrogen atmosphere. The mixture was heated at reflux for 16 hours, then quenched with saturated ammonium chloride (5 mL) and 2 M HCl (10 mL). (CAUTION: vigorous gas evolution!). Organic layer was separated; aqueous layer was extracted three times with ethyl acetate (45 mL each); combined extracts were washed twice with saturated sodium bicarbonate (20 mL each), dried over anhydrous Na₂SO₄, evaporated, and purified by silica gel chromatography to yield 2,6-dimethylbenzyl alcohol (0.50 g, 51%) as an white solid. $^1$H NMR (400 MHz, CDCl₃): δ 7.08 (m, 3 H, Ph-H), 4.70 (s, 2 H, Ph-CH₂), 4.05 (br s, 1 H, OH), 2.40 (s, 6 H, CH₃).

3',5'-O-Bis-(tert-butyldimethylsilyl)-5-(2,6-dimethylbenzyloxy)methyl-2'-deoxyuridine (dU.n11): Compound dU.x0 (230 mg, 0.36 mmol) and 2,6-dimethylbenzyl alcohol (0.49 g, 3.60 mmol) were heated neat at 118-122° C. for one hour under a nitrogen atmosphere. The mixture was cooled down to room temperature, dissolved in minimum amount of ethyl acetate, and purified by silica gel chromatography to yield 3',5'-O-bis-(tert-butyldimethylsilyl)-5-(2,6-dimethylbenzyloxy)methyl-2'-deoxyuridine dU.n11 (170 mg, 80%). $^1$H NMR (400 MHz, CDCl₃): δ 8.94 (s, 1 H, 3-NH), 7.63 (s, 1 H, H-6), 7.07 (m, 3 H, Ph-H), 6.28 (dd, J=7.6 and 5.6 Hz, 1 H, H-1'), 4.63 (s, 2 H, CH₂O), 4.38 (m, 1 H, H-3'), 4.32 (AB d, J=11.6 Hz, 1 H, 5-CH₂a), 4.27 (AB d, J=11.6 Hz, 1 H, 5-CH₂b), 3.92 (m, 1 H, H-4'), 3.74 (m, 2 H, H-5'a and H-5'b), 2.39 (s, 6 H, 2 CH₃), 2.24 (m, 1 H, H-2'a), 2.00 (m, 1 H, H-2'b), 0.90 (s, 9 H, (CH₃)₃C), 0.89 (s, 9 H, (CH₃)₃C), 0.11 (s, 3 H, CH₃Si), 0.09 (s, 3 H, CH₃Si), 0.08 (s, 3 H, CH₃Si), 0.06 (s, 3 H, CH₃Si).

5-(2,6-Dimethylbenzyloxy)methyl-2'-deoxyuridine (dU.n12): To a solution of compound dU.n11 (131 mg, 0.22 mmol) in THF (4 mL), a solution of tetra-n-butylammonium fluoride trihydrate (171 mg, 0.54 mmol) in THF (2 mL) was added. The mixture was stirred at room temperature for 30 minutes, then concentrated in vacuo and purified by silica gel

144 column chromatography to give 5-(2,6-dimethylbenzyloxy)methyl-2'-deoxyuridine dU.n12 (108 mg, 67%). $^1$H NMR (400 MHz, CD₃OD): δ 8.08 (s, 1 H, H-6), 7.02 (m, 3 H, Ph-H), 6.26 (t, 1 H, J=6.8 Hz, H-1'), 4.61 (s, 2 H, CH₂O), 4.38 (m, 1 H, H-3'), 4.33 (AB d, J=11.6 Hz, 1 H, 5-CH₂a), 4.15 (AB d, J=11.6 Hz, 1 H, 5-CH₂b), 3.91 (m, 1 H, H-4'), 3.77 (AB dd, J=12.0 and 3.2 Hz, 1 H, H-5'a), 3.70 (AB dd, J=12.0 and 3.6 Hz, 1 H, H-5'a, H-5'b), 2.36 (s, 6 H, CH₃), 2.24 (m, 2 H, H-2'a and H-2'b); $^{13}$C NMR (100 MHz, CD₃OD): δ 163.80 (C), 150.76 (C), 140.85 (CH), 137.81 (C), 133.73 (C), 127.81 (CH), 127.72 (CH), 110.82 (C), 87.56 (CH), 85.22 (CH), 70.74 (CH), 66.33 (CH₂), 64.47 (CH₂), 61.38 (CH₂), 40.02 (CH₂), 18.36 (CH₃).

5-(2,6-Dimethylbenzyloxy)methyl-2-deoxyuridine-5'-triphosphate (WW6p015): POCl₃ (11 μL, 0.12 mmol) was added to a solution of compound dU.n12 (30 mg, 0.08 mmol) and proton sponge (34 mg, 0.16 mmol) in trimethylphosphate (0.4 mL) and the reaction was stirred at 0° C. under a nitrogen atmosphere for two hours. A solution of bis-tri-n-butylammonium pyrophosphate (285 mg, 0.5 mmol) and tri-n-butylamine (120 μL) in anhydrous DMF (1.2 mL) was added. After 30 minutes of stirring, triethylammonium bicarbonate buffer (1 M, pH 7.5; 10 mL) was added. The reaction was stirred for one hour at room temperature and then concentrated in vacuo. The residue was dissolved in a mixture of water (5 mL) and acetonitrile (5 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate were combined and lyophilized to yield 5-(2,6-dimethylbenzyloxy)methyl-2'-deoxyuridine-5'-triphosphate WW6p015. $^1$H NMR (400 MHz, D₂O): δ 8.0 (s, 1 H, H-6), 7.16 (m, 1 H, Ph-H), 7.07 (m, 3 H, Ph-H), 6.30 (t, 1 H, J=7.2 Hz, H-1'), 4.64 (m, 3 H, Ph-CH₂ and H-3'), 4.47 (AB d, 1 H, J=7.2 Hz, 5-CH₂a), 4.40 (AB d, 1 H, J=7.2 Hz, 5-CH₂b), 4.20 (m, 3 H, H-4' and H-5'), 2.38 (m, 2 H, H-2'), 2.33 (s, 6 H, CH₃); $^{31}$P NMR (162 Hz, D₂O): δ-8.94 (d, J=19.4 Hz), −10.78 (d, J=19.4 Hz), −22.08 (d, J=19.4 Hz).

Synthesis of 5-(3-phenyl-2-propenyloxy)methyl-2'-deoxyuridine and reaction to its 5'-triphosphate Scheme 37. Synthesis of
5-(3-phenyl-2-propenyloxy)methyl-2'-deoxyuridine-5'-triphosphate.

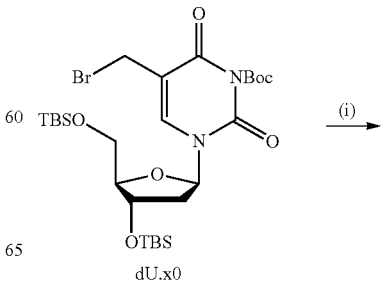

dU.x0

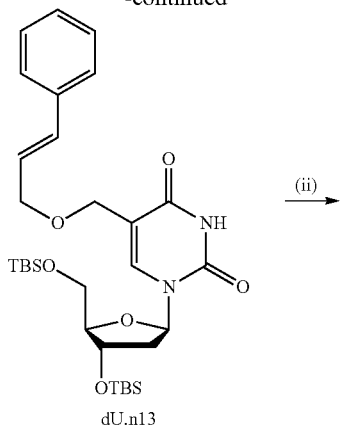

dU.n13

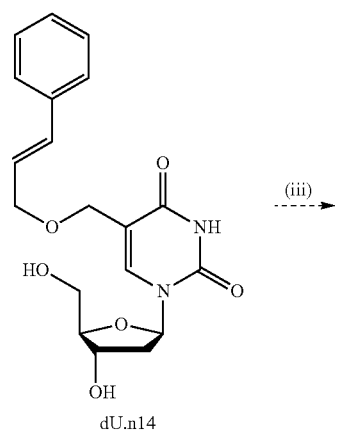

dU.n14

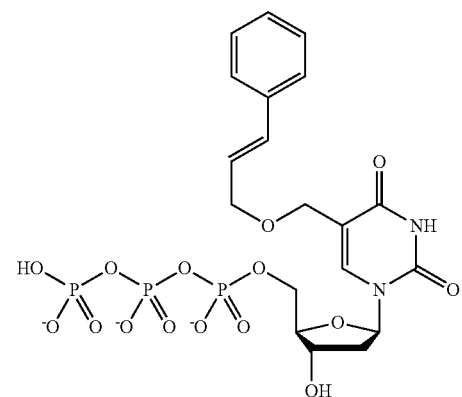

(i) cinnamoyl alcohol, neat, 104° C., 36%;
(ii) n-Bu₄NF, THF, room temperature, 76%;
(iii) POCl₃, proton sponge, (MeO)₃PO, 0° C.; (n-Bu₃NH)₂H₂P₂O₇, n-Bu₃N, DMF; 1M HNEt₃HCO₃.

3',5'-O-Bis-(tert-butyldimethylsilyl)-5-(3-phenyl-2-propenyloxy)methyl-2'-deoxyuridine (dU.n13): Compound dU.x0 (500 mg, 0.77 mmol) and cinnamyl alcohol (331 mg, 2.17 mmol) was heated neat at 104° C. for one hour under a nitrogen atmosphere. The mixture was cooled down to room temperature, dissolved in minimum amount of ethyl acetate, and purified by silica gel chromatography to yield 3',5'-O-bis-(tert-butyldimethylsilyl)-5-(3-phenyl-2-propenyloxy)methyl-2'-deoxyuridine dU.n13 (169 mg, 36%). $^1$H NMR (400 MHz, CDCl₃): δ 8.32 (s, 3-NH), 7.68 (s, 1 H, H-6), 7.31 (m, 5 H, Ph-H), 6.64 (d, J=16.0 Hz, 1 H, =CH), 6.28 (m, 2 H, H-1' and =CH), 4.40 (m, 1 H, H-3'), 4.28 (m, 2 H, 5-CH₂a and 5-CH₂b), 4.23 (m, 2 H, CH₂O), 3.94 (m, 1 H, H-4'), 3.80 (AB dd, J=11.2 and 3.2 Hz, 1 H, H-5'a), 3.75 (AB dd, J=11.2 and 3.2 Hz, 1 H, H-5'b), 2.27 (m, 1 H, H-2'a), 2.01 (m, 1 H, H-2'b), 0.90 (s, 9 H, (CH₃)₃C), 0.88 (s, 9 H, (CH₃)₃C), 0.08 (s, 3 H, CH₃Si), 0.07 (s, 3 H, CH₃Si), 0.05 (2 s, 6 H, (CH₃)₂Si); $^{13}$C NMR (100 MHz, CDCl₃): δ 162.56 (C), 150.04 (C), 138.34 (CH), 136.58 (C), 133.06 (CH), 128.54 (CH), 127.76 (CH), 126.55 (CH), 125.60 (CH), 111.80 (C), 87.92 (CH), 85.28 (CH), 72.27 (CH), 71.67 (CH₂), 64.40 (CH₂), 62.99 (CH₂), 41.24 (CH₂), 25.96 (C(CH₃)₃), 25.76 (C(CH₃)₃), 18.42 (C), 18.01 (C), −4.65 (CH₃), −4.82 (CH₃), −5.40 (CH₃), −5.50 (CH₃).

5-(3-Phenyl-2-propenyloxy)methyl-2'-deoxyuridine (dU.n14): To a solution of compound dU.n13 (138 mg, 0.23 mmol) in THF (2 mL) a solution of tetra-n-butylammonium fluoride trihydrate (321 mg, 0.73 mmol) in THF (2 mL) was added. The mixture was stirred at room temperature for one hour, then concentrated in vacuo and purified by silica gel column chromatography to give 5-(3-phenyl-2-propenyloxy)methyl-2'-deoxyuridine dU.n14 (65 mg, 76%) as a waxy solid. $^1$H NMR (400 MHz, DMSO-d₆): δ 11.39 (br s, 1 H, D₂O exchangeable, NH), 7.93 (s, 1 H, H-6), 7.44 (m, 2 H, Ph-H), 7.32 (m, 2 H, Ph-H), 7.23 (m, 1 H, Ph-H), 6.64 (d, J=16.0 Hz, 1 H, =CH), 6.34 (dt, J=16.0 and 5.7 Hz, 1 H, =CH), 6.16 (t, 1 H, J=6.7 Hz, H-1'), 5.24 (d, J=3.9 Hz, 1 H, D₂O exchangeable, 3'-OH), 5.04 (t, J=4.9 Hz, 1 H, D₂O exchangeable, 5'-OH), 4.22 (m, 1 H, H-3'), 4.18 (s, 2 H, 5-CH₂a and 5-CH₂b), 4.11 (d, J=5.7 Hz, 2 H, CH₂), 3.77 (m, 1 H, H-4'), 3.57 (m, 2 H, H-5'a and H-5'b), 2.09 (dd, J=6.5 and 4.9 Hz, 2 H, H-2'a and H-2'b).

5-(3-Phenyl-2-propenyloxy)methyl-2'-deoxyuridine-5'-triphosphate: This compound has not been made, but it may be synthesized according the following method, or a modified version thereof: POCl₃ (9 μL, 0.1 mmol) could be added to a solution of compound dU.n14 (28 mg, 0.066 mmol) and proton sponge (28 mg, 0.13 mmol) in trimethylphosphate (0.4 mL), and the reaction could then be stirred at 0° C. under a nitrogen atmosphere for two hours. A solution of bis-tri-n-butylammonium pyrophosphate (285 mg, 0.6 mmol) and tri-n-butylamine (120 μL) in anhydrous DMF (1.2 mL) could then be added. After 30 minutes of stirring, triethylammonium bicarbonate buffer (1 M, pH 7.5; 10 mL) could be added. The reaction could then be stirred for one hour at room temperature and then concentrated in vacuo. The residue could then be dissolved in a mixture of water (6 mL) and acetonitrile (4 mL), filtered, and purified by anion exchange chromatography using a Q Sepharose FF column (2.5×10 cm) with a linear gradient of 25% acetonitrile/75% triethylammonium bicarbonate (TEAB, 0.1M) to 25% acetonitrile/75% TEAB (1.5 M) over 240 min at 4.5 ml/min. The fractions containing triphosphate could then be combined and lyophilized to yield 5-(3-phenyl-2-propenyloxy)methyl-2'-deoxyuridine-5'-triphosphate WW6p014.

Example 10

Chemical Cleavage Results of dU Analogs

Chemical cleavage of
5-(benzyloxy)methyl-2'-deoxyuridine

Scheme 38.
Chemical cleavage of 5-(benzyloxy)methyl-2'-deoxyuridine.

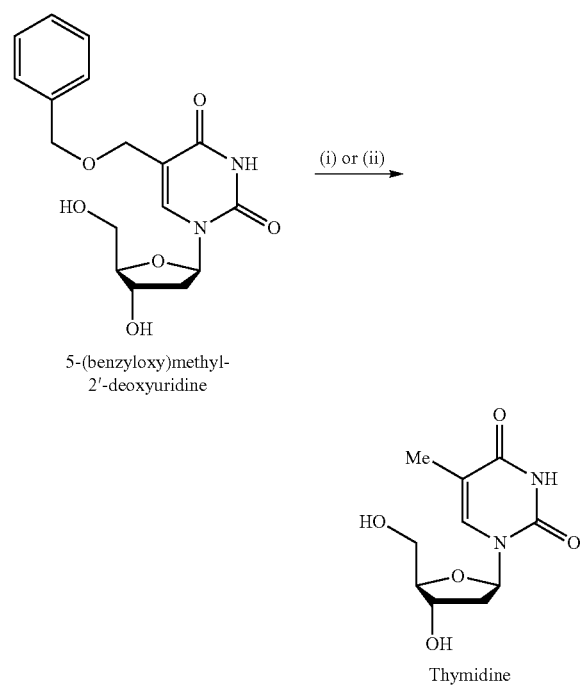

(i) H$_2$, Pd/C, ethanol, 30 minutes, 88%;
(ii) H$_2$, Na$_2$PdCl$_4$, anhydrous ethanol, 20 minutes.

Chemical Cleavage Using Heterogenous Palladium Catalyst: To a solution of 5-(benzyloxy)methyl-2'-deoxyuridine (29 mg, 0.082 mmol) in absolute ethanol (2 mL) under a nitrogen atmosphere was added 10 mg of palladium on activated carbon (10 wt. %, 10 mg) (CAUTION: flammable solid! Ensure handling in oxygen-free atmosphere). The mixture was flushed with hydrogen gas and stirred at room temperature for 30 minutes while being monitored by TLC every five minutes. The mixture was filtered, concentrated under reduced pressure, and dried under vacuum to yield thymidine (18 mg, 88%) that was identified by comparison to the authentic sample (TLC and $^1$H NMR).

Chemical Cleavage Using Homogenous Palladium Catalyst: To a solution of 5-(benzyloxy)methyl-2'-deoxyuridine (3.48 mg, 0.01 mmol) in absolute ethanol (0.1 mL) under a nitrogen atmosphere a solution of sodium tetrachloropalladate (II) (0.6 mg, 0.002 mmol) in absolute ethanol (0.9 mL) was added. The mixture was flushed with hydrogen gas and stirred at room temperature while being monitored by TLC every five minutes. After 20 minutes TLC indicated complete disappearance of starting material. The sole cleavage product was identified to be thymidine by comparison to the authentic sample on TLC.

Chemical cleavage of 5-(2-isopropylbenzyloxy)methyl-2'-deoxyuridine

Scheme 39.
Chemical cleavage of 5-(2-isopropylbenzyloxy)methyl-2'-deoxyuridine

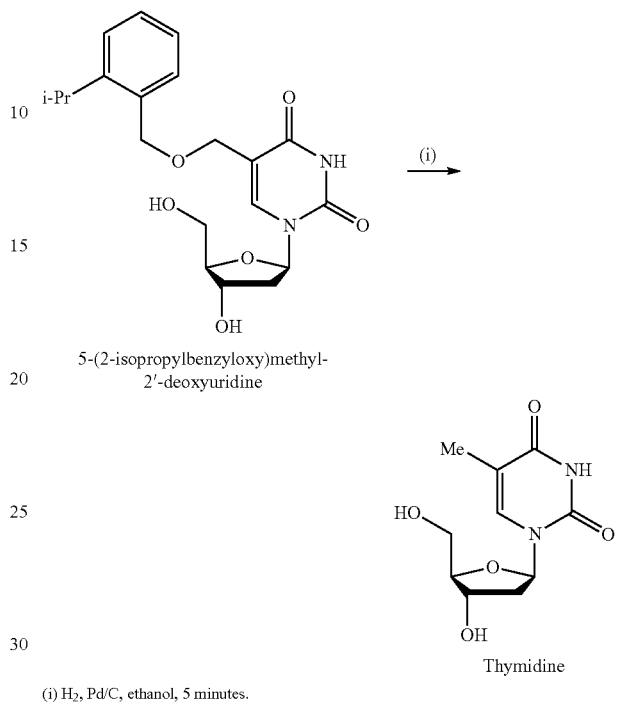

(i) H$_2$, Pd/C, ethanol, 5 minutes.

Chemical Cleavage Using Heterogenous Palladium Catalyst: To a solution of 5-(2-isopropylbenzyloxy)methyl-2'-deoxyuridine in absolute ethanol (10 mM, 1 mL) under a nitrogen atmosphere was added of palladium on activated carbon (10 wt. %, 2 mg) (CAUTION: flammable solid! Ensure handling in oxygen-free atmosphere). The mixture was flushed with hydrogen gas and stirred at room temperature for five minutes while being monitored by TLC every one minute. After five minutes TLC indicated complete disappearance of starting material. The sole cleavage product was identified to be thymidine by comparison to the authentic sample on TLC.

Chemical cleavage of
5-(2-phenylbenzyloxy)methyl-2'-deoxyuridine

Scheme 40. Chemical cleavage of
5-(2-phenylbenzyloxy)methyl-2'-deoxyuridine

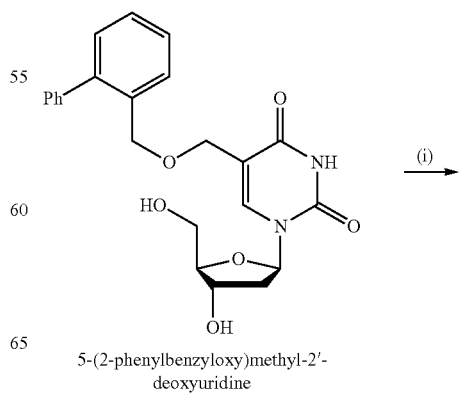

5-(2-phenylbenzyloxy)methyl-2'-deoxyuridine

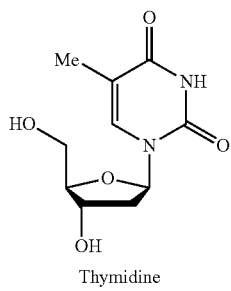

Thymidine (i) H₂, Pd/C, ethanol, 5 minutes.

Chemical Cleavage Using Heterogenous Palladium Catalyst: To solution of 5-(2-phenylbenzyloxy)methyl-2'-deoxyuridine in absolute ethanol (10 mM, 1 mL) under a nitrogen atmosphere was added palladium on activated carbon (10 wt. %, 2 mg) (CAUTION: flammable solid! Ensure handling in oxygen-free atmosphere). The mixture was flushed with hydrogen gas and stirred at room temperature for five minutes while being monitored by TLC every 1 minute. After five minutes TLC indicated complete disappearance of starting material. The sole cleavage product was identified to be thymidine by comparison to the authentic sample on TLC.

Chemical Cleavage of 5-(2,6-dimethylbenzyloxy)methyl-2'-deoxyuridine

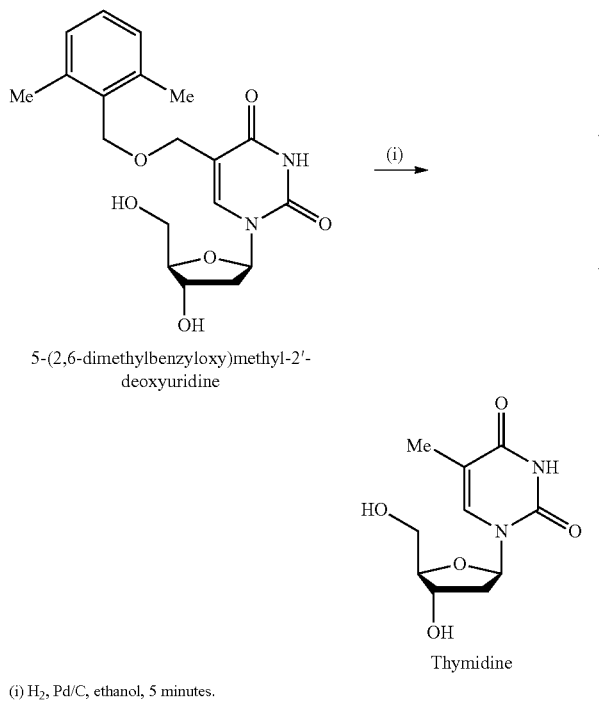

(i) H₂, Pd/C, ethanol, 5 minutes.

Chemical Cleavage Using Heterogenous Palladium Catalyst: To a solution of 5-(2,6-dimethylbenzyloxy)methyl-2'-deoxyuridine in absolute ethanol (10 mM, 1 mL) under a nitrogen atmosphere was added palladium on activated carbon (10 wt. %, 2 mg) (CAUTION: flammable solid! Ensure handling in oxygen-free atmosphere). The mixture was flushed with hydrogen gas and stirred at room temperature for five minutes while being monitored by TLC every 1 minute. After five minutes TLC indicated complete disappearance of starting material. The sole cleavage product was identified to be thymidine by comparison to the authentic sample on TLC.

Chemical cleavage of 5-(benzyloxy)methyl-2'-deoxyuridine

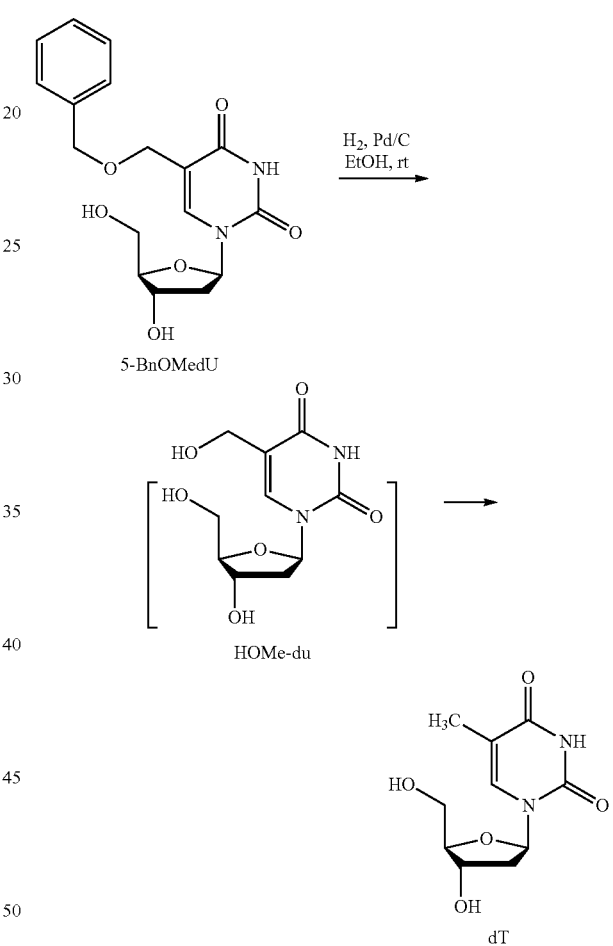

Figure 4:
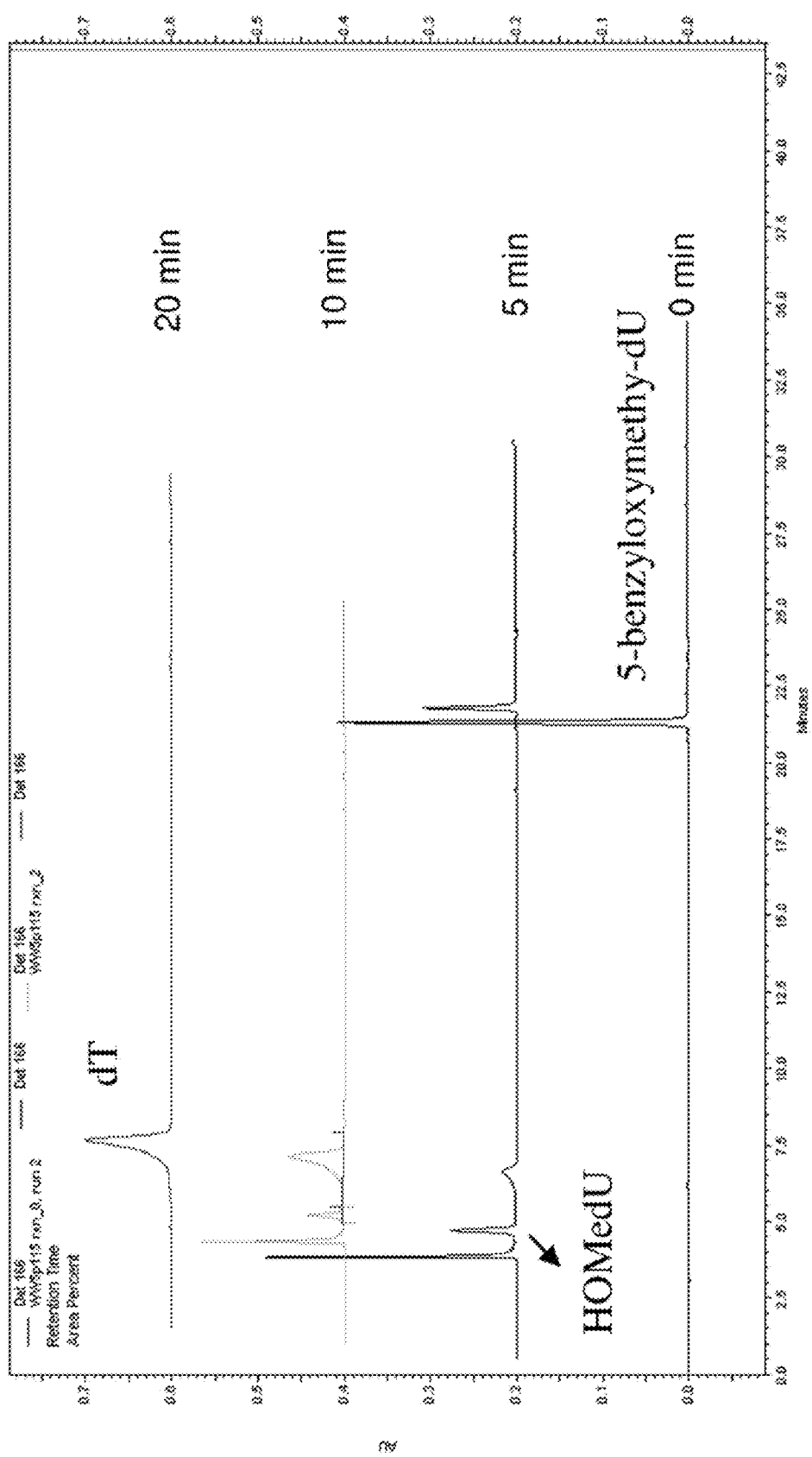
FIG. 4. HPLC stack trace of hydrogenolysis of 5-benzyloxymethyl-2'-deoxyuridine.

To a solution of 5-benzyloxy-2'-deoxyuridine (10 mg) in ethanol (1 mL) was added Pd/C (10%, 10 mg), and the mixture was stirred for five minutes. Hydrogen was introduced to the system via a balloon and the reaction mixture was stirred at room temperature. Aliquots (5 µL) were taken out from the reaction mixture at various time point intervals and were analyzed by thin layer chromatography and HPLC. Complete cleavage to thymidine was observed after ten minutes at room temperature (Scheme 42 and FIG. 4). The intermediate of the cleavage was identified to be 5-hydroxymethyl-dU generated from initial removal of benzyl group, and HOMedU was further reduced to thymidine.

Figure 5:
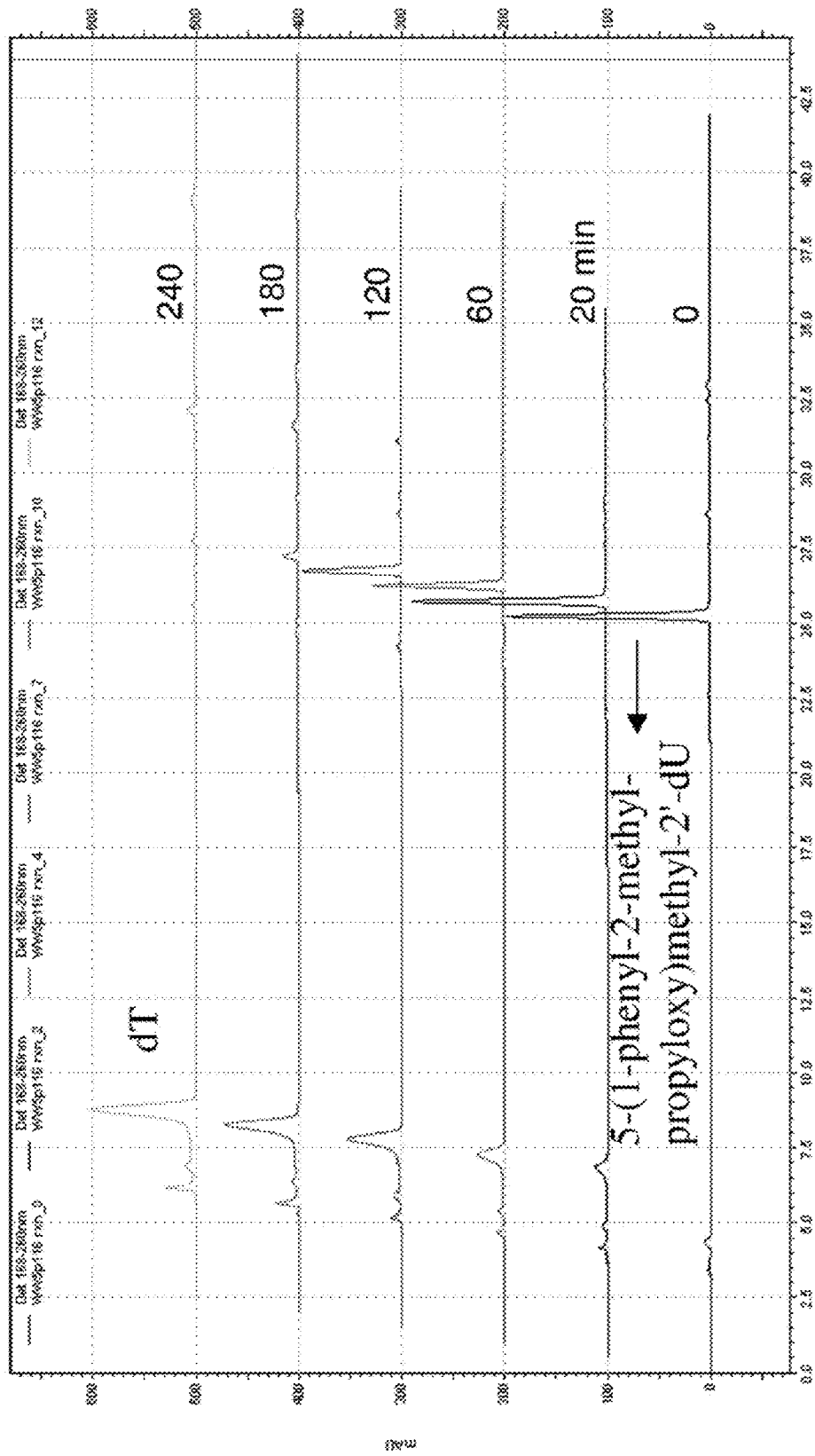
FIG. 5. HPLC stack trace of hydrogenolysis of 5-(1-phenyl-2-methyl-propyloxy)methyl-2'-deoxyuridine.

Cleavage of 5-(1-phenyl-2-methyl-propyloxy)methyl-2'-deoxyuridine using catalytic hydrogenolysis: To a solution of 5-(1-phenyl-2-methyl-propyloxy)methyl-2'-deoxyuridine (13 mg) in ethanol (3 mL) was added Pd/C (10%, 15 mg) and the mixture was stirred for five minutes. Hydrogen was introduced to the system via a balloon and the reaction mixture was stirred at room temperature. Aliquots (5 µL) were taken out from the reaction mixture various time point intervals and were analyzed by thin layer chromatography and HPLC. Complete cleavage to thymidine was observed after 240 minutes at room temperature (Scheme 43 and FIG. 5). The slow cleavage of the α-isopropyl substituted 5-benzyloxymethyl-dU may be caused by the steric hindrance presented by the substitution when the compound binds to the catalyst surface. Thus, the rate of chemical cleavage is substantially reduced for 5-benzyloxymethyluridine analogs when substituted of the α-carbon, which otherwise is important for termination and discrimination properties of these compounds. Without being bound by theory substitution of the 2-position of the benzyl ring, but not the α-carbon position can also affect termination properties (see Table 2), which provide faster cleaving nucleotides.

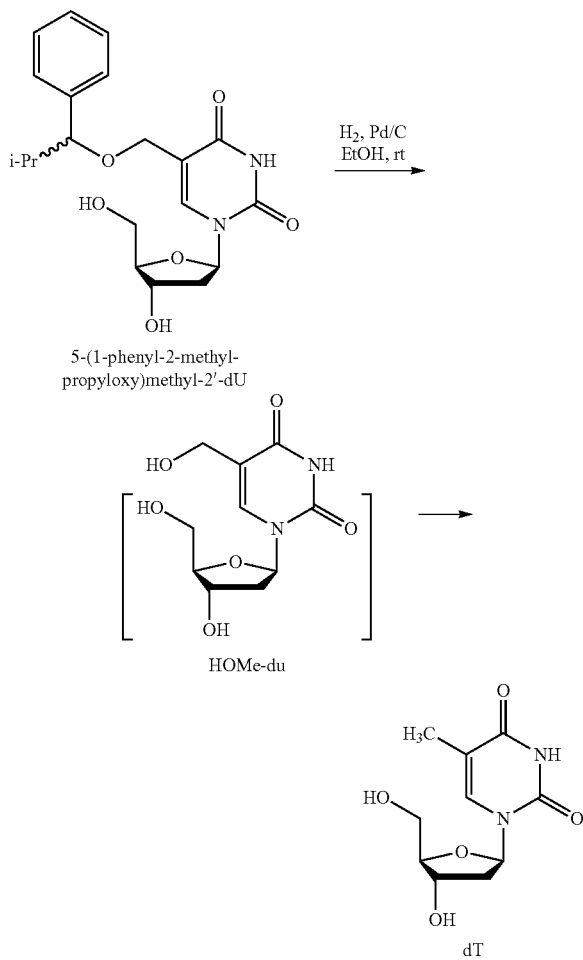

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

U.S. Pat. No. 4,439,356
U.S. Pat. No. 5,151,507
U.S. Pat. No. 5,188,934
U.S. Pat. No. 5,770,367
Barone et al., *Nucleosides, Nucleotides, and Nucleic Acids*, 20:1141-1145, 2001.
Bartholomew and Broom, *J. Chem. Soc. Chem. Commun.*, 38, 1975.
Beaulieu et al., *J. Med. Chem.*, 43:1094-1108, 2000.
Cameron and Frechet, *J. Am. Chem. Soc.*, 113:4303-4313, 1991.
Chaulk and MacMillan, *Nucleic Acids Res.*, 26:3173-3178, 1998.
Dong et al., *Org. Lett.*, 7:1043-1045, 2005.
Dressman et al., *Proc. Natl. Acad. Sci. USA*, 100:8817-8822, 2003.
European Patent Appln. 87310256.0
Flack, *Acta Cryst.*, A39:876-881, 1983.
Green and Wuts, *Protective Groups in organic Synthesis*, 3$^{rd}$ Ed. Wiley, NY, 1999.
Harris et al., *Science*, 320:106-109, 2008.
Hasan et al., *Tetrahedron*, 53:4247-4264, 1997.
Herm et al., *Chem. Eur. J.*, 8:1485-1499, 2002.
Hunkapiller et al., *Science*, 254:59-67, 1991.
Iafrate et al., *Nature Genet.*, 36:949-951, 2004.
International Human Genome Sequencing Consortium, *Nature*, 409:860-921, 2001.
Johnson et al., *Org. Lett.*, 6:4643-46, 2004.
Ju et al., *Proc. Natl. Acad. Sci. USA*, 103:19635-40, 2006.
Kanie et al., *Angew. Chem. Int. Ed.*, 39:4545-4547, 2000.
Kobayashi et al., *Science*, 304:1305-1308, 2004.
Lehninger, In: *Principles of Biochemistry*, 273-305, W.H. Freeman and Co., NY, 2005.
Levy et al., *PLoS Biol.*, 5:e254, 2007.
March's Advanced Organic Chemistry: Reactions, Mechanisms, and Structure, 2007.
Margulies et al, *Nature*, 437:376-380, 2005.
Mel'nik et al., *Bioorganicheskaya Khimiya*, 17:1101-1110, 1991.
Metzker et al., *Biotechniques*, 25:446-462, 1998.
Metzker et al., *Nucleic Acids Res.*, 22:4259-4267, 1994.
Metzker, *Genome Res.*, 15:1767-1776, 2005.
Ohtsuka et al., *Nucleic Acids Res.*, 1:1351-1357, 1974.
PCT Appln. PCT/US90/05565
Pease et al., *Proc. Natl. Acad. Sci. USA*, 91:5022-5026, 1994.
Pillai, Synthesis, 1-26, 1980.
Redon et al., *Nature*, 444:444-454, 2006.

Reichmanis et al., *J. Polymer Sci.*, 23:1-8, 1985.
Ronaghi et al., *Science*, 281:363-365, 1998.
Sanger et al., *Proc. Natl. Acad. Sci. USA*, 74:5463-5467, 1997.
Sapountzis et al., *J. Org. Chem.*, 70:2445-2454, 2005.
Sebat et al., *Science*, 305:525-528, 2004.
Seela and Peng, *J. Org. Chem.*, 71:81-90, 2006.
Service, *Science*, 282:1020-1021, 1998.
Smith et al., *J. Org. Chem.*, 55:2543-2545, 1990.
Stranger et al., *Science*, 315:848-853, 2007.
Tuzun et al., *Nature Genet.*, 37:727-732, 2005.
Wu et al., *Nucleic Acids Res.*, 35:6339-6349, 2007.
Wu et al., *Org. Lett.*, 6:2257-2260, 2004.
Zhi et al., *J. Med. Chem.*, 46:4104-4112, 2003.

What is claimed is:

1. A method of identifying a plurality of bases in a target nucleic acid, comprising the following steps:
 (i) attaching the 5'-end of a primer to a solid surface;
 (ii) hybridizing a target nucleic acid to the primer attached to the solid surface;
 (iii) adding a compound of the formula:

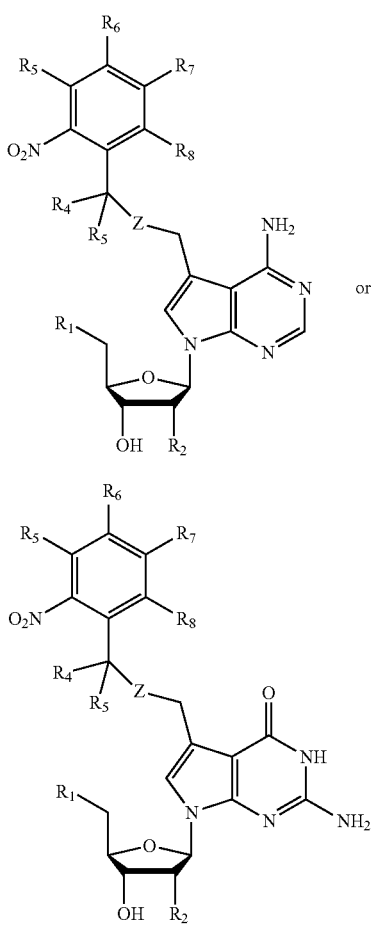

wherein:
 Z is —O—, —S—, —NH—, —OC(O)O—, —NHC(O)O—, —OC(O)NH— or —NHC(O)NH—;
 $R_1$ is triphosphate or α-thiotriphosphate;
 $R_2$ is hydrogen or hydroxy;
 $R_3$ and $R_4$ are each independently:
  hydrogen, hydroxy, halo or amino; or
  $alkyl_{(C \leq 12)}$, $alkenyl_{(C \leq 12)}$, $alkynyl_{(C \leq 12)}$, $aryl_{(C \leq 12)}$, $aralkyl_{(C \leq 12)}$, $heteroaryl_{(C \leq 12)}$, $heteroaralkyl_{(C \leq 12)}$, $alkoxy_{(C \leq 12)}$, $aryloxy_{(C \leq 12)}$, $aralkoxy_{(C \leq 12)}$, $hetero-aryloxy_{(C \leq 12)}$, $heteroaralkoxy_{(C \leq 12)}$, $alkylamino_{(C \leq 12)}$, $dialkylamino_{(C \leq 12)}$, $arylamino_{(C \leq 12)}$, $aralkylamino_{(C \leq 12)}$, or a substituted version of any of these groups; or
 $R_5$, $R_7$, and $R_8$ are each independently:
  hydrogen, hydroxy, halo, amino, nitro, cyano or mercapto;
  $alkyl_{(C \leq 12)}$, $alkenyl_{(C \leq 12)}$, $alkynyl_{(C \leq 12)}$, $aryl_{(C \leq 12)}$, $aralkyl_{(C \leq 12)}$, $heteroaryl_{(C \leq 12)}$, $heteroaralkyl_{(C \leq 12)}$, $acyl_{(C \leq 12)}$, $alkoxy_{(C \leq 12)}$, $alkenyloxy_{(C \leq 12)}$, $alkynyl-oxy_{(C \leq 12)}$, $aryloxy_{(C \leq 12)}$, $aralkoxy_{(C \leq 12)}$, $heteroaryloxy_{(C \leq 12)}$, $heteroaralkoxy_{(C \leq 12)}$, $acyloxy_{(C \leq 12)}$, $alkylamino_{(C \leq 12)}$, $dialkylamino_{(C \leq 12)}$, $alkoxyamino_{(C \leq 12)}$, $alkenylamino_{(C \leq 12)}$, $alkynylamino_{(C \leq 12)}$, $arylamino_{(C \leq 12)}$, $aralkylamino_{(C \leq 12)}$, $heteroaryl-amino_{(C \leq 12)}$, $heteroaralkylamino_{(C \leq 12)}$, $alkylsulphonylamino_{(C \leq 12)}$, $amido_{(C \leq 12)}$, $alkylthio_{(C \leq 12)}$, $alkenylthio_{(C \leq 12)}$, $alkynylthio_{(C \leq 12)}$, $arylthio_{(C \leq 12)}$, $aralkylthio_{(C \leq 12)}$, $heteroarylthio_{(C \leq 12)}$, $heteroaralkyl-thio_{(C \leq 12)}$, $acylthio_{(C \leq 12)}$, $thioacyl_{(C \leq 12)}$, $alkyl-sulfonyl_{(C \leq 12)}$, $arylsulfonyl_{(C \leq 12)}$, $alkyl-ammonium_{(C \leq 12)}$, $alkylsulfonium_{(C \leq 12)}$, $alkyl-silyl_{(C \leq 12)}$, or a substituted version of any of these groups;
 $R_6$ is a -linker-reporter;
or a salt thereof;
 (iv) adding a nucleic acid replicating enzyme to the hybridized primer/target nucleic acid complex to incorporate the compound of step (iii) into the growing primer strand, wherein the incorporated compound of step (iii) terminates the polymerase reaction at an efficiency of between about 70% to about 100%;
 (v) washing the solid surface to remove unincorporated components;
 (vi) detecting the reporter group of the incorporated compound of step (iii);
 (vii) a photochemical cleavage step to remove the terminating moiety of the incorporated compound, wherein the terminating moiety has the formula:

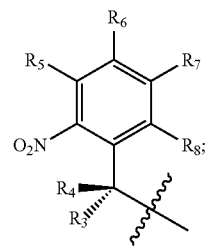

(viii) washing the solid surface to remove the cleaved terminating moiety; and
 (ix) repeating steps (iii) through (viii) one or more times to identify the plurality of bases in the target nucleic acid.

2. A method of identifying a plurality of bases in a target nucleic acid, comprising the following steps:
 (i) attaching the 5'-end of a target nucleic acid to a solid surface;
 (ii) hybridizing a primer to the target nucleic acid attached to the solid surface;

(iii) adding a compound of the formula:

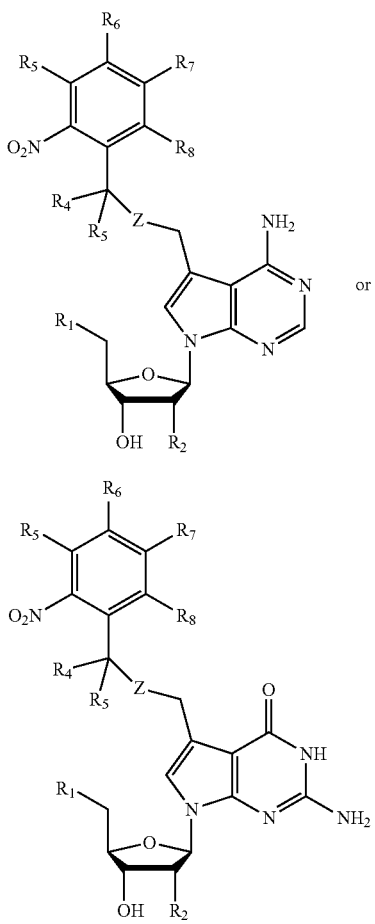

wherein:
Z is —O—, —S—, —NH—, —OC(O)O—, —NHC(O)O—, —OC(O)NH— or —NHC(O)NH—;
$R_1$ is triphosphate or α-thiotriphosphate;
$R_2$ is hydrogen or hydroxy;
$R_3$ and $R_4$ are each independently:
hydrogen, hydroxy, halo or amino; or
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, alkoxy$_{(C \leq 12)}$, aryloxy$_{(C \leq 12)}$, aralkoxy$_{(C \leq 12)}$, hetero-aryloxy$_{(C \leq 12)}$, heteroaralkoxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, or a substituted version of any of these groups; or
$R_5$, $R_7$, and $R_8$ are each independently:
hydrogen, hydroxy, halo, amino, nitro, cyano or mercapto;
alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, alkenyloxy$_{(C \leq 12)}$, alkynyl-oxy$_{(C \leq 12)}$, aryloxy$_{(C \leq 12)}$, aralkoxy$_{(C \leq 12)}$, heteroaryloxy$_{(C \leq 12)}$, heteroaralkoxy$_{(C \leq 12)}$, acyloxy$_{(C \leq 12)}$, alkylamino$_{(C \leq 12)}$, dialkylamino$_{(C \leq 12)}$, alkoxyamino$_{(C \leq 12)}$, alkenylamino$_{(C \leq 12)}$, alkynylamino$_{(C \leq 12)}$, arylamino$_{(C \leq 12)}$, aralkylamino$_{(C \leq 12)}$, heteroaryl-amino$_{(C \leq 12)}$, heteroaralkylamino$_{(C \leq 12)}$, alkylsulphonylamino$_{(C \leq 12)}$, amido$_{(C \leq 12)}$, alkylthio$_{(C \leq 12)}$, alkenylthio$_{(C \leq 12)}$, alkynylthio$_{(C \leq 12)}$, arylthio$_{(C \leq 12)}$, aralkylthio$_{(C \leq 12)}$, heteroarylthio$_{(C \leq 12)}$, heteroaralkyl-thio$_{(C \leq 12)}$, acylthio$_{(C \leq 12)}$, thioacyl$_{(C \leq 12)}$, alkyl-sulfonyl$_{(C \leq 12)}$, arylsulfonyl$_{(C \leq 12)}$, alkyl-ammonium$_{(C \leq 12)}$, alkylsulfonium$_{(C \leq 12)}$, alkyl-silyl$_{(C \leq 12)}$, or a substituted version of any of these groups;
$R_6$ is a -linker-reporter;
or a salt thereof;

(iv) adding a nucleic acid replicating enzyme to the hybridized primer/target nucleic acid complex to incorporate the compound of step (iii) into the growing primer strand, wherein the incorporated compound of step (iii) terminates the polymerase reaction at an efficiency of between about 70% to about 100%;

(v) washing the solid surface to remove unincorporated components;

(vi) detecting the reporter group of the incorporated compound of step (iii);

(vii) optionally adding one or more chemical compounds to permanently cap unextended primers;

(viii) a photochemical cleavage step to remove the terminating moiety of the incorporated compound, wherein the terminating moiety has the formula:

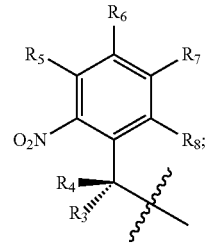

(ix) washing the solid surface to remove the cleaved terminating moiety; and (x) repeating steps (iii) through (ix) one or more times to identify the plurality of bases in the target nucleic acid.

3. The method of claim 1, wherein the compound is incorporated by a nucleic acid replicating enzyme that is a DNA polymerase.

4. The method of claim 1, wherein the photo-cleavage is performed using a wavelength of light ranging between 300 nm to 400 nm.

5. The method of claim 1, wherein Z is —O—.

6. The method of claim 1, wherein $R_1$ is a triphosphate.

7. The method of claim 1, wherein $R_1$ is α-thiotriphosphate.

8. The method of claim 1, wherein $R_2$ is hydrogen.

9. The method of claim 1, wherein $R_3$ is alkyl$_{(C \leq 12)}$ or a substituted version thereof.

10. The method of claim 1, wherein $R_3$ is selected from the group consisting of methyl, ethyl, n-propyl, isopropyl and tert-butyl.

11. The method of claim 1, wherein $R_3$ is tert-butyl.

12. The method of claim 1, wherein $R_4$ is hydrogen.

13. The method of claim 1, wherein $R_5$ is hydrogen.

14. The method of claim 1, wherein the linker of the -linker-reporter is:

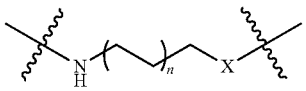

wherein
  X is
    —O—, —S—, or —NH—; or
    alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, or a substituted version of any of these groups; and
  n is an integer from 0-12.

15. The method of claim 14, wherein X is —C≡C—.
16. The method of claim 14, wherein n is zero.
17. The method of claim 14, wherein the reporter is:

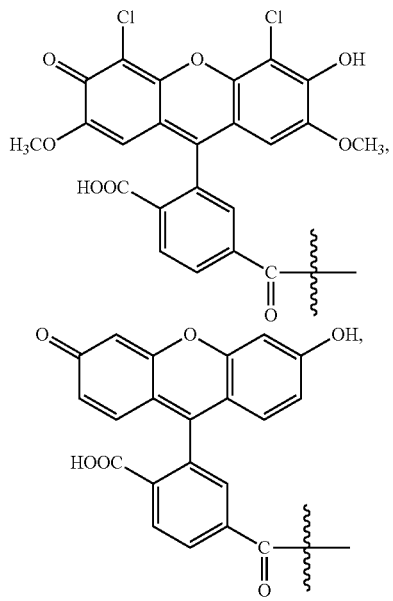

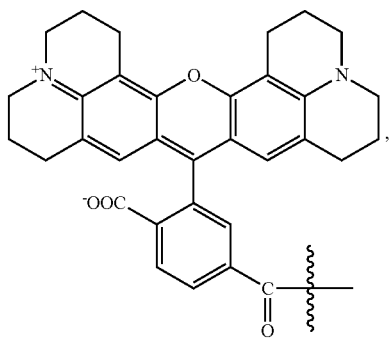

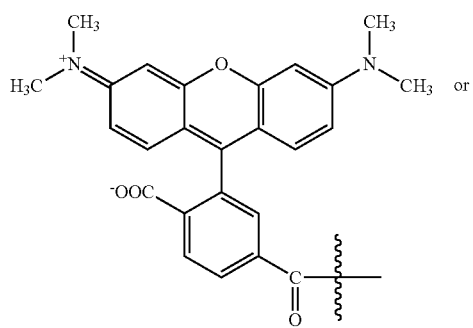

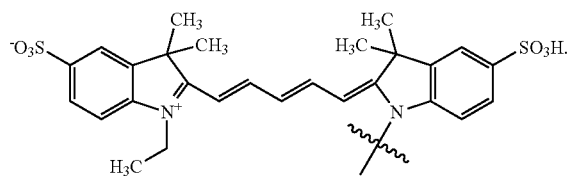

18. The method of claim 1, wherein $R_7$ is hydrogen.
19. The method of claim 1, wherein $R_8$ is hydrogen.

* * * * *

UNITED STATES PATENT AND TRADEMARK OFFICE
CERTIFICATE OF CORRECTION

PATENT NO. : 9,200,319 B2  
APPLICATION NO. : 14/519616  
DATED : December 1, 2015  
INVENTOR(S) : Vladislav A. Litosh et al.

Page 1 of 1

It is certified that error appears in the above-identified patent and that said Letters Patent is hereby corrected as shown below:

In the claims

In claim 1, column 153, lines 24-59, delete the entire contents of lines 24-59 and insert -- 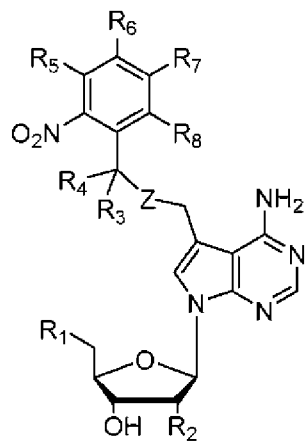 (A) or 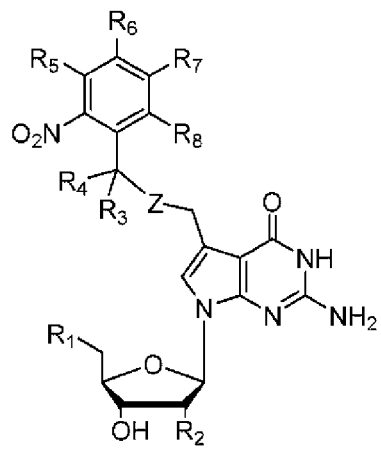 (B) -- therefor.

In claim 2, column 155, lines 4-39, delete the entire contents of lines 4-39 and insert -- 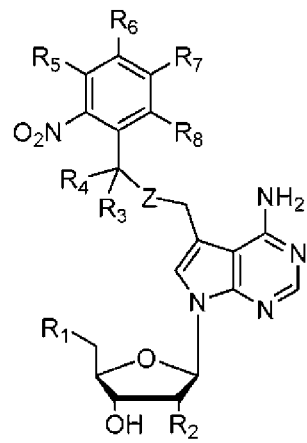 (A) or 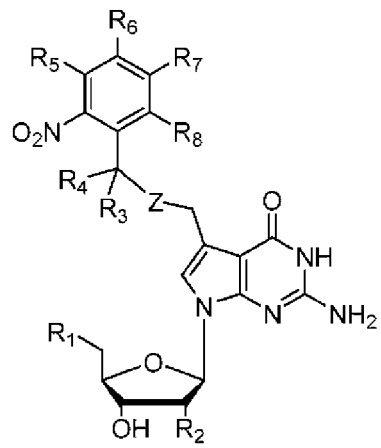 (B) -- therefor.

Signed and Sealed this  
Twenty-sixth Day of April, 2016

Michelle K. Lee  
*Director of the United States Patent and Trademark Office*